(12) United States Patent
Horiguchi et al.

(10) Patent No.: US 10,597,371 B2
(45) Date of Patent: Mar. 24, 2020

(54) POLYMERIZABLE COMPOUND AND OPTICAL ISOMER

(71) Applicant: DIC Corporation, Tokyo (JP)

(72) Inventors: Masahiro Horiguchi, Kita-adachi-gun (JP); Yutaka Kadomoto, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/547,949

(22) PCT Filed: Feb. 16, 2016

(86) PCT No.: PCT/JP2016/054399
§ 371 (c)(1),
(2) Date: Aug. 1, 2017

(87) PCT Pub. No.: WO2016/136533
PCT Pub. Date: Sep. 1, 2016

(65) Prior Publication Data
US 2018/0022716 A1 Jan. 25, 2018

(30) Foreign Application Priority Data
Feb. 24, 2015 (JP) ................................. 2015-033948

(51) Int. Cl.
| | | |
|---|---|---|
| C09K 19/38 | (2006.01) |
| C07D 277/82 | (2006.01) |
| C07D 409/14 | (2006.01) |
| C07D 417/12 | (2006.01) |
| C07C 243/20 | (2006.01) |
| C07C 243/22 | (2006.01) |
| C07C 323/52 | (2006.01) |
| C07D 209/56 | (2006.01) |
| C07D 241/42 | (2006.01) |
| C07D 263/58 | (2006.01) |
| C07D 277/84 | (2006.01) |
| C07D 303/27 | (2006.01) |
| C07D 317/46 | (2006.01) |
| C07D 333/58 | (2006.01) |
| C07D 401/12 | (2006.01) |
| C07D 403/12 | (2006.01) |
| C07D 405/12 | (2006.01) |
| C07D 413/14 | (2006.01) |
| C07D 417/14 | (2006.01) |
| C07D 495/04 | (2006.01) |
| C07D 513/04 | (2006.01) |
| C08F 22/10 | (2006.01) |
| C09K 19/32 | (2006.01) |
| C09K 19/34 | (2006.01) |

(52) U.S. Cl.
CPC .......... *C07D 277/82* (2013.01); *C07C 243/20* (2013.01); *C07C 243/22* (2013.01); *C07C 323/52* (2013.01); *C07D 209/56* (2013.01); *C07D 241/42* (2013.01); *C07D 263/58* (2013.01); *C07D 277/84* (2013.01); *C07D 303/27* (2013.01); *C07D 317/46* (2013.01); *C07D 333/58* (2013.01); *C07D 401/12* (2013.01); *C07D 403/12* (2013.01); *C07D 405/12* (2013.01); *C07D 409/14* (2013.01); *C07D 413/14* (2013.01); *C07D 417/12* (2013.01); *C07D 417/14* (2013.01); *C07D 495/04* (2013.01); *C07D 513/04* (2013.01); *C08F 22/10* (2013.01); *C09K 19/32* (2013.01); *C09K 19/322* (2013.01); *C09K 19/3491* (2013.01); *C09K 19/3497* (2013.01); *C09K 2019/328* (2013.01)

(58) Field of Classification Search
CPC ..................................................... C09K 19/34
See application file for complete search history.

(56) References Cited

U.S. PATENT DOCUMENTS

| | | |
|---|---|---|
| 5,445,854 A | 8/1995 | Newsham et al. |
| 2012/0224245 A1 | 9/2012 | Adlem et al. |
| 2014/0107247 A1 | 4/2014 | Sakamoto et al. |
| 2014/0142266 A1 | 5/2014 | Sakamoto et al. |
| 2014/0200320 A1 | 7/2014 | Sakamoto et al. |

(Continued)

FOREIGN PATENT DOCUMENTS

| | | |
|---|---|---|
| JP | 2010-31223 A | 2/2010 |
| JP | 2013-509458 A | 3/2013 |

(Continued)

OTHER PUBLICATIONS

International Search Report dated May 17, 2016, issued in counterpart International Application No. PCT/JP2016/054399 (2 pages).

(Continued)

Primary Examiner — Chanceity N Robinson
(74) Attorney, Agent, or Firm — Westerman, Hattori, Daniels & Adrian, LLP

(57) ABSTRACT

The present invention provides a polymerizable compound having high storage stability without causing crystal precipitation when added to a polymerizable composition. The present invention also provides a polymerizable composition containing the compound. When the filmy polymer produced through polymerization of the polymerizable composition is irradiated with UV light, it hardly discolors or peels from substrate. Further, the present invention provides a polymer produced through polymerization of the polymerizable composition and an optically anisotropic body using the polymer.

9 Claims, No Drawings

(56) References Cited

U.S. PATENT DOCUMENTS

| | | | |
|---|---|---|---|
| 2015/0175564 A1* | 6/2015 | Sakamoto | C07D 417/12 526/257 |
| 2015/0183902 A1 | 7/2015 | Sakamoto et al. | |
| 2015/0274872 A1 | 10/2015 | Sakamoto et al. | |
| 2015/0277010 A1 | 10/2015 | Aimatsu et al. | |
| 2015/0285979 A1* | 10/2015 | Aimatsu | C09K 19/02 349/194 |
| 2016/0002374 A1 | 1/2016 | Sakamoto et al. | |
| 2016/0200841 A1 | 7/2016 | Sakamoto | |
| 2016/0257659 A1 | 9/2016 | Sakamoto et al. | |
| 2017/0008833 A1 | 1/2017 | Sakamoto et al. | |
| 2017/0260150 A1* | 9/2017 | Nose | C07D 263/58 |

FOREIGN PATENT DOCUMENTS

| | | | |
|---|---|---|---|
| JP | 2016-113583 A | 6/2016 | |
| WO | 2012/141245 A1 | 10/2012 | |
| WO | 2012/147904 A1 | 11/2012 | |
| WO | 2013/180217 A1 | 12/2013 | |
| WO | 2014/010325 A1 | 1/2014 | |
| WO | WO-2014010325 A1 * | 1/2014 | C07D 417/12 |
| WO | 2014/065176 A1 | 5/2014 | |
| WO | 2014/065243 A1 | 5/2014 | |
| WO | 2014/069515 A1 | 5/2014 | |
| WO | WO-2014069515 A1 * | 5/2014 | C09K 19/02 |
| WO | 2014/126113 A1 | 8/2014 | |
| WO | 2014/132978 A1 | 9/2014 | |
| WO | WO-2014132978 A1 * | 9/2014 | G02B 5/3083 |
| WO | 2015/025793 A1 | 2/2015 | |
| WO | 2015/064698 A1 | 5/2015 | |
| WO | 2015/122385 A1 | 8/2015 | |
| WO | 2016/056542 A1 | 4/2016 | |
| WO | 2016/088749 A1 | 6/2016 | |

OTHER PUBLICATIONS

Notification of Reasons for Refusal dated Jan. 24, 2017, issued in counterpart Japanese Patent Application No. 2016-567448, w/English translation (8 pages).

Decision to Grant a Patent dated May 25, 2017, issued in counterpart Japanese Patent Application No. 2016-567448, w/English translation (6 pages).

* cited by examiner

POLYMERIZABLE COMPOUND AND OPTICAL ISOMER

TECHNICAL FIELD

The present invention relates to a compound having a polymerizable group, a polymerizable composition containing the compound, a polymerizable liquid crystal composition and an optically anisotropic body using the polymerizable liquid crystal composition.

BACKGROUND ART

A compound having a polymerizable group (polymerizable compound) is used for various optical materials. For example, after a polymerizable composition containing a polymerizable compound is aligned in a liquid-crystal state, it can be polymerized to produce a polymer having a uniform alignment. Such a polymer can be used for polarizers, retarders and the like necessary for displays. In many cases, for satisfying required optical properties, polymerization speed, solubility, melting point, glass transition temperature, polymer transparency, mechanical strength, surface hardness, heat resistance and lightproofness, a polymerizable composition containing two or more kinds of polymerizable compounds is used. In such a case, the polymerizable compounds to be used are desired to impart good physical properties to the polymerizable composition without having any negative influence on the other properties.

For improving the viewing angle of a liquid crystal display, it is desired to reduce the wavelength dispersion characteristic of birefringence of a retardation film, or to reverse it. As a material for the purpose, various polymerizable liquid crystal compounds having a reversed wavelength dispersion characteristic or a low wavelength dispersion characteristic have been developed. However, such a polymerizable compound causes crystal precipitation when added to a polymerizable composition and the storage stability thereof is insufficient (PTL 2 and PTL 3). On the other hand, in the case where a polymerizable composition is applied onto a substrate and polymerized thereon and the resultant filmy polymer is irradiated with UV light, there occur a problem that the filmy polymer often discolors or peels off from the substrate (PTL 1 to PTL 3). When the discolored or peeled film is used, for example, in a display, the brightness of the picture plane may be uneven, or the color may be unnatural, or intended optical characteristics could not be obtained, and there occurs a problem that the quality of display products is significantly lowered. Consequently, development of a polymerizable liquid crystal compound having a reversed wavelength dispersion property or a low wavelength dispersion property capable of solving the problems is desired.

CITATION LIST

Patent Literature

PTL 1: WO2012-147904A1
PTL 2: WO2014-010325A1
PTL 3: JP-A-2010-031223

SUMMARY OF INVENTION

Technical Problem

The problem that the present invention is to solve is to provide a polymerizable compound capable of having high storage stability without causing crystal precipitation when added to a polymerizable composition, and to provide a polymerizable composition containing the polymerizable compound and capable of giving a filmy polymer through polymerization, in which the resultant filmy polymer is hardly discolored and peeled from a substrate when irradiated with UV light. Further, the present invention is to provide a polymer obtained through polymerization of the polymerizable composition and to provide an optically anisotropic body using the polymer.

Solution to Problem

The present inventors have assiduously studied for the purpose of solving the above-mentioned problems and, as a result, have developed a compound represented by the following general formula (I). Specifically, the present invention provides a compound represented by the general formula (I):

[Chem. 1]

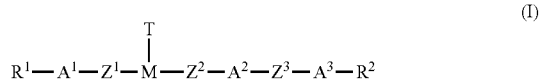

(In the formula, $R^1$ and $R^2$ each independently represent a hydrogen atom or a hydrocarbon group having 1 to 80 carbon atoms, which may have a substituent, and one or more of arbitrary carbon atoms thereof may be substituted with a hetero atom, provided that at least one of $R^1$ and $R^2$ represents a group including a polymerizable group;

$A^1$, $A^2$ and $A^3$ each independently represent a 1,4-phenylene group, a 1,4-cyclohexylene group, a pyridine-2,5-diyl group, a pyrimidine-2,5-diyl group, a naphthalene-2,6-diyl group, a naphthalane-1,4-diyl group, a tetrahydronaphthalene-2,6-diyl group, a decahydronaphthalane-2,6-diyl group or a 1,3-dioxane-2,5-diyl group, which may be unsubstituted or substituted with one or more of substituents L's;

$Z^1$, $Z^2$ and $Z^3$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C— or a single bond;

M represents an optionally-substituted trivalent aromatic group;

T represents a group selected from the following formula (T-1) or formula (T-2):

[Chem. 2]

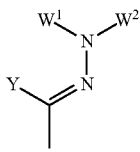
(T-1)

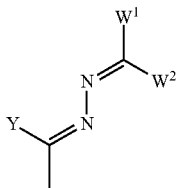
(T-2)

(wherein $W^1$ represents a group including an aromatic group and/or a non-aromatic group optionally substituted and having 1 to 80 carbon atoms, in which the aromatic group may be a hydrocarbon ring or a hetero ring, the non-aromatic group may be a hydrocarbon group or a hydrocarbon group where one or more of arbitrary carbon atoms is substituted with a hetero atom (provided that the oxygen atoms therein do not directly bond to each other), and the group may be unsubstituted or substituted with one or more of substituents $L^W$'s, $W^2$ represents a hydrogen atom, or a linear or branched alkyl group having 1 to 20 carbon atoms, in which one —$CH_2$— or two or more of (—$CH_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and one or more of arbitrary hydrogen atoms in the alkyl group may be substituted with a fluorine atom, or $W^2$ represents a group including an aromatic group and/or a non-aromatic group optionally substituted and having 1 to 80 carbon atoms, in which the aromatic group may be a hydrocarbon ring or a hetero ring, and the non-aromatic group may be a hydrocarbon group or a hydrocarbon group where one or more of arbitrary carbon atoms is substituted with a hetero atom (provided that the oxygen atoms therein do not directly bond to each other), and the group may be unsubstituted or substituted with one or more of substituents $L^W$'s, or $W^2$ may represent a group represented by $P^W$—$(Sp^W$-$X^W)_{kW}$—, where $P^W$ represents a polymerizable group, $Sp^W$ represents a spacer group or a single bond, and plural $Sp^W$'s, if any, may be the same or different, $X^W$ represents —O—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, plural $X^W$'s, if any, may be the same or different (provided that $P^W$—$(Sp^W$-$X^W)_{kW}$— does not contain an —O—O— bond), kW represents an integer of 0 to 10, and $W^1$ and $W^2$ may together form a cyclic structure, $L^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more of (—$CH_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and one or more of arbitrary hydrogen atoms in the alkyl group may be substituted with a fluorine atom, or $L^W$ represents a group represented by $P^{LW}$—$(Sp^{LW}$-$X^{LW})_{kLW}$— where $p^{LW}$ represents a polymerizable group, $Sp^{LW}$ represents a spacer group or a single bond, plural $Sp^{LW}$'s, if any, may be the same or different, $X^{LW}$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, plural $X^{LW}$'s, if any, may be the same or different (provided that $P^{LW}$—$(Sp^{LW}$-$X^{LW})_{kLW}$— does not contain an —O—O— bond), kLW represents an integer of 0 to 10, and plural $L^W$'s, if any, in the compound may be the same or different, Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more of (—$CH_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and one or more of arbitrary hydrogen atoms in the alkyl group may be substituted with a fluorine atom, or Y represents a group represented by $P^Y$—$(S^Y$—$X^Y)_{kY}$— where $P^Y$ represents a polymerizable group, $Sp^Y$ represents a spacer group or a single bond, plural $Sp^Y$'s, if any, may be the same or different, $X^Y$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, plural $X^Y$'s, if any, may be the same or different (provided that $P^Y$-$(Sp^Y$-$X^Y)_{kY}$— does not contain an —O—O— bond), and kY represents an integer of 0 to 10);

L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more of (—$CH_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and one or more of arbitrary hydrogen atoms in the alkyl group may be substituted with a fluorine atom, or L represents a group represented by $P^L$-$(Sp^L$-$X^L)_{kL}$— where $P^L$ represents a polymerizable group, $Sp^L$ represents a spacer group or a single bond, plural $Sp^L$'s, if any, may be the same or different, $X^L$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, plural $X^L$'s, if any, may be the same or different (provided that $P^L$-$(Sp^L$-$X^L)_{kL}$— does not contain an —O—O— bond), kL represents an integer of 0 to 10, plural L's, if any, in the compound may be the same or different; and the group that links T-M may be a single bond or a double bond; and the present invention also provides a polymerizable composition containing the compound, and resins, resin additives, oils, filters, adhesives, pressure-sensitive adhesives, oils and fats, inks, medicines, cosmetics, detergents, building materials, wrapping or packaging materials, liquid crystal materials, organic EL materials, organic semiconductor materials, electronic materials, display devices, electronic devices, communication instruments, automobile parts, airplane parts, machine parts, agricultural chemicals and foods using the compound, as well as products using them, and further provides a polymerizable liquid crystal composition, a polymer obtained by polymerizable the polymerizable liquid crystal composition, and an optically anisotropic body using the polymer.

Advantageous Effects of Invention

The compound of the present invention has high storage stability when constituting a polymerizable composition, and is useful as a constituent member of a polymerizable composition. An optically anisotropic body using a polymerizable liquid crystal composition that contains the compound of the present invention is, when irradiated with UV light, hardly discolored or peeled from a substrate, and is therefore useful for use in an optical material such as an retardation film, etc.

DESCRIPTION OF EMBODIMENTS

The present invention provides a reverse dispersion compound represented by the general formula (I), and also provides a polymerizable composition containing the compound, and resins, resin additives, oils, filters, adhesives, pressure-sensitive adhesives, oils and fats, inks, medicines, cosmetics, detergents, building materials, wrapping or packaging materials, liquid crystal materials, organic EL materials, organic semiconductor materials, electronic materials, display devices, electronic devices, communication instruments, automobile parts, airplane parts, machine parts, agricultural chemicals and foods using the compound, as well as products using them, and further provides a polymerizable liquid crystal composition, a polymer obtained by polymerizable the polymerizable liquid crystal composition, and an optically anisotropic body using the polymer.

In a graph where the wavelength λ of an incident light running into a retardation film is plotted on a horizontal axis and the birefringence Δn of the film is on the vertical axis, and in the case where the birefringence Δn decreases with the reduction in the wavelength λ, the film is generally called a "reverse wavelength dispersion" or "reverse dispersion" film by those skilled in the art. In the present invention, a compound to constitute a retardation film that shows a reverse dispersion property is referred to as a reverse dispersion compound.

In the general formula (I), $R^1$ and $R^2$ each independently represent a hydrogen atom or a hydrocarbon group optionally having a substituent and having 1 to 80 carbon atoms, in which one or more of arbitrary carbon atoms may be substituted with a hetero atom, but from the viewpoint of mechanical strength of the film formed using the compound, at least one of $R^1$ and $R^2$ preferably represents a group including a polymerizable group, and from the viewpoint of mechanical strength and liquid crystallinity, more preferably, the groups represented by $R^1$ and $R^2$ each independently represent a group represented by the following general formula (I-R):

[Chem. 3].

$$P\text{-}(Sp\text{-}X)_k\text{—} \qquad (I\text{-}R)$$

(In the formula, P represents a polymerizable group, Sp represents a spacer group or a single bond, and plural Sp's, if any, may be the same or different, X represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, and plural X's, if any, may be the same or different (provided that P—$(Sp\text{-}X)_k$— does not contain an —O—O— bond), k represents an integer of 0 to 10).

In the formula (I-R), P represents a polymerizable group and is preferably a group selected from the following formula (P-1) to formula (P-20):

[Chem. 4]

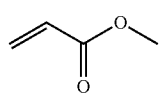

(P-1)

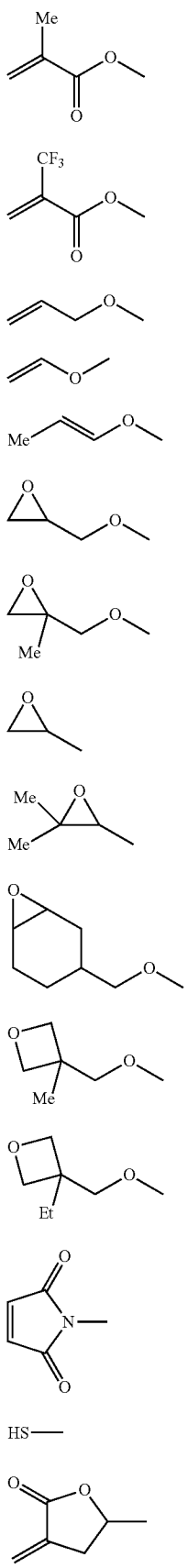
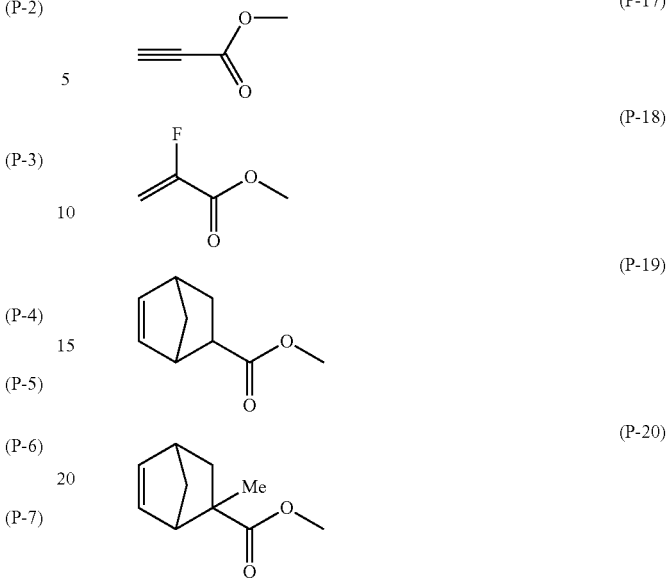

(P-2)
(P-3)
(P-4)
(P-5)
(P-6)
(P-7)
(P-8)
(P-9)
(P-10)
(P-11)
(P-12)
(P-13)
(P-14)
(P-15)
(P-16)
(P-17)
(P-18)
(P-19)
(P-20)

These polymerizable groups polymerize through radical polymerization, radical addition polymerization, cationic polymerization or anionic polymerization. In particular, when the polymerization method is in a mode of UV polymerization, the formula (P-1), the formula (P-2), the formula (P-3), the formula (P-4), the formula (P-5), the formula (P-7), the formula (P-11), the formula (P-13), the formula (P-15) or the formula (P-18) is preferred, the formula (P-1), the formula (P-2), the formula (P-7), the formula (P-11) or the formula (P-13) is more preferred, the formula (P-1), the formula (P-2) or the formula (P-3) is even more preferred, and the formula (P-1) or the formula (P-2) is especially preferred.

In the general formula (I-R), Sp represents a spacer group or a single bond, and plural Sp's, if any, may be the same or different. The spacer group may be unsubstituted or substituted with one or more of the following substituents $L^W$'s. The spacer group is preferably an alkylene group having 1 to 20 carbon atoms in which one —$CH_2$— or two or more of (—$CH_2$—)'s which are not adjacent to each other may be each independently substituted with —O—, —COO—, —OCO—, —OCO—O—, —CO—NH—, —NH—CO—, —CH=CH— or —C≡C—. From the viewpoint of easy availability of raw materials and easiness in synthesis, more preferably, plural Sp's, if any, may be the same or different and each independently represent an alkylene group having 1 to 10 carbon atoms in which one —$CH_2$— or two or more of (—$CH_2$—)'s which are not adjacent to each other may be each independently substituted with —O—, —COO— or —OCO—, or represent a single bond, and even more preferably they each independently represent an alkylene group having 1 to 10 carbon atoms or a single bond, and especially preferably, plural groups, if any, may be the same or different and each independently represent an alkylene group having 1 to 8 carbon atoms.

In the general formula (I-R), X represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C— or a single bond, and plural X's, if any, may be the same or different (provided that P—(Sp-X)$_k$— does not contain an —O—O— bond). From the viewpoint of easy availability of raw materials and easiness in synthesis, preferably, plural groups, if any, may be the same or different and each independently represent —O—, —S—, —OCH$_2$—, —CH$_2$O—, —COO—, —OCO—, —CO—S—, —S—CO—, —O—CO—O—, —CO—NH—, —NH—CO—, —COO—CH$_2$CH$_2$—, —OCO—CH$_2$CH$_2$—, —CH$_2$CH$_2$—COO—, —CH$_2$CH$_2$—OCO— or a single bond, more preferably —O—, —OCH$_2$—, —CH$_2$O—, —COO—, —OCO—, —COO—CH$_2$CH$_2$—, —OCO—CH$_2$CH$_2$—, —CH$_2$CH$_2$—COO—, —CH$_2$CH$_2$—OCO— or a single bond, and even more preferably, plural groups, if any, may the same or different, and each independently represent —O—, —COO—, —OCO— or a single bond.

In the general formula (I-R), k represents an integer of 0 to 10, but is preferably an integer of 0 to 5, more preferably an integer of 0 to 2, especially preferably 1.

In the general formula (I), R$^1$ and R$^2$ each independently represent a hydrogen atom or a hydrocarbon group having 1 to 80 carbon atoms and optionally having a substituent, in which one or more of arbitrary carbon atoms may be substituted with a hetero atom, but at least one of R$^1$ and R$^2$ represents a group including a polymerizable group. In the case where R$^1$ or R$^2$ represents a group not including a polymerizable group, R$^1$ or R$^2$ preferably represents, from the viewpoint of liquid crystallinity and easiness in synthesis, each independently a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which one —CH$_2$— or two or more of (—CH$_2$—)'s which are not adjacent to each other may be each independently substituted with —O—, —S—, —CO—, —COO—, —OCO—, —CO—S—, —S—CO—, —O—CO—O—, —CO—NH—, —NH—CO— or —C≡C—. More preferably, R$^1$ or R$^2$ each independently represents a hydrogen atom, a fluorine atom, a chlorine atom, a cyano group, or a linear or branched alkyl group having 1 to 12 carbon atoms in which one —CH$_2$— or two or more of (—CH$_2$—)'s which are not adjacent to each other may be each independently substituted with —O—, —COO—, —OCO— or —O—CO—O—, even more preferably a hydrogen atom, a fluorine atom, a chlorine atom, a cyano group, or a linear alkyl group or a linear alkoxy group having 1 to 12 carbon atoms, and especially preferably a linear alkyl group or a linear alkoxy group having 1 to 12 carbon atoms.

In the general formula (I), A$^1$, A$^2$ and A$^3$ each independently represent a 1,4-phenylene group, a 1,4-cyclohexylene group, a pyridine-2,5-diyl group, a pyrimidine-2,5-diyl group, a naphthalene-2,6-diyl group, a naphthalane-1,4-diyl group, a tetrahydronaphthalene-2,6-diyl group, a decahydronaphthalane-2,6-diyl group or a 1,3-dioxane-2,5-diyl group, which may be unsubstituted or substituted with one or more substituents of the following substituents L$^W$'s.

The substituent L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH$_2$— or two or more of (—CH$_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—, and one or more of arbitrary hydrogen atoms in the alkyl group may be substituted with a fluorine atom, or L represents a group represented by P$^L$-(Sp$^L$-X$^L$)$_{kL}$— where p$^L$ represents a polymerizable group, Sp$^L$ represents a spacer group or a single bond, plural Sp$^L$'s, if any, may be the same or different, X$^L$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C— or a single bond, plural X$^L$'s, if any, may be the same or different (provided that P$^L$-(Sp$^L$-X$^L$)$_{kL}$— does not contain an —O—O— bond), kL represents an integer of 0 to 10, and plural L's, if any, in the compound may be the same or different.

From the viewpoint of liquid crystallinity and easiness in synthesis, L is preferably a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon atoms, in which one or more of arbitrary hydrogen atoms may be substituted with a fluorine atom and one —CH$_2$— or two or more of (—CH$_2$—)'s which are not adjacent to each other may be each independently substituted with a group selected from —O—, —S—, —CO—, —COO—, —OCO—, —O—CO—O—, —CH═CH—, —CF═CF— or —C≡C—, more preferably a fluorine atom, a chlorine atom, or a linear or branched alkyl group having 1 to 12 carbon atoms, in which one or more of arbitrary hydrogen atoms may be substituted with a fluorine atom and one —CH$_2$— or two or more of (—CH$_2$—)'s which are not adjacent to each other may be each independently substituted with a group selected from —O—, —COO— or —OCO—, even more preferably a fluorine atom, a chlorine atom, or a linear or branched alkyl or alkoxy group having 1 to 12 carbon atoms in which one or more of arbitrary hydrogen atoms may be substituted with a fluorine atom, and especially preferably a fluorine atom, a chlorine atom, or a linear alkyl or a linear alkoxy group having 1 to 8 carbon atoms.

From the viewpoint of easy availability of raw materials and easiness in synthesis, A$^1$, A$^2$ and A$^3$ preferably represent each independently a 1,4-phenylene group, a 1,4-cyclohexylene group or a naphthalene-2,6-diyl group which is unsubstituted or optionally substituted with one or more of substituents L's, more preferably each independently represent a group selected from the following formula (A-1) to formula (A-11):

[Chem. 5]

(A-1) 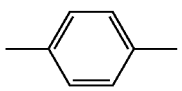

(A-2) 

(A-3) 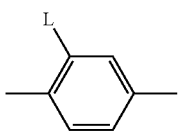

(A-4) 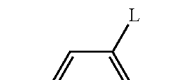

(A-5) 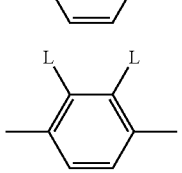

(A-6) 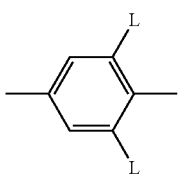

(A-7) 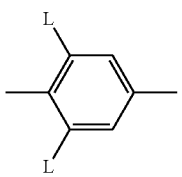

(A-8) 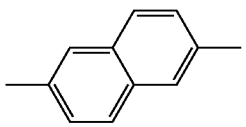

(A-9) 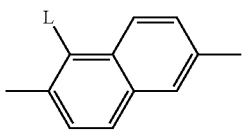

(A-10) 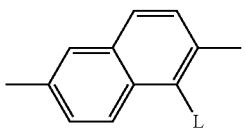

(A-11) 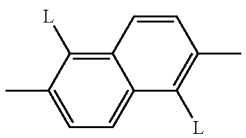

Even more preferably, they represent each independently a group selected from the formula (A-1) to the formula (A-8), and especially preferably a group selected from the formula (A-1) to the formula (A-4).

In the general formula (I), $Z^1$, $Z^2$ and $Z^3$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C— or a single bond, and from the viewpoint of liquid crystallinity of the compound, and easy availability of raw materials and easiness in synthesis, they preferably represent each independently —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C— or a single bond, more preferably each independently represent —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH=CH—, —C≡C— or a single bond, even more preferably each independently represent —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO— or a single bond, and especially preferably each independently represent —COO—, —OCO— or a single bond.

From the viewpoint that the filmy polymer exposed to UV light is hardly peeled from a substrate, $Z^2$ preferably represents —OCH$_2$—, —CH$_2$O—, —COO—, —OCO—, —CF$_2$O—, —OCF$_2$—, —CH$_2$CH$_2$—, —CF$_2$CF$_2$—, —COO—CH$_2$CH$_2$—, —OCO—CH$_2$CH$_2$—, —CH$_2$CH$_2$—COO—, —CH$_2$CH$_2$—OCO— or a single bond, more preferably —OCH$_2$—, —CH$_2$O—, —COO—, —OCO—, —CH$_2$CH$_2$—, —COO—CH$_2$CH$_2$—, —OCO—CH$_2$CH$_2$—, —CH$_2$CH$_2$—COO—, —CH$_2$CH$_2$—OCO— or a single bond, even more preferably —OCH$_2$—, —CH$_2$O—, —COO—, —OCO—, —CH$_2$CH$_2$— or a single bond, further more preferably —COO—, —OCO—, —CH$_2$CH$_2$— or a single bond, and especially preferably —COO—, —OCO— or a single bond.

In the general formula (I), M represents an optionally-substituted tri-valent aromatic group, and from the viewpoint of liquid crystallinity of the compound, easy availability of raw materials and easiness in synthesis, M is preferably a group selected from the following formula (M-1) or formula (M-2):

[Chem. 6]

(M-1)

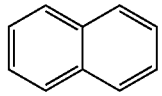
(M-2)

(These formulae may have a chemical bond in any arbitrary position, and in these, any arbitrary —CH═ may be each independently substituted with —N═. Here, the wording "may have a chemical bond in any arbitrary position" means that, for example, since M is a trivalent group, the formula may have three chemical bonds at any arbitrary positions. (Hereinunder in the present invention, the wording "may have a chemical bond in any arbitrary position" shall have the same meaning as above.) These groups may be unsubstituted or substituted with one or more of substituents $L^{M}$'s, and $L^{M}$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH$_2$— or two or more of (—CH$_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—, and one or more of arbitrary hydrogen atoms in the alkyl group may be substituted with a fluorine atom, and plural $L^{M}$'s, if any, may be the same or different). The group represented by the above formula (M-1) is preferably a group selected from the following formula (M-1-1) or formula (M-1-2):

[Chem. 7]

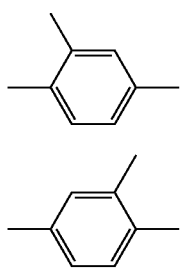

(M-1-1)

(M-1-2)

(These groups may be unsubstituted or substituted with one or more of the above-mentioned substituents $L^{M}$'s), and the group represented by the above formula (M-2) is preferably a group selected from the following formula (M-2-1) to formula (M-2-4):

[Chem. 8]

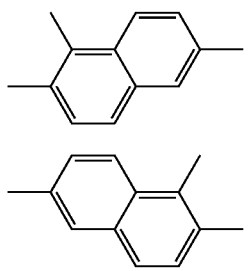

(M-2-1)

(M-2-2)

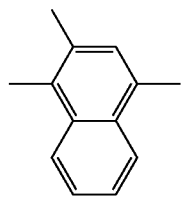

(M-2-3)

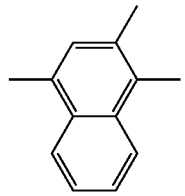

(M-2-4)

(These groups may be unsubstituted or substituted with one or more of the above-mentioned substituents $L^{M}$'s). From the viewpoint that the filmy polymer exposed to UV light is hardly discolored and hardly peeled from a substrate, M is more preferably a group selected from the above-mentioned formulae (M-1-1), (M-1-2), (M-2-3) and (M-2-4), which may be unsubstituted or substituted with one or more of the above-mentioned substituents $L^{M}$'s, even more preferably M is a group selected from the above-mentioned, unsubstituted formulae (M-1-1), (M-1-2), (M-2-3) and (M-2-4), and especially preferably M is a group selected from the above-mentioned, unsubstituted formulae (M-1-1) and (M-1-2).

In the general formula (I), T represents a group selected from the following formula (T-1) or formula (T-2):

[Chem. 9]

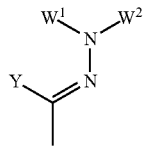

(T-1)

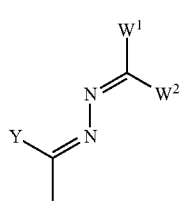

(T-2)

(In the formulae, $W^1$ represents a group including an aromatic group and/or a non-aromatic group optionally substituted and having 1 to 80 carbon atoms, in which the aromatic group may be a hydrocarbon ring or a hetero ring, the non-aromatic group may be a hydrocarbon group or a hydrocarbon group where one or more of arbitrary carbon atoms is substituted with a hetero atom (provided that the oxygen atoms therein do not directly bond to each other), and the group may be unsubstituted or substituted with one or more of substituents $L^{W}$'s, $W^2$ represents a hydrogen atom, or a linear or branched alkyl group having 1 to 20 carbon atoms, in which one —CH$_2$— or two or more of (—CH$_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and any hydrogen atom in the alkyl group may be substituted with a fluorine atom, or W² represents a group including an aromatic group and/or a non-aromatic group optionally substituted and having 1 to 80 carbon atoms, in which the aromatic group may be a hydrocarbon ring or a hetero ring, and the non-aromatic group may be a hydrocarbon group or a hydrocarbon group where one or more of arbitrary carbon atoms is substituted with a hetero atom (provided that the oxygen atoms therein do not directly bond to each other), and the group may be unsubstituted or substituted with one or more of substituents $L^W$'s, or W² may represent a group represented by $P^W\text{-}(Sp^W\text{-}X^W)_{kW}$—, where $P^W$ represents a polymerizable group, $Sp^W$ represents a spacer group or a single bond, and plural $Sp^W$'s, if any, may be the same or different, $X^W$ represents -O—, —S—, —OCH₂—, —CH₂O—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C— or a single bond, plural $X^W$'s, if any, may be the same or different (provided that $P^W\text{-}(Sp^W\text{-}X^W)_{kW}$— does not contain an —O—O— bond), kW represents an integer of 0 to 10, and W¹ and W² may together form a cyclic structure, $L^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH₂— or two or more of (—CH₂—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and one or more of arbitrary hydrogen atoms in the alkyl group may be substituted with a fluorine atom, or $L^W$ represents a group represented by $P^{LW}\text{-}(Sp^{LW}\text{-}X^{LW})_{kLW}$— where $P^{LW}$ represents a polymerizable group, $Sp^{LW}$ represents a spacer group or a single bond, plural $Sp^{LW}$'s, if any, may be the same or different, $X^{LW}$ represents —O—, —S—, —OCH₂—, —CH₂O—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C— or a single bond, plural $X^{LW}$'s, if any, may be the same or different (provided that $P^{LW}\text{-}(Sp^{LW}\text{-}X^{LW})_{kLW}$— does not contain an —O—O— bond), kLW represents an integer of 0 to 10, and plural $L^W$'s, if any, in the compound may be the same or different, Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH₂— or two or more of (—CH₂—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and any hydrogen atom in the alkyl group may be substituted with a fluorine atom, or Y represents a group represented by $P^Y\text{-}(Sp^Y\text{-}X^Y)_{kY}$— where $P^Y$ represents a polymerizable group, $Sp^Y$ represents a spacer group or a single bond, plural $Sp^Y$'s, if any, may be the same or different, $X^Y$ represents —O—, —S—, —OCH₂—, —CH₂O—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C— or a single bond, plural $X^Y$'s, if any, may be the same or different (provided that $P^Y\text{-}(Sp^Y\text{-}X^Y)_{kY}$— does not contain an —O—O— bond), kY represents an integer of 0 to 10)).

In the above formula (T-1) or formula (T-2), from the viewpoint of liquid crystallinity and easiness in synthesis, Y preferably represent a hydrogen atom, a fluorine atom, a chlorine atom, a nitro group, a cyano group, or a linear or branched alkyl group having 1 to 20 carbon atoms, in which one or more of arbitrary hydrogen atoms may be substituted with a fluorine atom and one —CH₂— or two or more of (—CH₂—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, or a group represented by $P^Y\text{-}(Sp^Y\text{-}X^Y)_{kY}$—, Y is more preferably a hydrogen atom, or a linear or branched alkyl group having 1 to 12 carbon atoms, in which one or more of arbitrary hydrogen atoms may be substituted with a fluorine atom and one —CH₂— or two or more of (—CH₂—)'s which are not adjacent to each other may be each independently substituted with —O—, —COO— or —OCO—, Y is even more preferably a hydrogen atom, or a linear or branched alkyl group having 1 to 12 carbon atoms in which one or more of arbitrary hydrogen atoms may be substituted with a fluorine atom, Y is further more preferably a hydrogen atom, or a linear alkyl group having 1 to 12 carbon atoms, and Y is especially preferably a hydrogen atom.

W¹ represents a group including an aromatic group and/or a non-aromatic group optionally substituted and having 1 to 80 carbon atoms, in which the aromatic group may be a hydrocarbon ring or a hetero ring, the non-aromatic group may be a hydrocarbon group or a hydrocarbon group where one or more of arbitrary carbon atoms is substituted with a hetero atom (provided that the oxygen atoms therein do not directly bond to each other), and the group may be unsubstituted or substituted with one or more of substituents $L^W$'s. From the viewpoint of easy availability of raw materials and easiness in synthesis, the aromatic group included in $W^1$ is preferably a group selected from the following formulae (W-1) to (W-20) which may be unsubstituted or substituted with one or more of the above-mentioned substituents $L^W$'s.

[Chem. 10]

(W-1)
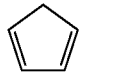

(W-2)

(W-3)
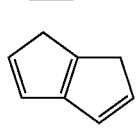

(W-4)
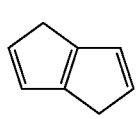

(W-5)
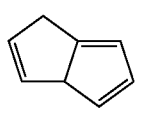

(W-6)
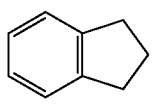

(W-7)
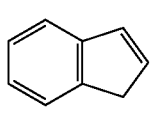

(W-8)
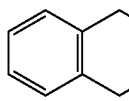

(W-9)
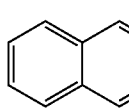

(W-10)
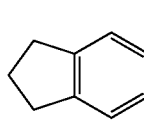

(W-11)
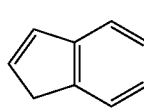

(W-12)
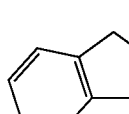

(W-13)
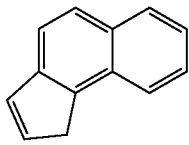

(W-14)
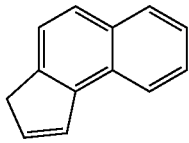

(W-15)
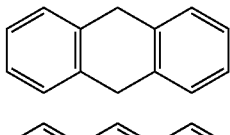

(W-16)
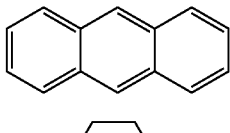

(W-17)
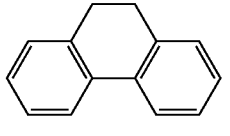

(W-18)
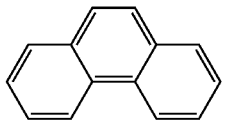

(W-19)
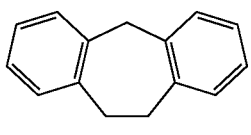

(W-20)
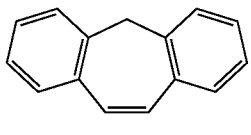

(In the formulae, the cyclic structure may have a chemical bond at any arbitrary position, and two or more aromatic groups selected from these groups may be bonded via a single bond to form a group, any arbitrary —CH═ may be each independently substituted with —N═, —CH$_2$— may be each independently substituted with —O—, —S—, —NR$^T$— (where R$^T$ represents a hydrogen atom, or an alkyl group having 1 to 20 carbon atoms), —CS— or —CO—, but does not contain an —O—O— bond. These groups may be unsubstituted or substituted with one or more of substituents $L^W$'s.) The group represented by the above formula (W-1) is preferably a group selected from the following formulae (W-1-1) to (W-1-7) which may be unsubstituted or substituted with one or more of the above-mentioned substituents $L^W$'s.

[Chem. 11]

(W-1-1)

-continued (W-1-2) 

(W-1-3) 

(W-1-4) 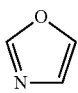

(W-1-5) 

(W-1-6) 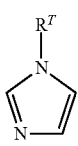

(W-1-7) 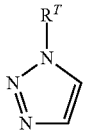

(In these formulae, these groups may have a chemical bond at any arbitrary position, and $R^T$ represents a hydrogen atom or an alkyl group having 1 to 8 carbon atoms.) The group represented by the above-mentioned formula (W-2) is preferably a group selected from the following formulae (W-2-1) to (W-2-8) which may be unsubstituted or substituted with one or more of the above-mentioned substituents $L^W$'s.

[Chem. 12]

(W-2-1) 

(W-2-2) 

(W-2-3) 

(W-2-4) 

(W-2-5) 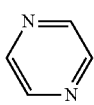

-continued (W-2-6) 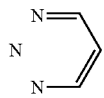

(W-2-7) 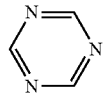

(W-2-8) 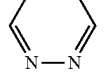

(In the formulae, these groups may have a chemical bond at any arbitrary position). The group represented by the above-mentioned formula (W-3) is preferably a group selected from the following formulae (W-3-1) to (W-3-6) which may be unsubstituted or substituted with one or more of the above-mentioned substituents $L^W$'s.

[Chem. 13]

(W-3-1) 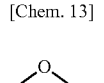

(W-3-2) 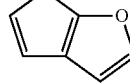

(W-3-3) 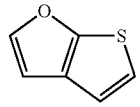

(W-3-4) 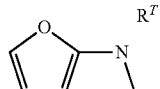

(W-3-5) 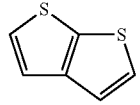

(W-3-6) 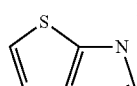

(In the formulae, these groups may have a chemical bond at any arbitrary position, and $R^T$ represents a hydrogen atom or an alkyl group having 1 to 8 carbon atoms.) The group represented by the above-mentioned formula (W-4) is preferably a group selected from the following formulae (W-4-1) to (W-4-9) which may be unsubstituted or substituted with one or more of the above-mentioned substituents $L^W$'s.

[Chem. 14]

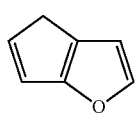 (W-4-1)

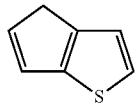 (W-4-2)

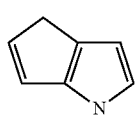 (W-4-3)

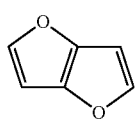 (W-4-4)

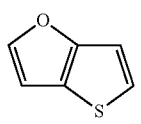 (W-4-5)

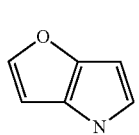 (W-4-6)

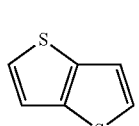 (W-4-7)

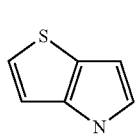 (W-4-8)

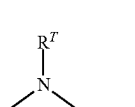 (W-4-9)

[Chem. 15]

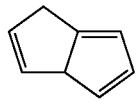 (W-5-1)

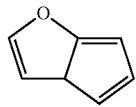 (W-5-2)

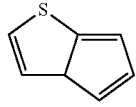 (W-5-3)

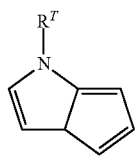 (W-5-4)

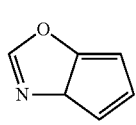 (W-5-5)

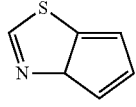 (W-5-6)

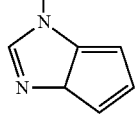 (W-5-7)

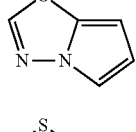 (W-5-8)

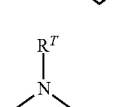 (W-5-9)

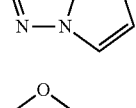 (W-5-10)

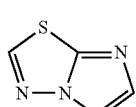 (W-5-11)

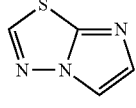 (W-5-12)

(In the formulae, these groups may have a chemical bond at any arbitrary position, and $R^T$ represents a hydrogen atom or an alkyl group having 1 to 8 carbon atoms.) The group represented by the above-mentioned formula (W-5) is preferably a group selected from the following formulae (W-5-1) to (W-5-13) which may be unsubstituted or substituted with one or more of the above-mentioned substituents $L^W$'s.

(W-5-13)

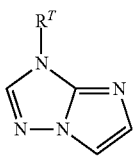

(In the formulae, these groups may have a chemical bond at any arbitrary position, and $R^T$ represents a hydrogen atom or an alkyl group having 1 to 8 carbon atoms.) The group represented by the above-mentioned formula (W-6) is preferably a group selected from the following formulae (W-6-1) to (W-6-12) which may be unsubstituted or substituted with one or more of the above-mentioned substituents $L^W$'s.

[Chem. 16]

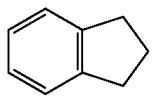
(W-6-1)

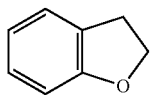
(W-6-2)

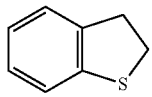
(W-6-3)

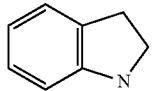
(W-6-4)

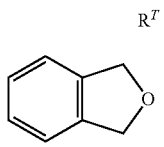
(W-6-5)

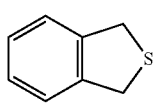
(W-6-6)

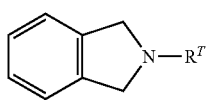
(W-6-7)

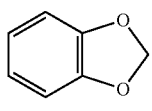
(W-6-8)

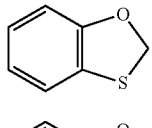
(W-6-9)

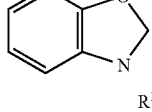
(W-6-10)

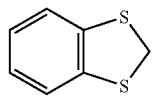
(W-6-11)

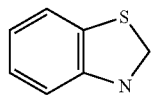
(W-6-12)

(In the formulae, these groups may have a chemical bond at any arbitrary position, and $R^T$ represents a hydrogen atom or an alkyl group having 1 to 8 carbon atoms.) The group represented by the above-mentioned formula (W-7) is preferably a group selected from the following formulae (W-7-1) to (W-7-8) which may be unsubstituted or substituted with one or more of the above-mentioned substituents $L^W$'s.

[Chem. 17]

(W-7-1)

(W-7-2)

(W-7-3)

(W-7-4)

(W-7-5)

(W-7-6)

(W-7-7)

(W-7-8)

(In the formulae, these groups may have a chemical bond at any arbitrary position, and $R^T$ represents a hydrogen atom or an alkyl group having 1 to 8 carbon atoms.) The group represented by the above-mentioned formula (W-8) is preferably a group selected from the following formulae (W-8-1)

to (W-8-19) which may be unsubstituted or substituted with one or more of the above-mentioned substituents $L^W$'s.

[Chem. 18]

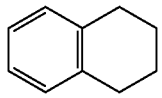
(W-8-1)

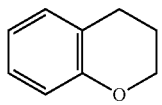
(W-8-2)

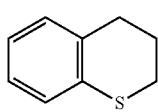
(W-8-3)

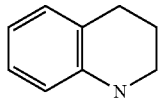
$R^T$
(W-8-4)

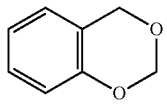
(W-8-5)

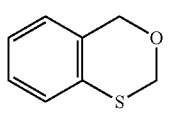
(W-8-6)

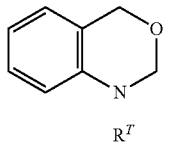
$R^T$
(W-8-7)

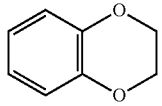
(W-8-8)

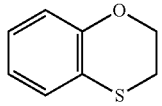
(W-8-9)

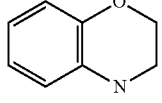
$R^T$
(W-8-10)

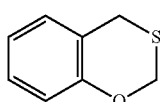
(W-8-11)

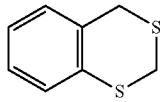
(W-8-12)

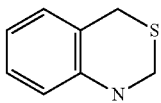
(W-8-13)

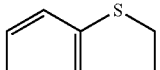
$R^T$
(W-8-14)

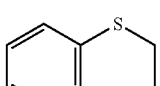
(W-8-15)

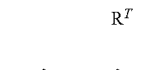
$R^T$
(W-8-16)

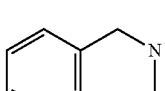
$R^T$
(W-8-17)

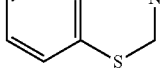
$R^T$
(W-8-18)

$R^T$
(W-8-19)

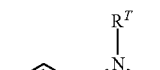
$R^T$ (In the formulae, these groups may have a chemical bond at any arbitrary position, and $R^T$ represents a hydrogen atom or an alkyl group having 1 to 8 carbon atoms.) The group represented by the above-mentioned formula (W-9) is preferably a group selected from the following formulae (W-9-1) to (W-9-7) which may be unsubstituted or substituted with one or more of the above-mentioned substituents $L^W$'s.

[Chem. 19]

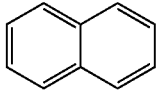
(W-9-1)

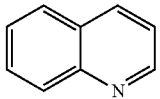
(W-9-2)

-continued
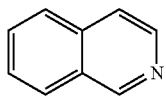 (W-9-3)
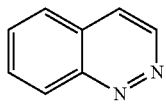 (W-9-4)
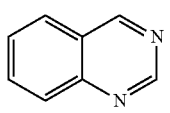 (W-9-5)
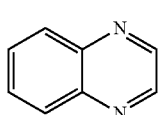 (W-9-6)
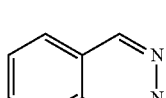 (W-9-7)
(In the formulae, these groups may have a chemical bond at any arbitrary position.) The group represented by the above-mentioned formula (W-10) is preferably a group selected from the following formulae (W-10-1) to (W-10-16) which may be unsubstituted or substituted with one or more of the above-mentioned substituents $L^W$'s.
[Chem. 20]
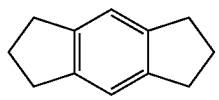 (W-10-1)
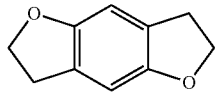 (W-10-2)
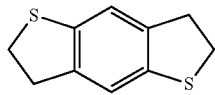 (W-10-3)
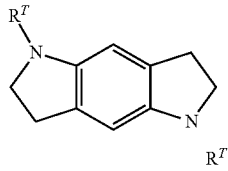 (W-10-4)
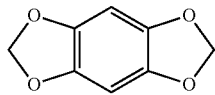 (W-10-5)
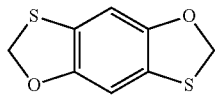 (W-10-6)
-continued
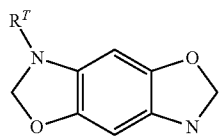 (W-10-7)
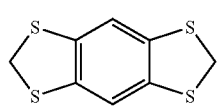 (W-10-8)
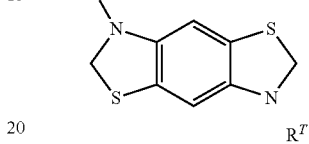 (W-10-9)
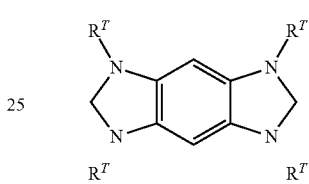 (W-10-10)
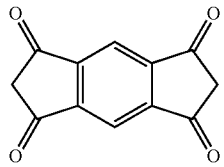 (W-10-11)
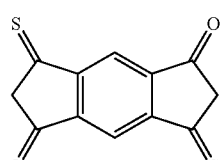 (W-10-12)
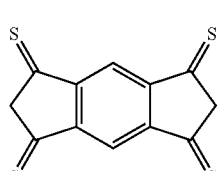 (W-10-13)
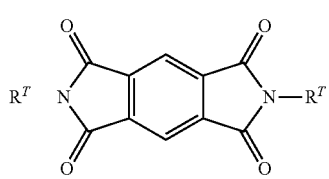 (W-10-14)
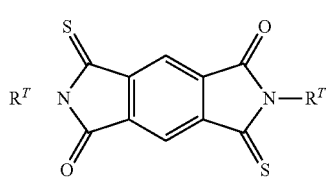 (W-10-15)

-continued

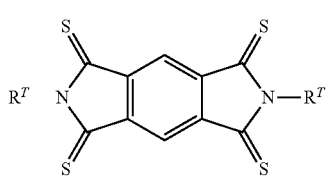
(W-10-16)

(In the formulae, these groups may have a chemical bond at any arbitrary position, and $R^T$ represents a hydrogen atom or an alkyl group having 1 to 8 carbon atoms.) The group represented by the above-mentioned formula (W-11) is preferably a group selected from the following formulae (W-11-1) to (W-11-10) which may be unsubstituted or substituted with one or more of the above-mentioned substituents $L^W$'s.

[Chem. 21]

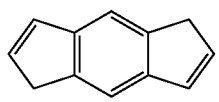
(W-11-1)

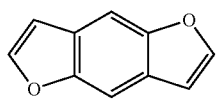
(W-11-2)

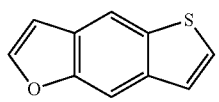
(W-11-3)

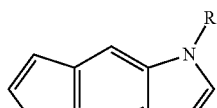
(W-11-4)

(W-11-5)

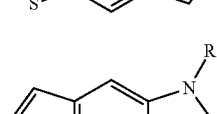
(W-11-6)

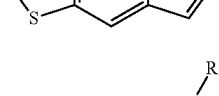
(W-11-7)

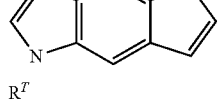
(W-11-8)

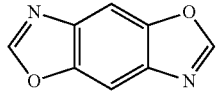
(W-11-9)

-continued

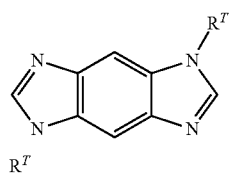
(W-11-10)

(In the formulae, these groups may have a chemical bond at any arbitrary position, and $R^T$ represents a hydrogen atom or an alkyl group having 1 to 8 carbon atoms.) The group represented by the above-mentioned formula (W-12) is preferably a group selected from the following formulae (W-12-1) to (W-12-4) which may be unsubstituted or substituted with one or more of the above-mentioned substituents $L^W$'s.

[Chem. 22]

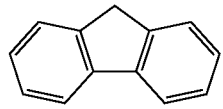
(W-12-1)

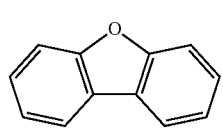
(W-12-2)

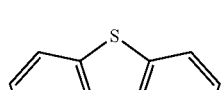
(W-12-3)

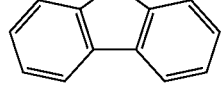
(W-12-4)

(In the formulae, these groups may have a chemical bond at any arbitrary position, and $R^T$ represents a hydrogen atom or an alkyl group having 1 to 8 carbon atoms.) The group represented by the above-mentioned formula (W-13) is preferably a group selected from the following formulae (W-13-1) to (W-13-8) which may be unsubstituted or substituted with one or more of the above-mentioned substituents $L^W$'s.

[Chem. 23]

(W-13-1)

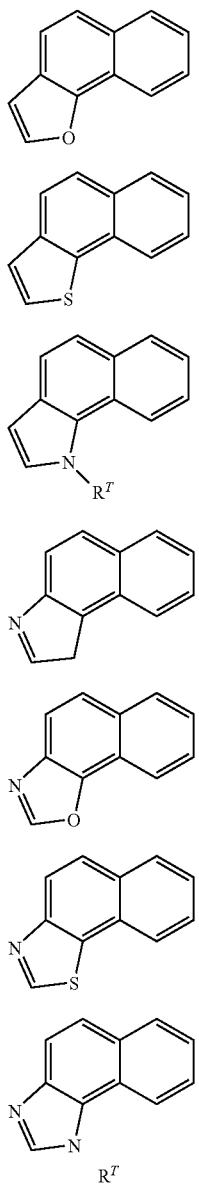

(In the formulae, these groups may have a chemical bond at any arbitrary position, and $R^T$ represents a hydrogen atom or an alkyl group having 1 to 8 carbon atoms.) The group represented by the above-mentioned formula (W-14) is preferably a group selected from the following formulae (W-14-1) to (W-14-8) which may be unsubstituted or substituted with one or more of the above-mentioned substituents $L^W$'s.

[Chem. 24]

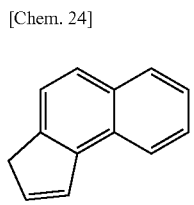

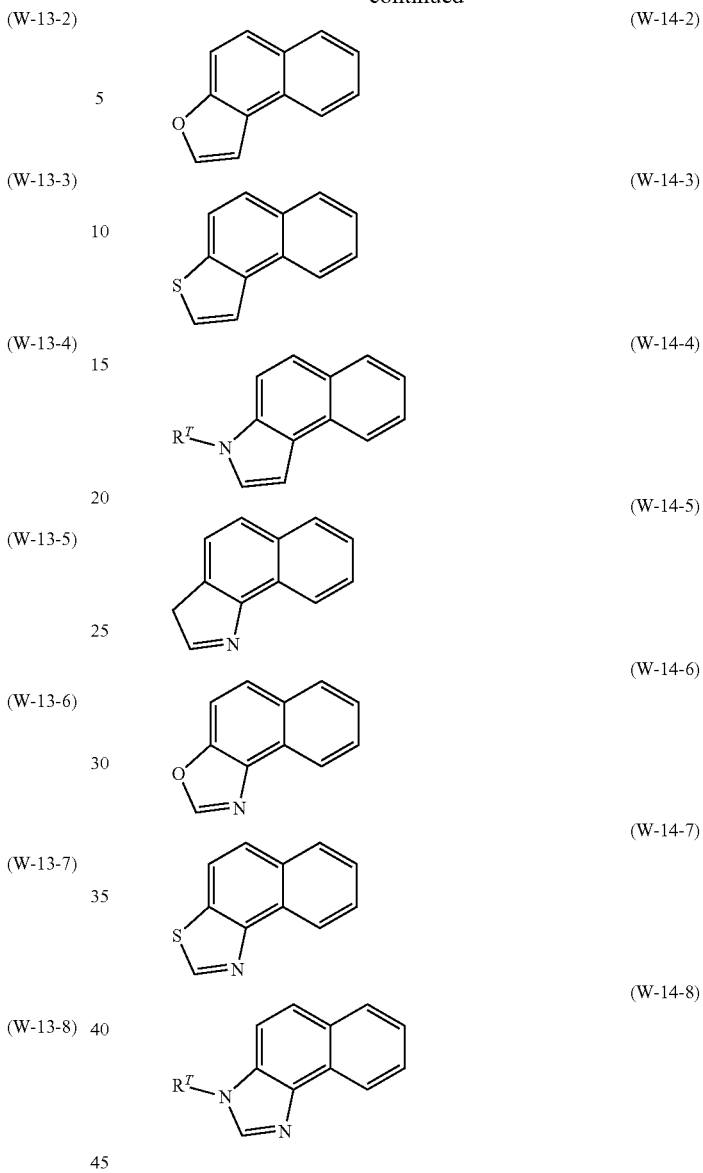

(In the formulae, these groups may have a chemical bond at any arbitrary position, and $R^T$ represents a hydrogen atom or an alkyl group having 1 to 8 carbon atoms.) The group represented by the above-mentioned formula (W-15) is preferably a group selected from the following formulae (W-15-1) to (W-15-10) which may be unsubstituted or substituted with one or more of the above-mentioned substituents $L^W$'s.

[Chem. 25]

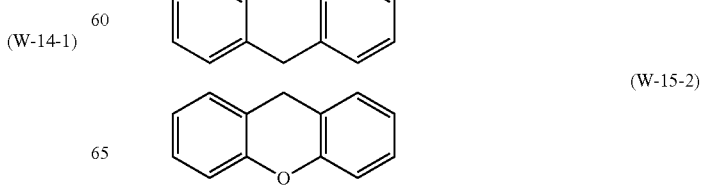

-continued (W-15-3)
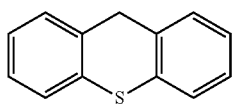

(W-15-4)
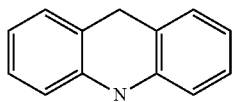
$R^T$ (W-15-5)
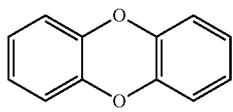

(W-15-6)
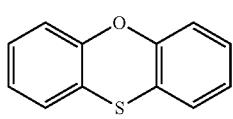

(W-15-7)
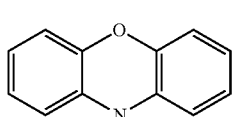
$R^T$ (W-15-8)
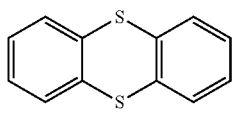

(W-15-9)
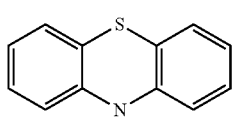
$R^T$ (W-15-10)
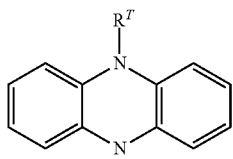
$R^T$ (In the formulae, these groups may have a chemical bond at any arbitrary position, and $R^T$ represents a hydrogen atom or an alkyl group having 1 to 8 carbon atoms.) The group represented by the above-mentioned formula (W-16) is preferably a group selected from the following formulae (W-16-1) to (W-16-8) which may be unsubstituted or substituted with one or more of the above-mentioned substituents $L^W$'s.

[Chem. 26]

(W-16-1)
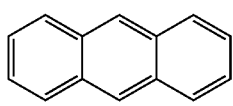

(W-16-2)
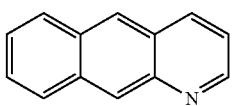

(W-16-3)
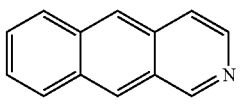

(W-16-4)
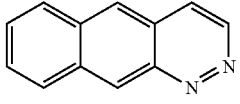

(W-16-5)
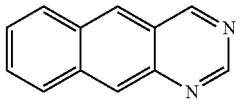

(W-16-6)
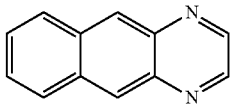

(W-16-7)
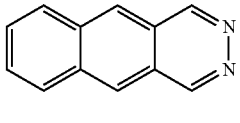

(W-16-8)
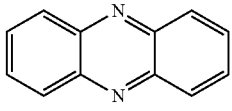

(In the formulae, these groups may have a chemical bond at any arbitrary position.) The group represented by the above-mentioned formula (W-17) is preferably a group selected from the following formulae (W-17-1) to (W-17-4) which may be unsubstituted or substituted with one or more of the above-mentioned substituents $L^W$'s.

[Chem. 27]

(W-17-1)
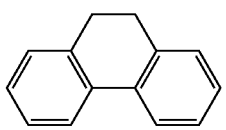

(W-17-2)
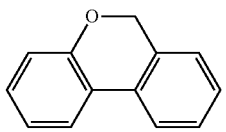

(W-17-3)
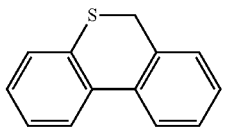

(W-17-4)

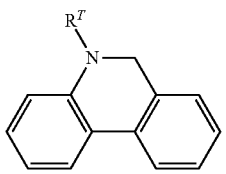

(In the formulae, these groups may have a chemical bond at any arbitrary position, and $R^T$ represents a hydrogen atom or an alkyl group having 1 to 8 carbon atoms.) The group represented by the above-mentioned formula (W-18) is preferably a group selected from the following formulae (W-18-1) to (W-18-4) which may be unsubstituted or substituted with one or more of the above-mentioned substituents $L^W$'s.

[Chem. 28]

(W-18-1)

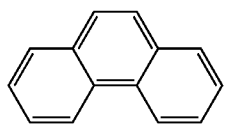

(W-18-2)

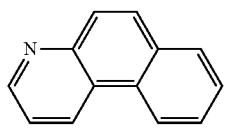

(W-18-3)

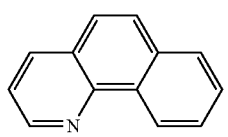

(W-18-4)

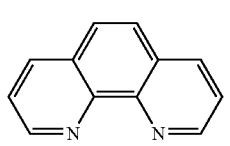

(In the formulae, these groups may have a chemical bond at any arbitrary position.) The group represented by the above-mentioned formula (W-19) is preferably a group selected from the following formulae (W-19-1) to (W-19-16) which may be unsubstituted or substituted with one or more of the above-mentioned substituents $L^W$'s.

[Chem. 29]

(W-19-1)

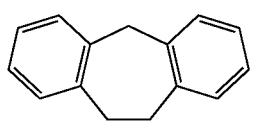

(W-19-2)

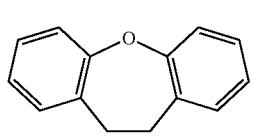

(W-19-3)

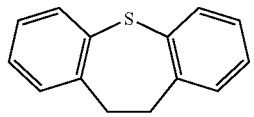

(W-19-4)

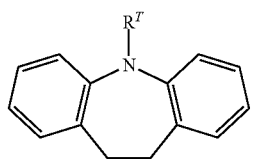

(W-19-5)

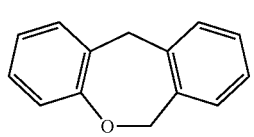

(W-19-6)

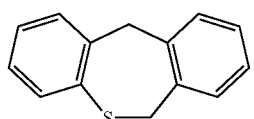

(W-19-7)

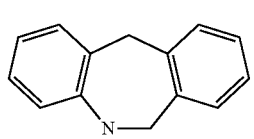

(W-19-8)

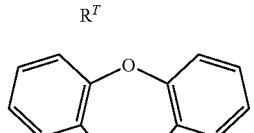

(W-19-9)

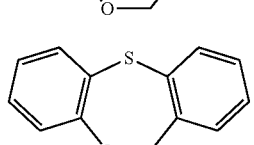

(W-19-10)

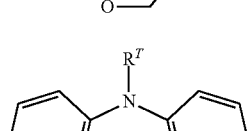

(W-19-11)

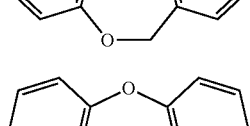

(W-19-12)

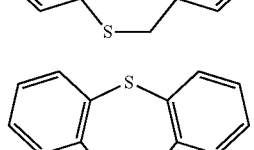

(W-19-13)

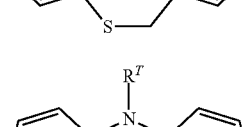

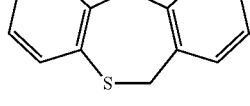

-continued (W-19-14)
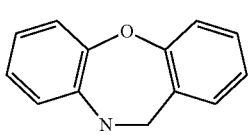

(W-19-15)
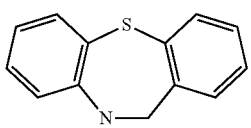

(W-19-16)
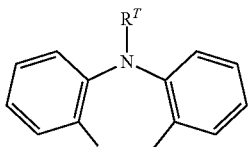

(In the formulae, these groups may have a chemical bond at any arbitrary position, and $R^T$ represents a hydrogen atom or an alkyl group having 1 to 8 carbon atoms.) The group represented by the above-mentioned formula (W-20) is preferably a group selected from the following formulae (W-20-1) to (W-20-4) which may be unsubstituted or substituted with one or more of the above-mentioned substituents $L^W$'s.

[Chem. 30]

(W-20-1)
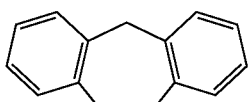

(W-20-2)
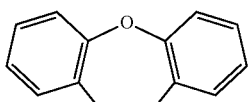

(W-20-3)
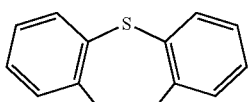

(W-20-4)
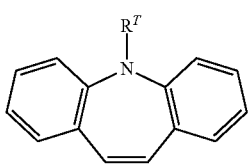

(In the formulae, these groups may have a chemical bond at any arbitrary position, and $R^T$ represents a hydrogen atom or an alkyl group having 1 to 8 carbon atoms.) From the viewpoint of solubility in solvent, liquid crystallinity and reverse wavelength dispersion, $W^1$ is more preferably a group selected from the following formulae (W-7-7-1) to (W-14-7-1):

[Chem. 31]

(W-7-7-1)
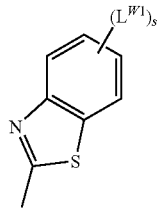

(W-7-6-1)
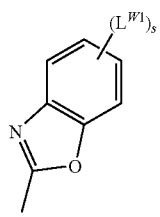

(W-9-1-1)
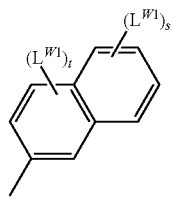

(W-9-1-2)
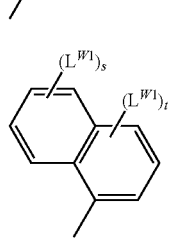

(W-12-1-1)
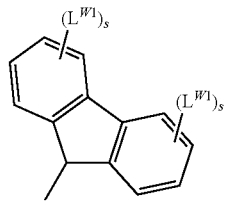

(W-13-7-1)
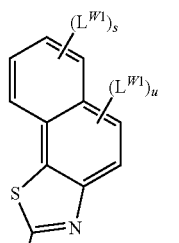

(W-14-7-1)
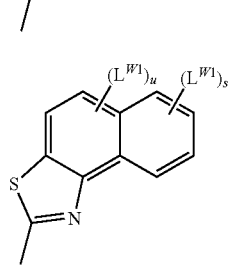

(In the formulae, $L^{W1}$ represents a fluorine atom, a chlorine atom, a nitro group, a cyano group, or a linear or branched alkyl group having 1 to 20 carbon atoms, in which one —$CH_2$— or two or more of (—$CH_2$—)'s which are not adjacent to each other may be each independently substituted with —O—, —S—, —CO—, —COO— or —OCO—, and one or more of arbitrary hydrogen atoms in the alkyl group may be substituted with a fluorine atom, plural $L^{W1}$'s, if any, in the compound may be the same or different, s represents an integer of 0 to 4, t represents an integer of 0 to 3, and u represents an integer of 0 to 2.) $W^1$ is even more preferably a group selected from the following formulae (W-7-7-1-1) to (W-14-7-1-1):

[Chem. 32]

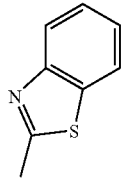
(W-7-7-1-1)

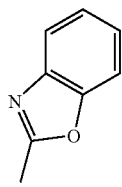
(W-7-6-1-1)

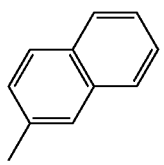
(W-9-1-1-1)

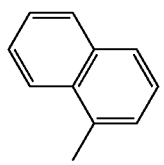
(W-9-1-2-1)

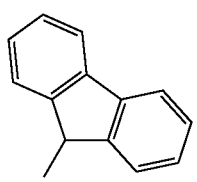
(W-12-1-1-1)

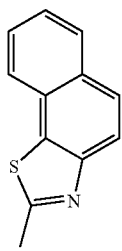
(W-13-7-1-1)

-continued

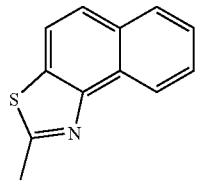
(W-14-7-1-1)

$W^1$ is especially preferably a group of the above formula (W-7-7-1-1).

$W^2$ represents a hydrogen atom, or a linear or branched alkyl group having 1 to 20 carbon atoms, in which one or more of arbitrary hydrogen atoms may be substituted with a fluorine atom, and one —$CH_2$— or two or more of (—$CH_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, or $W^2$ represents a group including an aromatic group and/or a non-aromatic group optionally substituted and having 1 to 80 carbon atoms, in which the aromatic group may be a hydrocarbon ring or a hetero ring, and the non-aromatic group may be a hydrocarbon group or a hydrocarbon group where one or more of arbitrary carbon atoms is substituted with a hetero atom (provided that the oxygen atoms therein do not directly bond to each other), and the group may be unsubstituted or substituted with one or more of substituents $L^{W}$'s, or $W^2$ may represent a group represented by $P^W$-$(Sp^W$-$X^W)_{kW}$—, and $W^1$ and $W^2$ may together form a cyclic structure.

In the case where reverse dispersion and liquid crystallinity are considered to be important, $W^2$ is preferably a hydrogen atom.

In the case where degradation proofness in long-term storage in solvent, degradation proofness in long-term storage in composition or retardation stability in film are considered to be important, $W^2$ is preferably a linear or branched alkyl group having 1 to 20 carbon atoms, in which one or more of arbitrary hydrogen atoms may be substituted with a fluorine atom, and one —$CH_2$— or two or more of (—$CH_2$—)'s which are not adjacent to each other may be each independently substituted with —O—, —CO—, —COO— or —OCO—, or a group represented by $P^W$-$(Sp^W$-$X^W)_{kW}$—. Among the above-mentioned groups, $W^2$ is more preferably a linear alkyl group having 1 to 12 carbon atoms, in which one —$CH_2$— or two or more of (—$CH_2$—)'s which are not adjacent to each other may be each independently substituted with —O—, or a group represented by $P^W$-$(Sp^W$-$X^W)_{kW}$—. Preferred structures of $P^W$ are the same as those described for P. $Sp^W$ is preferably a spacer group, and from the viewpoint of liquid crystallinity, easy availability of raw materials and easiness in synthesis, plural $Sp^W$'s, if any, may be the same or different and are preferably each independently an alkylene group having 1 to 20 carbon atoms, in which one —$CH_2$— or two or more of (—$CH_2$—)'s which are not adjacent to each other may be each independently substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—

CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF— or —C≡C—. More preferably, plural these groups, if any, may be the same or different and each independently represent a linear alkylene group having 1 to 20 carbon atoms, in which one —CH$_2$— or two or more of (—CH$_2$—)'s which are not adjacent to each other may be each independently substituted with —O—, —COO—, —OCO— or —OCO—O—. Even more preferably, plural these groups, if any, may be the same or different and each independently represent a linear alkylene group having 1 to 12 carbon atoms, in which one —CH$_2$— or two or more of (—CH$_2$—)'s which are not adjacent to each other may be each independently substituted with —O—. From the viewpoint of liquid crystallinity and solubility in solvent, Sp$^W$ is especially preferably a linear alkylene group having 1 to 12 carbon atoms, in which one —CH$_2$— or two or more of (—CH$_2$—)'s which are not adjacent to each other may be each independently substituted with —O—. From the viewpoint of easy availability of raw materials and easiness in synthesis, plural X$^W$'s, if any, may be the same or different and each independently preferably represents —O—, —S—, —OCH$_2$—, —CH$_2$O—, —COO—, —OCO—, —CO—S—, —S—CO—, —O—CO—O—, —COO—CH$_2$CH$_2$—, —OCO—CH$_2$CH$_2$—, —CH$_2$CH$_2$—COO—, —CH$_2$CH$_2$—OCO— or a single bond, more preferably each independently represents —O—, —COO—, —OCO— or a single bond, and especially preferably a single bond. kw is, from the viewpoint of liquid crystallinity and easy availability of raw materials, preferably an integer of 1 to 3, and from the viewpoint of curing shrinkage of film formed of the compound, kw is more preferably 1.

The group directly bonding to the N atom in the group represented by P$^W$-(Sp$^W$-X$^W$)$_{kW}$— is, from the viewpoint of easiness in synthesis, preferably —CH$_2$—.

The group represented by P$^W$-(Sp$^W$-X$^W$)$_{kW}$— is, from the viewpoint of time-dependent stability of retardation and reverse wavelength dispersion, and of peeling resistance from substrate in long-term irradiation with UV light, preferably a group selected from the following formula (Pw-1), (Pw-2) or (Pw-3):

[Chem. 33]

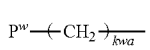 (Pw-1)

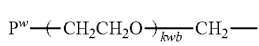 (Pw-2)

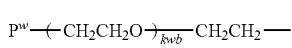 (Pw-3)

(In the formulae, kwa represents an integer of 0 to 20, and kwb represents an integer of 1 to 10). In the formula (Pw-1), kwa is, from the viewpoint of liquid crystallinity, more preferably an integer of 2 to 12, even more preferably an integer of 2 to 8. In the formula (Pw-2) and the formula (Pw-3), kwb is, from the viewpoint of liquid crystallinity, more preferably an integer of 1 to 3, and even more preferably 1 or 2.

In the case where W$^2$ represents a group including an aromatic group and/or a non-aromatic group which may be substituted and which has 1 to 80 carbon atoms, preferred structures of W$^2$ are the same as those described for W$^1$.

W$^1$ and W$^2$ may together form a cyclic structure, and in the case, the cyclic group represented by —NW$^1$W$^2$ is preferably represents a group selected from the following formulae (W-21) to (W-42) which may be unsubstituted or substituted with one or more of the above-mentioned substituents L$^W$'s.

[Chem. 34]

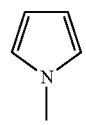 (W-21)

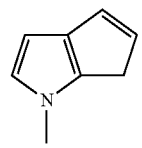 (W-22)

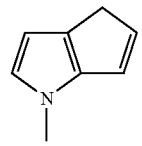 (W-23)

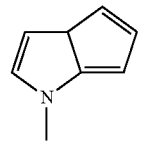 (W-24)

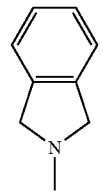 (W-25)

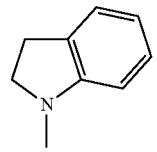 (W-26)

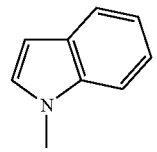 (W-27)

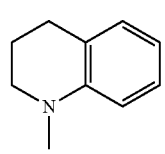 (W-28)

-continued (W-29) 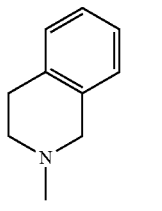

(W-30) 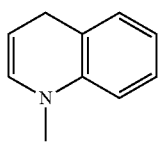

(W-31) 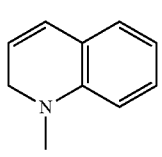

(W-32) 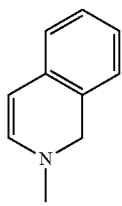

(W-33) 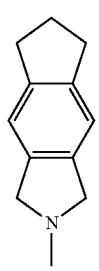

(W-34) 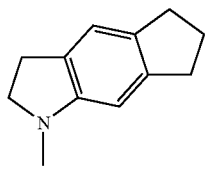

(W-35) 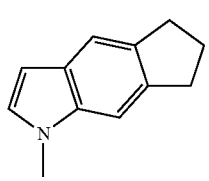

(W-36) 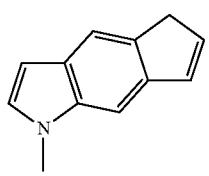

-continued (W-37) 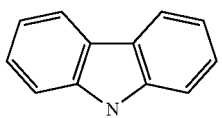

(W-38) 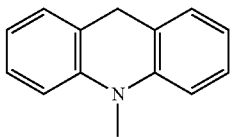

(W-39) 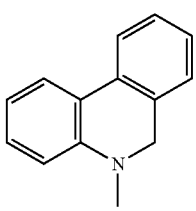

(W-40) 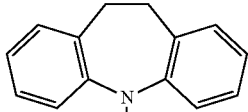

(W-41) 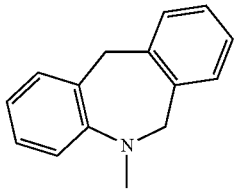

(W-42) 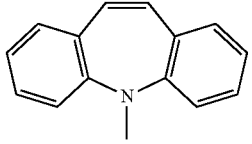

(In the formulae, any arbitrary —CH═ may be substituted with —N═, —CH$_2$— may be each independently represented with —O—, —S—, —NR$^T$— (where R$^T$ represents a hydrogen atom or an alkyl group having 1 to 20 carbon atoms), —CS— or —CO—, but does not contain an —O—O— bond. These groups may be unsubstituted or substituted with one or more of the above-mentioned substituents L$^W$'s). The group represented by the above formula (W-21) is preferably a group selected from the following formulae (W-21-1) to (W-21-3) which may be unsubstituted or substituted with one or more of the above-mentioned substituents L$^W$'s,

[Chem. 35]

(W-21-1) 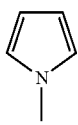

(W-21-2)

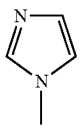

(W-21-3)

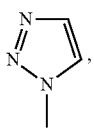

the group represented by the above formula (W-22) is preferably a group selected from the following formulae (W-22-1) to (W-22-4) which may be unsubstituted or substituted with one or more of the above-mentioned substituents L's,

[Chem. 36]

(W-22-1)

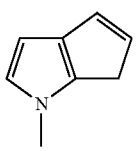

(W-22-2)

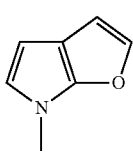

(W-22-3)

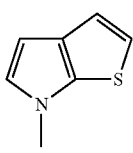

(W-22-4)

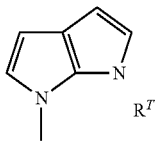

(wherein $R^T$ is preferably a hydrogen atom or an alkyl group having 1 to 8 carbon atoms), the group represented by the above formula (W-23) is preferably a group selected from the following formulae (W-23-1) to (W-23-4) which may be unsubstituted or substituted with one or more of the above-mentioned substituents $L^W$'s,

[Chem. 37]

(W-23-1)

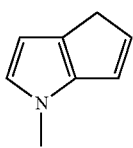

(W-23-2)

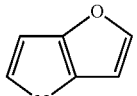

(W-23-3)

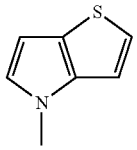

(W-23-4)

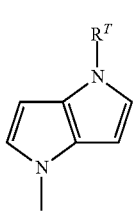

(wherein $R^T$ represents a hydrogen atom or an alkyl group having 1 to 8 carbon atoms), the group represented by the above formula (W-24) is preferably a group selected from the following formulae (W-24-1) to (W-24-4) which may be unsubstituted or substituted with one or more of the above-mentioned substituents $L^W$'s,

[Chem. 38]

(W-24-1)

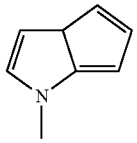

(W-24-2)

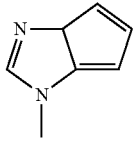

(W-24-3)

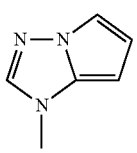

(W-24-4)

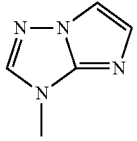

the group represented by the above formula (W-25) is preferably a group selected from the following formulae (W-25-1) to (W-25-3) which may be unsubstituted or substituted with one or more of the above-mentioned substituents $L^W$'s,

[Chem. 39]

(W-25-1)

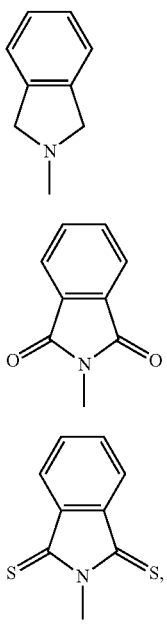

(W-25-2)

(W-25-3)

the group represented by the above formula (W-26) is preferably a group selected from the following formulae (W-26-1) to (W-26-4) which may be unsubstituted or substituted with one or more of the above-mentioned substituents $L^W$'s,

[Chem. 40]

(W-26-1)

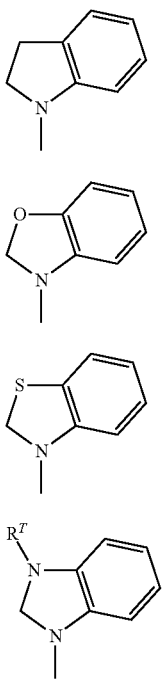

(W-26-2)

(W-26-3)

(W-26-4)

(wherein $R^T$ represents a hydrogen atom or an alkyl group having 1 to 8 carbon atoms), the group represented by the above formula (W-27) is preferably a group selected from the following formulae (W-27-1) to (W-27-3) which may be unsubstituted or substituted with one or more of the above-mentioned substituents $L^W$'s,

[Chem. 41]

(W-27-1)

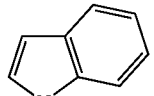

(W-27-2)

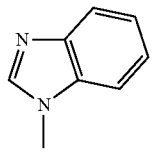

(W-27-3)

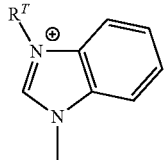

(wherein $R^T$ represents a hydrogen atom or an alkyl group having 1 to 8 carbon atoms), the group represented by the above formula (W-28) is preferably a group selected from the following formulae (W-28-1) to (W-28-7) which may be unsubstituted or substituted with one or more of the above-mentioned substituents $L^W$'s,

[Chem. 42]

(W-28-1)

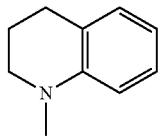

(W-28-2)

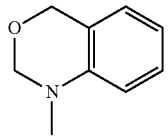

(W-28-3)

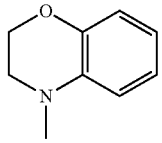

(W-28-4)

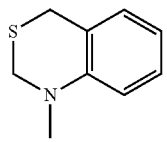

(W-28-5)

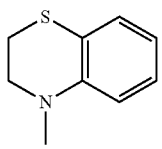

(W-28-6)

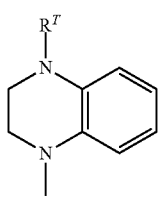

(W-28-7)

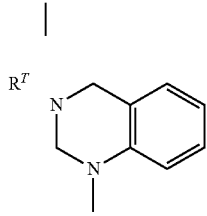

(wherein $R^T$ represents a hydrogen atom or an alkyl group having 1 to 8 carbon atoms), the group represented by the above formula (W-29) is preferably a group selected from the following formulae (W-29-1) to (W-29-4) which may be unsubstituted or substituted with one or more of the above-mentioned substituents $L^W$'s,

[Chem. 43]

(W-29-1)

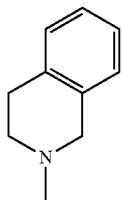

(W-29-2)

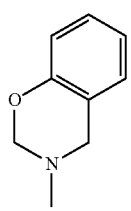

(W-29-3)

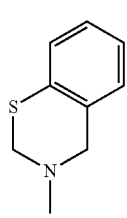

(W-29-4)

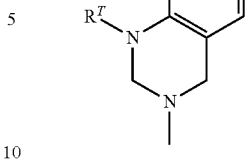

(wherein $R^T$ represents a hydrogen atom or an alkyl group having 1 to 8 carbon atoms), the group represented by the above formula (W-30) is preferably a group selected from the following formulae (W-30-1) to (W-30-6) which may be unsubstituted or substituted with one or more of the above-mentioned substituents $L^W$'s,

[Chem. 44]

(W-30-1)

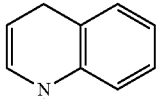

(W-30-2)

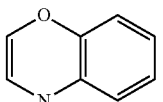

(W-30-3)

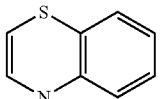

(W-30-4)

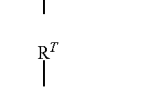

(W-30-5)

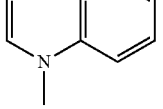

(W-30-6)

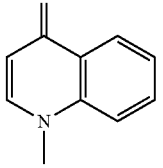

(wherein $R^T$ represents a hydrogen atom or an alkyl group having 1 to 8 carbon atoms), the group represented by the above formula (W-31) is preferably a group selected from the following formulae (W-31-1) to (W-31-3) which may be unsubstituted or substituted with one or more of the above-mentioned substituents $L^W$'s,

[Chem. 45]

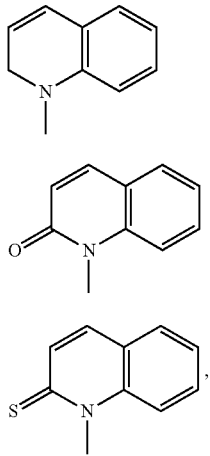

(W-31-1)

(W-31-2)

(W-31-3)

the group represented by the above formula (W-32) is preferably a group selected from the following formulae (W-32-1) to (W-32-3) which may be unsubstituted or substituted with one or more of the above-mentioned substituents $L^W$'s,

[Chem. 46]

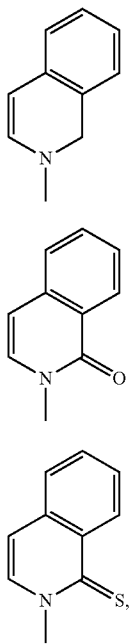

(W-32-1)

(W-32-2)

(W-32-3)

the group represented by the above formula (W-33) is preferably a group selected from the following formulae (W-33-1) to (W-33-4) which may be unsubstituted or substituted with one or more of the above-mentioned substituents $L^W$'s,

[Chem. 47]

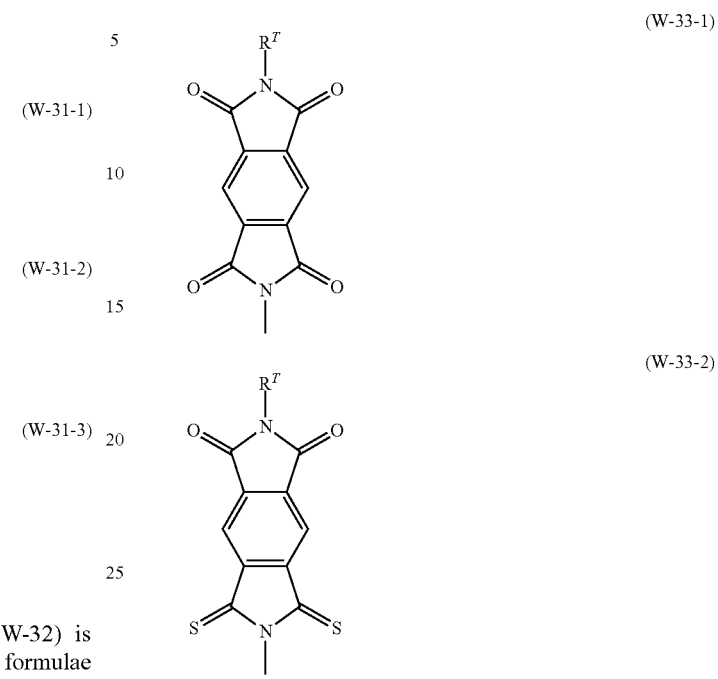

(W-33-1)

(W-33-2)

(W-33-3)

(W-33-4)

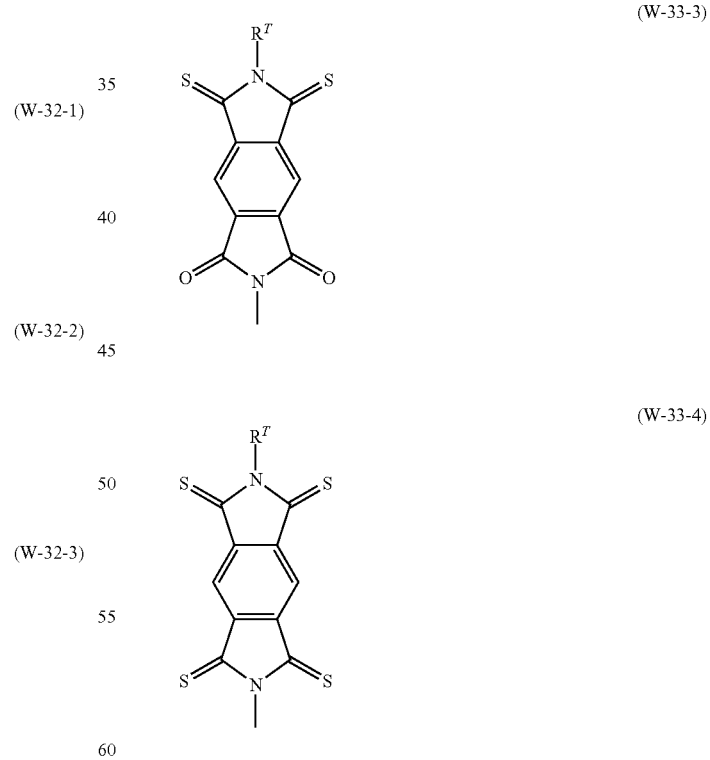

(wherein $R^T$ represents a hydrogen atom or an alkyl group having 1 to 8 carbon atoms), the group represented by the above formula (W-34) is preferably a group selected from the following formulae (W-34-1) to (W-34-5) which may be unsubstituted or substituted with one or more of the above-mentioned substituents $L^W$'s,

[Chem. 48]

(W-34-1)
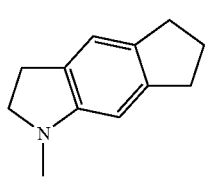

(W-34-2)
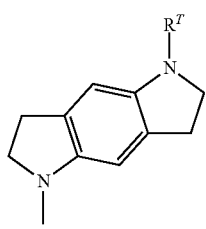

(W-34-3)
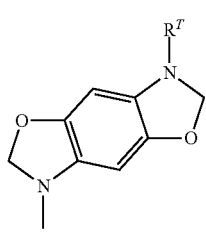

(W-34-4)
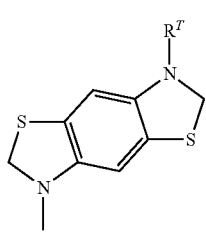

(W-34-5)
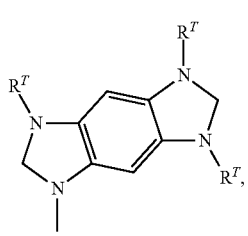

(wherein $R^T$ represents a hydrogen atom or an alkyl group having 1 to 8 carbon atoms), the group represented by the above formula (W-35) is preferably a group selected from the following formulae (W-35-1) to (W-35-3) which may be unsubstituted or substituted with one or more of the above-mentioned substituents $L^W$'s,

[Chem. 49]

(W-35-1)
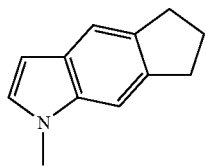

(W-35-2)
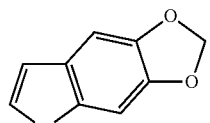

(W-35-3)
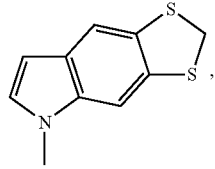

the group represented by the above formula (W-36) is preferably a group selected from the following formulae (W-36-1) to (W-36-5) which may be unsubstituted or substituted with one or more of the above-mentioned substituents $L^W$'s,

[Chem. 50]

(W-36-1)
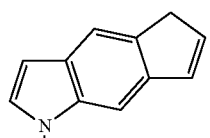

(W-36-2)
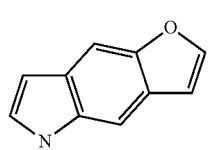

(W-36-3)
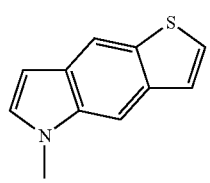

(W-36-4)
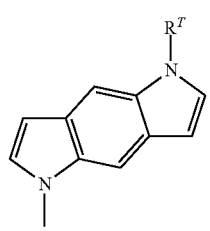

(W-36-5)
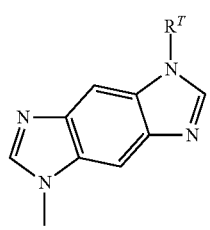

(wherein $R^T$ represents a hydrogen atom or an alkyl group having 1 to 8 carbon atoms), the group represented by the above formula (W-37) is preferably a group selected from the following formula (W-37-1) which may be unsubstituted or substituted with one or more of the above-mentioned substituents $L^W$'s,

[Chem. 51]

(W-37-1)

the group represented by the above formula (W-38) is preferably a group selected from the following formulae (W-38-1) to (W-38-6) which may be unsubstituted or substituted with one or more of the above-mentioned substituents $L^W$'s,

[Chem. 52]

(W-38-1)

(W-38-2)

(W-38-3)

(W-38-4)

(W-38-5)

(W-38-6)

(wherein $R^T$ represents a hydrogen atom or an alkyl group having 1 to 8 carbon atoms), the group represented by the above formula (W-39) is preferably a group selected from the following formulae (W-39-1) to (W-39-3) which may be unsubstituted or substituted with one or more of the above-mentioned substituents $L^W$'s,

[Chem. 53]

(W-39-1)

(W-39-2)

(W-39-3)

the group represented by the above formula (W-40) is preferably a group selected from the following formulae (W-40-1) to (W-40-4) which may be unsubstituted or substituted with one or more of the above-mentioned substituents $L^W$'s,

[Chem. 54]

(W-40-1)

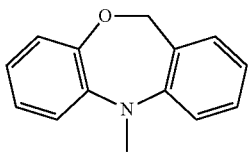
(W-40-2)

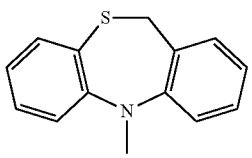
(W-40-3)

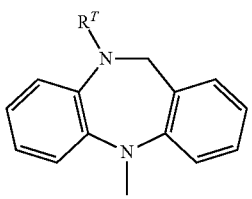
(W-40-4)

(wherein $R^T$ represents a hydrogen atom or an alkyl group having 1 to 8 carbon atoms), the group represented by the above formula (W-41) is preferably a group selected from the following formulae (W-41-1) to (W-41-4) which may be unsubstituted or substituted with one or more of the above-mentioned substituents $L^W$'s,

[Chem. 55]

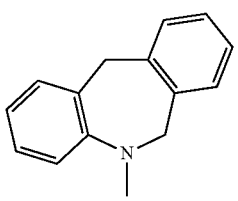
(W-41-1)

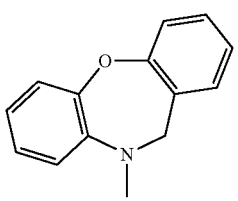
(W-41-2)

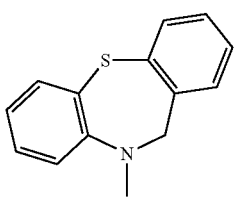
(W-41-3)

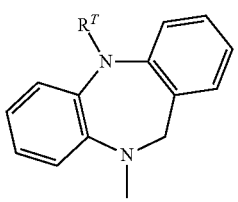
(W-41-4)

(wherein $R^T$ represents a hydrogen atom or an alkyl group having 1 to 8 carbon atoms), the group represented by the above formula (W-42) is preferably a group selected from the following formula (W-42-1):

[Chem. 56]

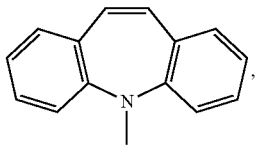
(W-42-1)

which may be unsubstituted or substituted with one or more of the above-mentioned substituents $L^W$'s.

From the viewpoint of easy availability of raw materials and easiness in synthesis, the cyclic group represented by —$NW^1W^2$ is more preferably a group selected from the formula (W-21-1), the formula (W-23-2), the formula (W-23-3), the formula (W-23-4), the formula (W-25-2), the formula (W-25-3), the formula (W-27-1), the formula (W-27-2), the formula (W-27-3), the formula (W-32-2), the formula (W-32-3), the formula (W-37-1), the formula (W-38-2), the formula (W-38-3), the formula (W-38-4) and the formula (W-42-1) which may be unsubstituted or substituted with one or more of the above-mentioned substituents $L^W$'s.

$W^1$ and $W^2$ may together form a cyclic structure, and in the case, the cyclic group represented by =$CW^1W^2$ is preferably a group selected form the following formulae (W-43) to (W-64) which may be unsubstituted or substituted with one or more of the above-mentioned substituents $L^W$'s.

[Chem. 57]

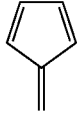
(W-43)

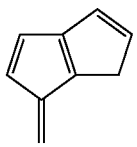
(W-44)

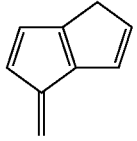
(W-45)

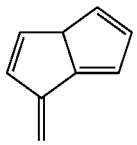
(W-46)

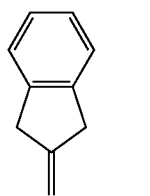 (W-47)
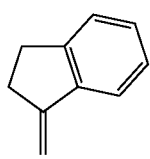 (W-48)
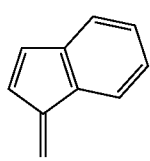 (W-49)
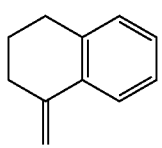 (W-50)
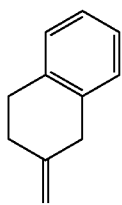 (W-51)
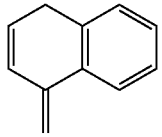 (W-52)
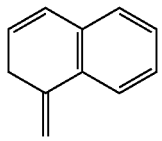 (W-53)
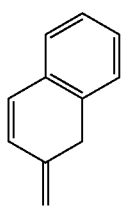 (W-54)
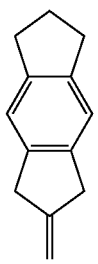 (W-55)
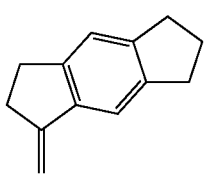 (W-56)
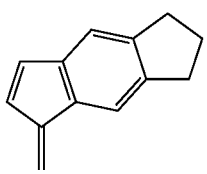 (W-57)
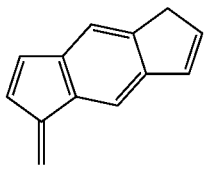 (W-58)
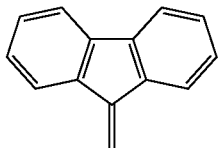 (W-59)
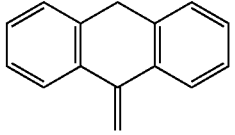 (W-60)
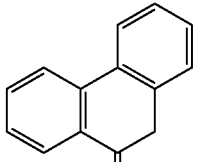 (W-61)
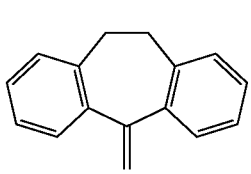 (W-62)

-continued (W-63)

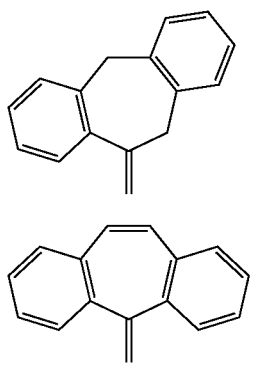

(W-64)

(In the formulae, any arbitrary —CH= may be each independently substituted with —N=, —CH$_2$— may be each independently substituted with —O—, —S—, —NR$^T$— (where R$^T$ represents a hydrogen atom or an alkyl group having 1 to 20 carbon atoms), —CS— or —CO—, but does not contain an —O—O— bond. These groups may be unsubstituted or substituted with one or more of the above-mentioned L$^W$'s.) The group represented by the above-mentioned formula (W-43) is preferably a group selected from the following formulae (W-43-1) to (W-43-3) which may be unsubstituted or substituted with one or more of the above-mentioned L$^W$'s.

[Chem. 58]

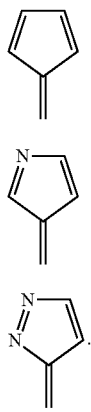

(W-43-1)

(W-43-2)

(W-43-3)

The group represented by the above-mentioned formula (W-44) is preferably a group selected from the following formulae (W-44-1) to (W-44-4) which may be unsubstituted or substituted with one or more of the above-mentioned L$^W$'s.

[Chem. 59]

(W-44-1)

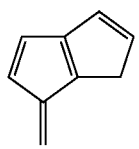

-continued (W-44-2)

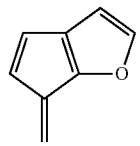

(W-44-3)

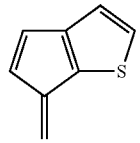

(W-44-4)

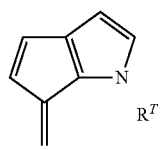

(In the formulae, R$^T$ represents a hydrogen atom or an alkyl group having 1 to 8 carbon atoms). The group represented by the above-mentioned formula (W-45) is preferably a group selected from the following formulae (W-45-1) to (W-45-4) which may be unsubstituted or substituted with one or more of the above-mentioned L$^W$'s.

[Chem. 60]

(W-45-1)

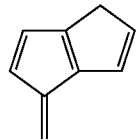

(W-45-2)

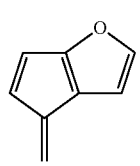

(W-45-3)

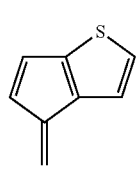

(W-45-4)

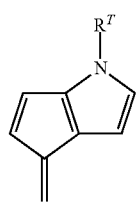

(In the formulae, R$^T$ represents a hydrogen atom or an alkyl group having 1 to 8 carbon atoms). The group represented by the above-mentioned formula (W-46) is preferably a group selected from the following formulae (W-46-1) to (W-46-4) which may be unsubstituted or substituted with one or more of the above-mentioned L$^W$'s.

[Chem. 61]

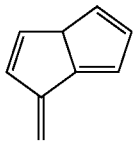
(W-46-1)

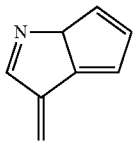
(W-46-2)

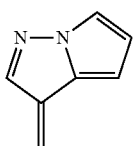
(W-46-3)

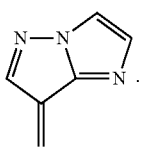
(W-46-4)

The group represented by the above-mentioned formula (W-47) is preferably a group selected from the following formulae (W-47-1) to (W-47-4) which may be unsubstituted or substituted with one or more of the above-mentioned $L^W$'s.

[Chem. 62]

(W-47-1)

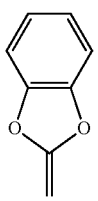
(W-47-2)

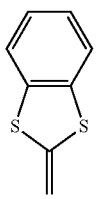
(W-47-3)

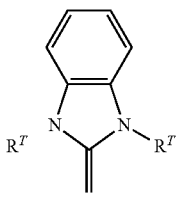
(W-47-4)

(In the formulae, $R^T$ represents a hydrogen atom or an alkyl group having 1 to 8 carbon atoms). The group represented by the above-mentioned formula (W-48) is preferably a group selected from the following formulae (W-48-1) to (W-48-4) which may be unsubstituted or substituted with one or more of the above-mentioned $L^W$'s.

[Chem. 63]

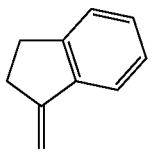
(W-48-1)

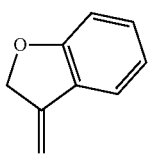
(W-48-2)

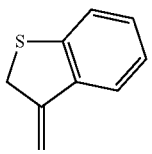
(W-48-3)

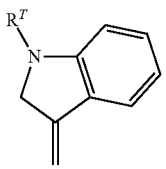
(W-48-4)

(In the formulae, $R^T$ represents a hydrogen atom or an alkyl group having 1 to 8 carbon atoms). The group represented by the above-mentioned formula (W-49) is preferably a group selected from the following formulae (W-49-1) to (W-49-3) which may be unsubstituted or substituted with one or more of the above-mentioned $L^W$'s.

[Chem. 64]

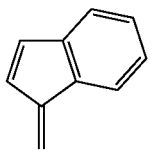
(W-49-1)

(W-49-2)

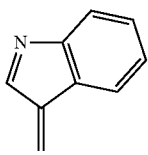

(W-49-3)

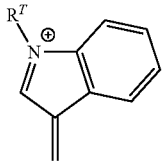

(In the formulae, $R^T$ represents a hydrogen atom or an alkyl group having 1 to 8 carbon atoms). The group represented by the above-mentioned formula (W-50) is preferably a group selected from the following formulae (W-50-1) to (W-50-7) which may be unsubstituted or substituted with one or more of the above-mentioned $L^W$'s.

[Chem. 65]

(W-50-1)

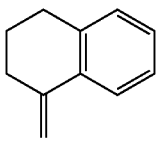

(W-50-2)

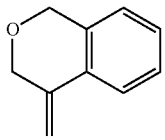

(W-50-3)

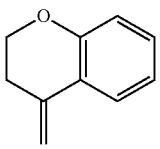

(W-50-4)

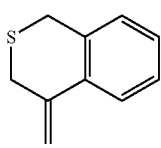

(W-50-5)

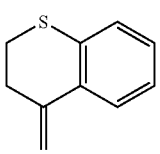

(W-50-6)

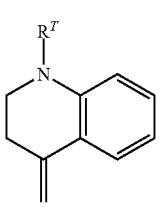

(W-50-7)

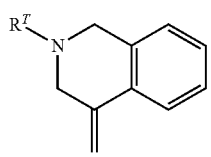

(In the formulae, $R^T$ represents a hydrogen atom or an alkyl group having 1 to 8 carbon atoms). The group represented by the above-mentioned formula (W-51) is preferably a group selected from the following formulae (W-51-1) to (W-51-4) which may be unsubstituted or substituted with one or more of the above-mentioned $L^W$'s.

[Chem. 66]

(W-51-1)

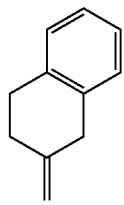

(W-51-2)

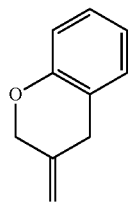

(W-51-3)

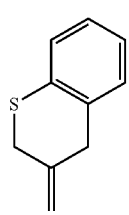

(W-51-4)

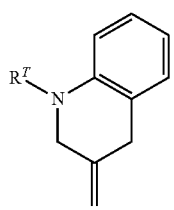

(In the formulae, $R^T$ represents a hydrogen atom or an alkyl group having 1 to 8 carbon atoms). The group represented by the above-mentioned formula (W-52) is preferably a group selected from the following formulae (W-52-1) to (W-52-6) which may be unsubstituted or substituted with one or more of the above-mentioned $L^W$'s.

[Chem. 67]

(W-52-1)
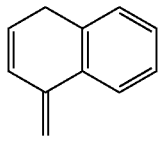

(W-52-2)
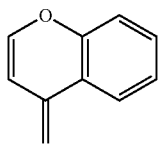

(W-52-3)
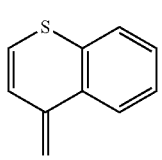

(W-52-4)
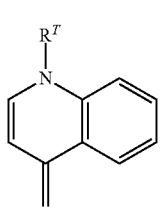

(W-52-5)
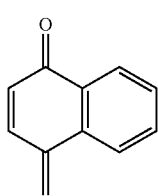

(W-52-6)
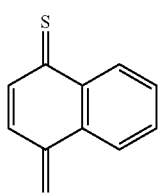

(In the formulae, $R^T$ represents a hydrogen atom or an alkyl group having 1 to 8 carbon atoms). The group represented by the above-mentioned formula (W-53) is preferably a group selected from the following formulae (W-53-1) to (W-53-3) which may be unsubstituted or substituted with one or more of the above-mentioned $L^W$'s.

[Chem. 68]

(W-53-1)
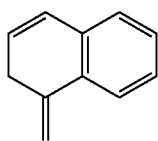

(W-53-2)
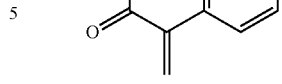

(W-53-3)
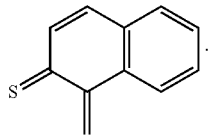

The group represented by the above-mentioned formula (W-54) is preferably a group selected from the following formulae (W-54-1) to (W-54-3) which may be unsubstituted or substituted with one or more of the above-mentioned $L^W$'s.

[Chem. 69]

(W-54-1)
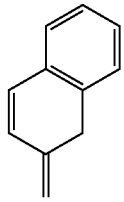

(W-54-2)
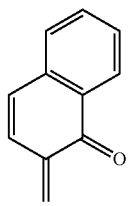

(W-54-3)
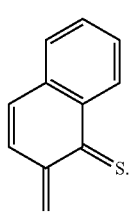

The group represented by the above-mentioned formula (W-55) is preferably a group selected from the following formulae (W-55-1) to (W-55-8) which may be unsubstituted or substituted with one or more of the above-mentioned $L^W$'s.

[Chem. 70]

(W-55-1)
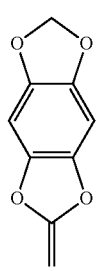

(W-55-2)
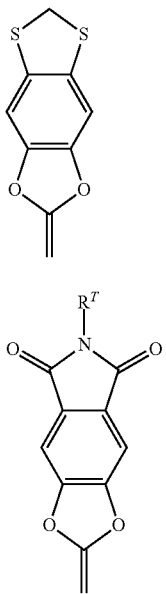
(W-55-3)
(W-55-4)
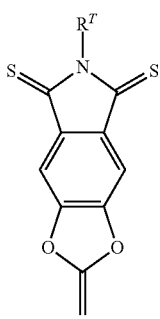
(W-55-5)
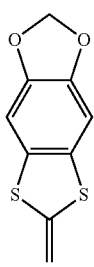
(W-55-6)
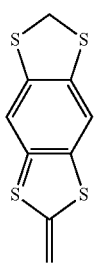
(W-55-7)
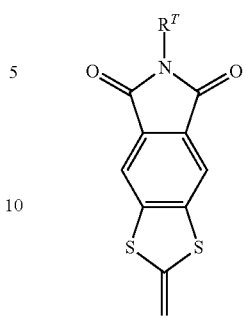
(W-55-8)
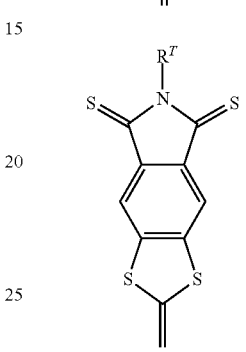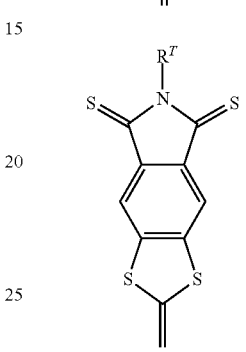
(In the formulae, $R^T$ represents a hydrogen atom or an alkyl group having 1 to 8 carbon atoms). The group represented by the above-mentioned formula (W-56) is preferably a group selected from the following formulae (W-56-1) to (W-56-5) which may be unsubstituted or substituted with one or more of the above-mentioned $L^W$'s.
[Chem. 71]
(W-56-1)
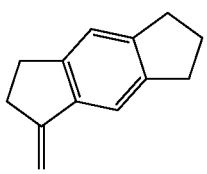
(W-56-2)
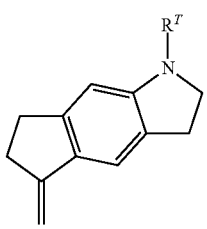
(W-56-3)
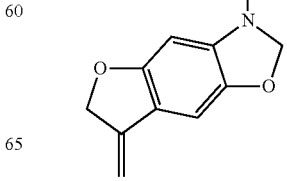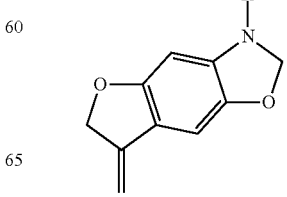

(W-56-4)

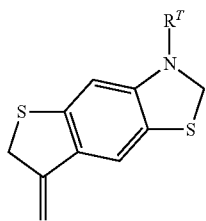

(W-56-5)

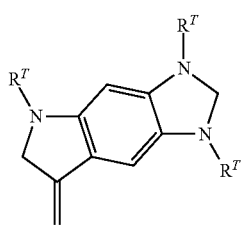

(In the formulae, $R^T$ represents a hydrogen atom or an alkyl group having 1 to 8 carbon atoms). The group represented by the above-mentioned formula (W-57) is preferably a group selected from the following formulae (W-57-1) to (W-57-3) which may be unsubstituted or substituted with one or more of the above-mentioned $L^W$'s.

[Chem. 72]

(W-57-1)

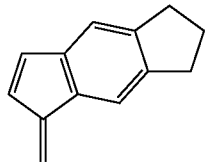

(W-57-2)

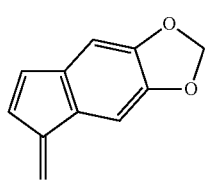

(W-57-3)

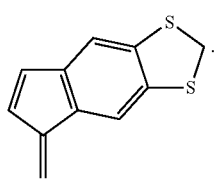

The group represented by the above-mentioned formula (W-58) is preferably a group selected from the following formulae (W-58-1) to (W-58-5) which may be unsubstituted or substituted with one or more of the above-mentioned $L^W$'s.

[Chem. 73]

(W-58-1)

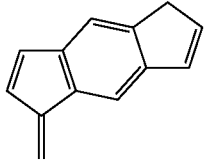

(W-58-2)

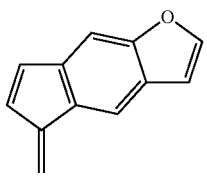

(W-58-3)

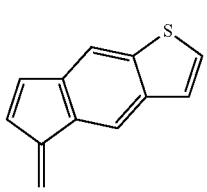

(W-58-4)

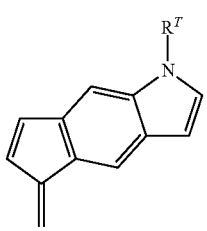

(W-58-5)

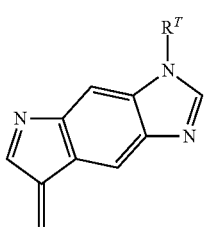

(In the formulae, $R^T$ represents a hydrogen atom or an alkyl group having 1 to 8 carbon atoms). The group represented by the above-mentioned formula (W-59) is preferably a group selected from the following formula (W-59-1) which may be unsubstituted or substituted with one or more of the above-mentioned $L^W$'s.

[Chem. 74]

(W-59-1)

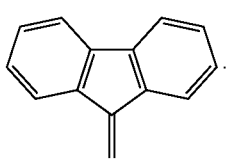

The group represented by the above-mentioned formula (W-60) is preferably a group selected from the following formulae (W-60-1) to (W-60-6) which may be unsubstituted or substituted with one or more of the above-mentioned $L^W$'s.

[Chem. 75]

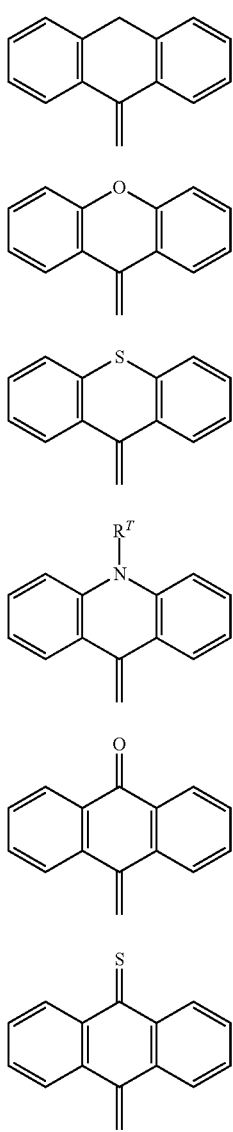

(W-60-1)
(W-60-2)
(W-60-3)
(W-60-4)
(W-60-5)
(W-60-6)

(In the formulae, $R^T$ represents a hydrogen atom or an alkyl group having 1 to 8 carbon atoms). The group represented by the above-mentioned formula (W-61) is preferably a group selected from the following formulae (W-61-1) to (W-61-3) which may be unsubstituted or substituted with one or more of the above-mentioned $L^W$'s.

[Chem. 76]

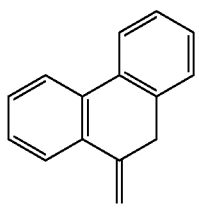

(W-61-1)

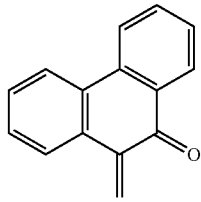

(W-61-2)

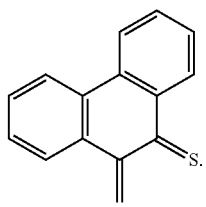

(W-61-3)

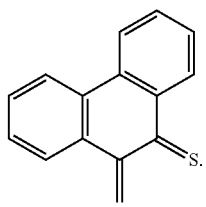

The group represented by the above-mentioned formula (W-62) is preferably a group selected from the following formulae (W-62-1) to (W-62-4) which may be unsubstituted or substituted with one or more of the above-mentioned $L^W$'s.

[Chem. 77]

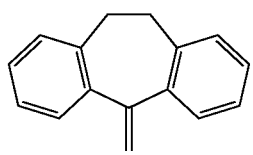

(W-62-1)

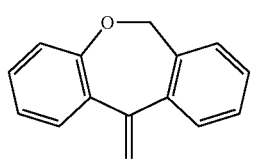

(W-62-2)

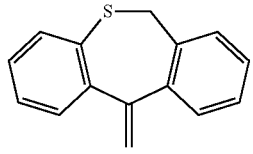

(W-62-3)

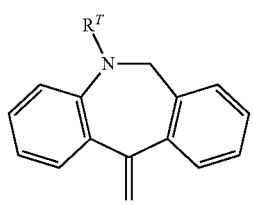

(W-62-4)

(In the formulae, $R^T$ represents a hydrogen atom or an alkyl group having 1 to 8 carbon atoms). The group represented by the above-mentioned formula (W-63) is preferably a group selected from the following formulae (W-63-1) to (W-63-4) which may be unsubstituted or substituted with one or more of the above-mentioned $L^W$'s.

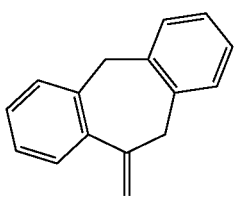
(W-63-1)

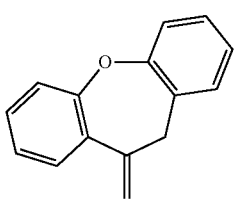
(W-63-2)

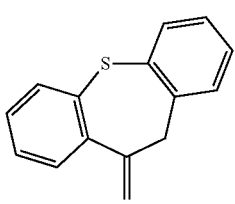
(W-63-3)

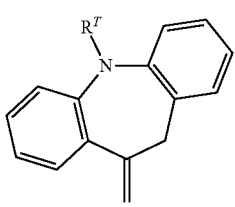
(W-63-4)

(In the formulae, $R^T$ represents a hydrogen atom or an alkyl group having 1 to 8 carbon atoms). The group represented by the above-mentioned formula (W-64) is preferably a group selected from the following formula (W-64-1):

[Chem. 79]

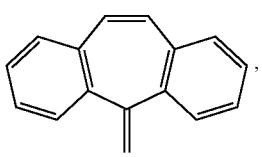
(W-64-1)

which may be unsubstituted or substituted with one or more of the above-mentioned $L^W$'s.

From the viewpoint of easy availability of raw materials and easiness in synthesis, the cyclic group represented by $=CW^1W^2$ is more preferably a group selected from the formula (W-44-2), the formula (W-44-3), the formula (W-45-2), the formula (W-45-3), the formula (W-47-3), the formula (W-47-4), the formula (W-59-1), the formula (W-60-2), the formula (W-60-3), the formula (W-60-4) and the formula (W-64-1) which may be unsubstituted or substituted with one or more of the above-mentioned substituents $L^W$'s, more preferably a group selected from the formula (W-59-1) and the formula (W-64-1) which may be unsubstituted or substituted with one or more of the above-mentioned substituents $L^W$'s, and even more preferably a group represented by the formula (W-59-1) which may be unsubstituted or substituted with one or more of the above-mentioned substituents $L^W$'s.

From the viewpoint of easy availability of raw materials and liquid crystallinity, $L^W$ is preferably a fluorine atom, a chlorine atom, a nitro group, a cyano group, a methylamino group, a dimethylamino group, a diethylamino group, a diisopropylamino group, or a linear or branched alkyl group having 1 to 20 carbon atoms, in which one or more of arbitrary hydrogen atoms may be substituted with a fluorine atom, and one —CH$_2$— or two or more of (—CH$_2$—)'s which are not adjacent to each other may be each independently substituted with —O—, —S—, —CO—, —COO—, —OCO—, —O—CO—O—, —CH=CH—, —CF=CF— or —C≡C—, more preferably a fluorine atom, a chlorine atom, a nitro group, a cyano group, a methylamino group, a dimethylamino group, or a linear or branched alkyl group having 1 to 20 carbon atoms, in which one or more of arbitrary hydrogen atoms may be substituted with a fluorine atom, and one —CH$_2$— or two or more of (—CH$_2$—)'s which are not adjacent to each other may be each independently substituted with —O—, —S— or —CO—, even more preferably a fluorine atom, a chlorine atom, a nitro group, a cyano group, a methylamino group, a dimethylamino group, or a linear alkyl group having 1 to 10 carbon atoms, in which one or more of arbitrary hydrogen atoms may be substituted with a fluorine atom, and one —CH$_2$— or two or more of (—CH$_2$—)'s which are not adjacent to each other may be each independently substituted with —O—, still more preferably a fluorine atom, a chlorine atom, a nitro group, a dimethylamino group, or a linear alkyl group having 1 or 2 carbon atoms, in which one or more of arbitrary hydrogen atoms may be substituted with a fluorine atom, and one —CH$_2$— or two or more of (—CH$_2$—)'s which are not adjacent to each other may be each independently substituted with —O—.

The total number of the π electrons contained in $W^1$ and $W^2$ is, from the viewpoint of wavelength dispersion property, storage stability, liquid crystallinity and easiness in synthesis, preferably 4 to 24.

Specifically, the compound represented by the general formula (I) is preferably a compound selected from the following general formulae (I-A) to (I-C).

[Chem. 80]

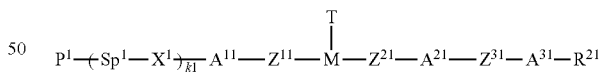
(I-A)

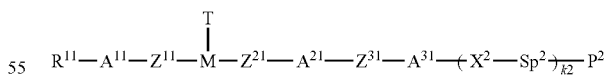
(I-B)

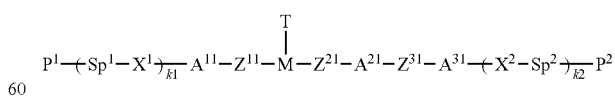
(I-C)

(In the formulae, $P^1$ and $P^2$ each have the same meanings as those of P in the general formula (I), $Sp^1$ and Sp each have the same meanings as those of Sp in the general formula (I), $X^1$ and $X^2$ each have the same meanings as those of X in the general formula (I), k1 and k2 each have the same meanings as those of k in the general formula (I), T and M each have the same meanings as those of T and M in the general formula (I), $A^{11}$, $A^{21}$ and $A^{31}$ each independently represent a group selected from the above-mentioned formulae (A-1) to (A-8), $Z^{11}$, $Z^{21}$ and $Z^{31}$ each independently represent —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO— or a single bond, $R^{11}$ and $R^{21}$ each independently represent a hydrogen atom, a fluorine atom, a chlorine atom, a cyano group, or a linear alkyl or alkoxy group having 1 to 12 carbon atoms).

In the case where the solubility of the compound and the curing shrinkage resistance of the film formed of the compound are considered to be important, the compound represented by the above general formula (I-A) or (I-B) is preferred, where alignment is additionally considered to be important, the compound represented by the general formula (I-A) is preferred, and where wavelength dispersion property is further additionally considered to be important, the compound represented by the general formula (I-B) is preferred.

In the case where the retardation stability of the formed film is considered to be important, the compound represented by the general formula (I-C) is preferred.

More specifically, the compound represented by the general formula (I-A) is more preferably a compound represented by the following general formula (I-A-1).

[Chem. 81]

(I-A-1)

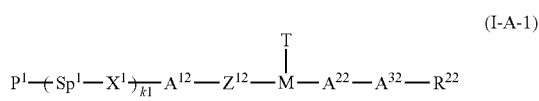

(In the formula, $P^1$, $Sp^1$, $X^1$ and k1 each have the same meanings as those of $P^1$, $Sp^1$, $X^1$ and k1 in the general formula (I-A), T and M each have the same meanings as those in the general formula (I), $A^{12}$ represents a group selected from the above-mentioned formula (A-1), formula (A-3) or formula (A-4), $A^{22}$ and $A^{32}$ each represent a group of the above-mentioned formula (A-2), $Z^{12}$ represents —OCH$_2$—, —CH$_2$O—, —COO— or —OCO—, $R^{22}$ represents a hydrogen atom, a fluorine atom, or a linear alkyl or alkoxy group having 1 to 12 carbon atoms.)

More specifically, the compound represented by the general formula (I-B) is more preferably a compound represented by the following general formula (I-B-1).

[Chem. 82]

(I-B-1)

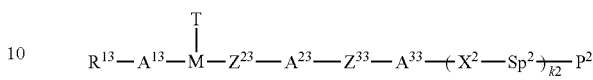

(In the formula, $P^2$, $Sp^2$, $X^2$ and k2 each have the same meanings as those of $P^2$, $Sp^2$, $X^2$ and k2 in the general formula (I-B), T and M each have the same meanings as those in the general formula (I), $A^{13}$ and $A^{23}$ each have the same meanings as those in the above formula (A-2), $A^{33}$ represents a group selected from the above formula (A-1), formula (A-3) or formula (A-4), $Z^{23}$ and $Z^{33}$ each represent —OCH$_2$—, —CH$_2$O—, —COO— or —OCO—, $R^{13}$ represents a hydrogen atom, a fluorine atom, or a linear alkyl or alkoxy group having 1 to 12 carbon atoms.)

More specifically, the compound represented by the general formula (I-C) is more preferably a compound represented by the following general formula (I-C-1).

[Chem. 83]

(I-C-1)

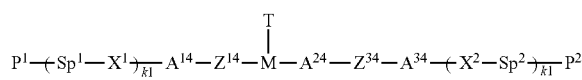

(In the formula, $P^1$, $Sp^1$, $X^1$ and k1 each have the same meanings as those of $P^1$, $Sp^1$, $X^1$ and k1 in the general formula (I-A), T and M each have the same meanings as those in the general formula (I), $A^{14}$ and $A^{34}$ each represent a group selected from the above formula (A-1), formula (A-3) or formula (A-4), $A^{24}$ represents a group selected from the above formulae (A-1) to (A-4), $Z^{14}$ and $Z^{34}$ each represent —OCH$_2$—, —CH$_2$O—, —COO— or —OCO—.)

Specifically, the compound represented by the general formula (I) is preferably a compound represented by the following formulae (I-1) to (I-133).

[Chem. 84]

(I-1)

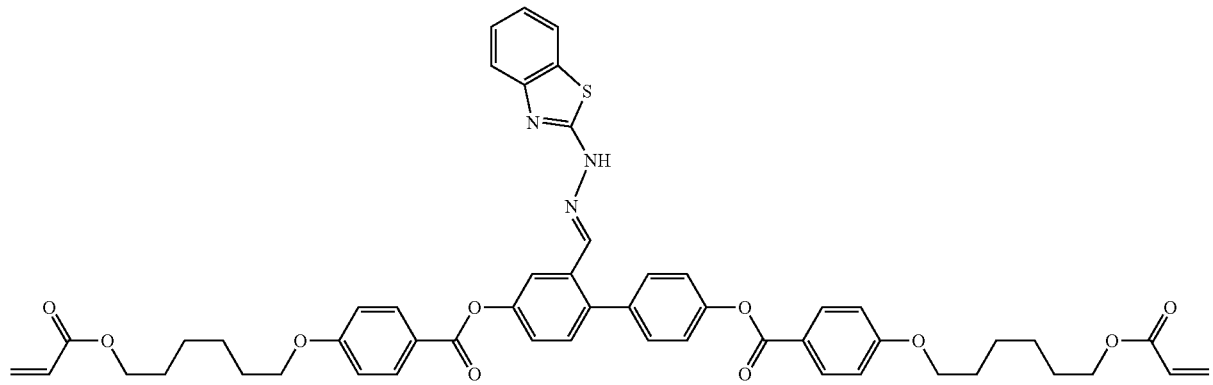

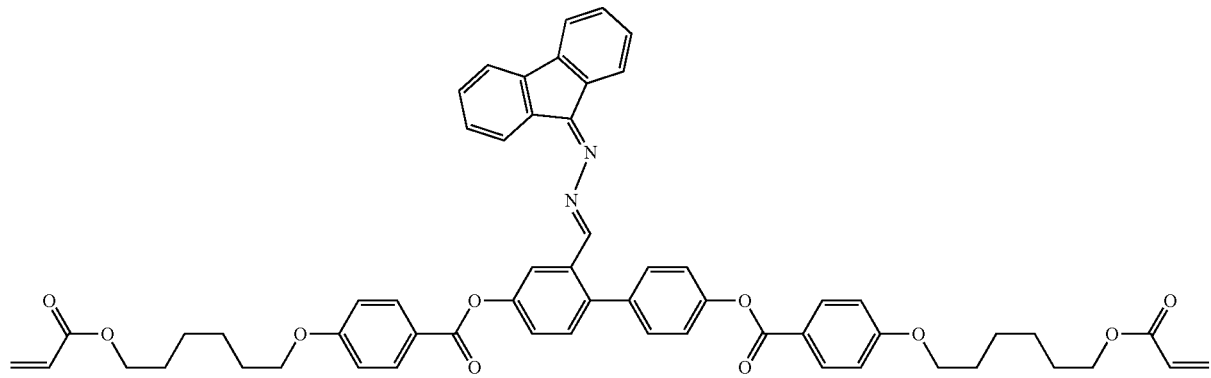
(I-2)
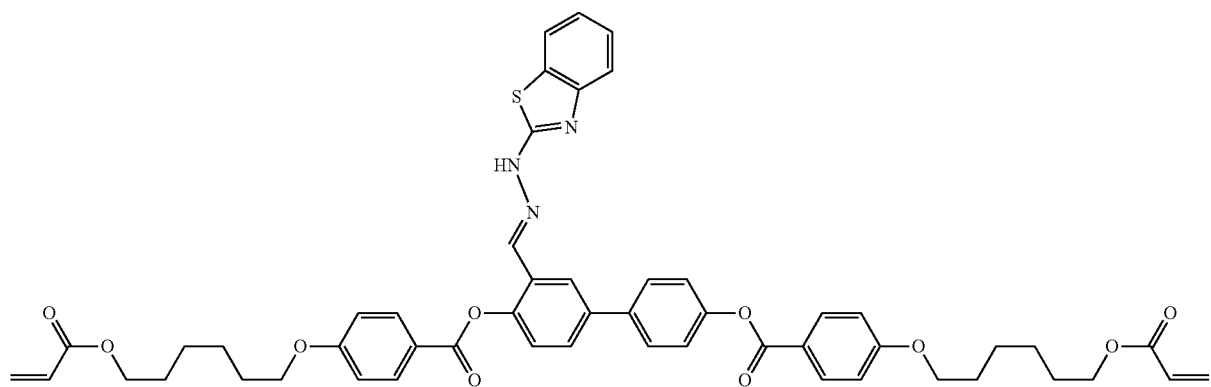
(I-3)
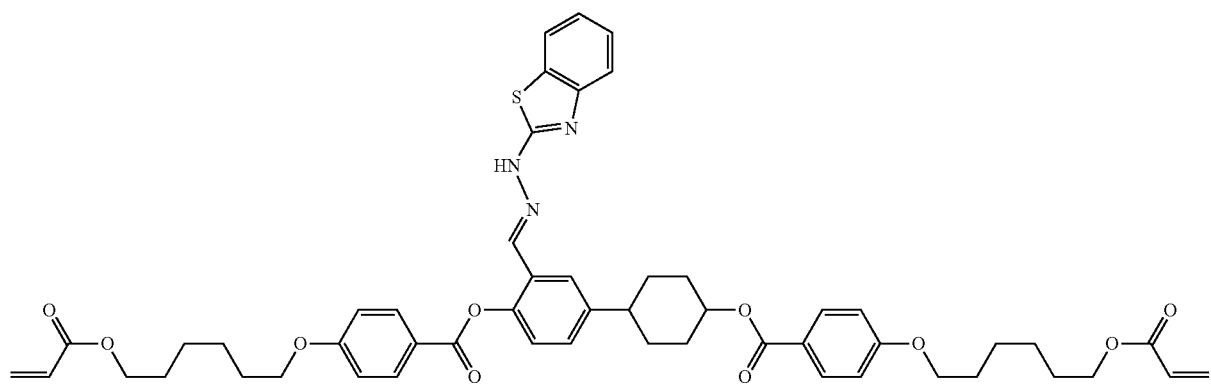
(I-4)

(I-5)
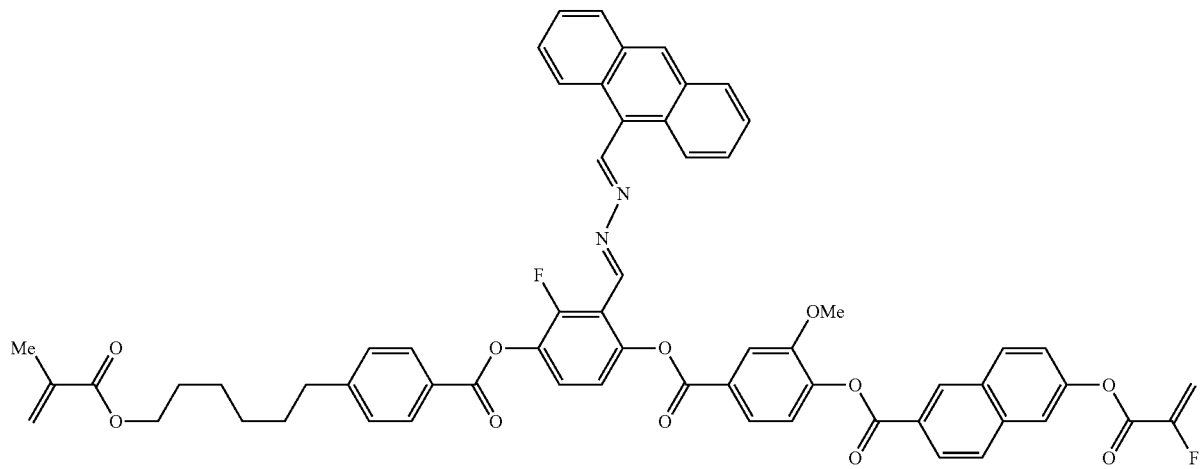
[Chem. 85]
(I-6)
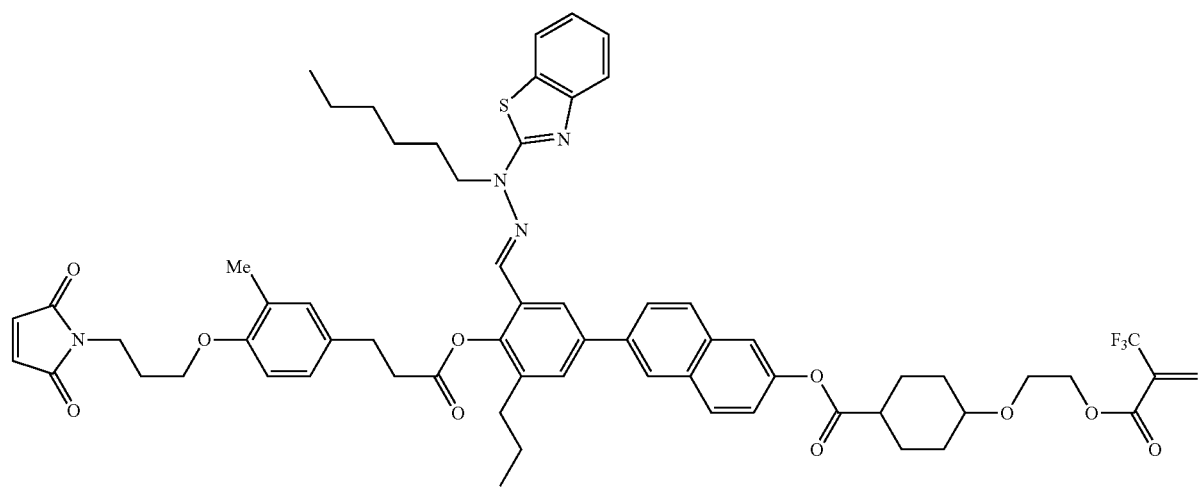
(I-7)
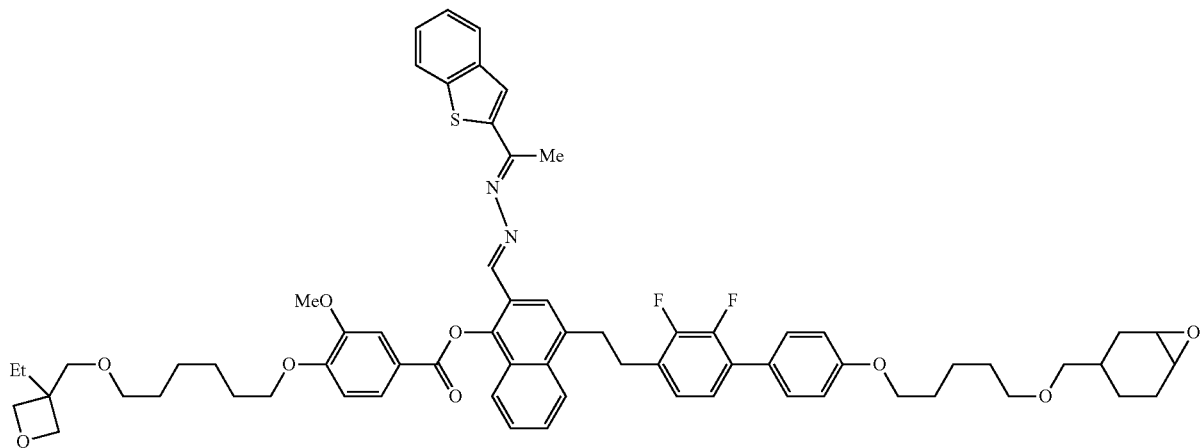

-continued
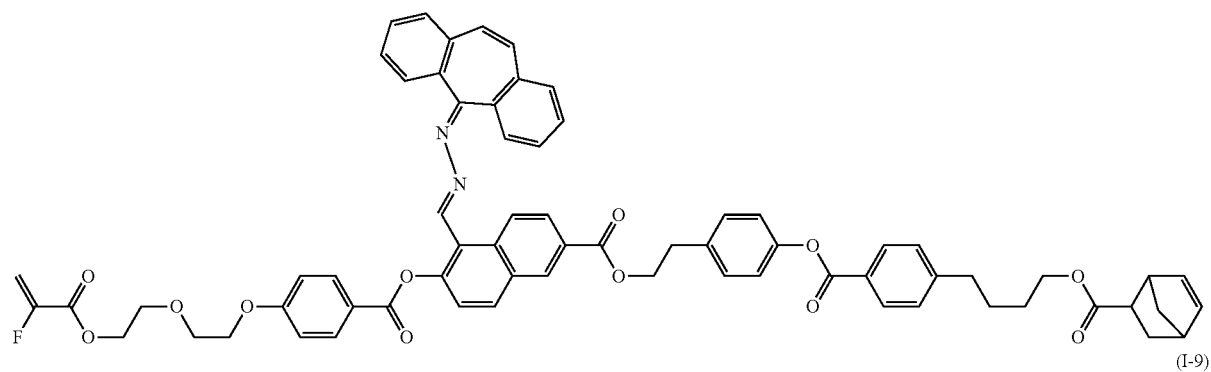
(I-8)
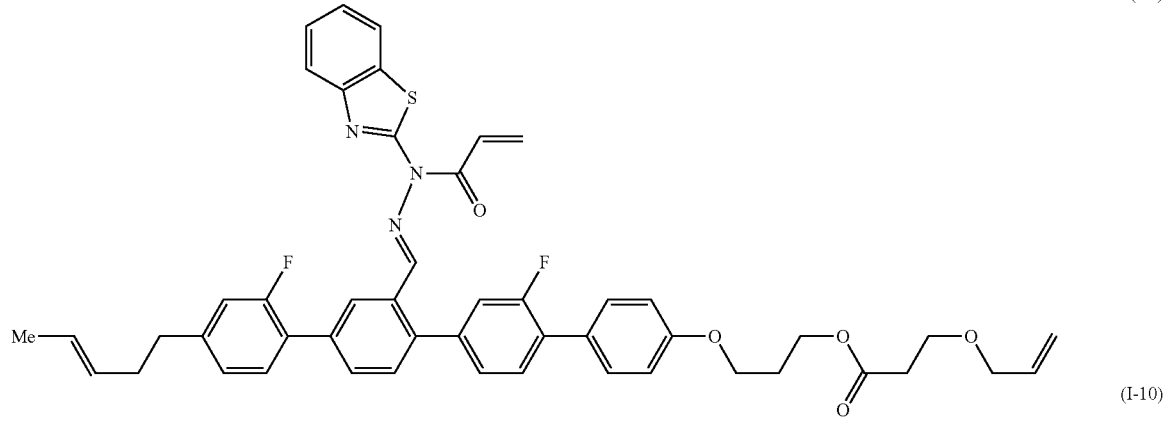
(I-9)
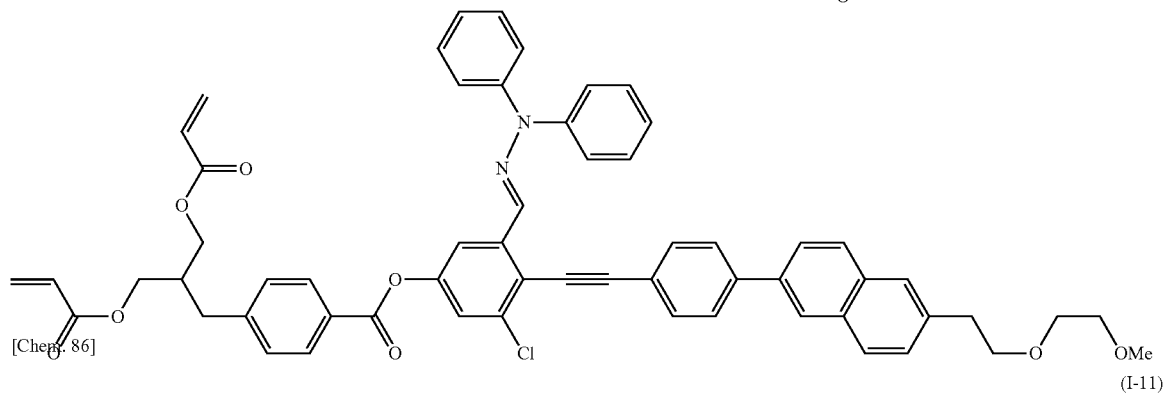
(I-10)
[Chem. 86]
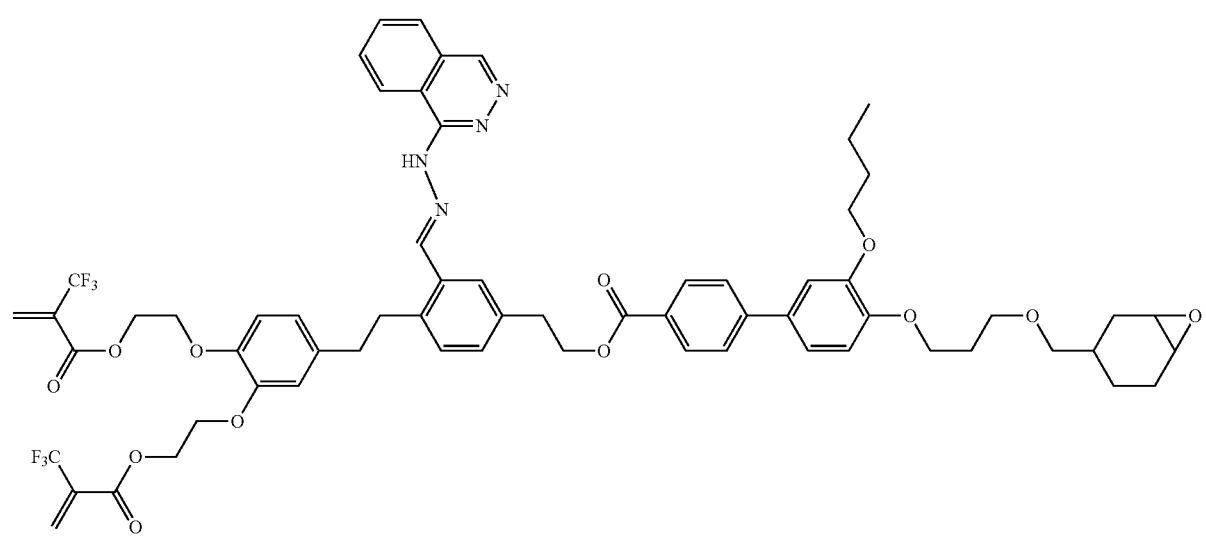
(I-11)

-continued
(I-12)
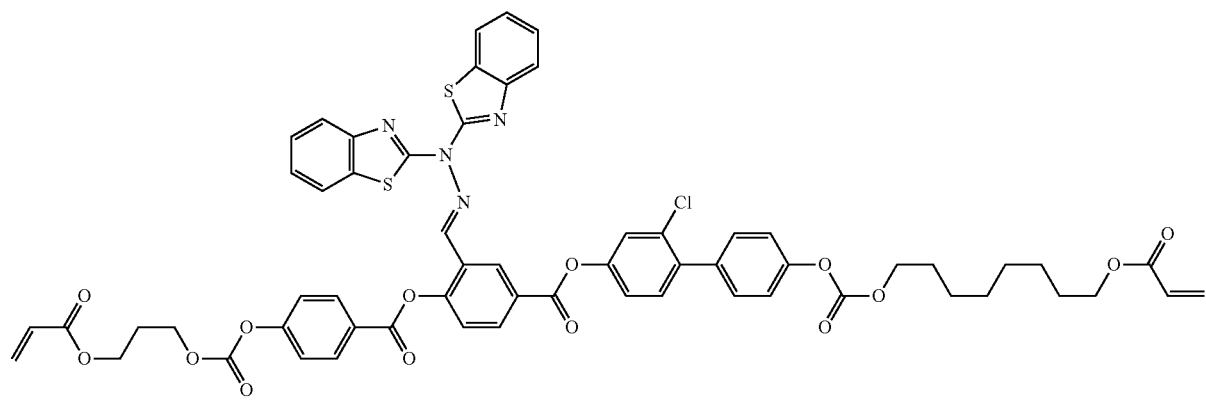
(I-13)
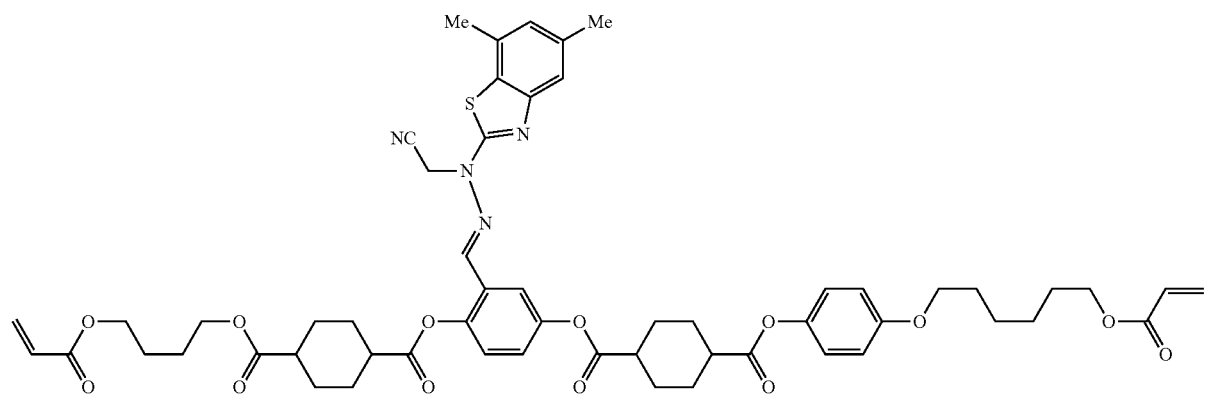
(I-14)
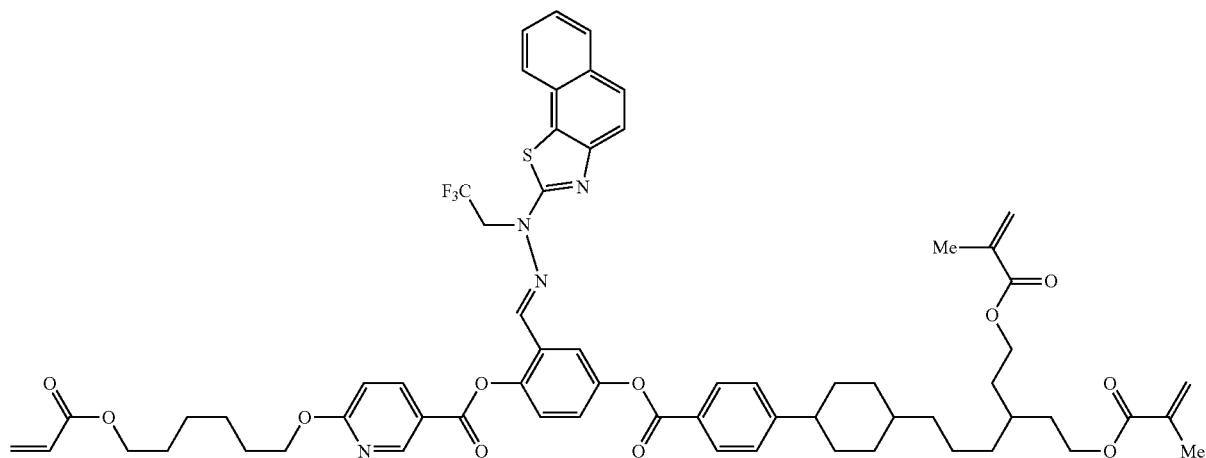

-continued
(I-15)
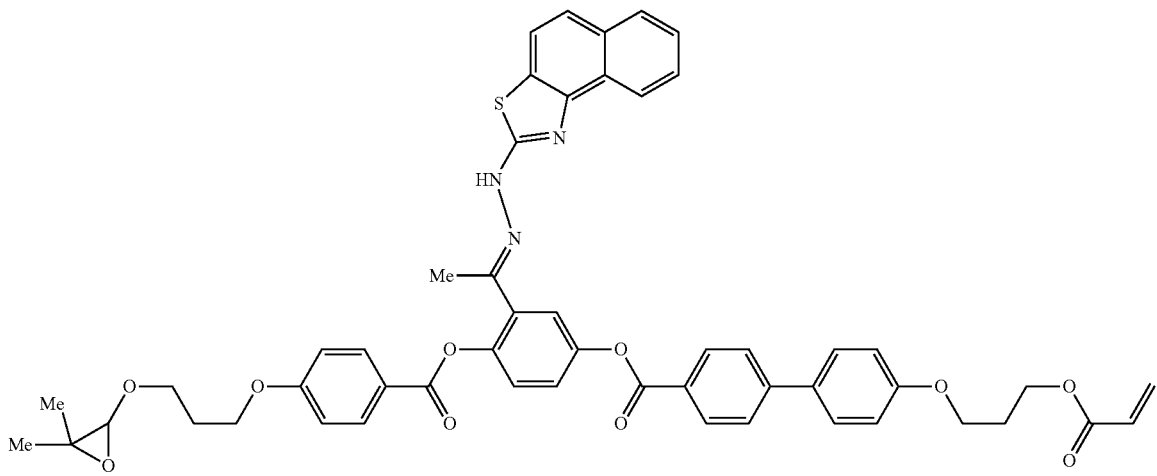
(I-16)
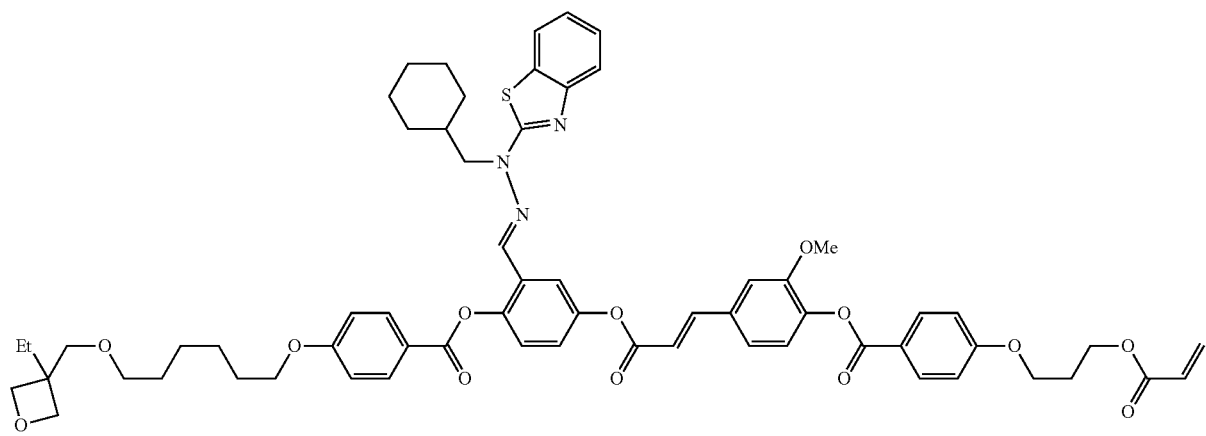
(I-17)
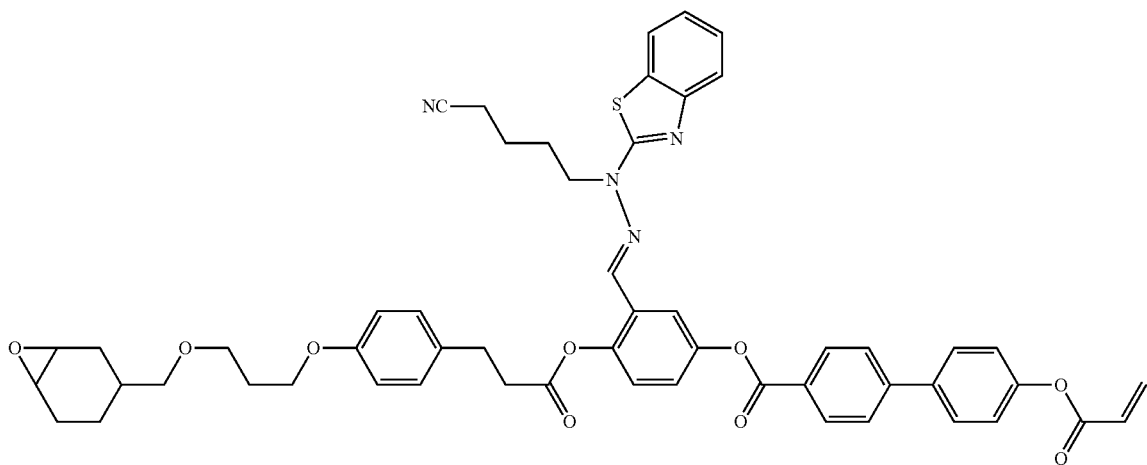

-continued
(I-18)
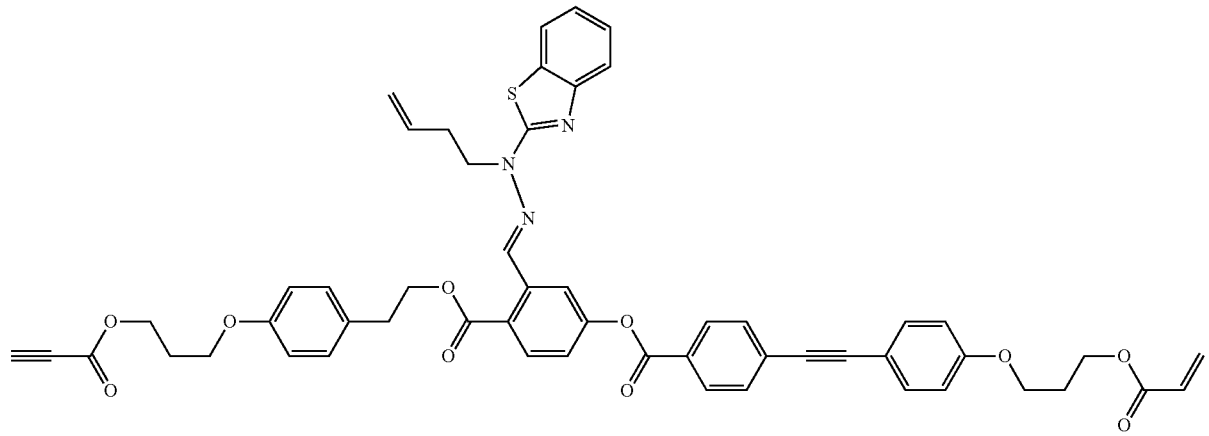
(I-19)
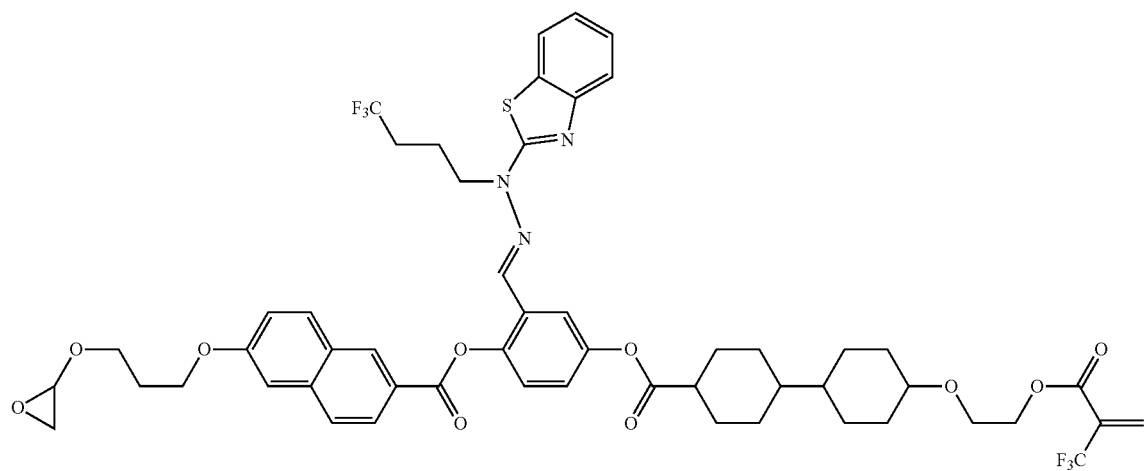
(I-20)
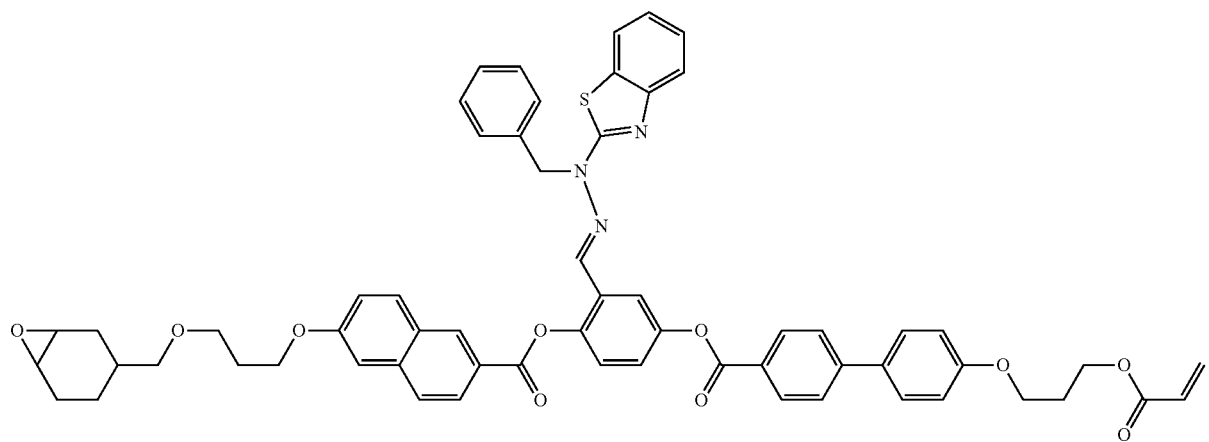

-continued
[Chem. 88]
(I-21)
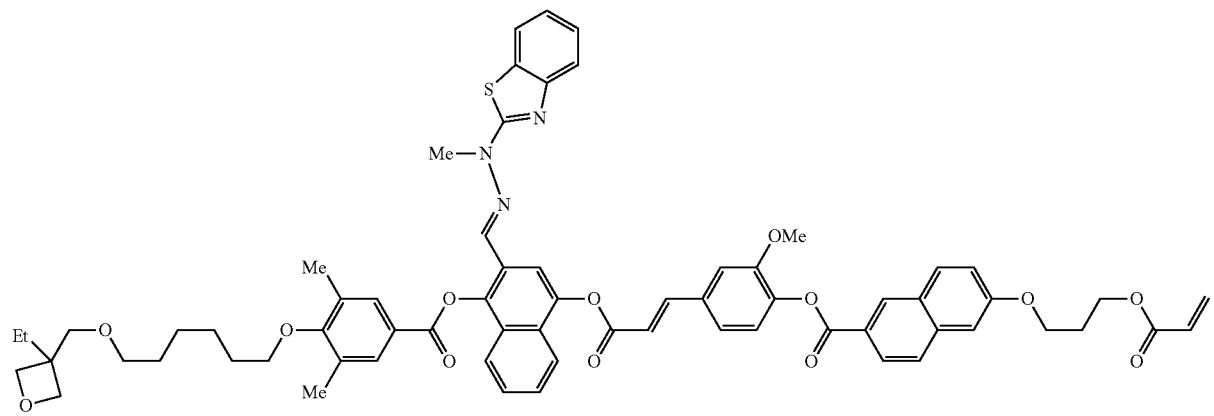
(I-22)
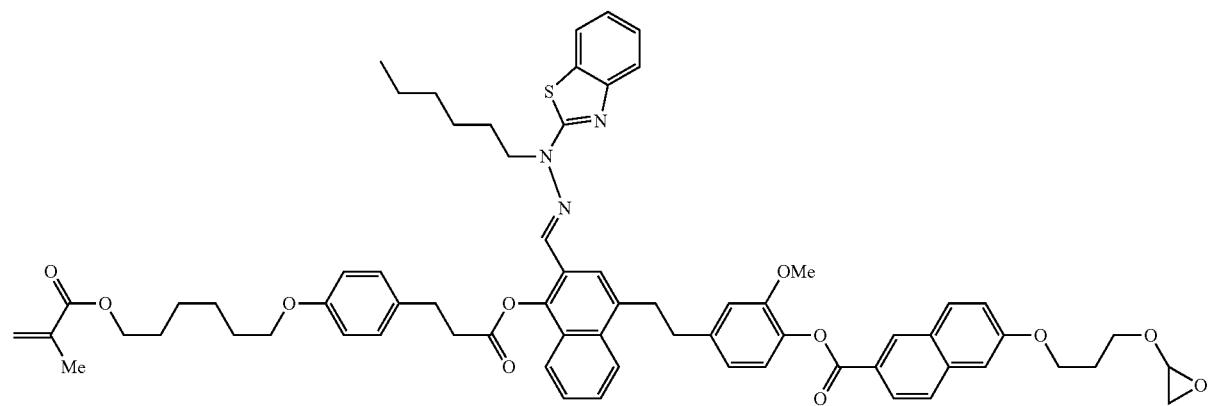
(I-23)
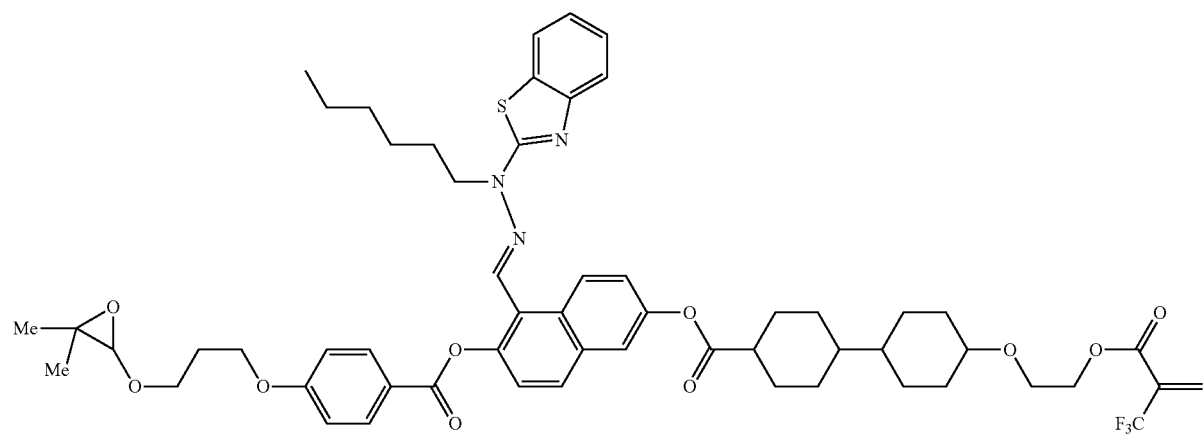

(I-24)
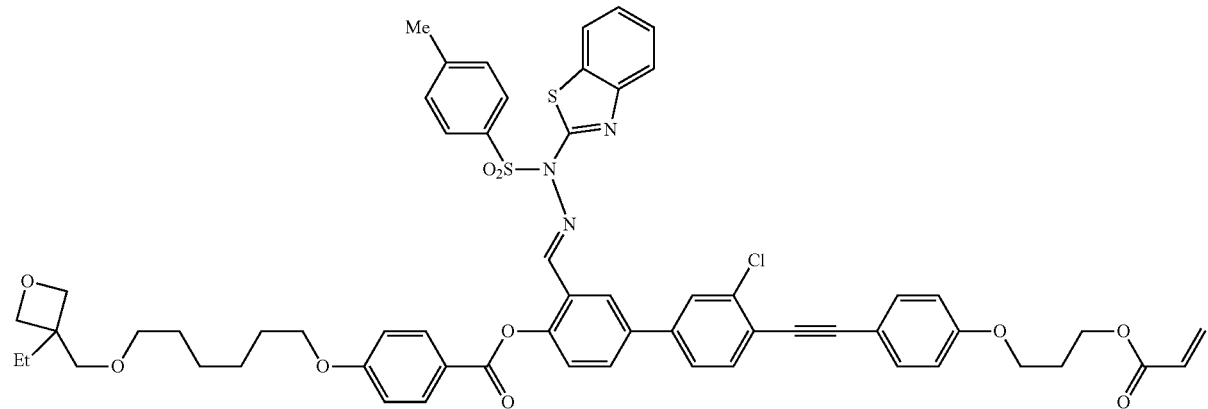
(I-25)
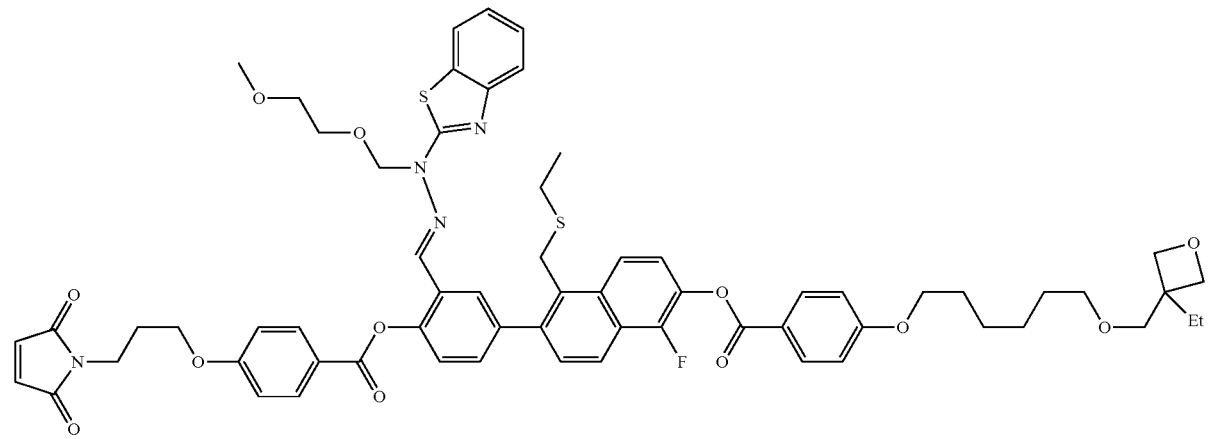
[Chem. 89]
(I-26)
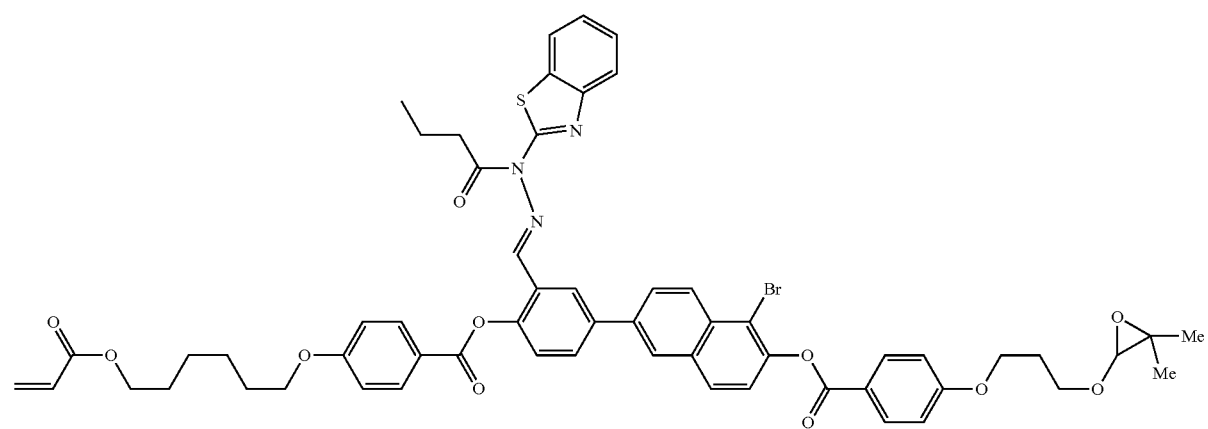

(I-27)
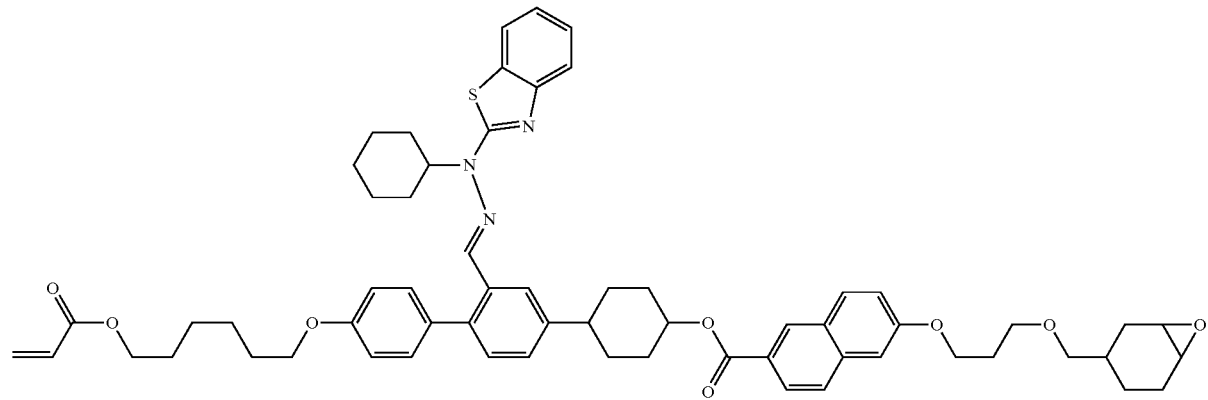
(I-28)
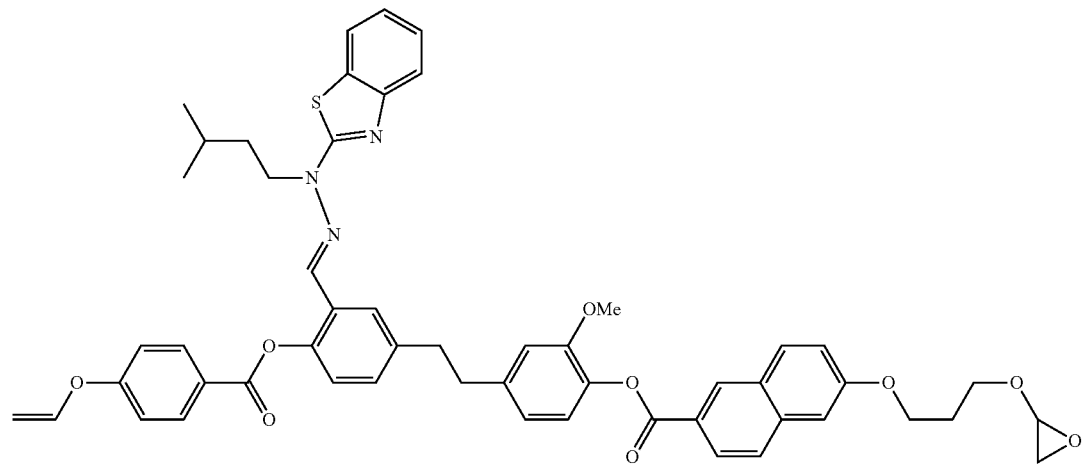
(I-29)
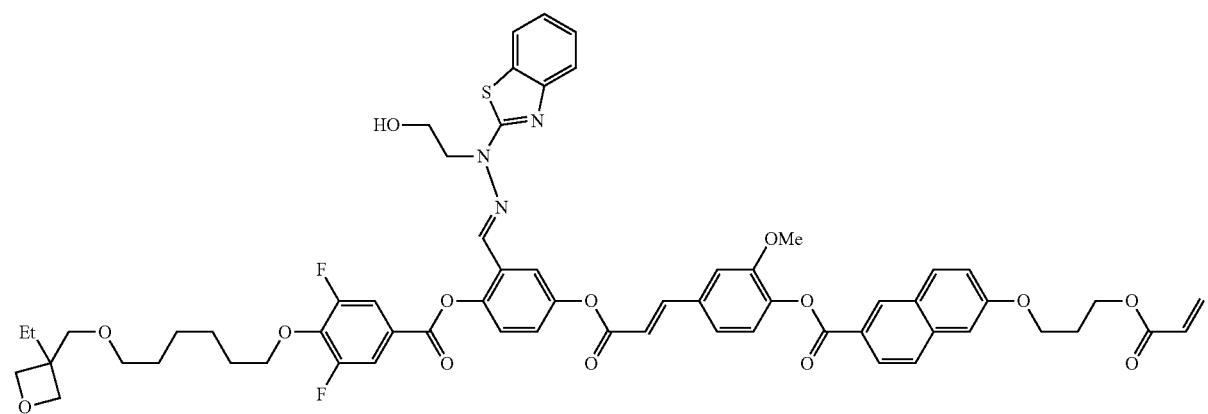

(I-30)
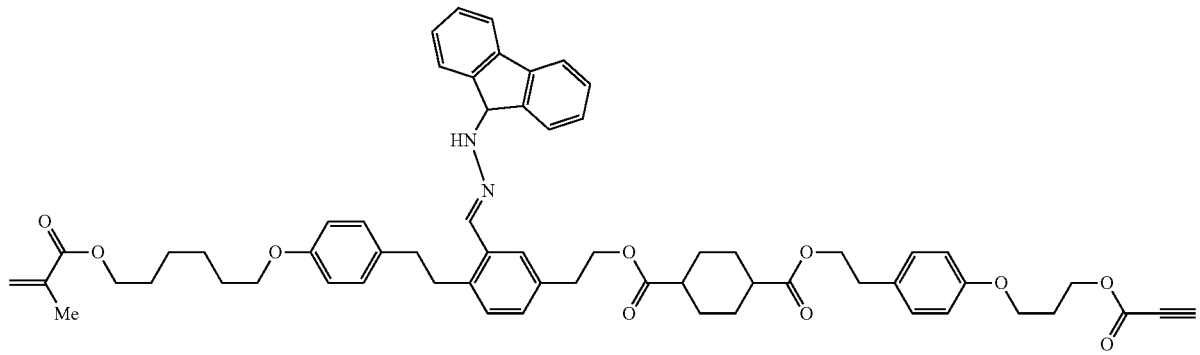
[Chem. 90]
(I-31)
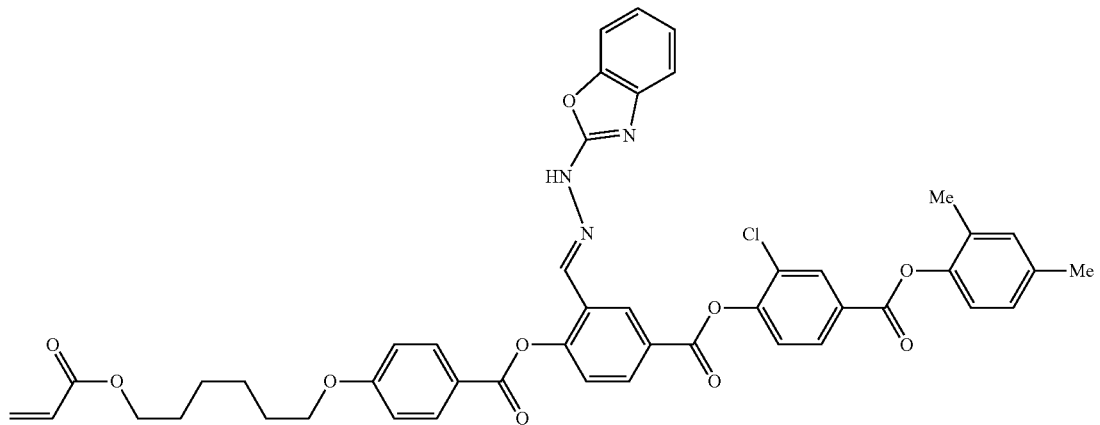
(I-32)
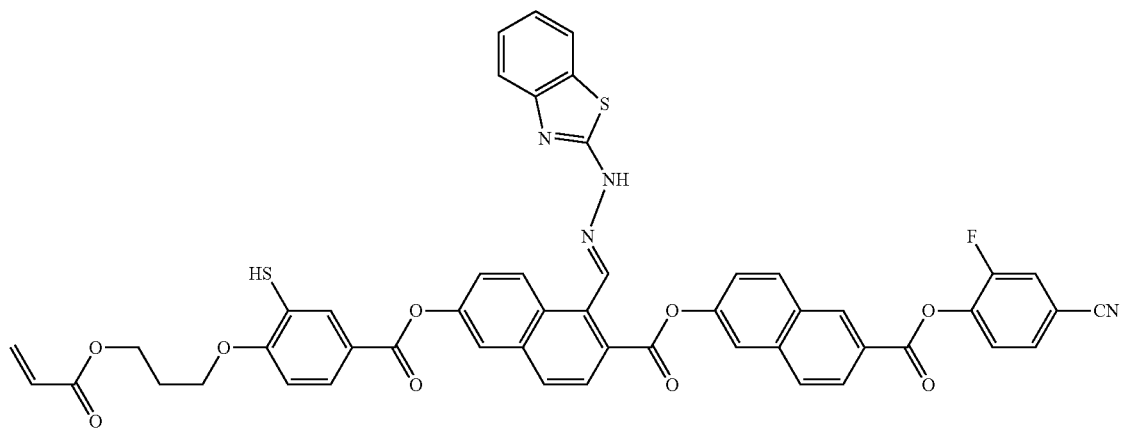

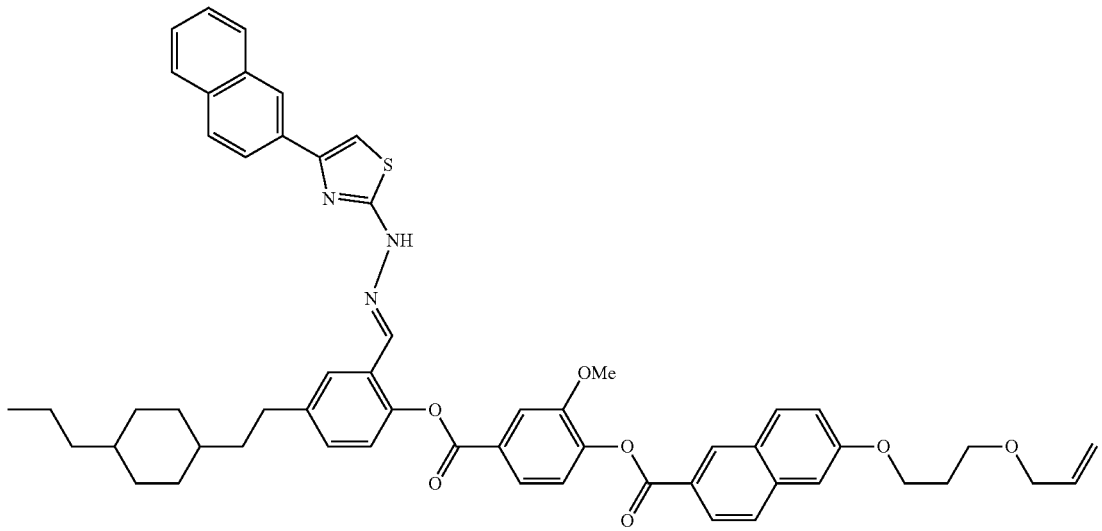
(I-33)
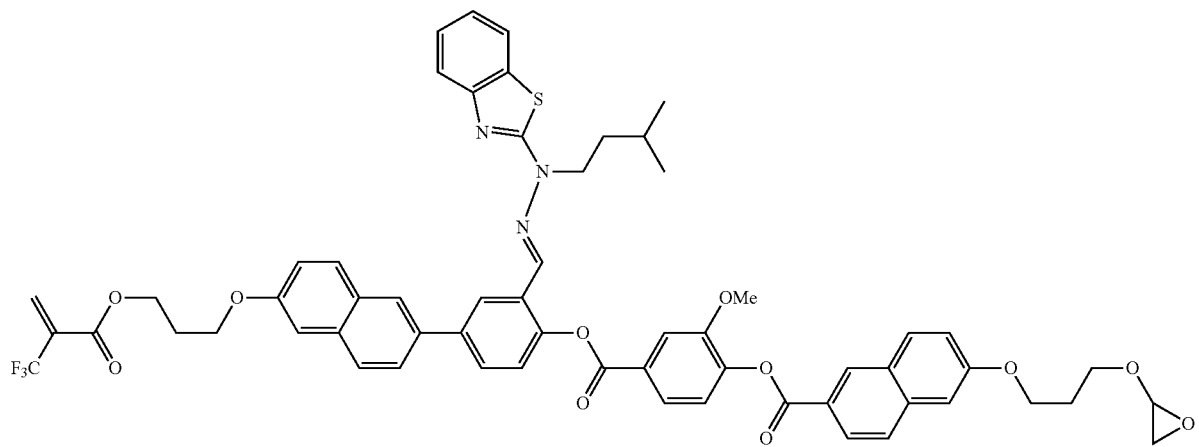
(I-34)
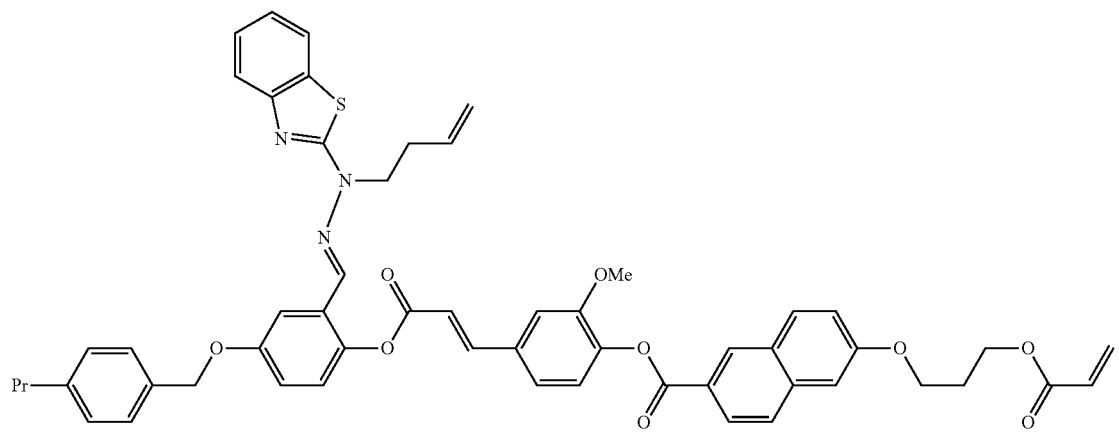
(I-35)

-continued
[Chem. 91]
(I-36)
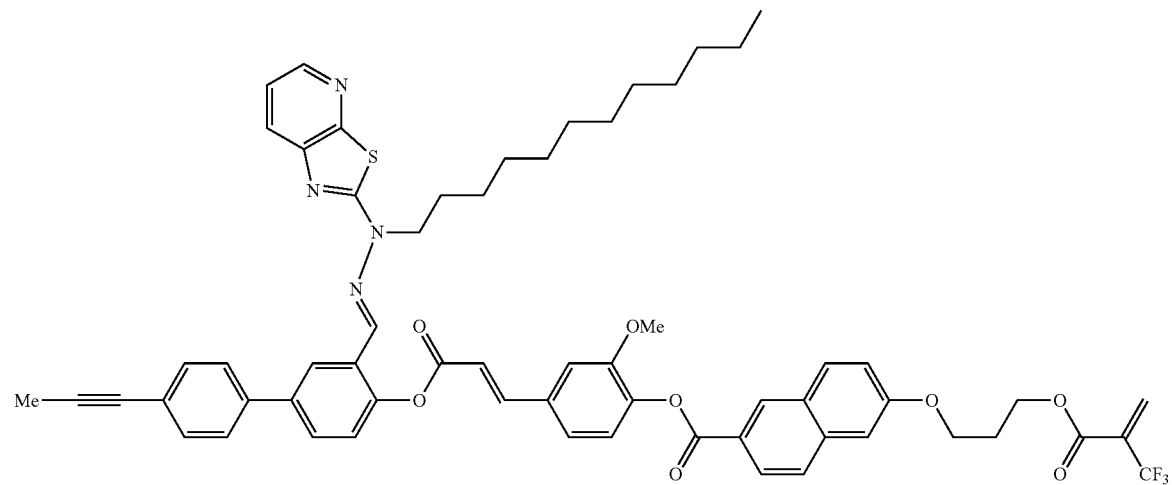
(I-37)
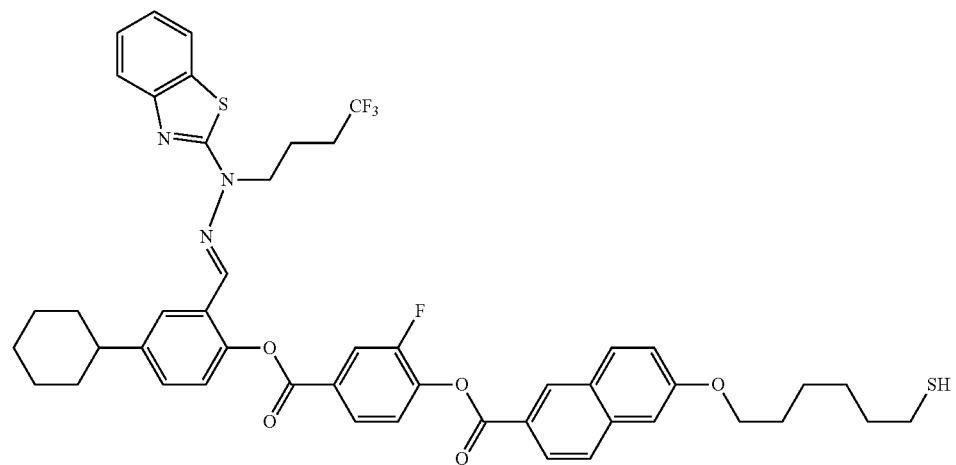
(I-38)
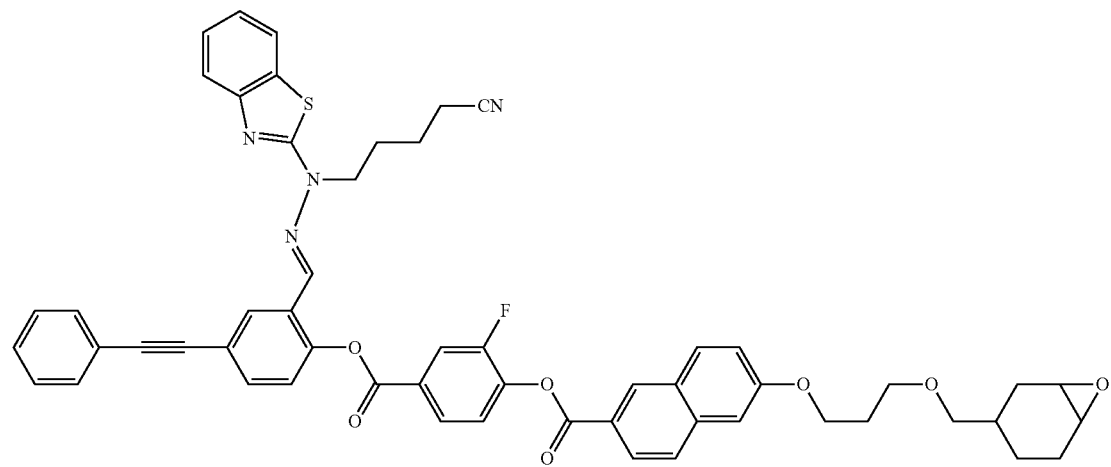

-continued
(I-39)
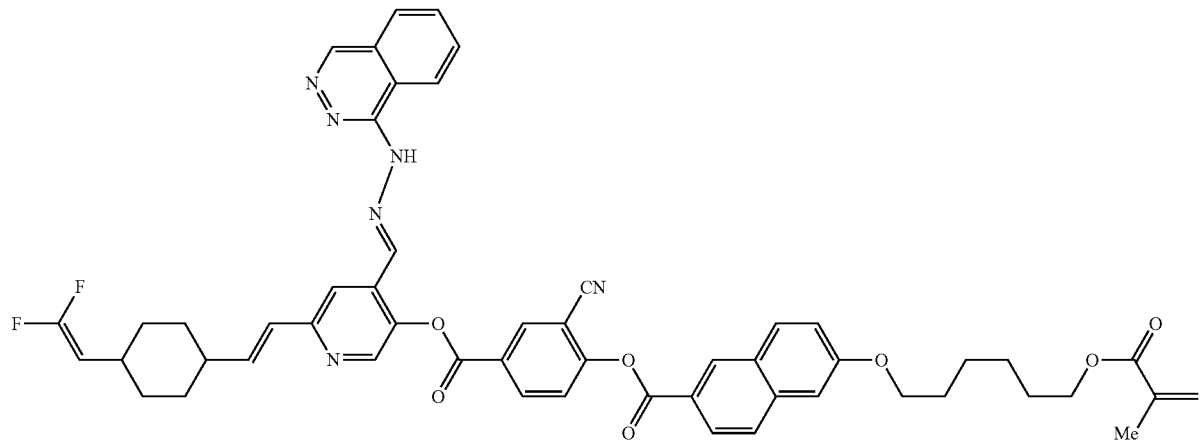
(I-40)
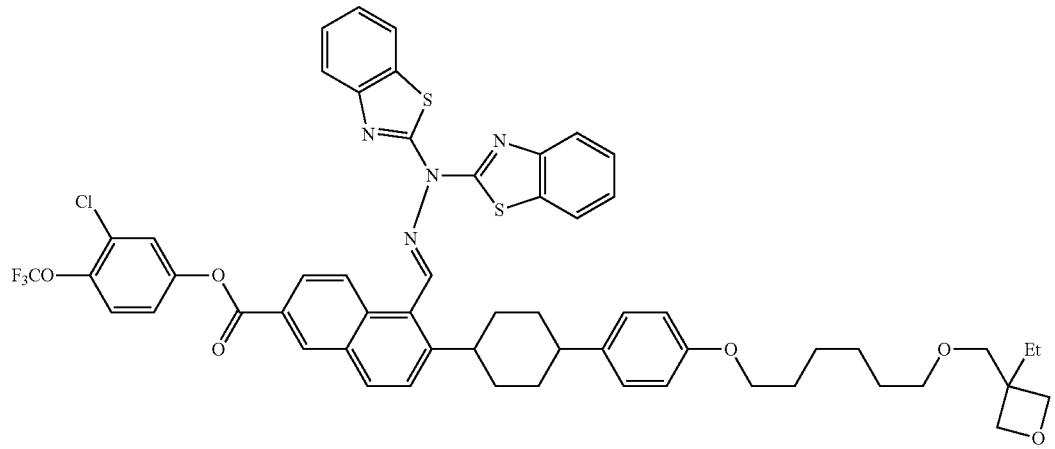
[Chem. 92]
(I-41)
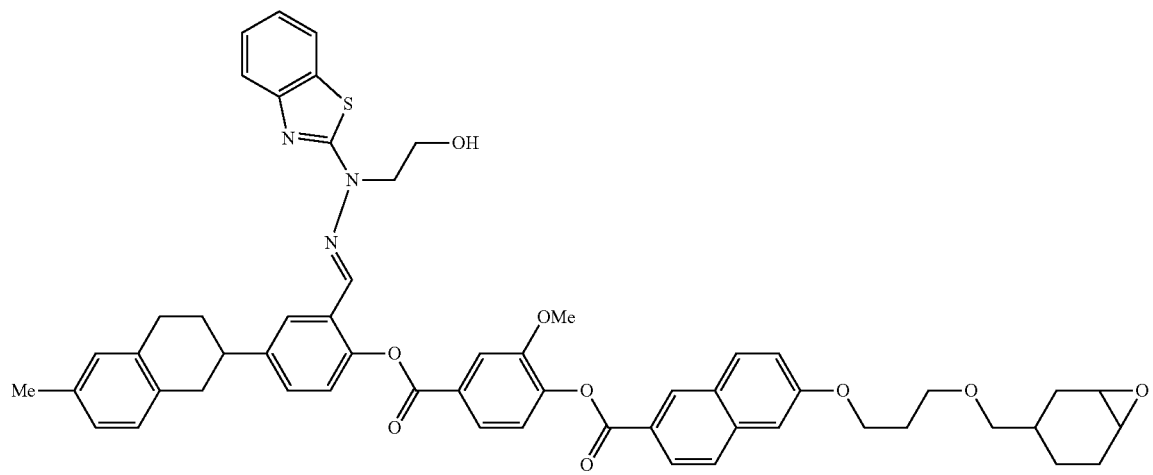

(I-42)
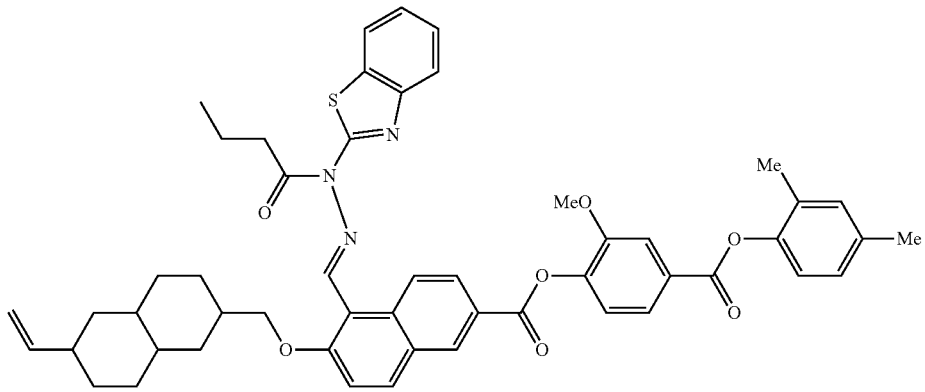
(I-43)
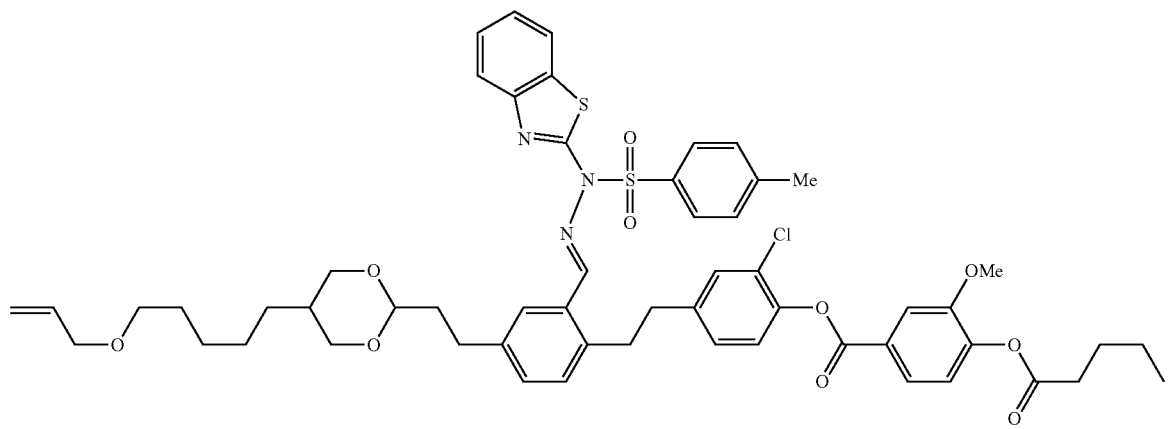
(I-44)
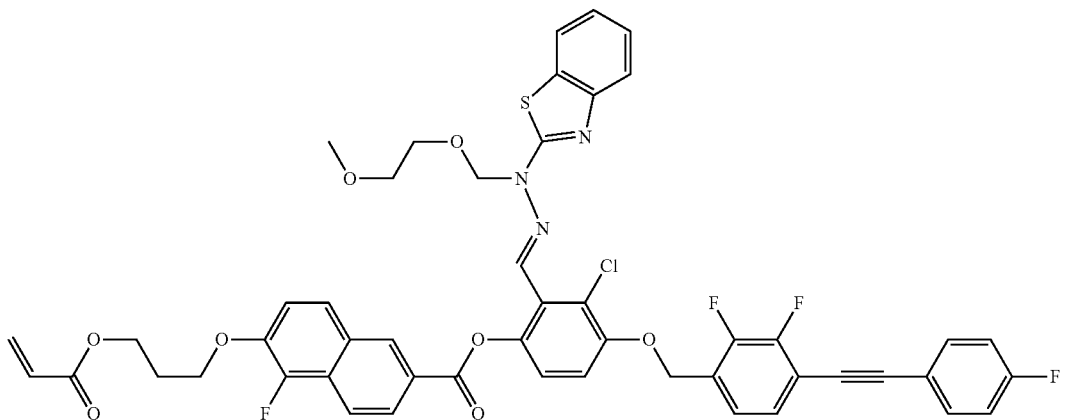

(I-45)
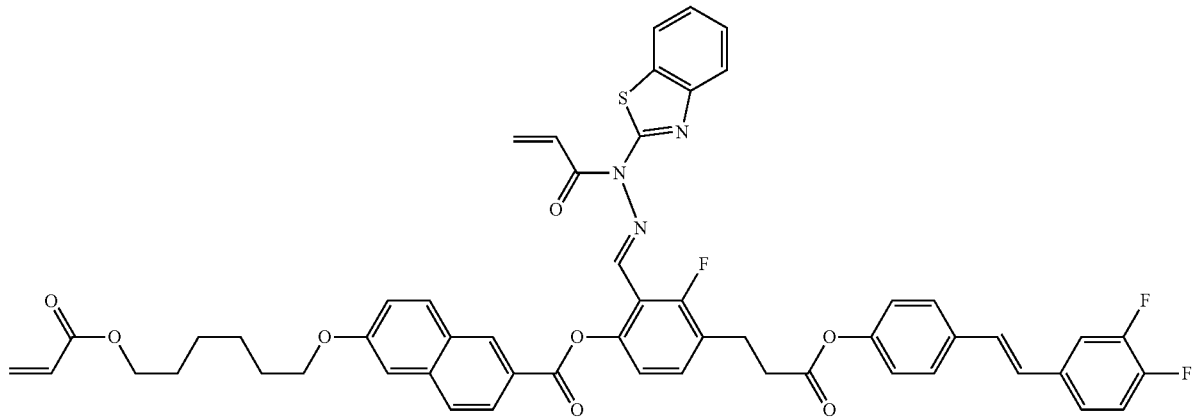
(I-46)
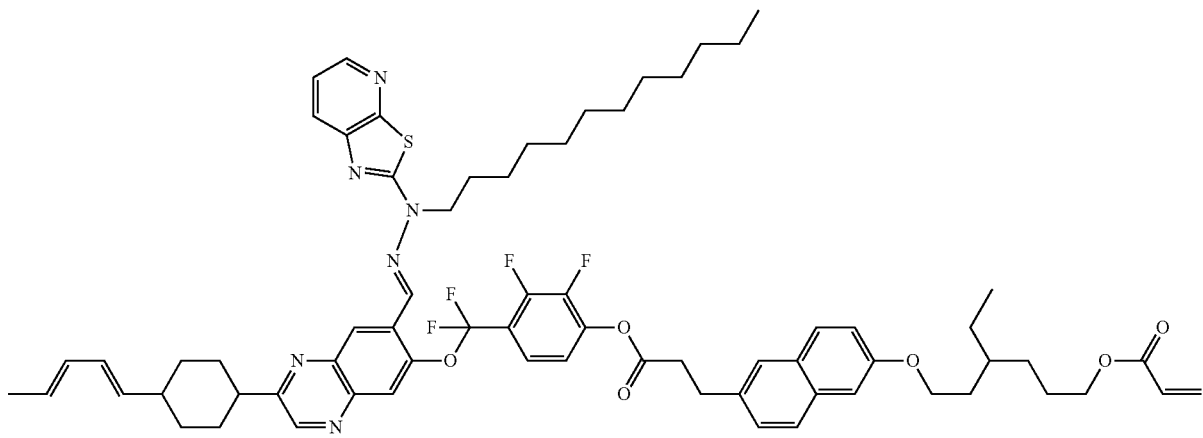
(I-47)
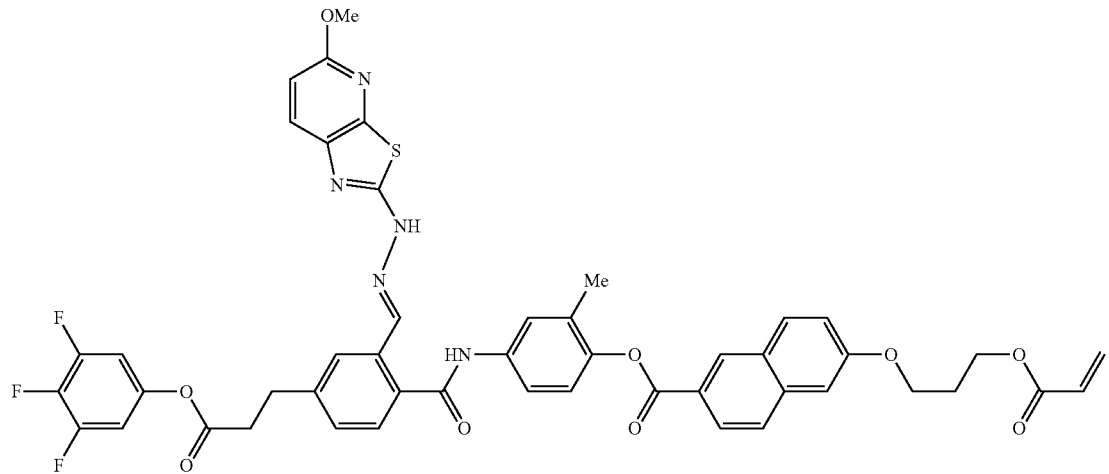

(I-48)
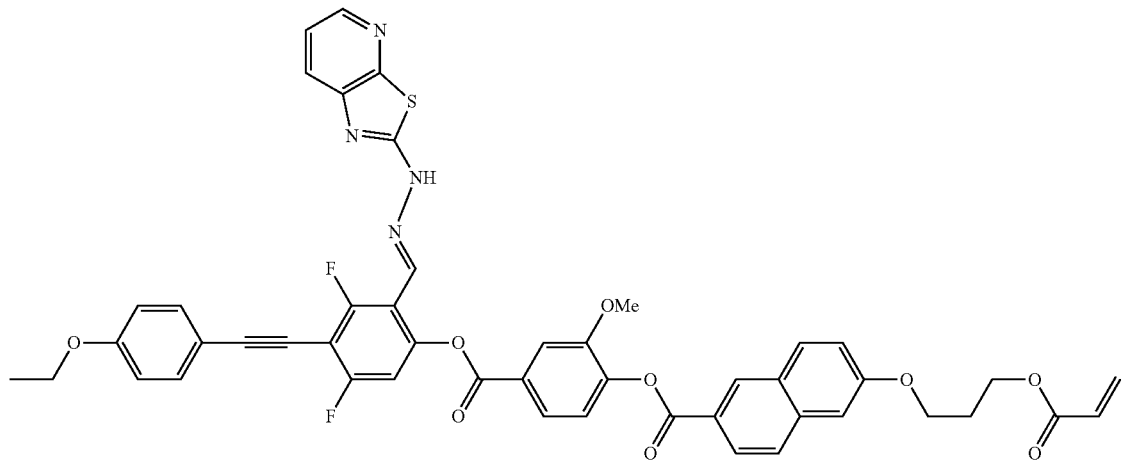
(I-49)
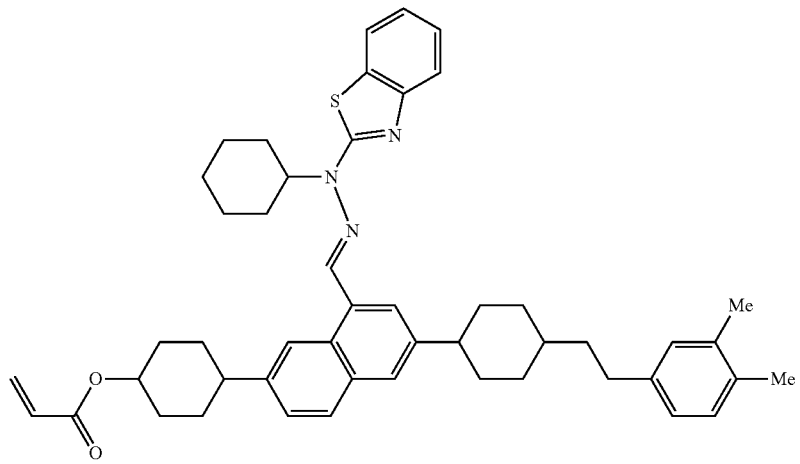
(I-50)
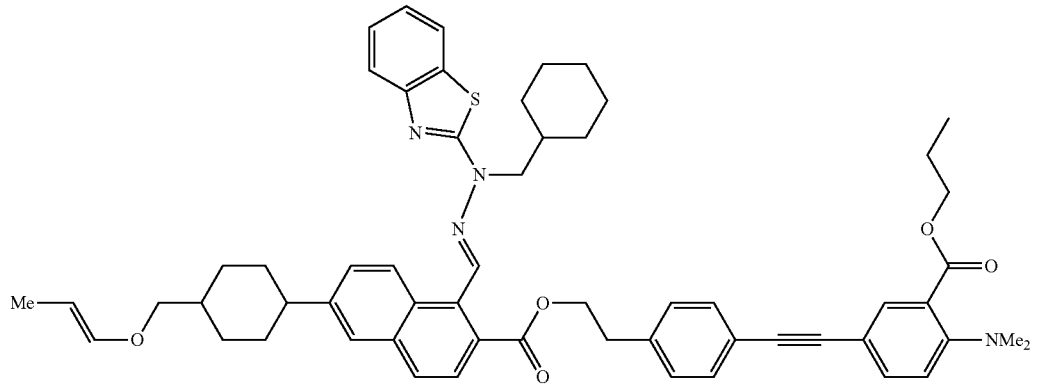

[Chem. 94]
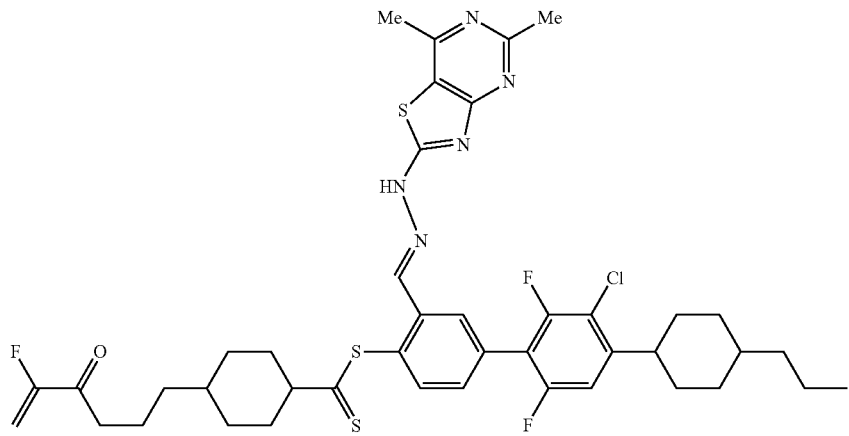
(I-51)
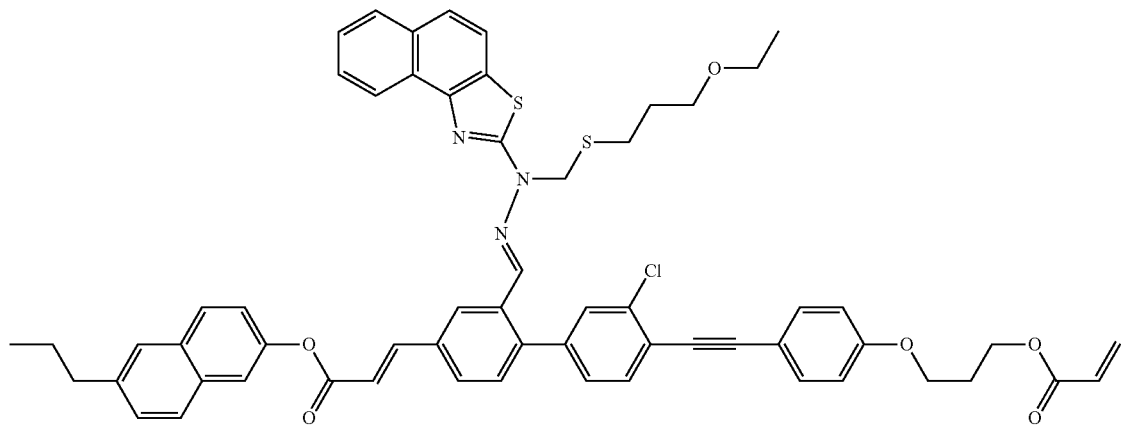
(I-52)
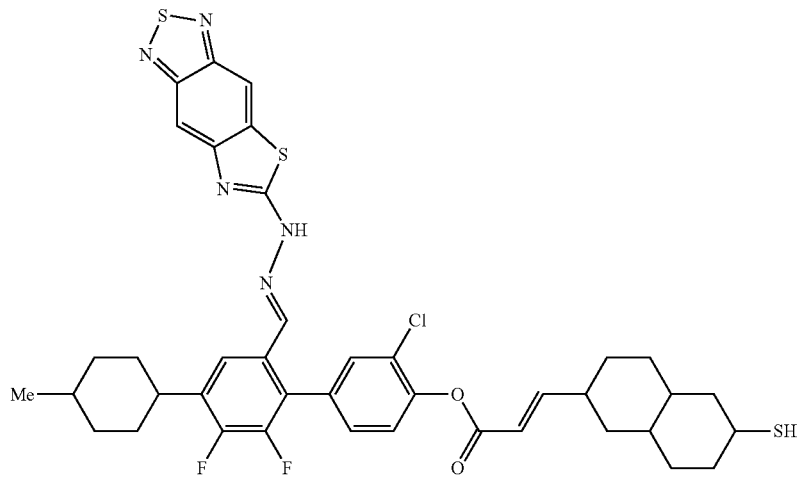
(I-53)

(I-54)
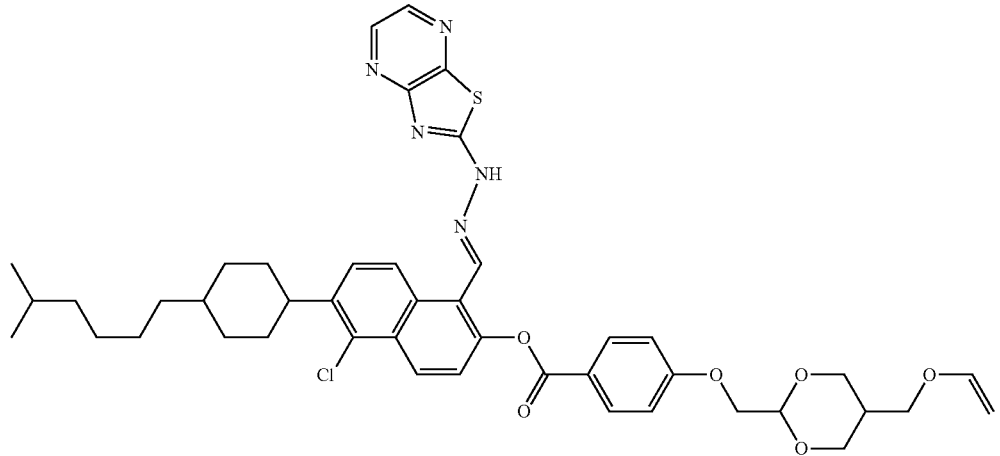
(I-55)
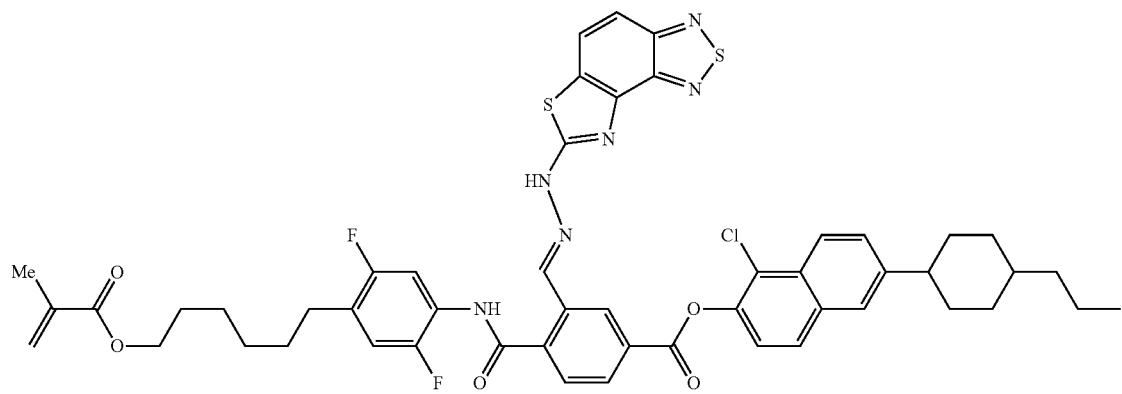
[Chem. 95]
(I-56)
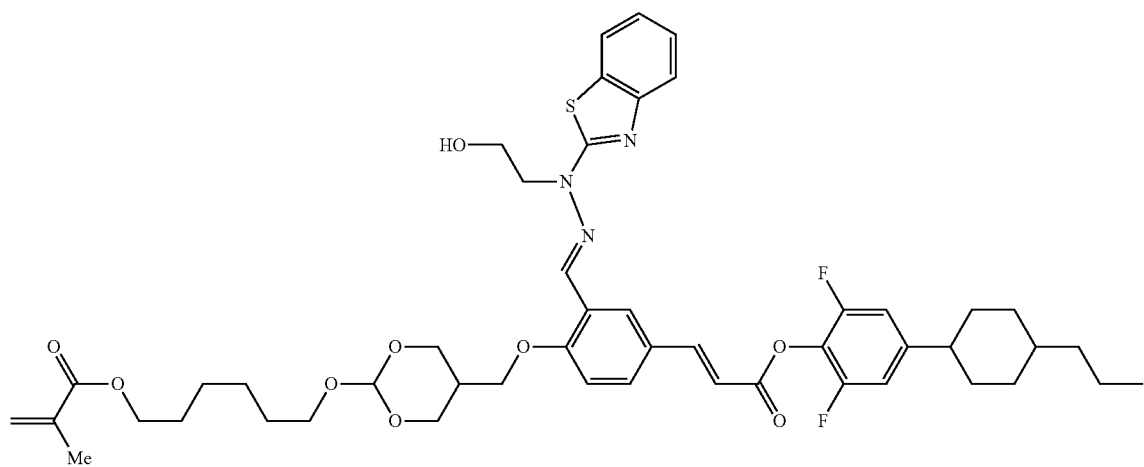

(I-57)
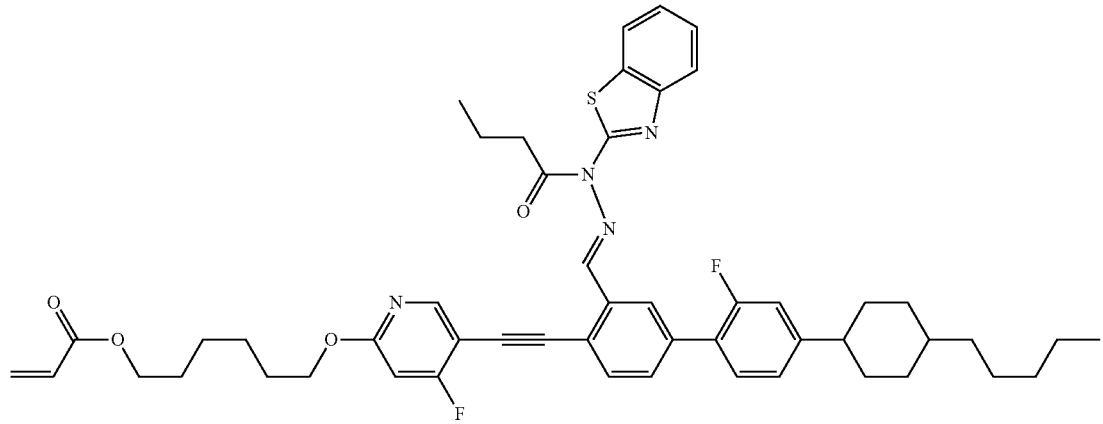
(I-58)
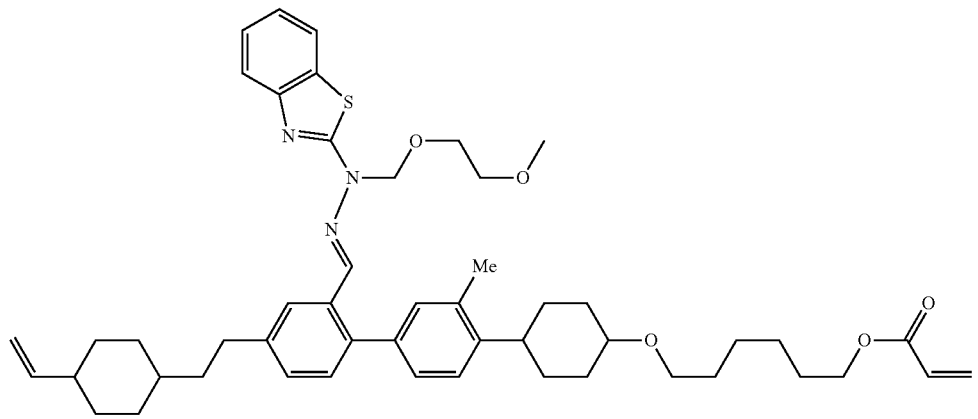
(I-59)
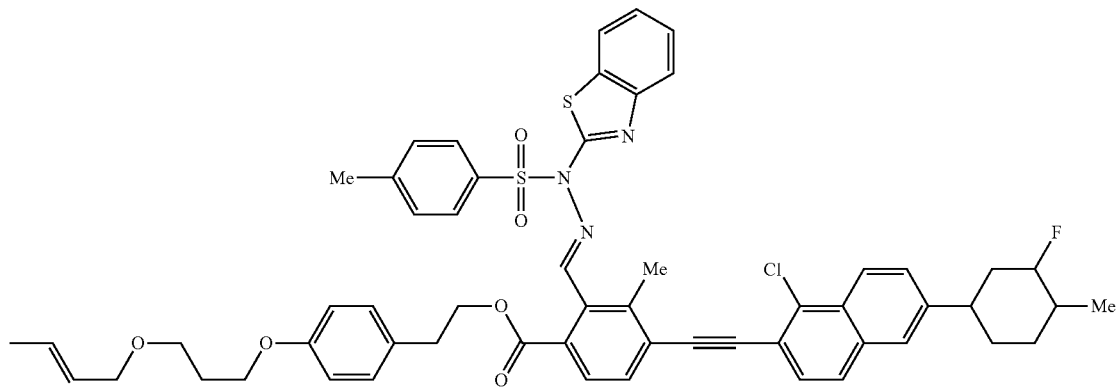

(I-60)
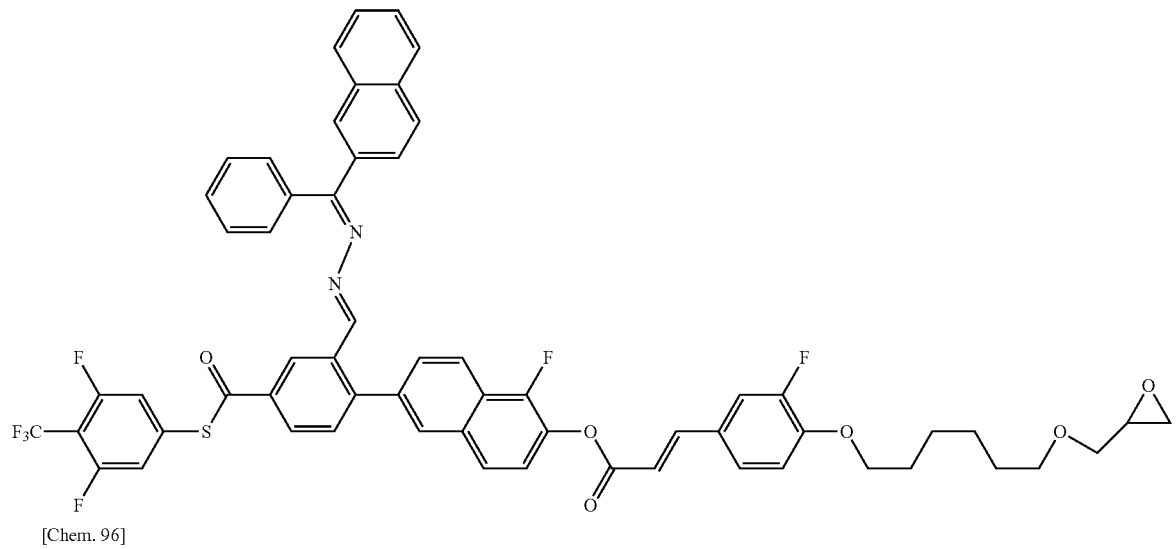
[Chem. 96]
(I-61)
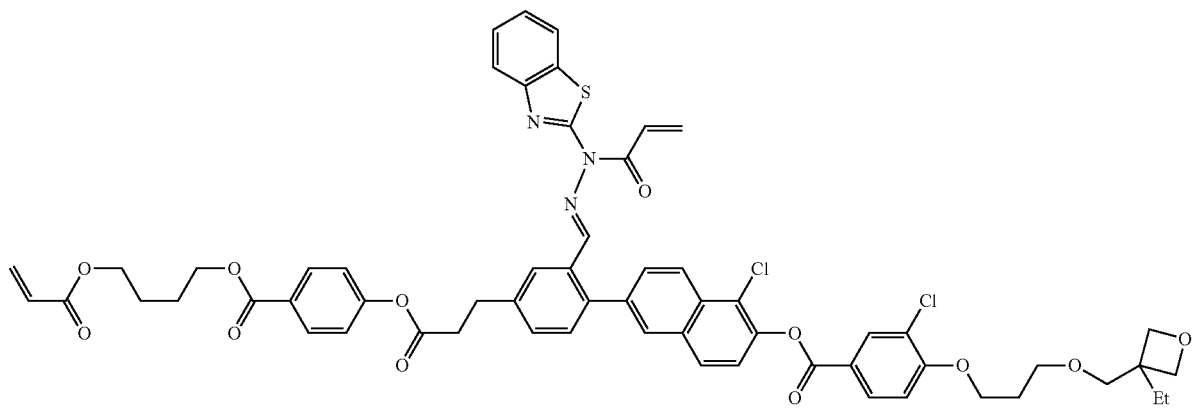
(I-62)
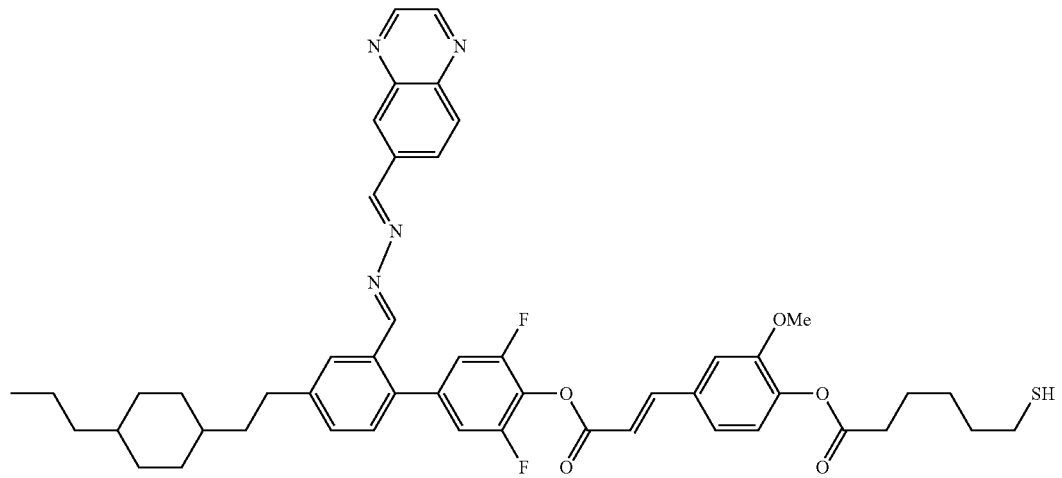

(I-63)
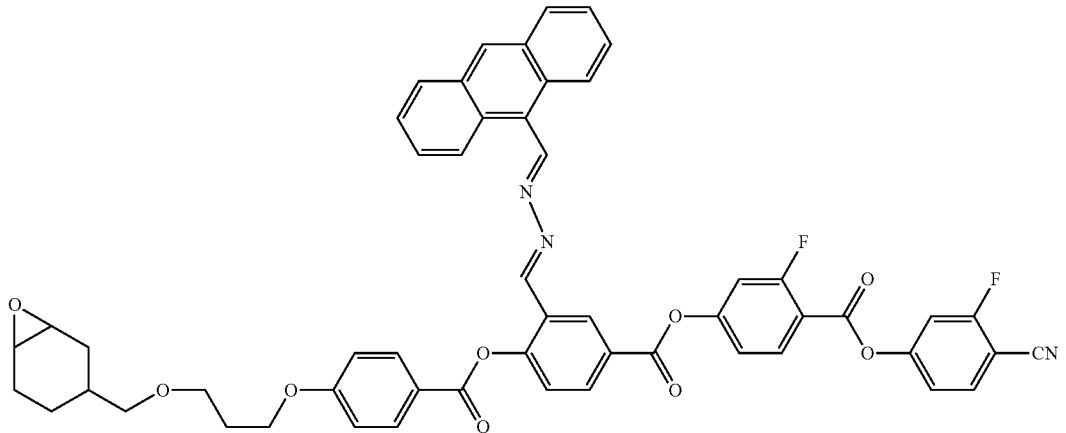
(I-64)
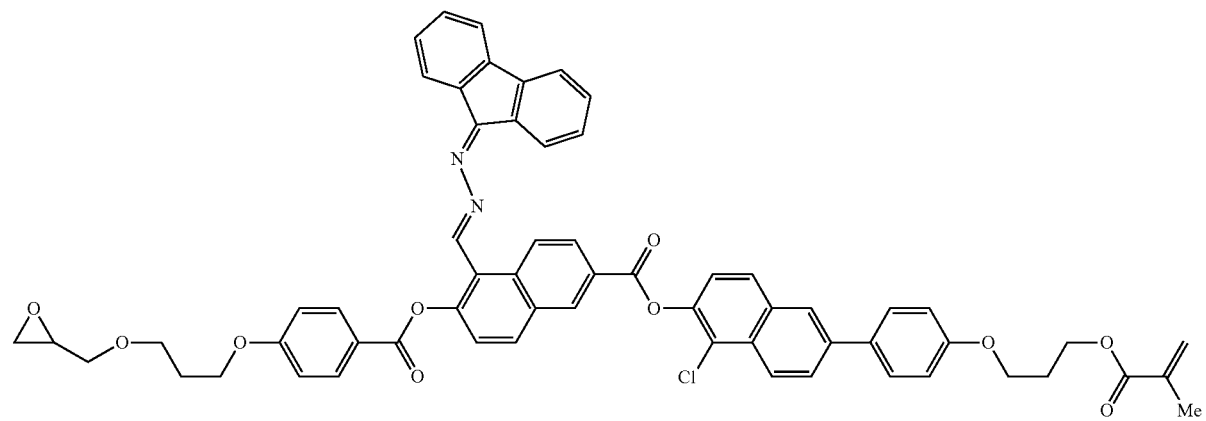
(I-65)
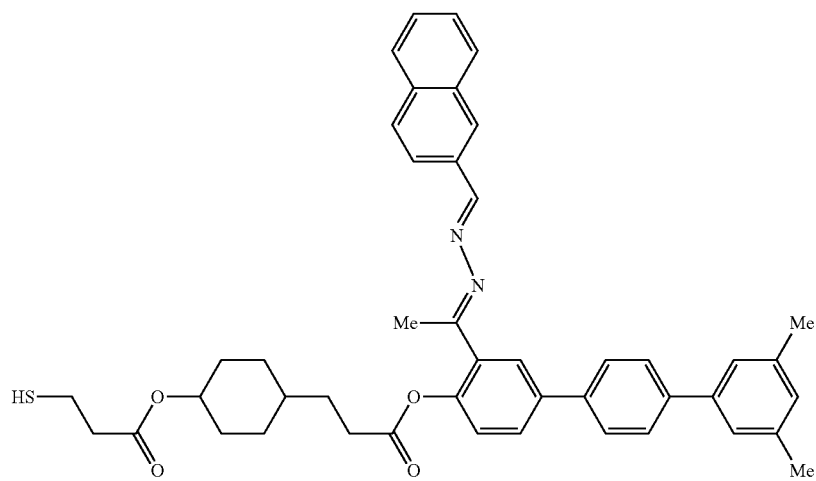

[Chem. 97]
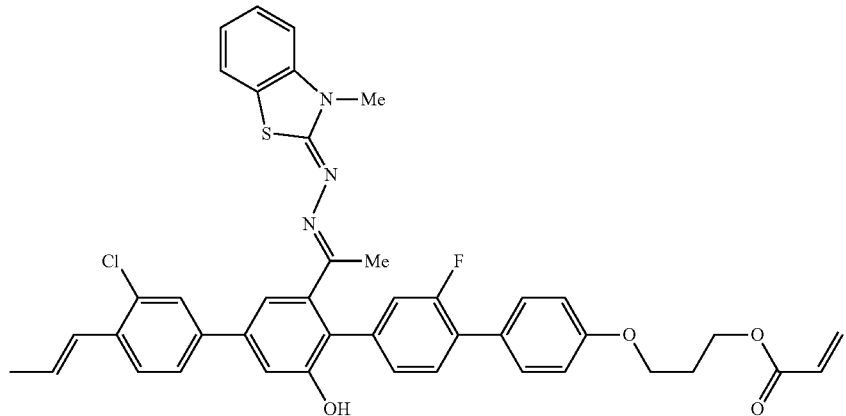
(I-66)
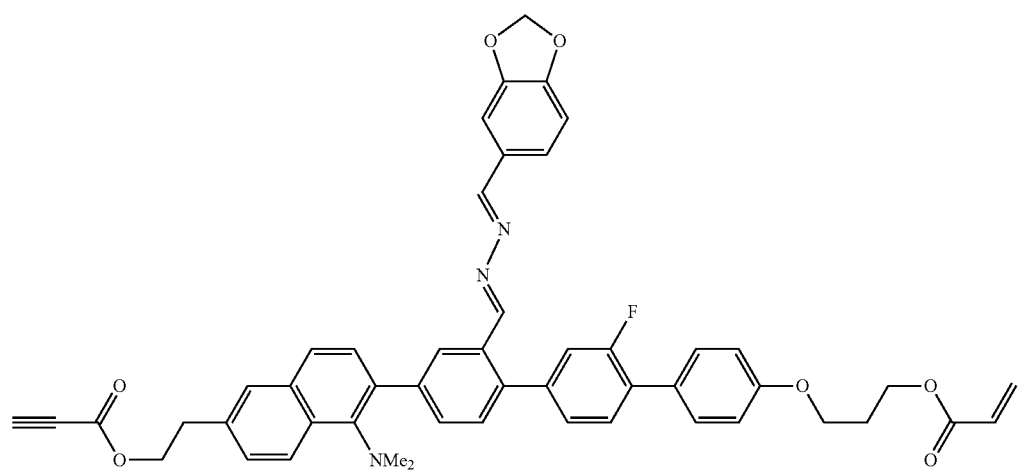
(I-67)
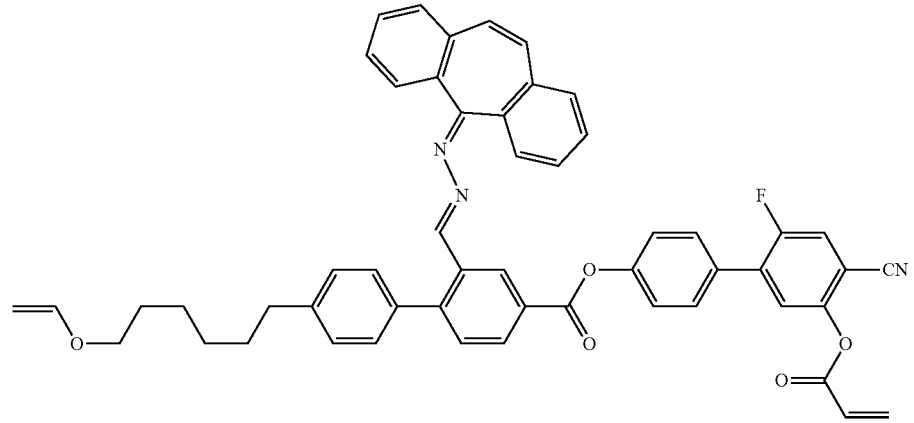
(I-68)

(I-69)
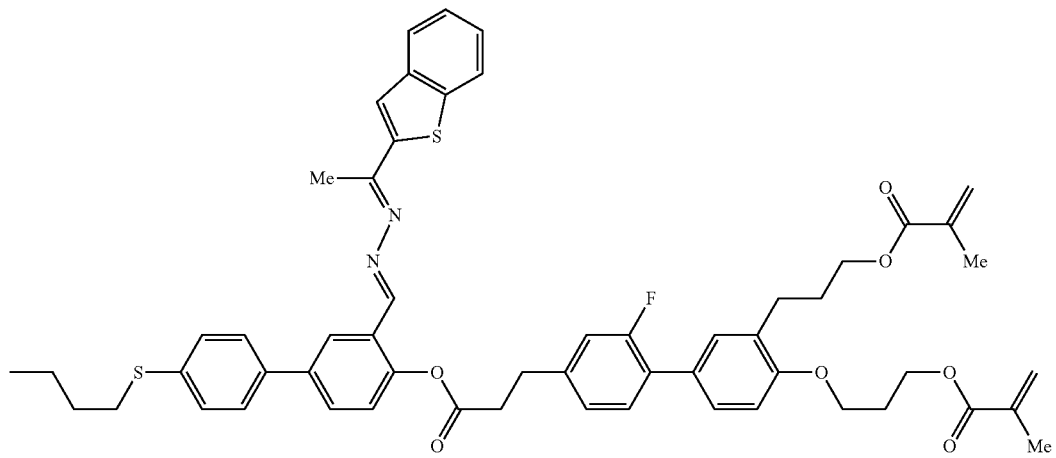
(I-70)
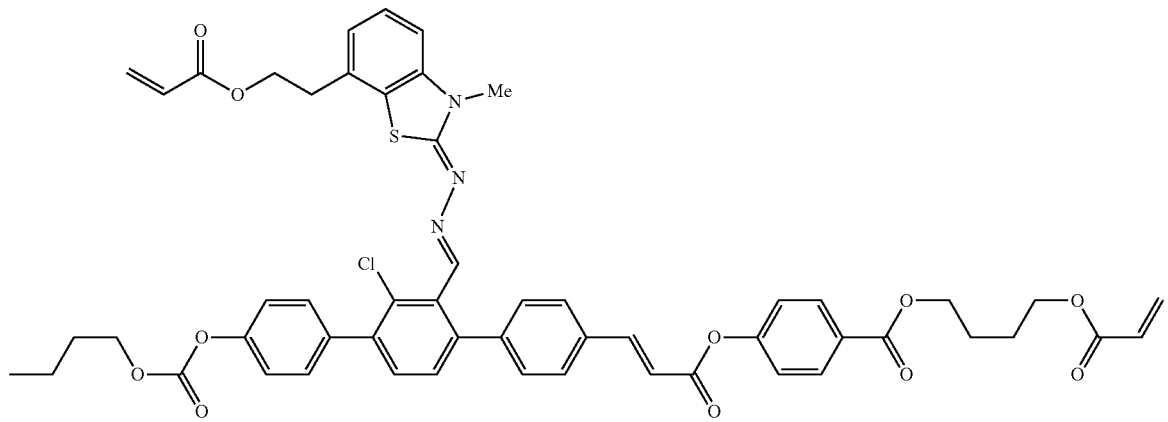
[Chem. 98]
(I-71)
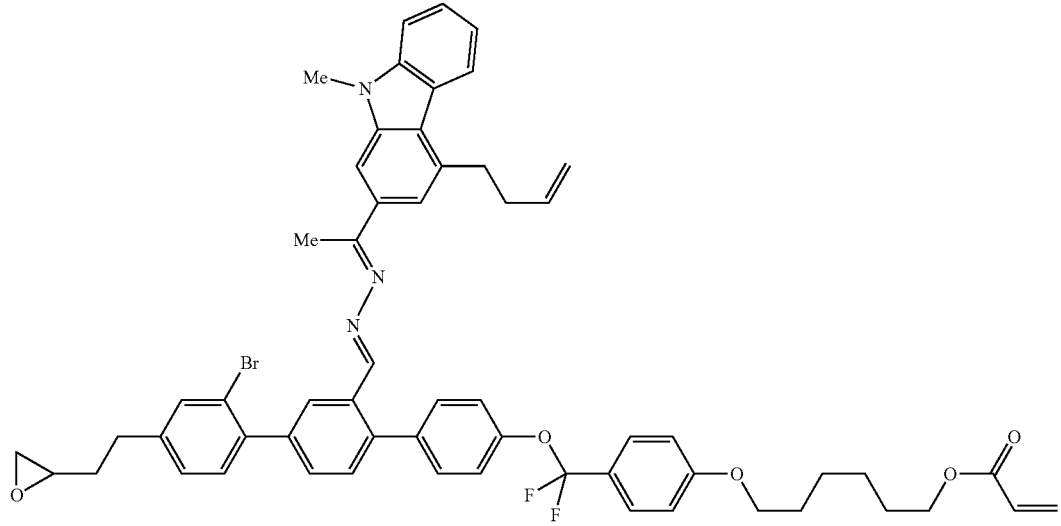

-continued
(I-72)
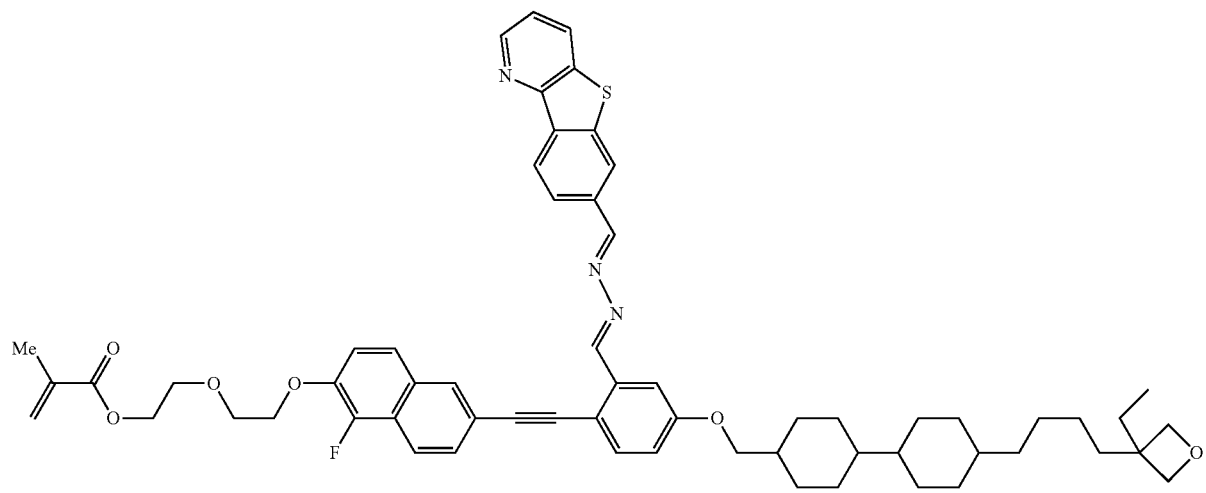
(I-73)
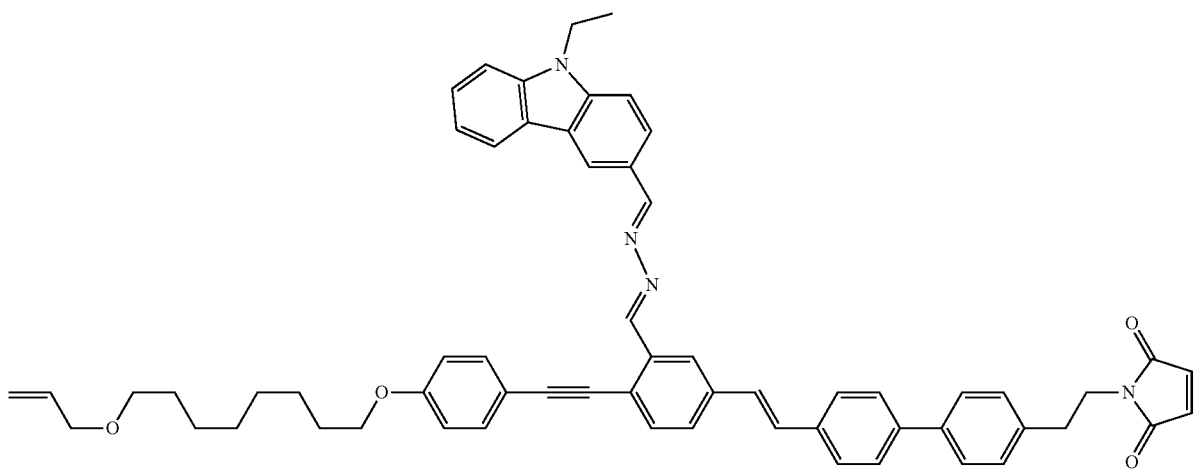
(I-74)
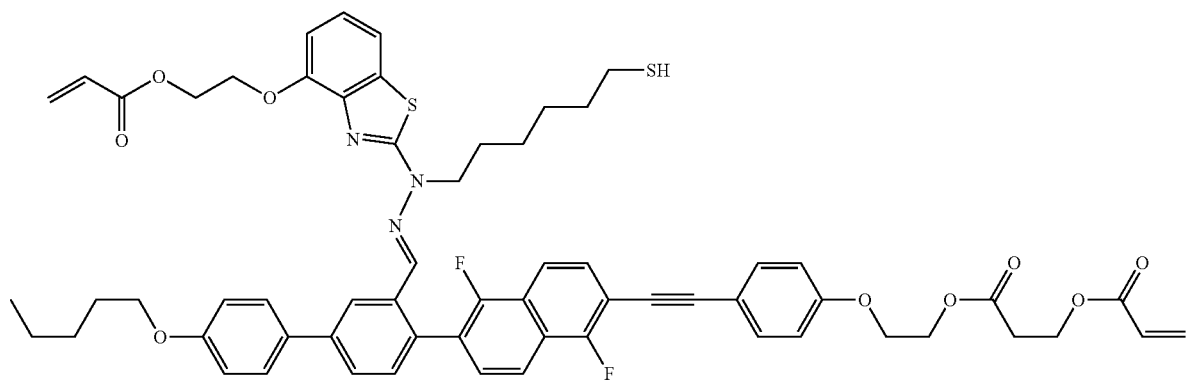

(I-75)
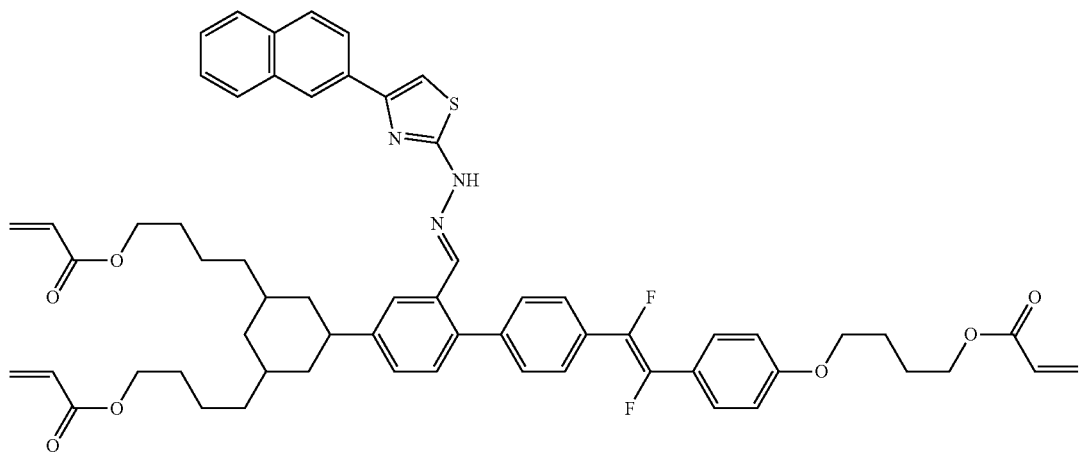
[Chem. 99]
(I-76)
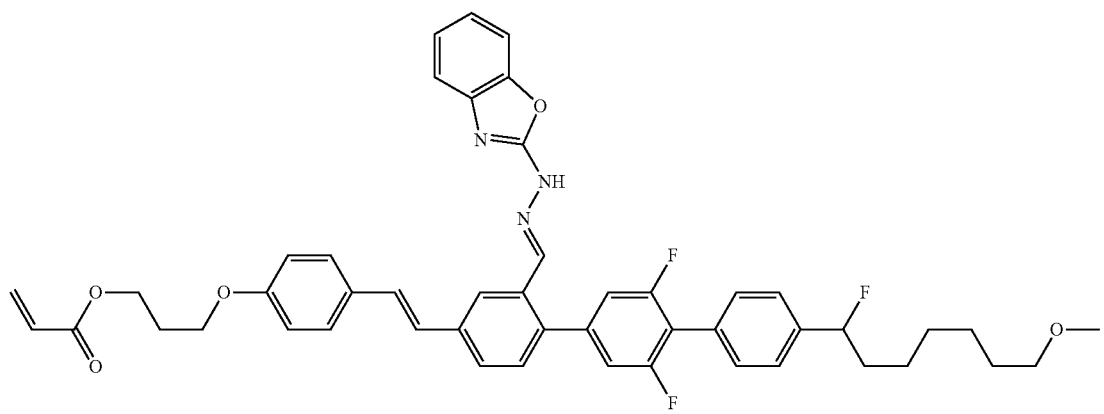
(I-77)
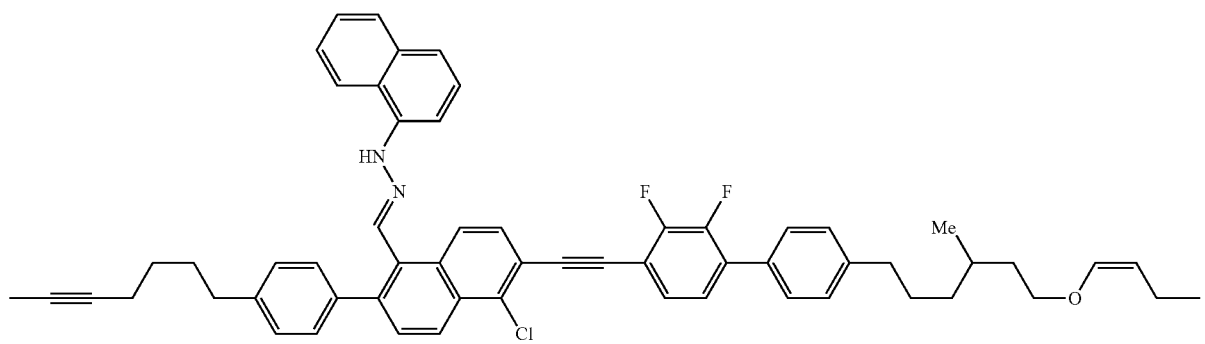
(I-78)
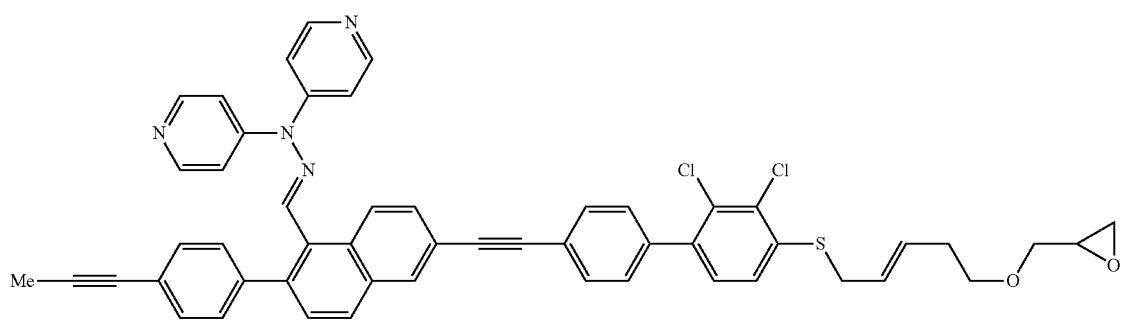

(I-79)
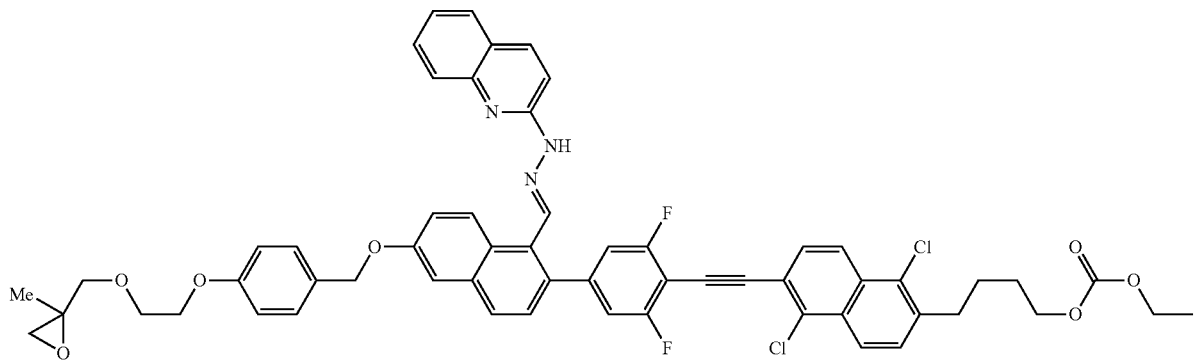
(I-80)
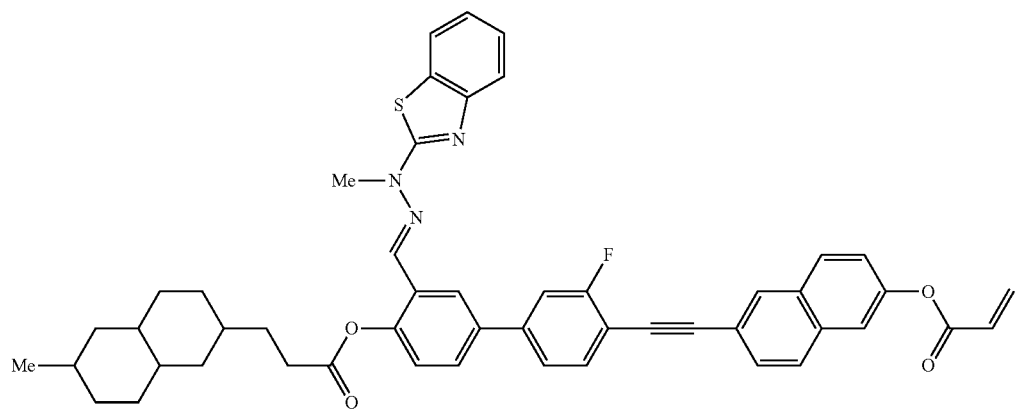
[Chem. 100]
(I-81)
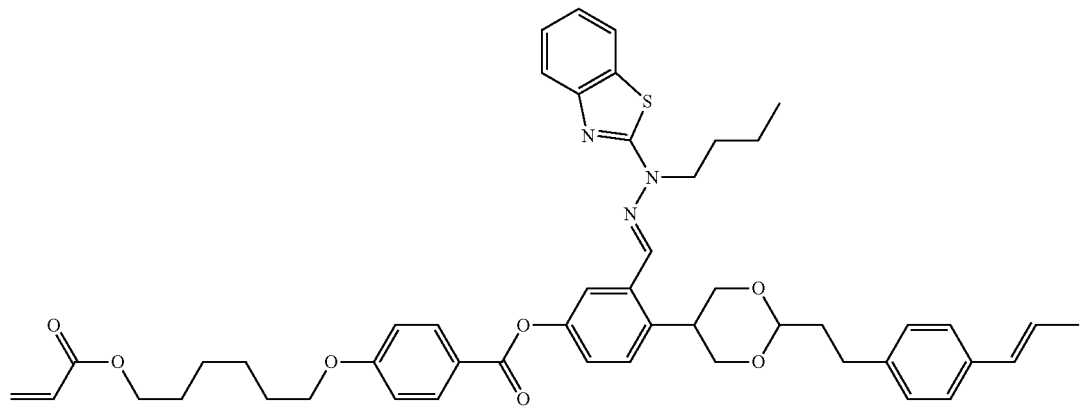

-continued
(I-82)
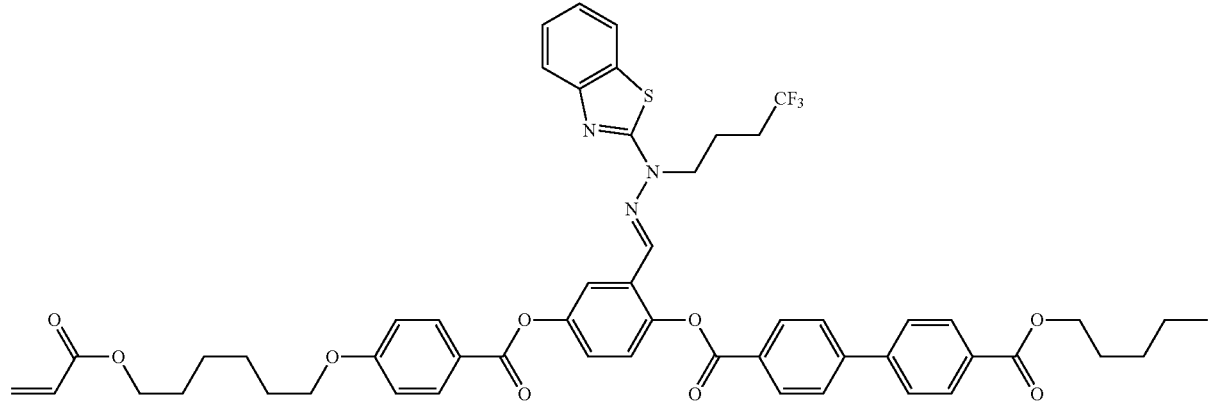
(I-83)
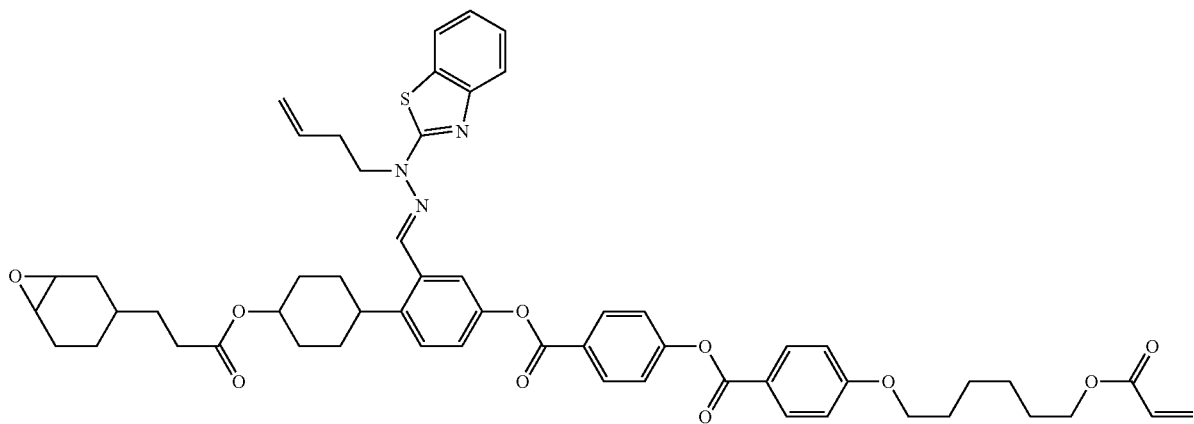
(I-84)
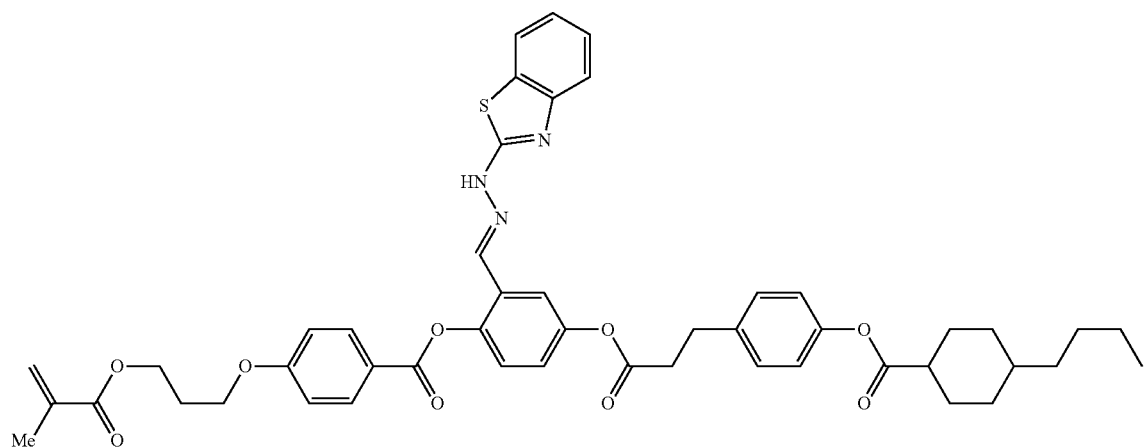

(I-85)
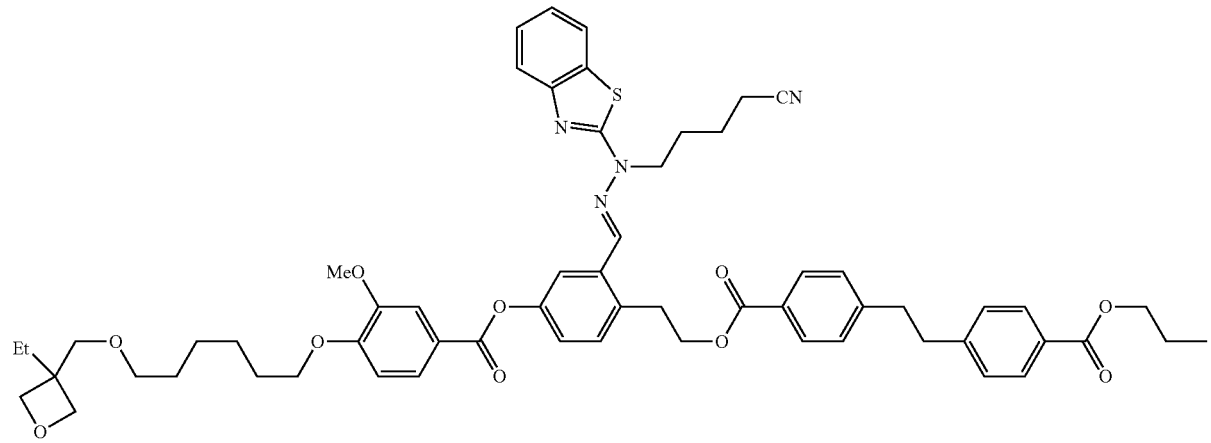
[Chem. 101]
(I-86)
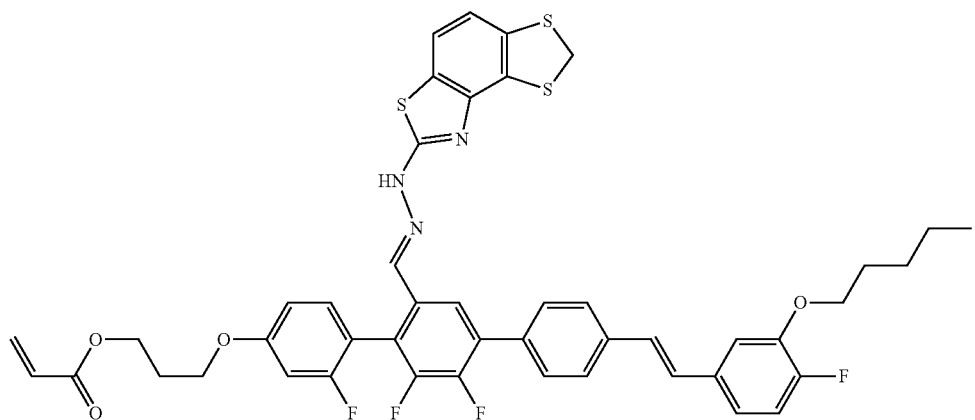
(I-87)
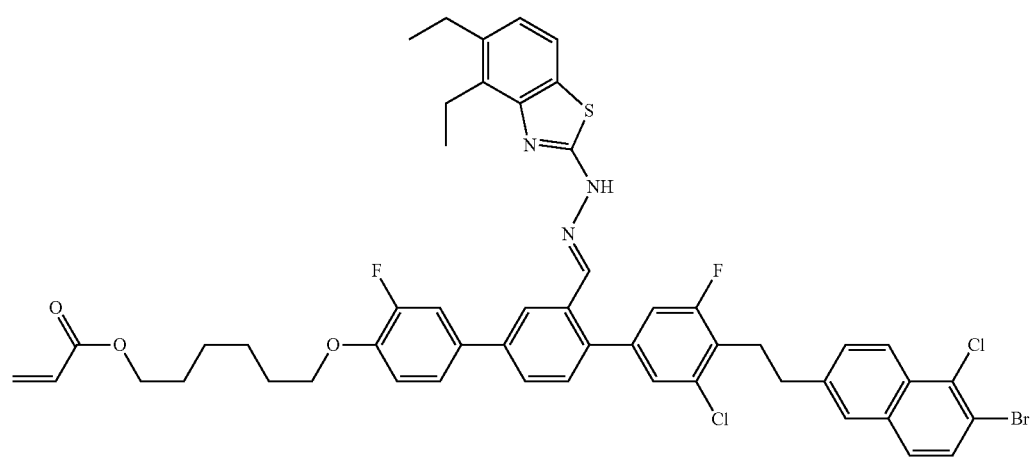

-continued
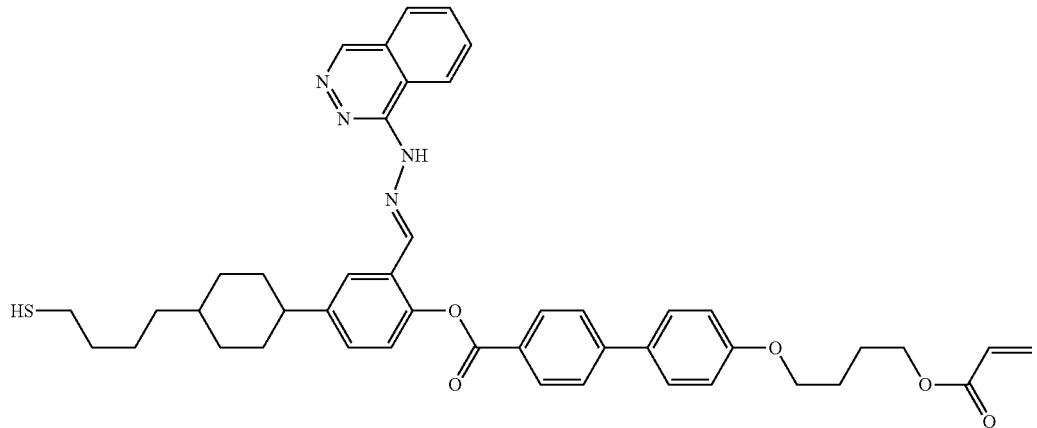
(I-88)
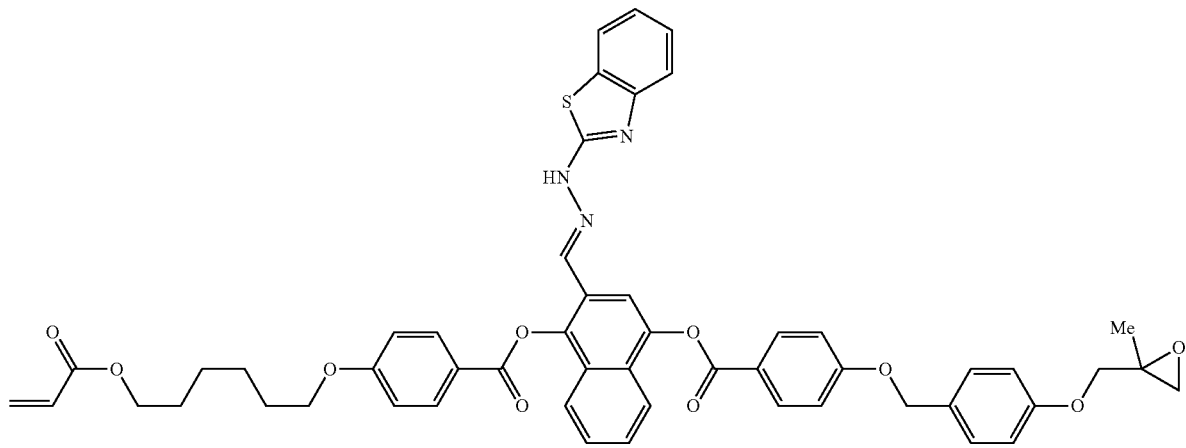
(I-89)
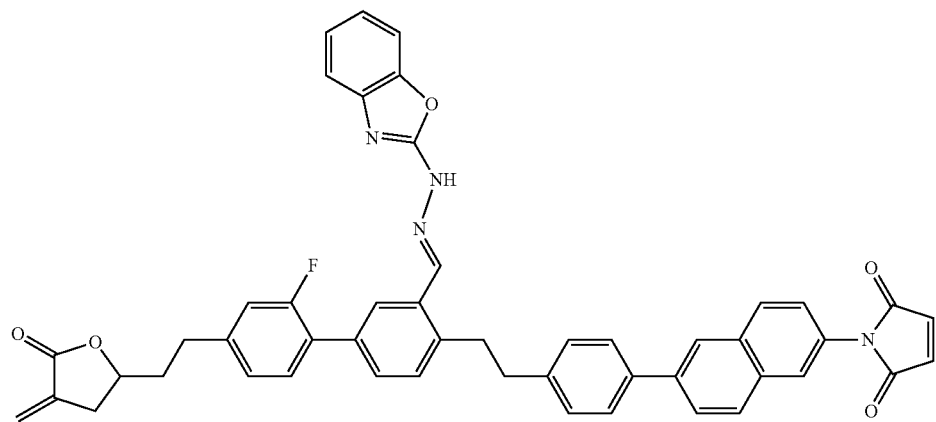
(I-90)

-continued
[Chem. 102]
(I-91)
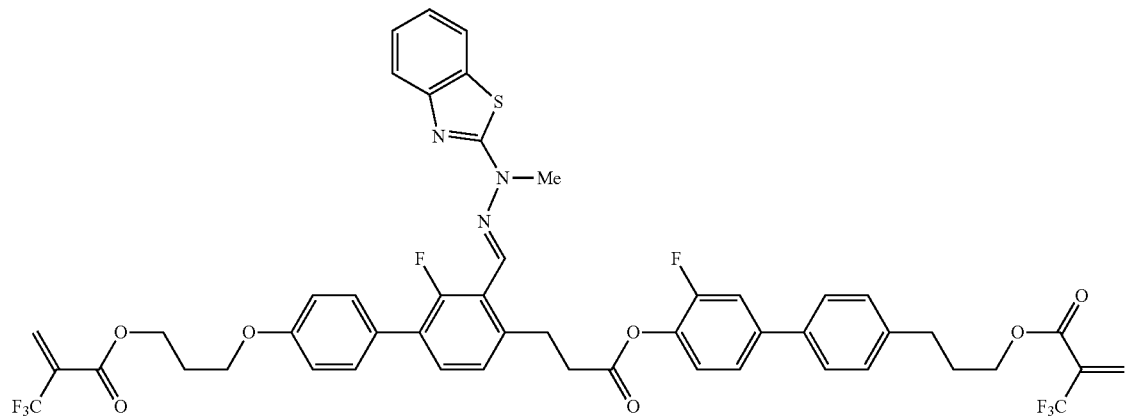
(I-92)
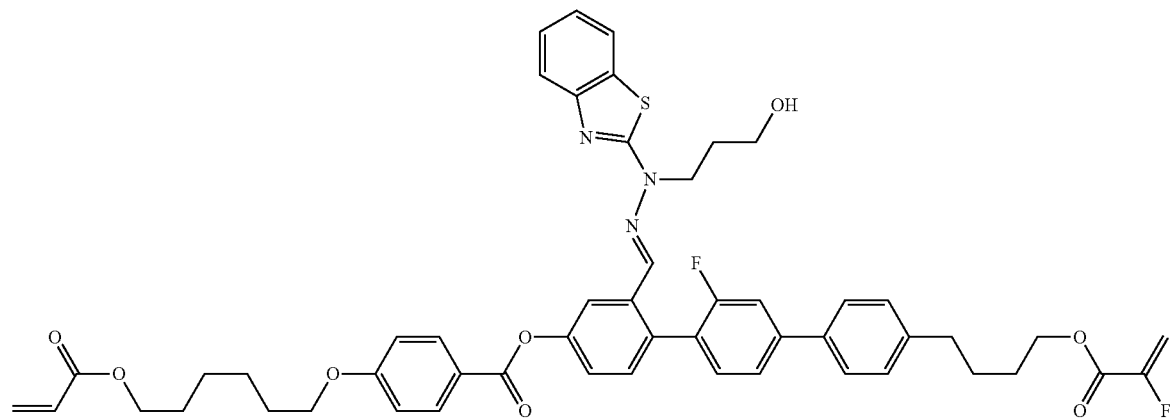
(I-93)
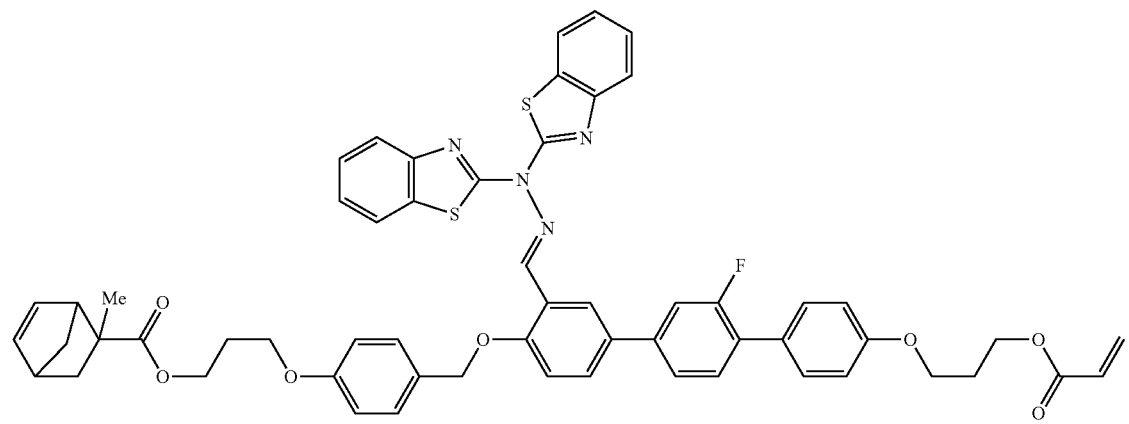

(I-94)
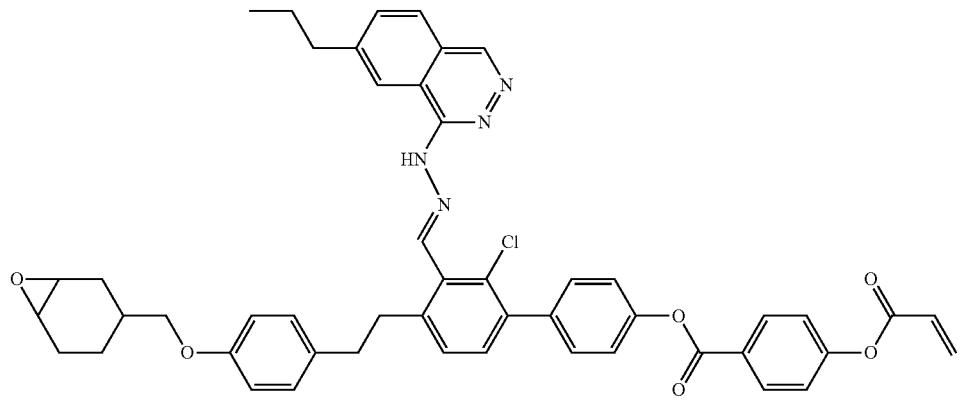
(I-95)
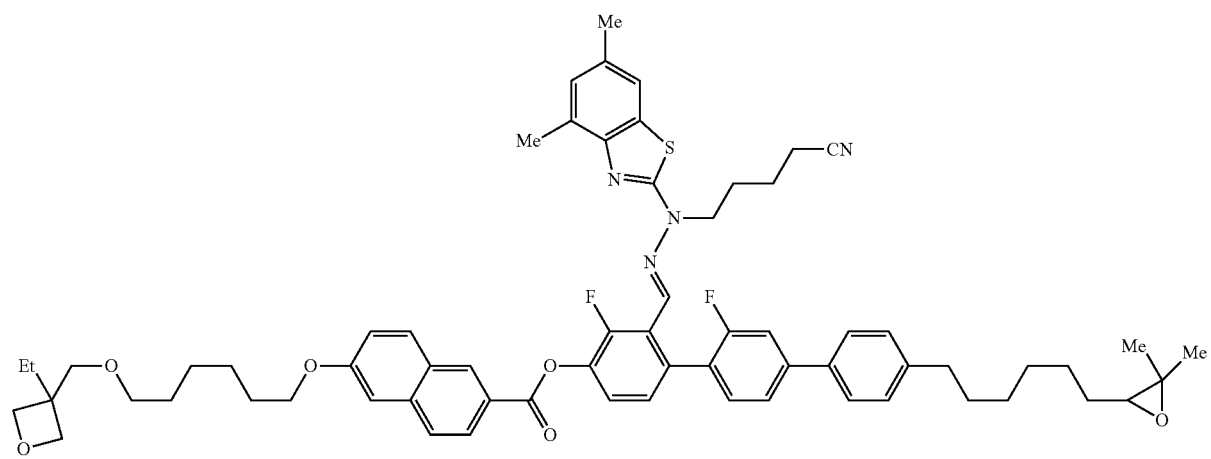
[Chem. 103]
(I-96)
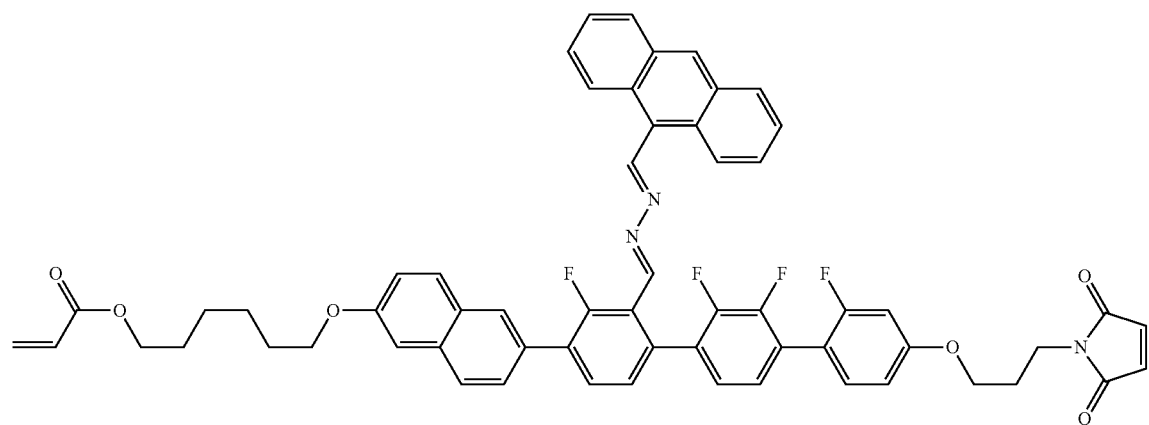

(I-97)
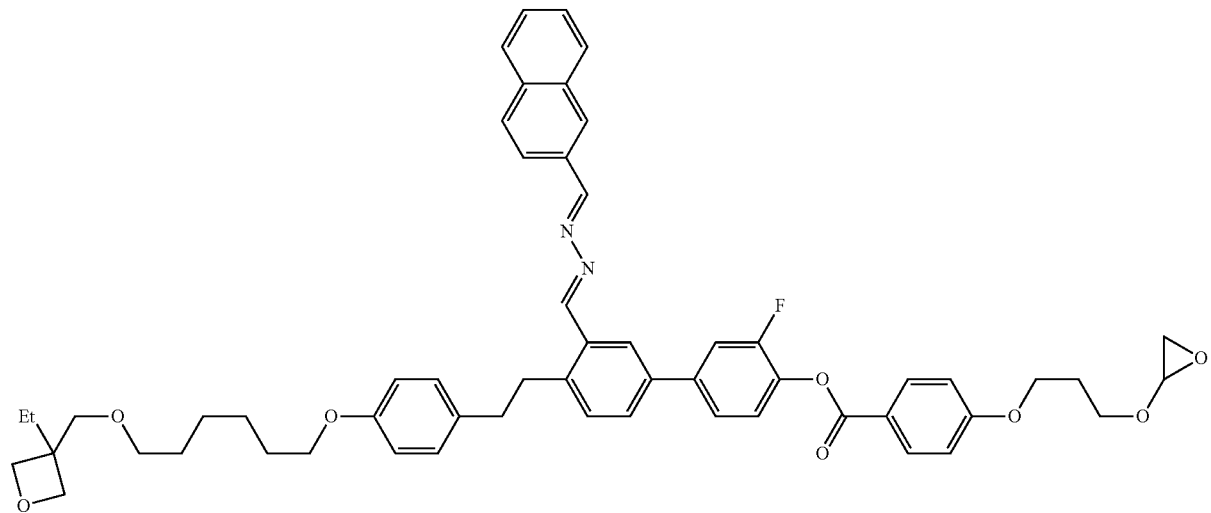
(I-98)
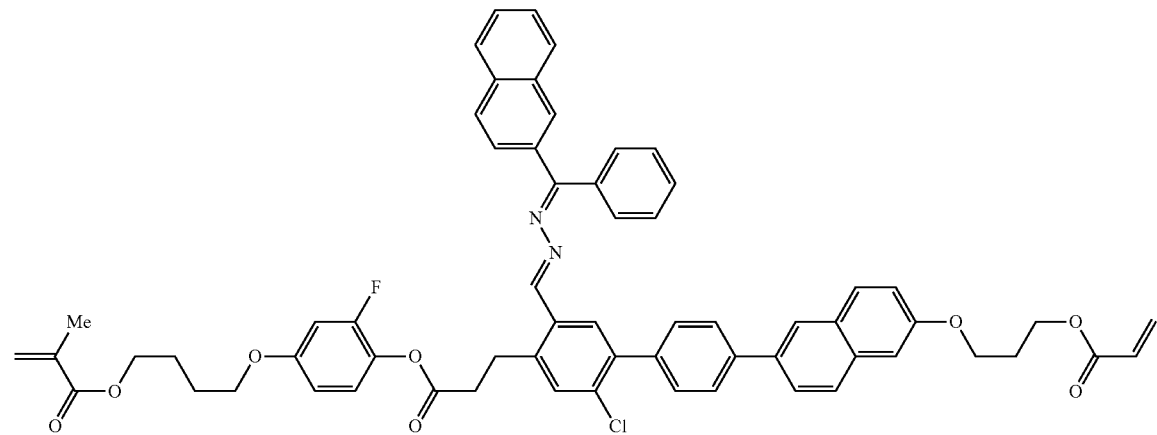
(I-99)
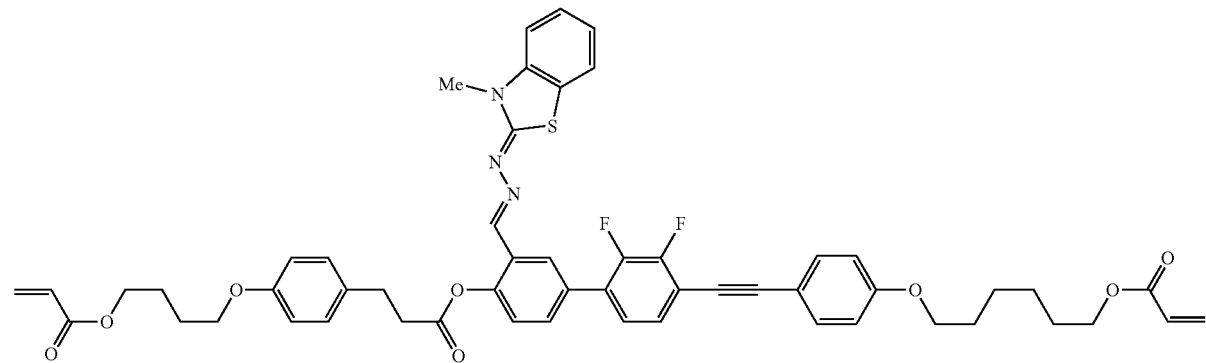

-continued
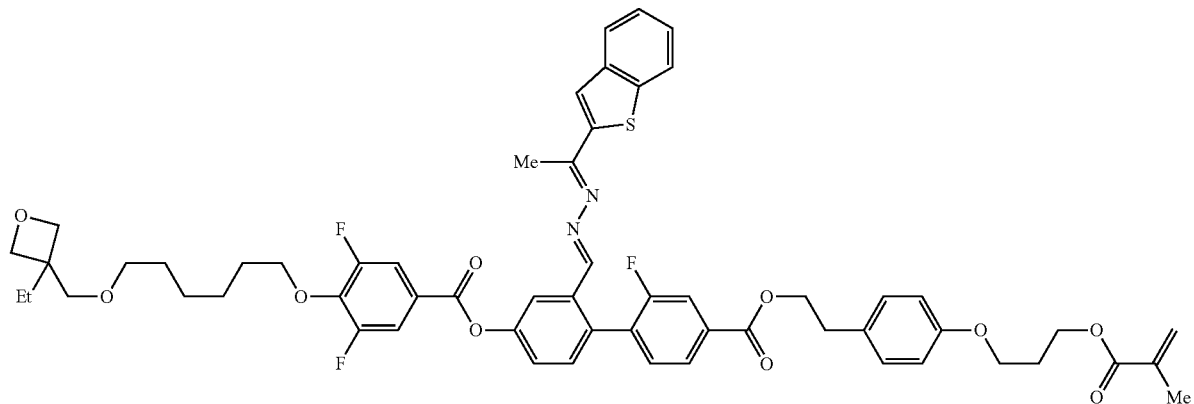
(I-100)
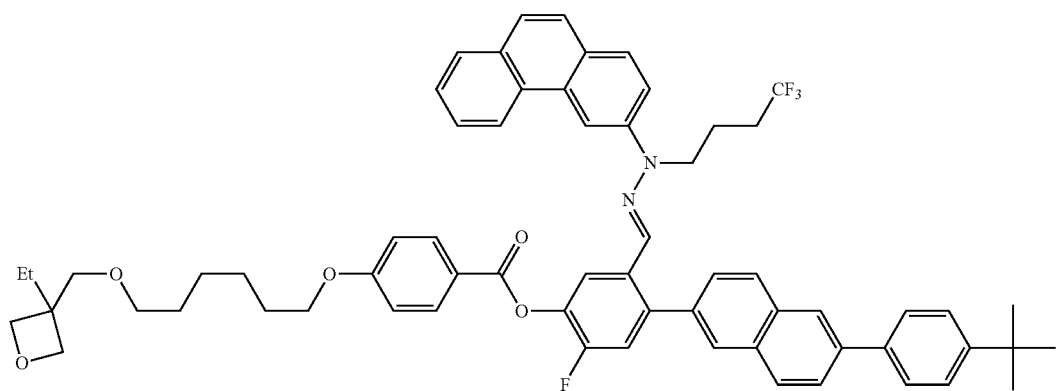
(I-101)
[Chem. 104]
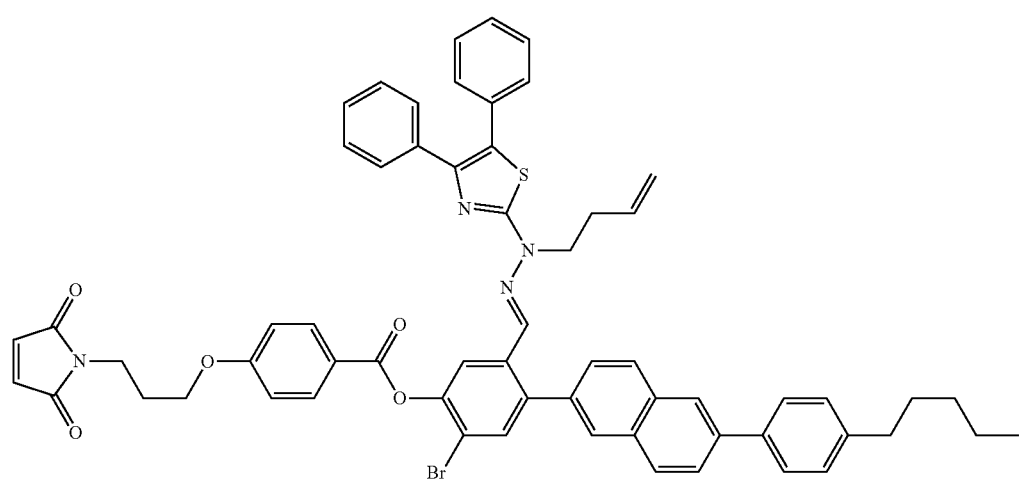
(I-102)

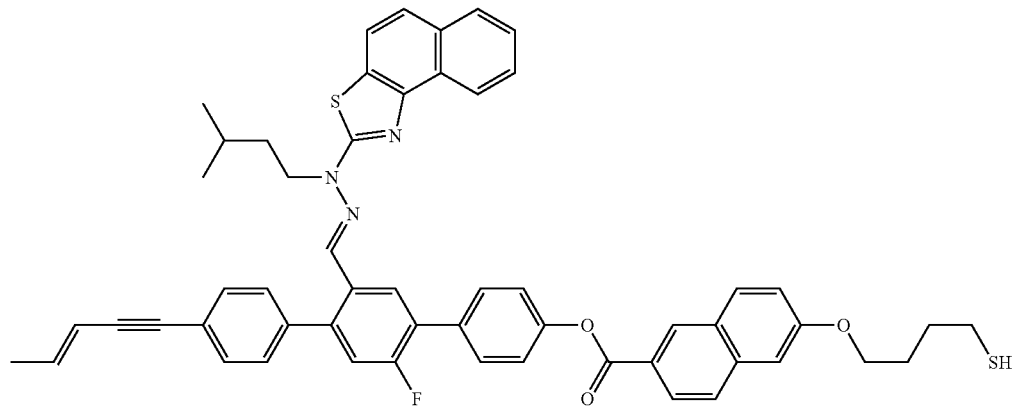
(I-103)
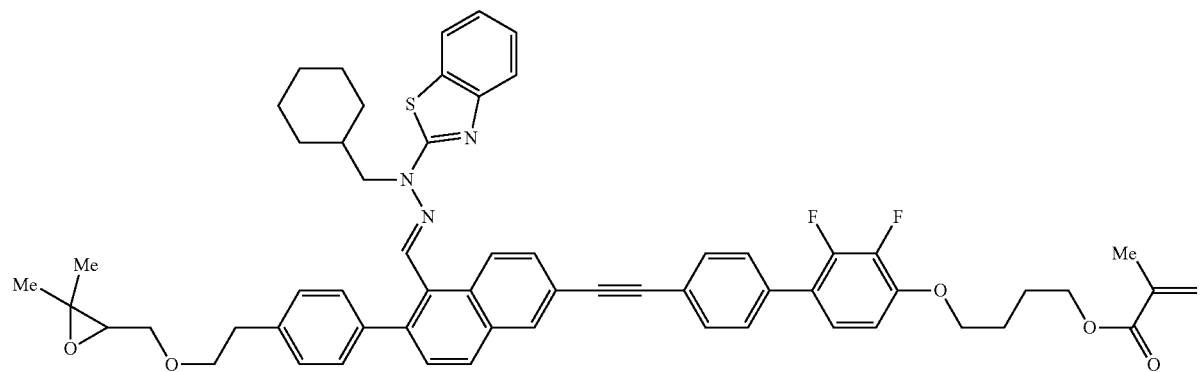
(I-104)
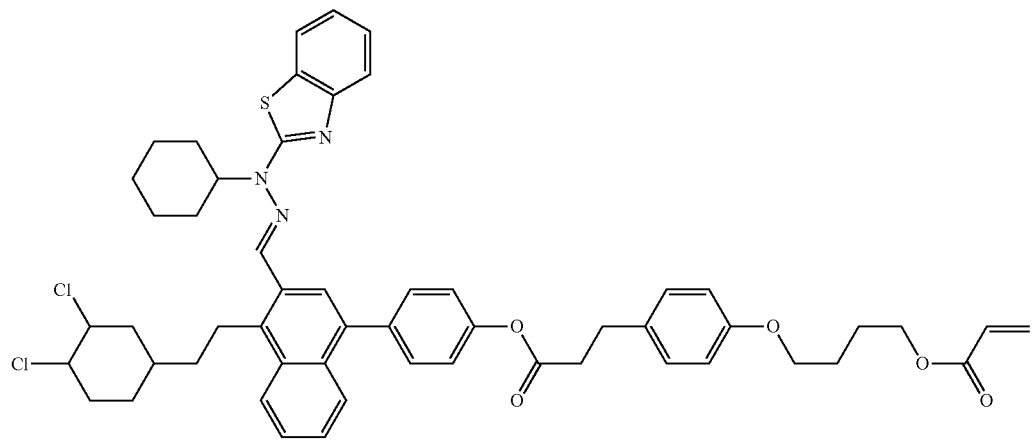
(I-105)

[Chem. 105]
(I-106)
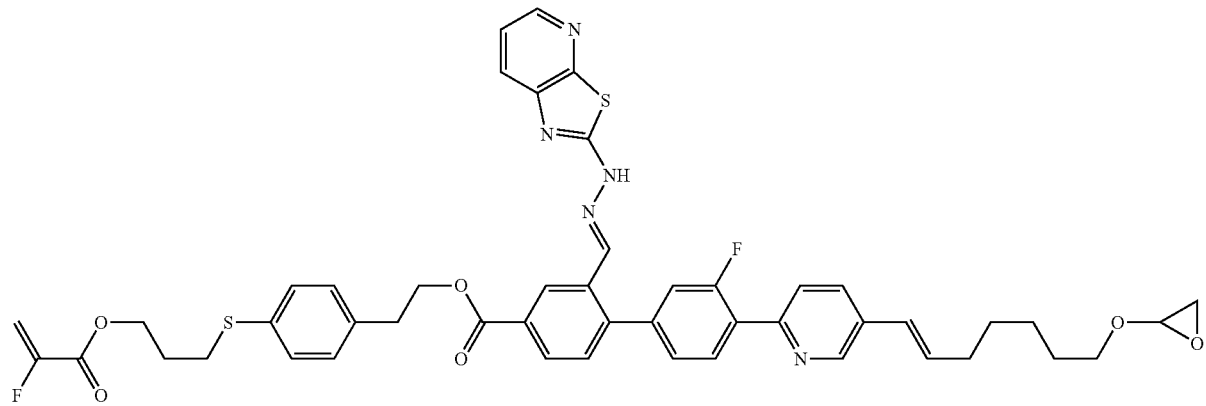
(I-107)
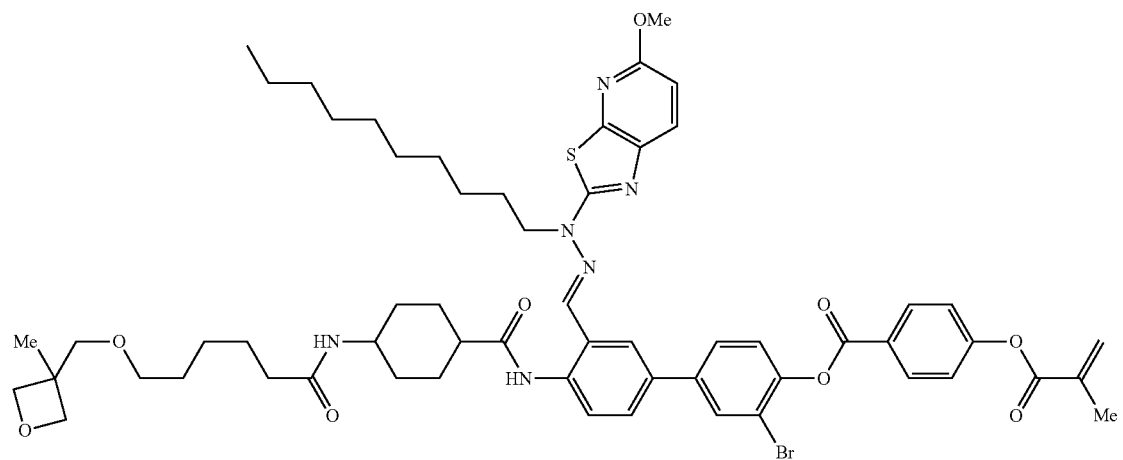
(I-108)
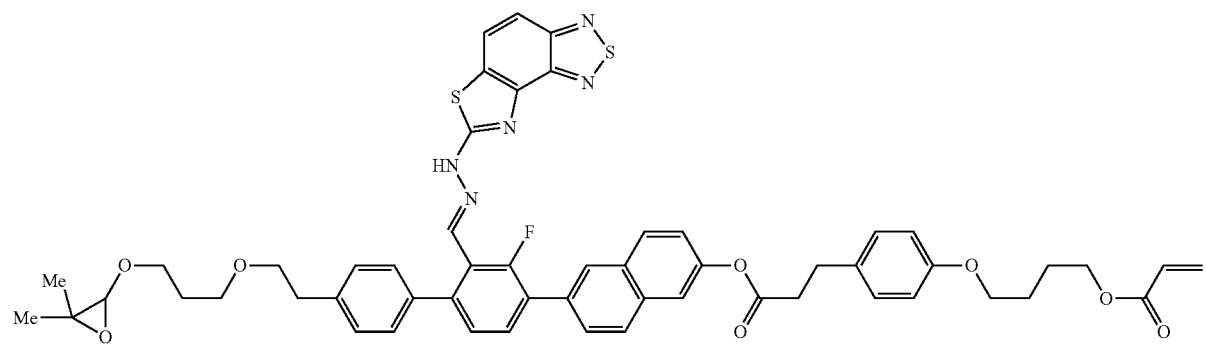

(I-109)
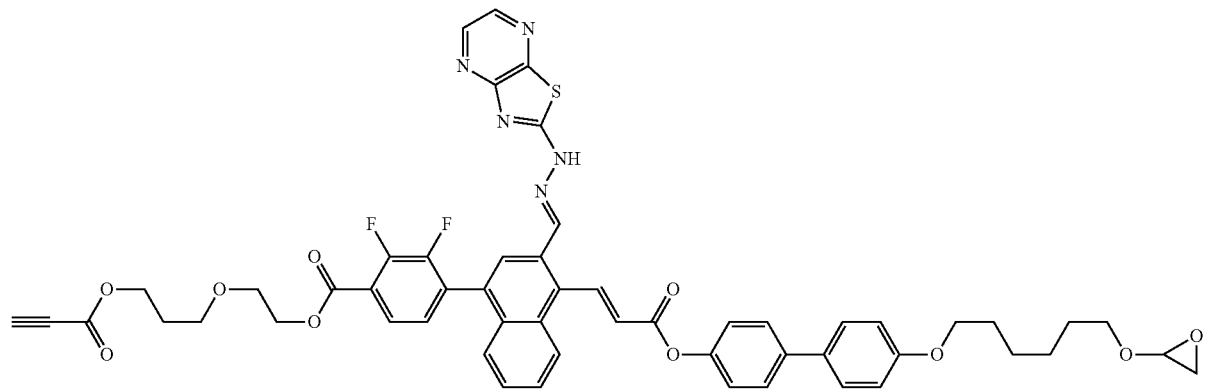
(I-110)
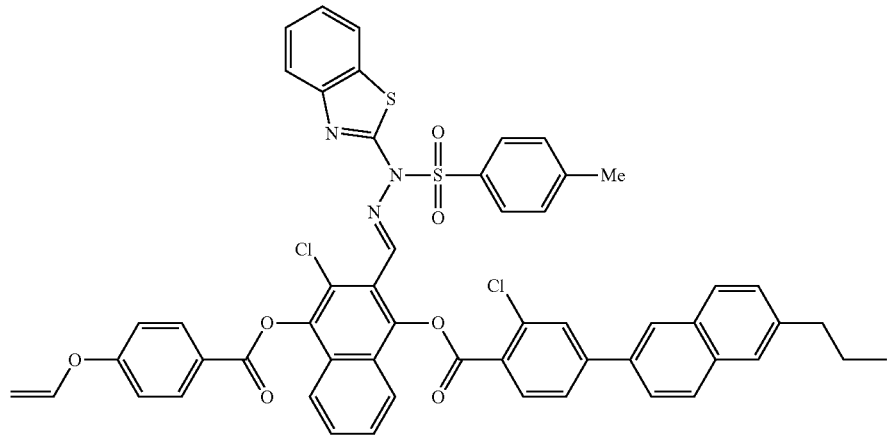
[Chem. 106]
(I-111)
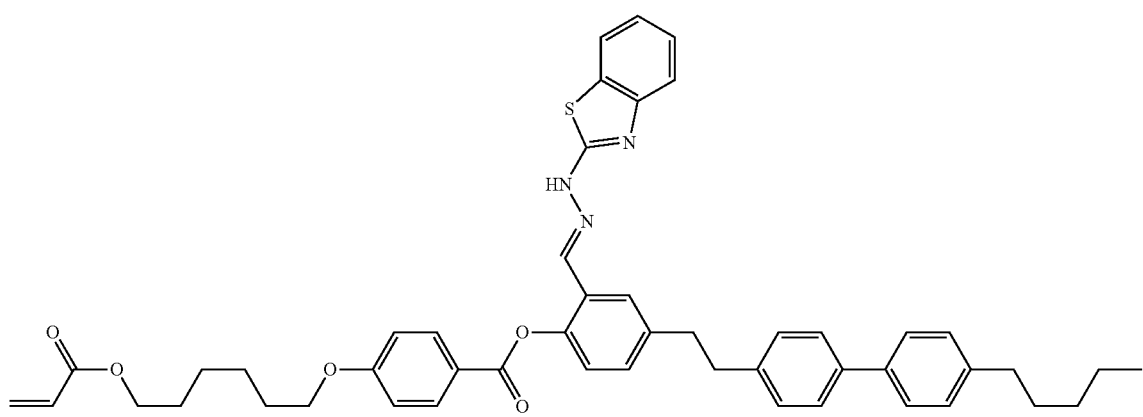

-continued
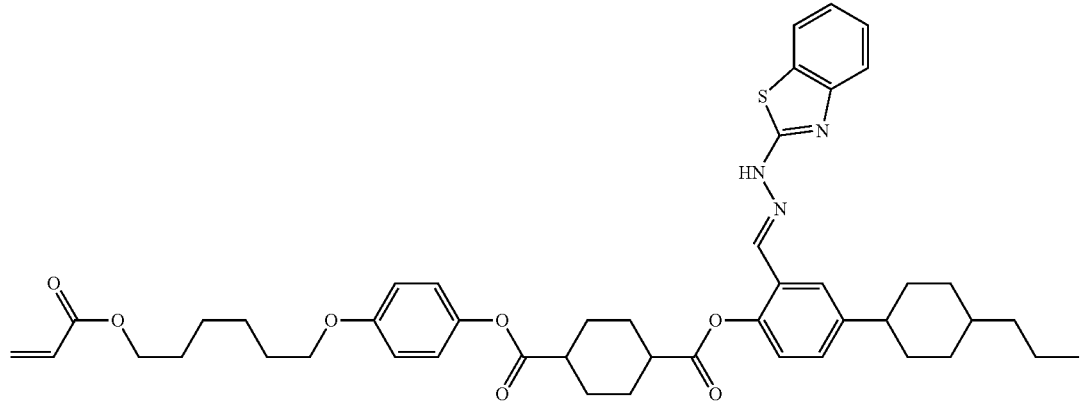
(I-112)
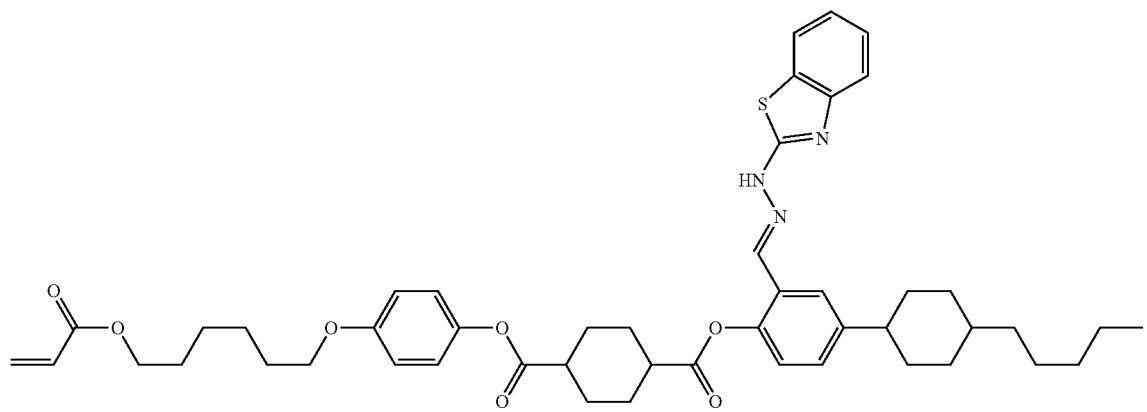
(I-113)
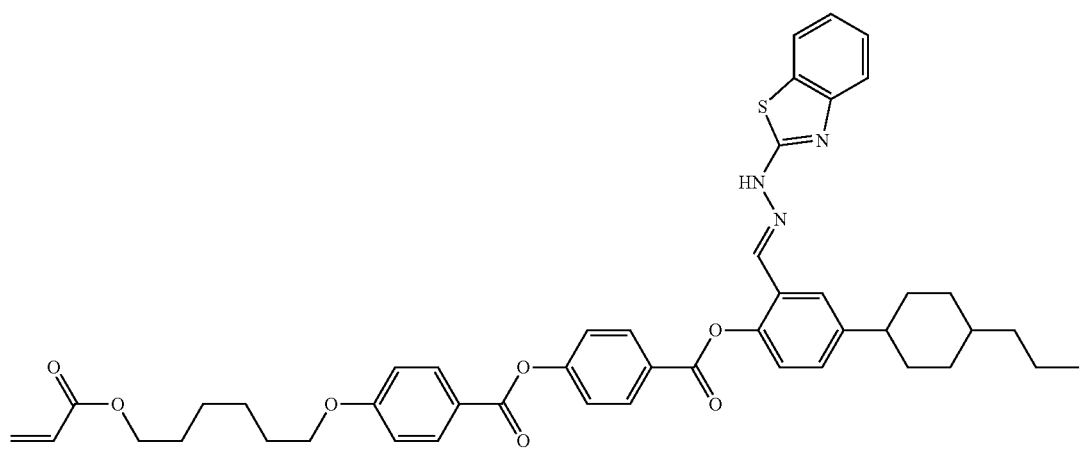
(I-114)

(I-115)
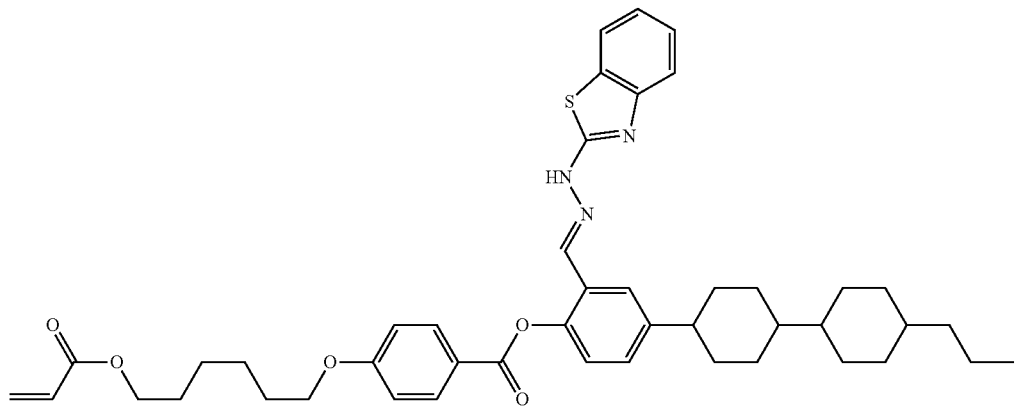
[Chem. 107]
(I-116)
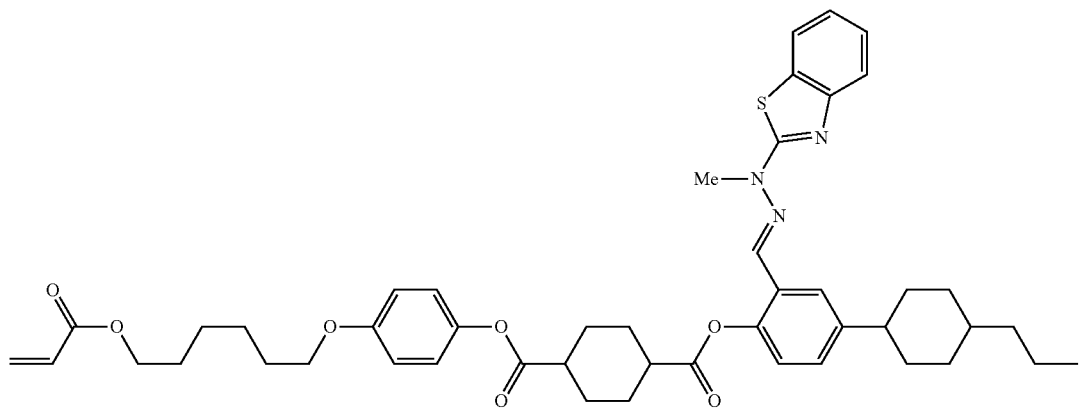
(I-117)
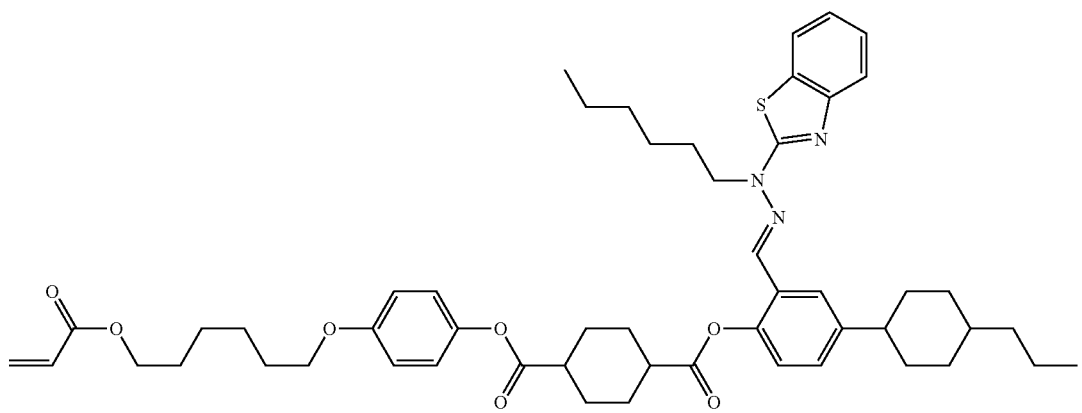

(I-118)
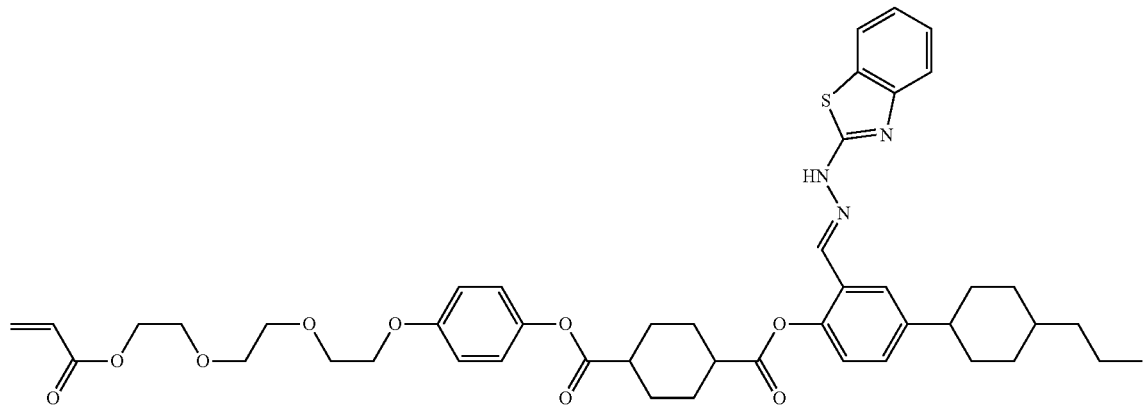
(I-119)
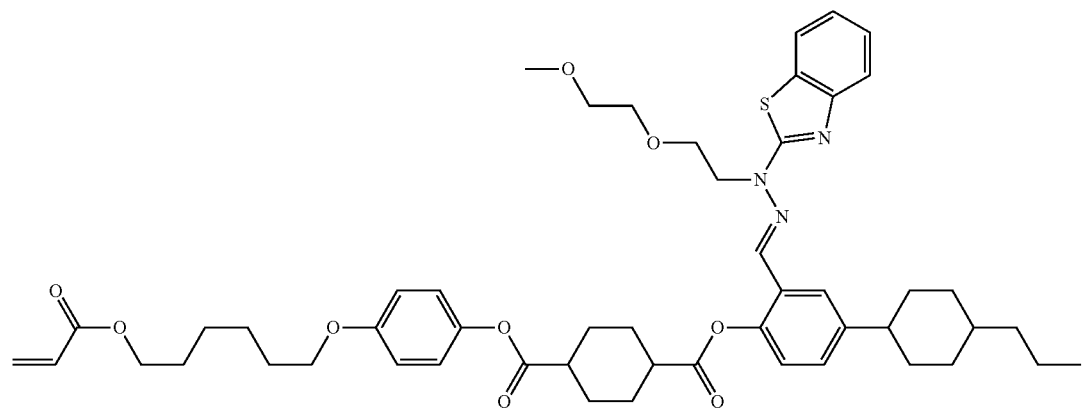
(I-120)
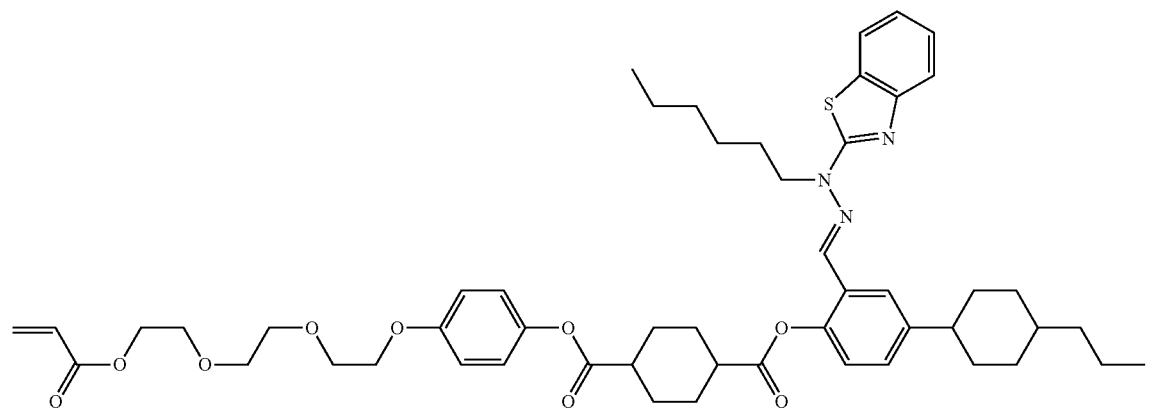

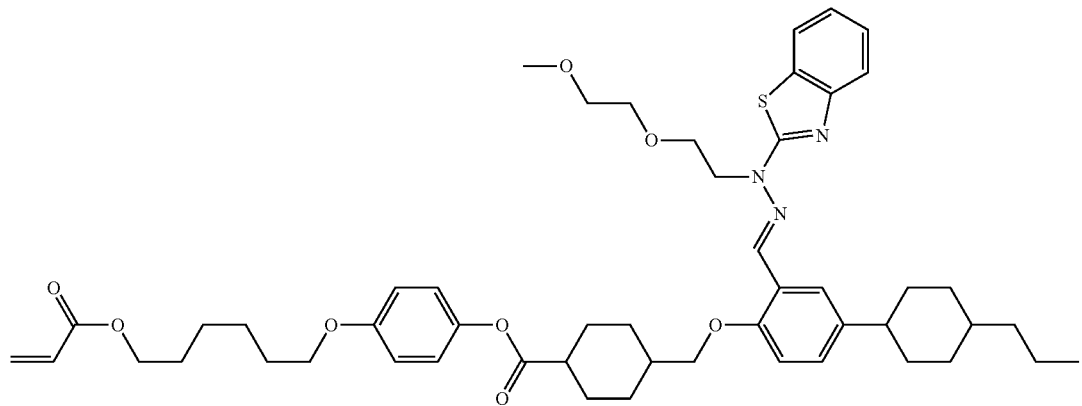
(I-121)
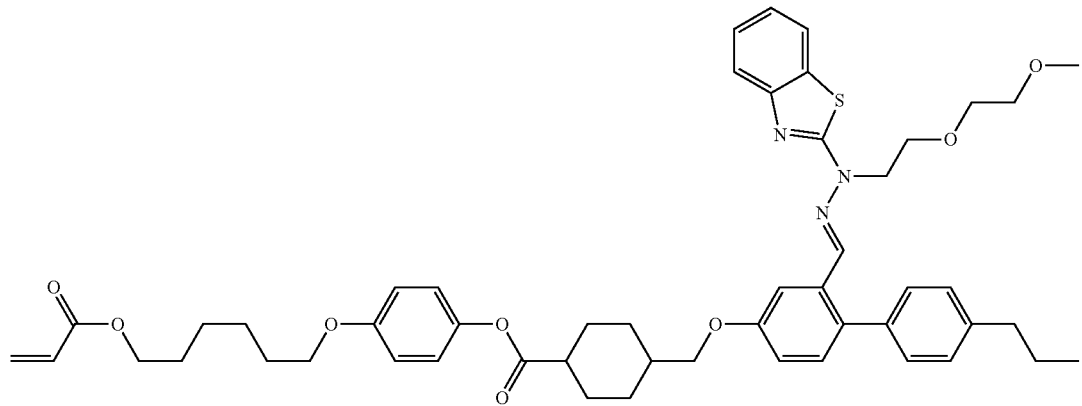
(I-122)
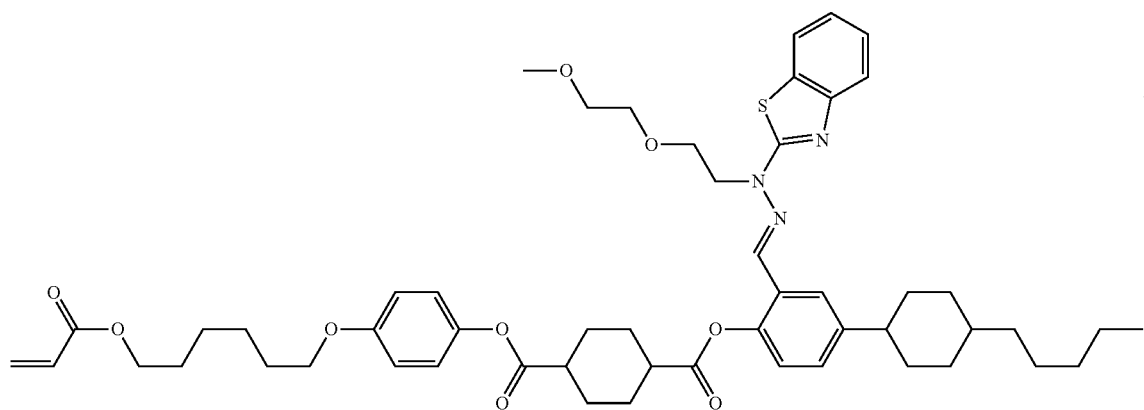
(I-123)

(I-124)
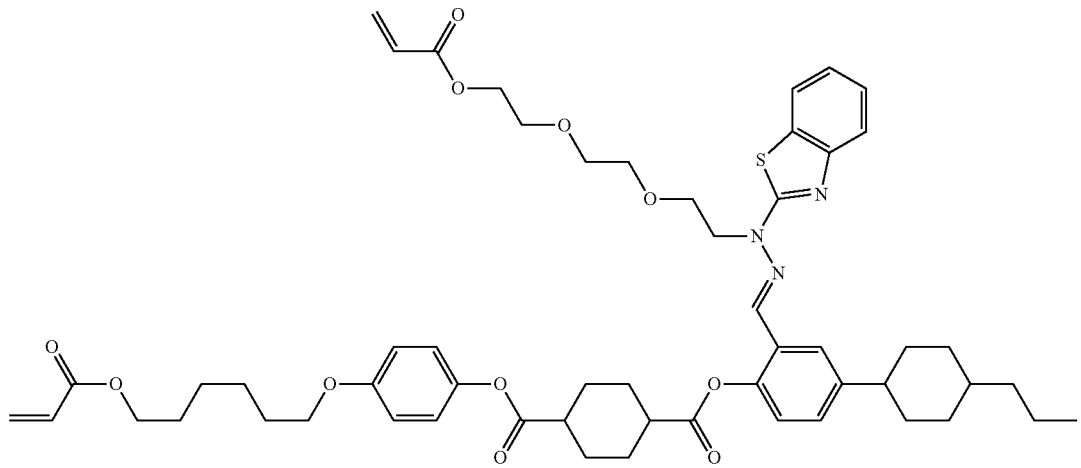
(I-125)
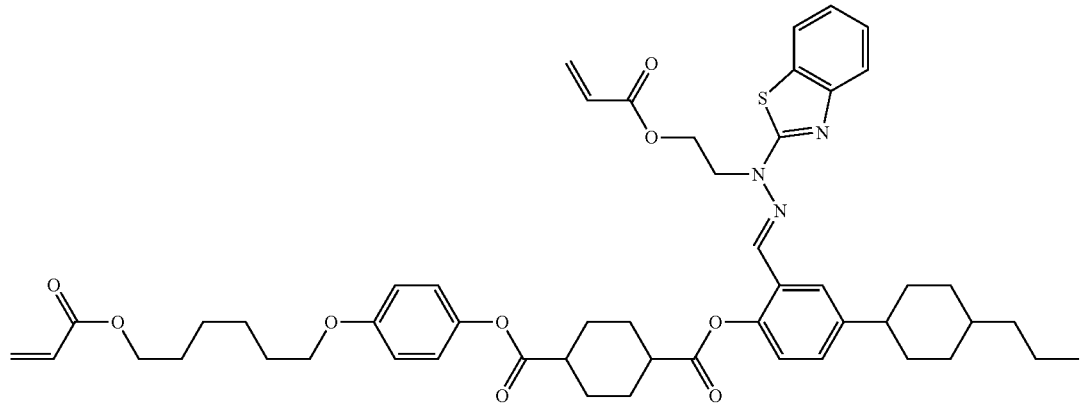
[Chem. 109]
(I-126)
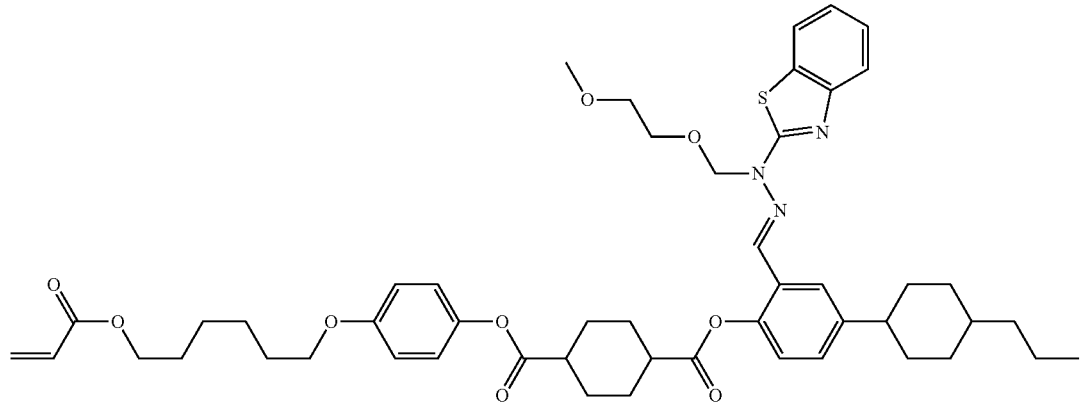

(I-127)
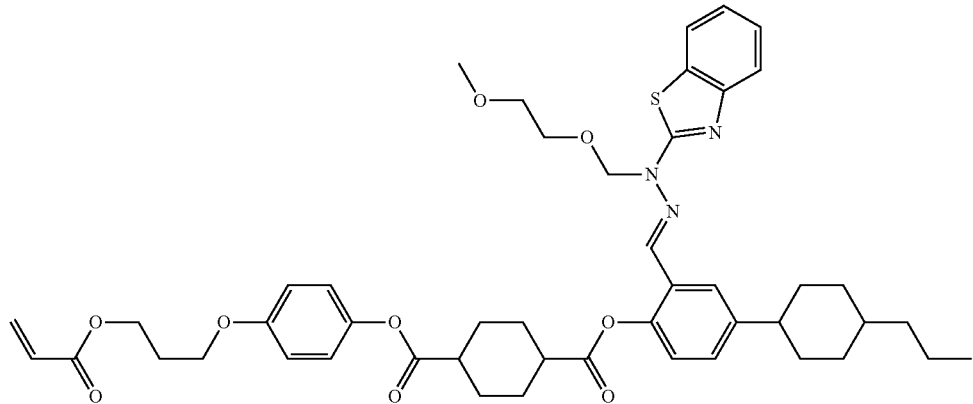
(I-128)
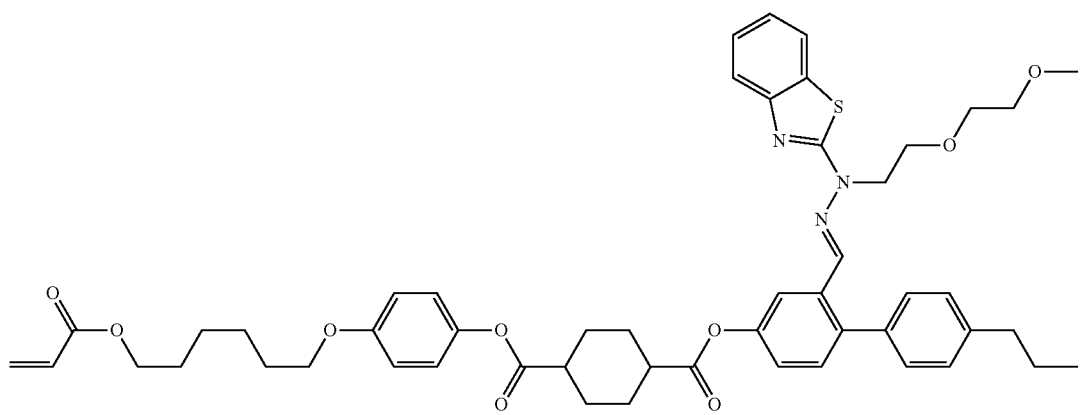
(I-129)
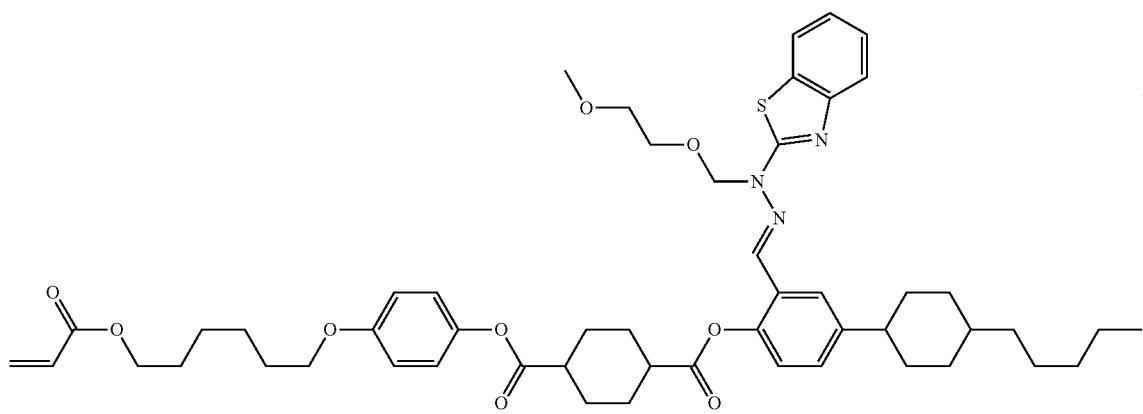

-continued
(I-130)
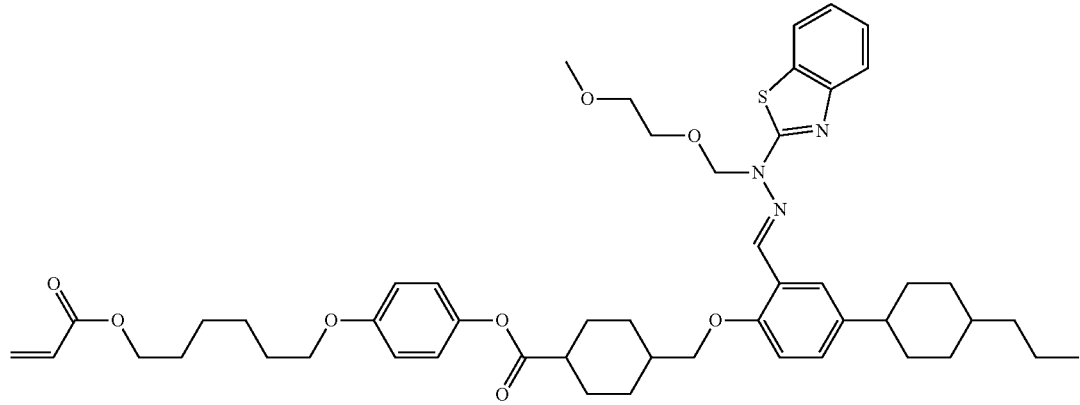
(I-131)
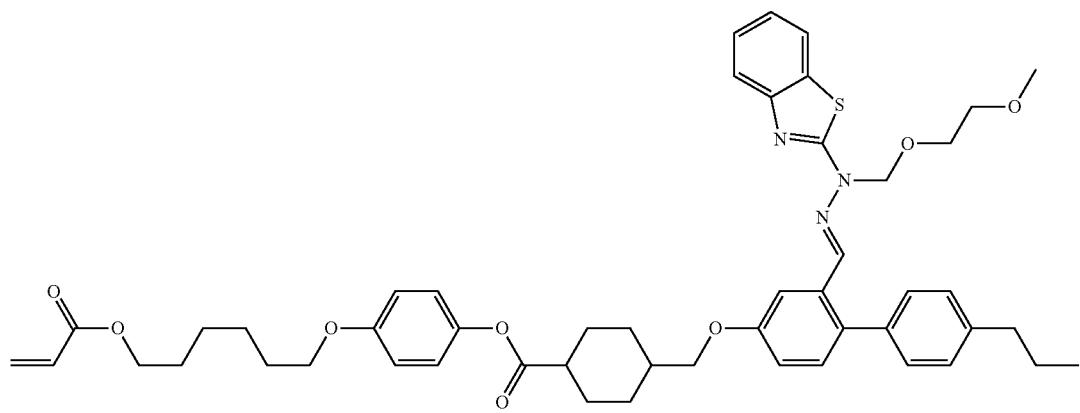
(I-132)
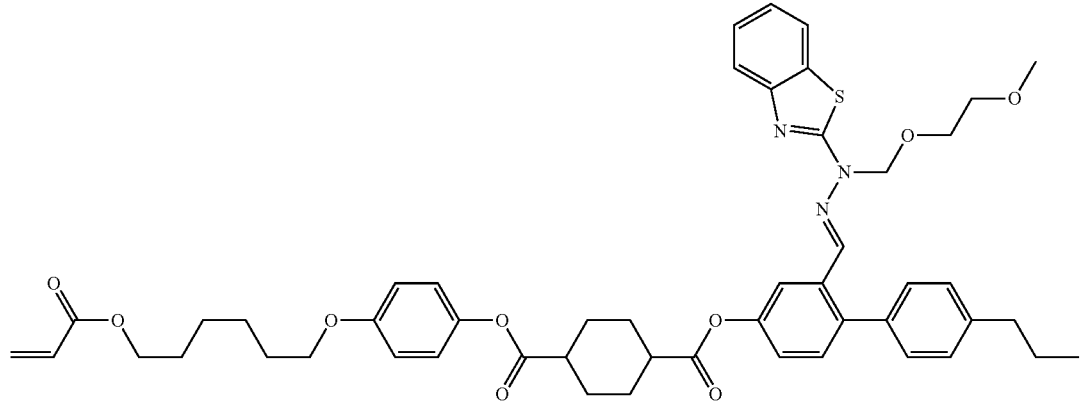

(I-133)
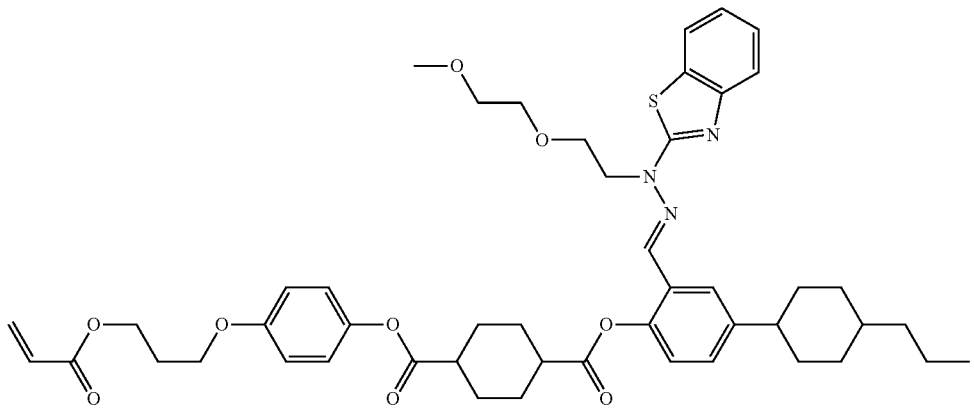
The compounds of the present invention can be produced according to the production methods mentioned below.
(Production Method 1) Production of compounds represented by the following formula (S-14):
[Chem. 111]
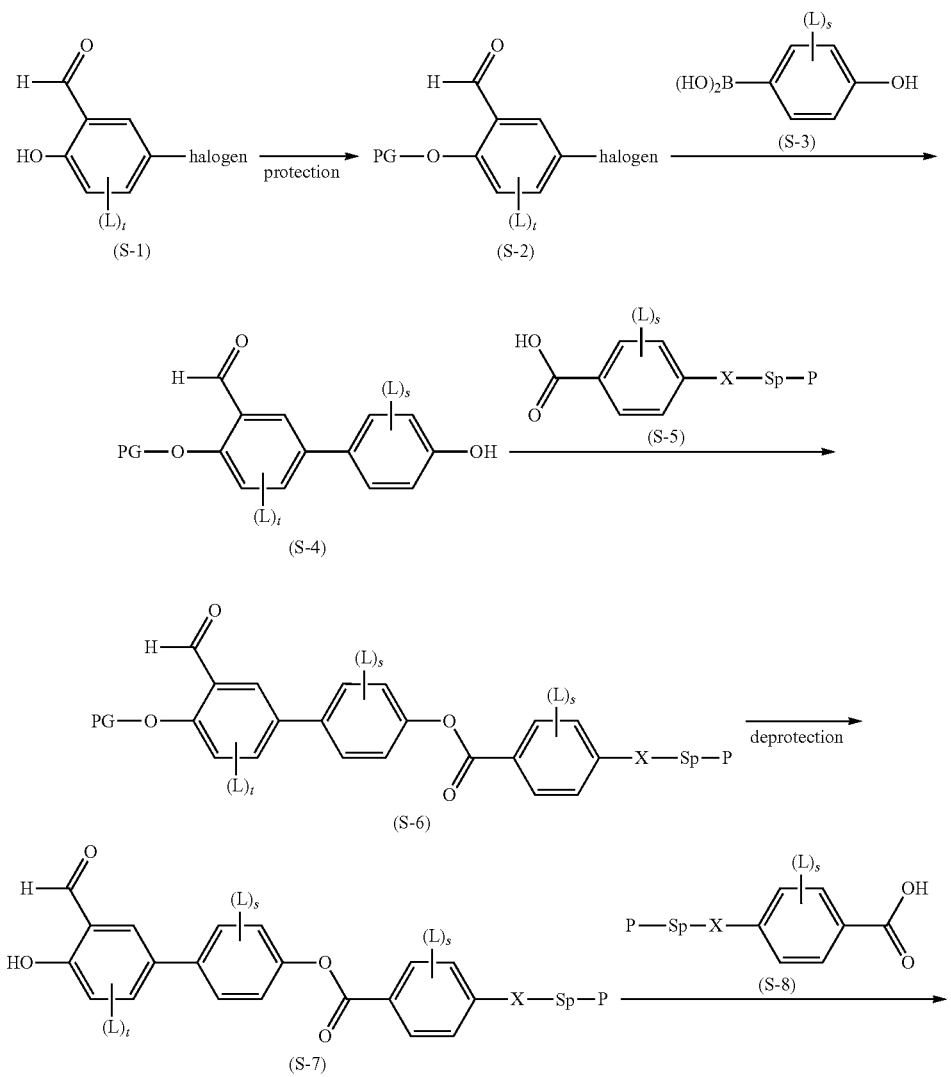

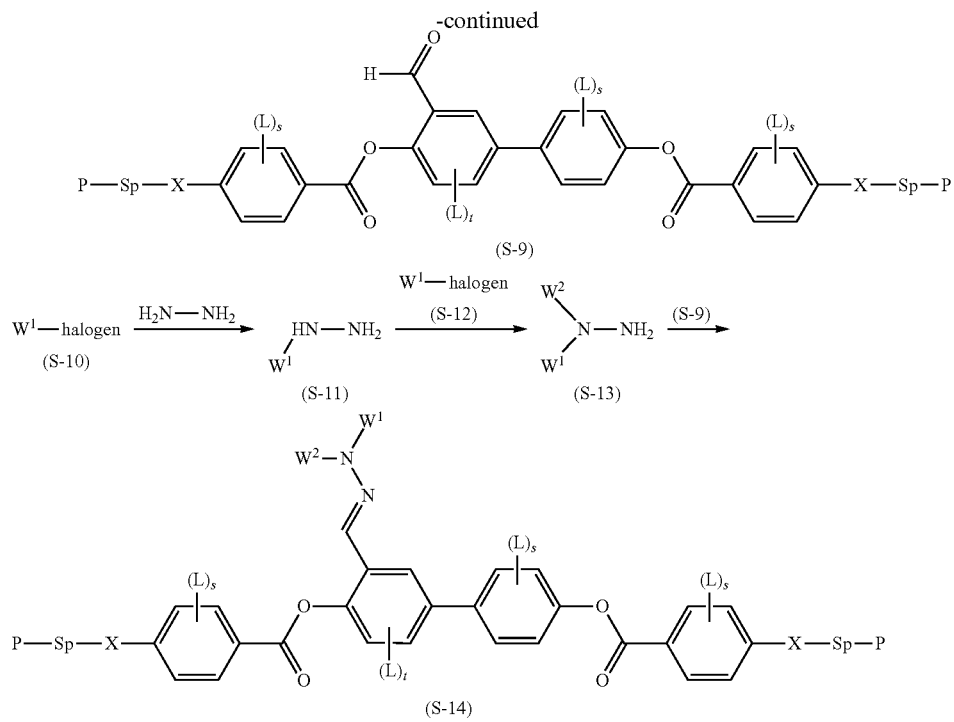

(In the formulae, P, Sp, X, L, $W^1$ and $W^2$ each independently have the same meanings as those defined in the general formula (I) and the general formula (I-R), s each independently represent an integer of 0 to 4, t represents an integer of 0 to 3, PG represents a protective group, halogen represents a halogen atom or a halogen equivalent.)

The hydroxyl group in the compound represented by the formula (S-1) is protected with a protective group (PG). The protective group (PG) is not specifically limited so far as it can stably protect the compound until the deprotection step, but is, for example, preferably any of the protective groups listed in GREENE'S PROTECTIVE GROUPS IN ORGANIC SYNTHESIS (Fourth Edition), written by PETER G. M. WUTS, THEODORA W. GREENE, John Wiley & Sons, Inc., Publication), etc. Specific examples of the protective group include a tetrahydropyranyl group.

The compound represented by the formula (S-2) is reacted with the compound represented by the formula (S-3) to give the compound represented by the formula (S-4). One reaction example is a method of crosscoupling the compounds, for example, in the presence of a metal catalyst and a base. Examples of the metal catalyst include [1,1'-bis(diphenylphosphino)ferrocene]palladium(II) dichloride, palladium(II) acetate, tetrakis(triphenylphosphine)palladium(0). Examples of the base include triethylamine, etc. Regarding the reaction condition, for example, the methods described in documents of Metal-Catalyzed Cross-Coupling Reactions (written by Armin de Meijere, Francois Diedrich, Wiley-VCH), Palladium Reagents and Catalysts: New Perspectives for the 21st Century (written by Jiro Tsuji, Wiley & Sons, Ltd.), Cross-Coupling Reactions: A Practical Guide (Topics in Current Chemistry) (written by S. L. Buchwald, K. Fugami, T. Hiyama, M. Kosugi, M. Miura, N. Miyaura, A. R. Muci, M. Nomura, E. Shirakawa, K. Tamao, Springer), etc.

The compound represented by the formula (S-4) is reacted with the compound represented by the formula (S-5) to give the compound represented by the formula (S-6). Regarding the reaction condition, for example, a method using a condensing agent may be referred to, or a method of converting the compound represented by the formula (S-5) into an acid chloride, a mixed acid anhydride or a carboxylic acid anhydride thereof, and then reacting it with the compound represented by the general formula (S-4) in the presence of a base may be employed. In the case of using a condensing agent, examples of the condensing agent include N,N'-dicyclohexylcarbodiimide, N,N'-diisopropylcarbodiimide, 1-ethyl-3-(3-dimethylaminopropyl)carbodiimide hydrochloride. Examples of the base include triethylamine, diisopropylethylamine, etc.

The protective group (PG) of the compound represented by the formula (S-6) is deprotected. The reaction condition for the deprotection is not specifically limited so far as the deprotection gives the compound represented by the formula (S-7), but is preferably any one listed in the above-mentioned documents.

The compound represented by the formula (S-7) is reacted with the compound represented by the formula (S-8) to give the compound represented by the formula (S-9). Regarding the reaction condition, those mentioned above are referred to.

The compound represented by the formula (S-10) is reacted with, for example, hydrazine monohydrate to give the compound represented by the formula (S-11).

The compound represented by the formula (S-11) is reacted with the compound represented by the formula (S-12) in the presence of a base to give the compound represented by the formula (S-13). Examples of the base include potassium carbonate, cesium carbonate, etc.

The compound represented by the formula (S-13) is reacted with the compound represented by the formula (S-9) in the presence of an acid catalyst to give the compound represented by the formula (S-14). Examples of the acid include p-toluenesulfonic acid, pyridinium p-toluenesulfonate, 10-camphor-sulfonic acid, etc.

(Production Method 2) Production of compounds represented by the following formula (S-28):
[Chem. 112]
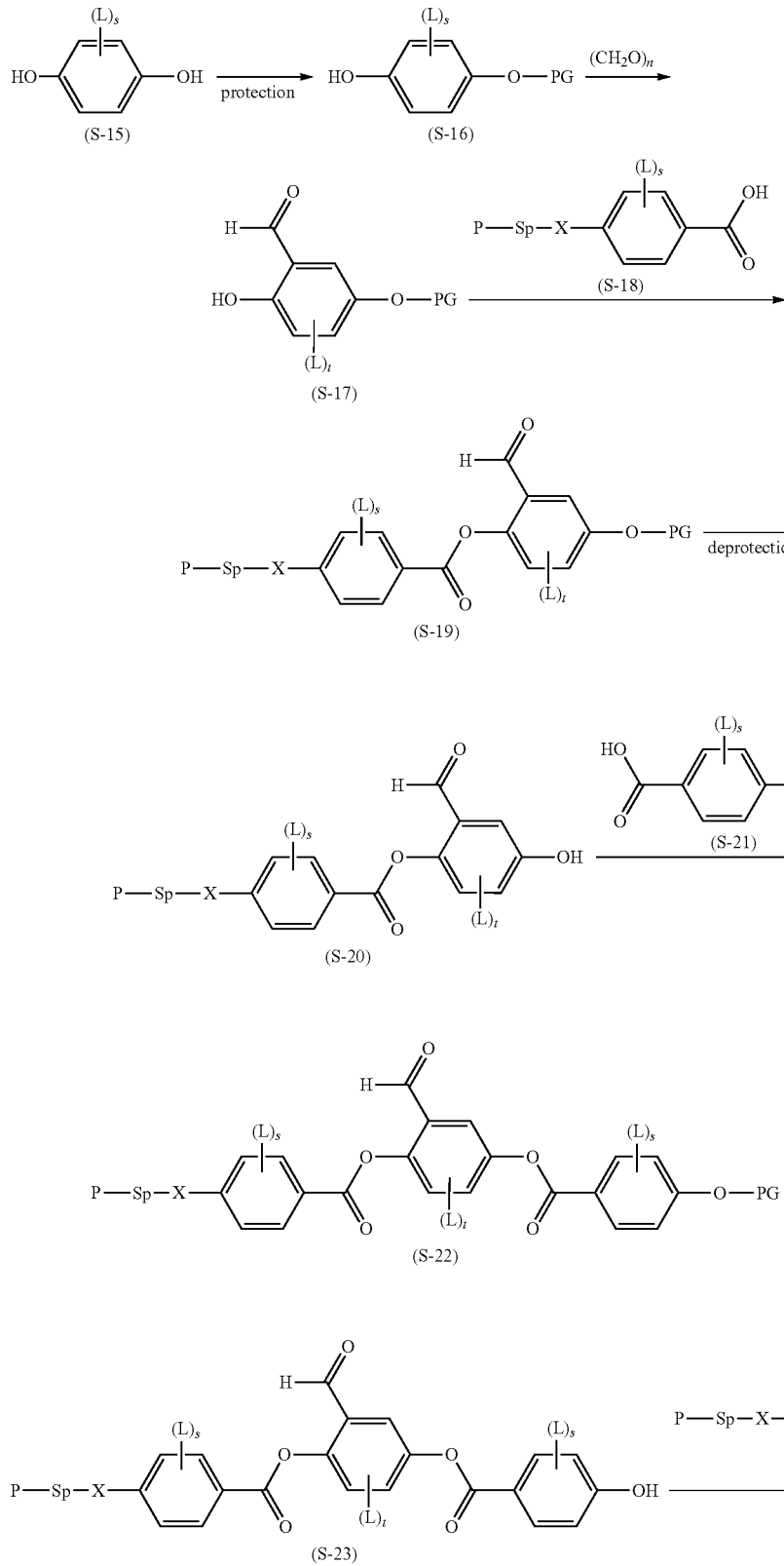

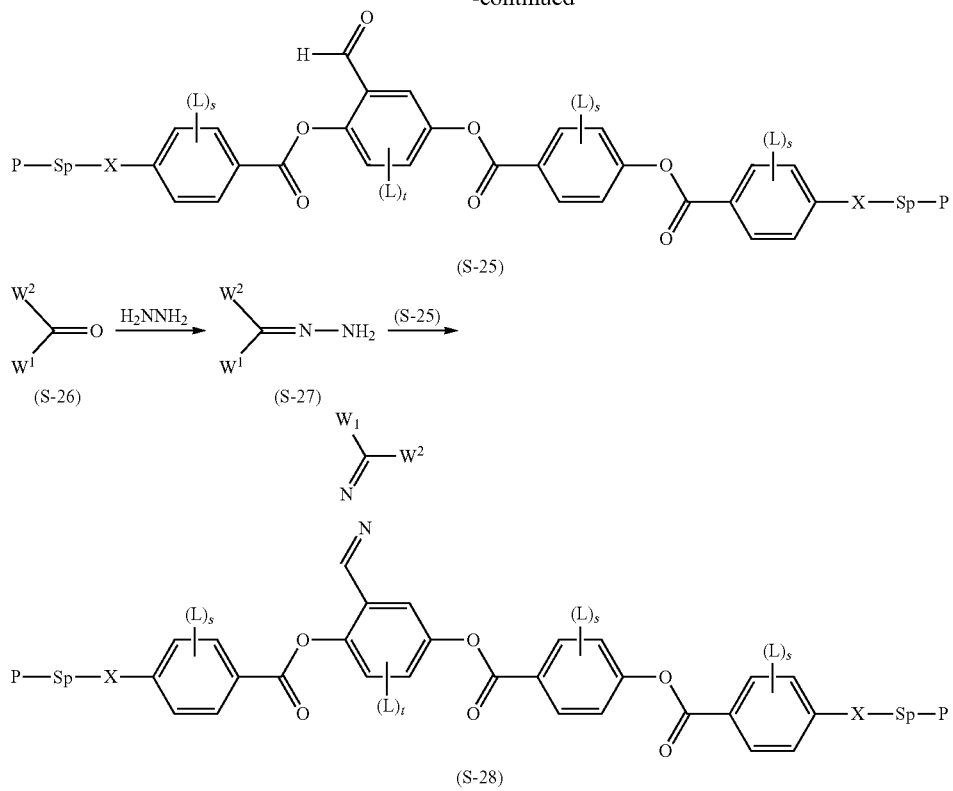

(In the formulae, P, Sp, X, L, $W^1$ and $W^2$ each independently have the same meanings as those defined in the general formula (I) and the general formula (I-R), s each independently represents an integer of 0 to 4, t represents an integer of 0 to 3, PG represents a protective group.)

The hydroxyl group in the compound represented by the formula (S-15) is protected with a protective group (PG). The protective group (PG) is not specifically limited so far as it can stably protect the compound until the deprotection step, but is, for example, preferably any of the protective groups listed in GREENE'S PROTECTIVE GROUPS IN ORGANIC SYNTHESIS (Fourth Edition), written by PETER G. M. WUTS, THEODORA W. GREENE, John Wiley & Sons, Inc., Publication), etc. Specific examples of the protective group include a tetrahydropyranyl group.

The compound represented by the formula (S-16) is formulated to give the compound represented by the formula (S-17). Regarding the reaction condition, for example, a method of reacting the compound with paraformaldehyde in the presence of magnesium chloride and a base is referred to. Examples of the base include triethylamine.

The compound represented by the formula (S-17) is reacted with the compound represented by the formula (S-18) to give the compound represented by the formula (S-19). The reaction condition may be, for example, the same as that in the production method 1.

The protective group (PG) of the compound represented by the formula (S-19) is deprotected. The reaction condition for the deprotection is not specifically limited so far as the deprotection gives the compound represented by the formula (S-20), but is preferably any one listed in the documents given in the section of production method 1.

The compound represented by the formula (S-20) is reacted with the compound represented by the formula (S-21) to give the compound represented by the formula (S-22). The reaction condition may be, for example, the same as that in the production method 1.

The protective group (PG) of the compound represented by the formula (S-22) is deprotected. The reaction condition for the deprotection is not specifically limited so far as the deprotection gives the compound represented by the formula (S-23), but is preferably any one listed in the documents given in the section of production method 1.

The compound represented by the formula (S-23) is reacted with the compound represented by the formula (S-24) to give the compound represented by the formula (S-25). The reaction condition may be, for example, the same as that in the production method 1.

The compound represented by the formula (S-26) is reacted with, for example, hydrazine monohydrate to give the compound represented by the formula (S-27).

The compound represented by the formula (S-27) is reacted with the compound represented by the formula (S-25) to give the compound represented by the formula (S-28). The reaction condition may be, for example, the same as that in the production method 1.

Regarding the reaction condition except those described in each step of the production method 1 and the production method 2, for example, the conditions described in documents of Experimental Chemistry Course (edited by the Chemical Society of Japan, published by Maruzen Co. Ltd.), Organic Syntheses (John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), Fiesers' Reagents for Organic Synthesis (John Wiley & Sons, Inc.), etc., or the conditions provided by on-line search services of SciFinder (Chemical Abstracts Service, American Chemical Society) or Reaxys (Elsevier Ltd.) and the like may be referred to.

A reaction solvent may be optionally used in each step. The solvent is not specifically limited so far as the intended compound is given, and examples thereof include tert-butyl alcohol, isobutyl alcohol, isopropyl alcohol, isopentyl alcohol, cyclohexanol, 1-butanol, 2-butanol, 1-octanol, 2-methoxyethanol, ethylene glycol, diethylene glycol, methanol, methylcyclohexanol, ethanol, propanol, chloroform, carbon tetrachloride, dichloromethane, 1,2-dichloroethane, 1,2-dichloroethylene, 1,1,2,2-tetrachloroethane, trichloroethylene, 1-chlorobutane, carbon disulfide, acetone, acetonitrile, benzonitrile, N,N-dimethylformamide, N,N-dimethylacetamide, dimethylsulfoxide, 1,3-dimethyl-2-imidazolidinone, diethyl ether, ethylene glycol monoethyl ether, ethylene glycol monoethyl ether acetate, ethylene glycol monobutyl ether, ethylene glycol monomethyl ether, diethylene glycol diethyl ether, o-dichlorobenzene, xylene, o-xylene, p-xylene, m-xylene, chlorobenzene, isobutyl acetate, isopropyl acetate, isoamyl acetate, ethyl acetate, butyl acetate, propyl acetate, pentyl acetate, methyl acetate, 2-methoxyethyl acetate, hexamethylphosphoric acid triamide, tris(dimethylamino) phosphine, cyclohexanone, 1,4-dioxane, dichloromethane, styrene, tetrachloroethylene, tetrahydrofuran, pyridine, 1-methyl-2-pyrrolidinone, 1,1,1-trichloroethane, toluene, hexane, pentane, cyclohexane, cyclopentane, heptane, benzene, methyl isobutyl ketone, tert-butyl methyl ether, methyl ethyl ketone, methylcyclohexanone, methyl butyl ketone, diethyl ketone, gasoline, coal tar naphtha, petroleum ether, petroleum naphtha, petroleum benzine, turpentine oil, mineral spirit, etc. In the case where the reaction is carried out in two phases of an organic solvent and water, a phase transfer catalyst may be added. Examples of the phase transfer catalyst include benzyltrimethylammonium chloride, polyoxyethylene(20) sorbitan monolaurate [Tween 20], sorbitan monooleate [Span 80], etc.

In each step, the product may be purified as needed. The purification method includes chromatography, recrystallization, distillation, sublimation, reprecipitation, adsorption, liquid-liquid separation treatment, etc. In the case where a purifying agent is used, the purifying agent includes silica gel, alumina, activated carbon, activated earth, Celite, zeolite, mesoporous silica, carbon nanotube, carbon nanohorn, binchotan charcoal, wood coal, graphene, ion-exchange resin, acid clay, silicon dioxide, diatomaceous earth, pearlite, cellulose, organic polymer, porous gel, etc.

The compound of the present invention is preferably used in a nematic liquid crystal composition, a smectic liquid crystal composition, a chiral-smectic liquid crystal composition and a cholesteric liquid crystal composition. Any other compound than those of the present invention may be added to the liquid crystal composition using the reactive compound of the present invention.

Specifically, preferred examples of the other polymerizable compound to be used as mixed with the polymerizable compound of the present invention include a compound represented by the following general formula (X-11),

[Chem. 113]

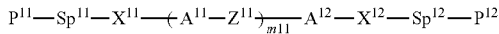

(X-11)

and/or a compound represented by the following general formula (X-12),

[Chem. 114]

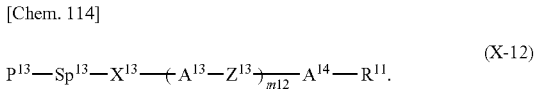

(X-12)

(In the formulae, $P^{11}$, $P^{12}$ and $P^{13}$ each independently represent a polymerizable group, $Sp^{11}$, $Sp^{12}$ and $Sp^{13}$ each independently represent a single bond or an alkylene group having 1 to 20 carbon atoms, and one —$CH_2$— or two or more of (—$CH_2$—)'s which are not adjacent to each other may be substituted with —O—, —COO—, —OCO— or —OCOO—, $X^{11}$, $X^{12}$ and $X^{13}$ each independently represent —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —CHS—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —CF=CF—, —C≡C— or a single bond, $Z^{11}$ and $Z^{12}$ each independently represent —O—, —S—, —$OCH_2$—, —$CH_2O$—, —COO—, —OCO—, —CO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —$CH_2CH_2$—, —$CH_2CF_2$—, —$CF_2CH_2$—, —$CF_2CF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —CF=CF—, —C≡C— or a single bond, $A^{11}$, $A^{12}$, $A^{13}$ and $A^{14}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group or a 1,3-dioxane-2,5-diyl group, and $A^{11}$, $A^{12}$, $A^{13}$ and $A^{14}$ may be each independently unsubstituted or substituted with an alkyl group, a halogenoalkyl group, an alkoxy group, a halogenoalkoxy group, a halogen atom, a cyano group or a nitro group, $R^{11}$ represents a hydrogen atom, a fluorine atom, a chlorine atom, a bromine atom, an iodine atom, a pentafluorosulfuranyl group, a cyano group, a nitro group, an isocyano group, a thioisocyano group, a linear or branched alkyl group having 1 to 20 carbon atoms, in which one —$CH_2$— or two or more of (—$CH_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, m11 and m12 each represent 0, 1, 2 or 3, and in the case where m11 and/or m12 are/is 2 or 3, two or three $A^{11}$, $A^{13}$, $Z^{11}$ and/or $Z^{12}$ may be the same or different.) More preferably, $P^{11}$, $P^{12}$ and $P^{13}$ each are an acryl group or a methacryl group. Specifically, the compound represented by the general formula (X-11) is preferably a compound represented by the following general formula (X-11a).

[Chem. 115]

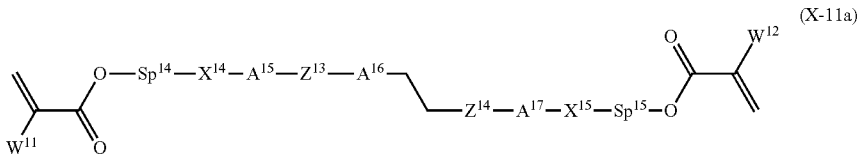

(In the formula, $W^{11}$ and $W^{12}$ each independently represent a hydrogen atom or a methyl group, $Sp^{14}$ and $Sp^{15}$ each independently represent an alkylene group having 2 to 18 carbon atoms, $X^{14}$ and $X^{15}$ each independently represent —O—, —COO—, —OCO— or a single bond, $Z^{13}$ and $Z^{14}$ each independently represent —COO— or —OCO—, $A^{15}$, $A^{16}$ and $A^{17}$ each independently represent a 1,4-phenylene group which may be unsubstituted or substituted with a fluorine atom, a chlorine atom, a linear or branched alkyl group having 1 to 4 carbon atoms, or a linear or branched alkoxy group having 1 to 4 carbon atoms). The compound is especially preferably a compound represented by the following formulae (X-11a-1) to (X-11a-4).

[Chem. 116]

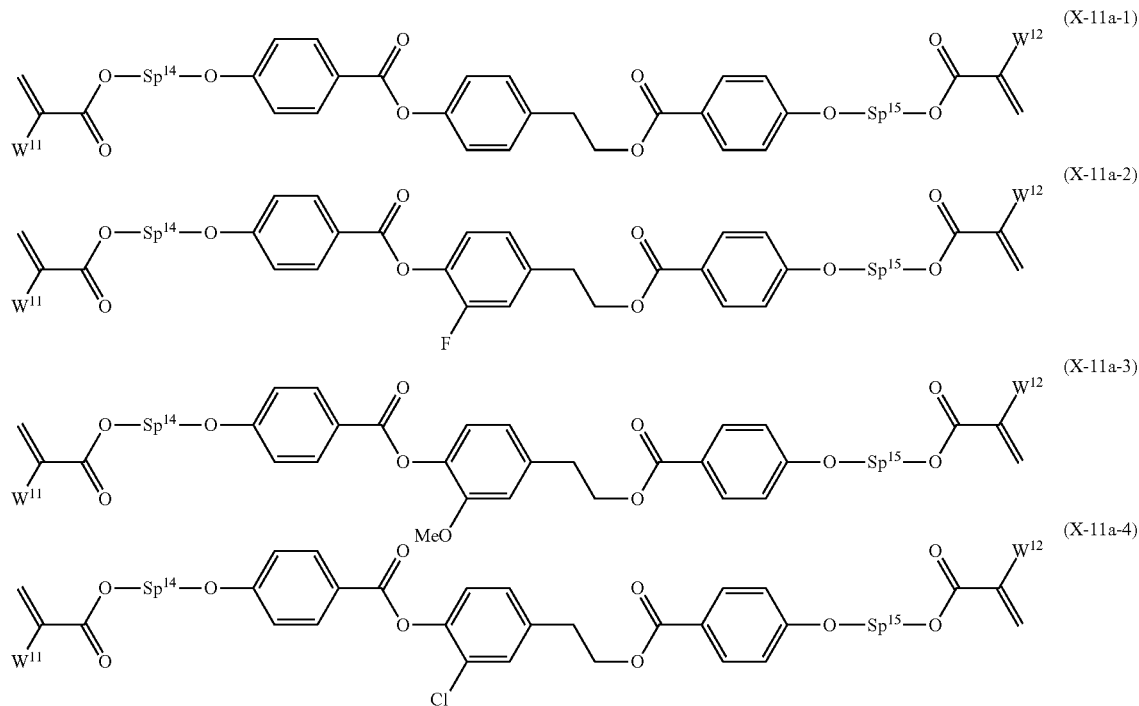

(In the formulae, $W^{11}$, $W^{12}$, $Sp^{14}$ and $Sp^{15}$ each have the same meanings as those in the general formula (X-11a). A compound represented by the formulae (X-11a-1) to (X-11a-4) where $Sp^{14}$ and $Sp^{15}$ each are independently an alkylene group having 2 to 8 carbon atoms is especially preferred.

In addition, preferred examples of the other bifunctional polymerizable compound include those represented by the following general formula (X-11b-1) to (X-11b-3).

[Chem. 117]

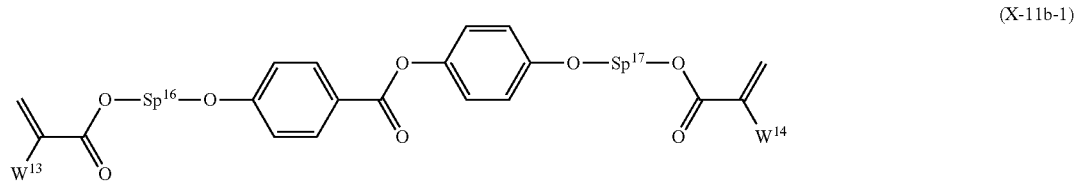

-continued

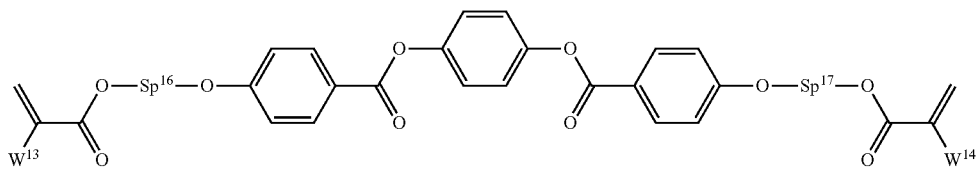
(X-11b-2)

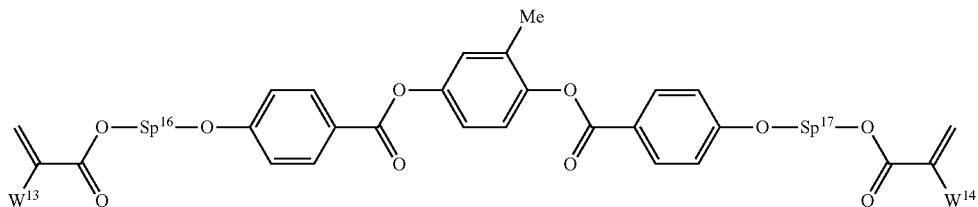
(X-11b-3)

(In the formulae, $W^{13}$ and $W^{14}$ each independently represent a hydrogen atom or a methyl group, $Sp^{16}$ and $Sp^{17}$ each independently represent an alkylene group having 2 to 18 carbon atoms.) A compound of the above formulae (X-11b-1) to (X-11b-3) where $Sp^{16}$ and $Sp^{17}$ each are independently an alkylene group having 2 to 8 carbon atoms is especially preferred.

Specifically, the compound represented by the general formula (X-12) include compounds represented by the following general formulae (X-12-1) to (X-12-7).

(In the formulae, $P^{14}$ represents a polymerizable group, $Sp^{18}$ represents a single bond or an alkylene group having 1 to 20 carbon atoms in which one —$CH_2$— or two or more of (—$CH_2$—)'s which are not adjacent to each other may be each substituted with —O—, —COO—, —OCO— or —O—CO—O—, $X^{16}$ represents a single bond, —O—, —COO— or —OCO—, $Z^{15}$ represents a single bond, —COO— or —OCO—, $L^1$ represents a fluorine atom, a chlorine atom, or a linear or branched alkyl group having 1 to 10 carbon atoms in which one —$CH_2$— or two or more

[Chem. 118]

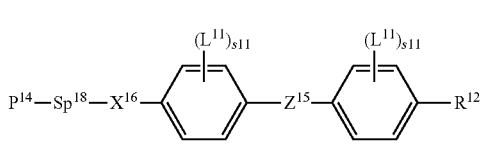
(X-12-1)

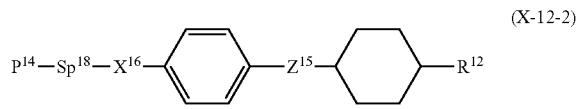
(X-12-2)

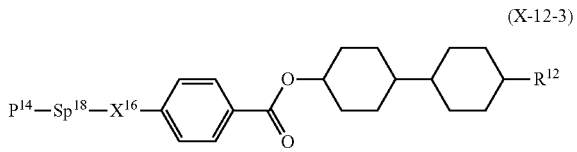
(X-12-3)

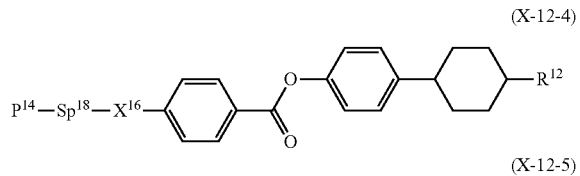
(X-12-4)

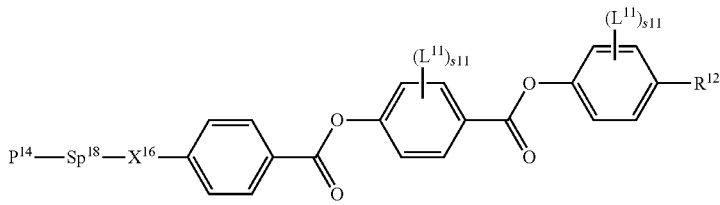
(X-12-5)

(X-12-6)

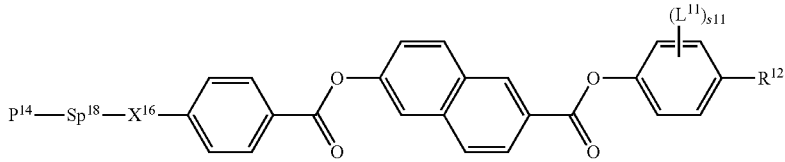

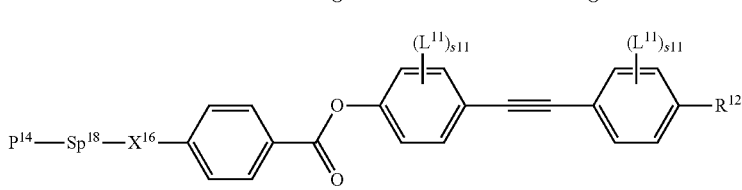
(X-12-7)

of (—CH₂—)'s which are not adjacent to each other may be each independently substituted with —O—, —COO— or —OCO—, s11 represents an integer of 0 to 4, $R^{12}$ represents a hydrogen atom, a fluorine atom, a chlorine atom, a cyano group, a nitro group, or a linear or branched alkyl group having 1 to 20 carbon atoms in which one —CH₂— or two or more of (—CH₂—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—.)

A non-liquid-crystalline polymerizable compound may be added to the polymerizable liquid crystal composition containing the compound of the present invention, within a range not significantly detracting from the liquid crystallinity of the composition. Specifically, a compound that is recognizable as a polymer-forming monomer or a polymer-forming oligomer in this technical field can be used with no specific limitation. Specific examples thereof include those described in "Photocurable Technique Data Book, Section of Materials (monomers, oligomers, photopolymerization initiators)" (supervised by Kunihiro Ichimura and Kiyoshi Katoh, Technonet).

Not using a photopolymerization initiator, the compound of the present invention can polymerize, but depending on the intended purpose, a photopolymerization initiator may be added thereto. In the case, the concentration of the photopolymerization initiator is preferably 0.1% by mass to 15% by mass of the compound of the present invention, more preferably 0.2% by mass to 10% by mass, even more preferably 0.4% by mass to 8% by mass. The photopolymerization initiator includes benzoin ethers, benzophenones, acetophenones, benzyl ketals, acylphosphine oxides, etc. Specific examples of the photopolymerization initiator include 2-methyl-1-(4-methylthiophenyl)-2-morpholinopropan-1-one (IRGACURE 907), [1-[4-(phenylthio)benzoyl]heptylidene]amino-benzoic acid (IRGACURE OXE01), etc. A thermal polymerization initiator includes azo compounds, peroxides, etc. Specific examples of the thermal polymerization initiator include 2,2'-azobis(4-methoxy-2,4-dimethylvaleronitrile), 2,2'-azobis(isobutyronitrile), etc. One kind of polymerization initiator may be used, or two or more kinds of polymerization initiators may be used as combined.

A stabilizer may be added to the liquid crystal composition of the present invention for improving the storage stability thereof. Examples of the usable stabilizer include hydroquinones, hydroquinone monoalkyl ethers, tert-butyl catechols, pyrogallols, thiophenols, nitro compounds, β-naphthylamines, β-naphthols, nitroso compounds, etc. In the case where a stabilizer is used, the amount thereof to be added is preferably within a range of 0.005% by mass to 1% by mass of the composition, more preferably 0.02% by mass to 0.8% by mass, even more preferably 0.03% by mass to 0.5% by mass. One kind of stabilizer may be used or two or more kinds of stabilizers may be used as combined. Specifically, preferred examples of the stabilizers include compounds represented by the following formulae (X-13-1) to (X-13-35).

[Chem. 119]

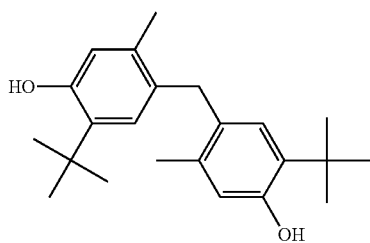

(X-13-1)

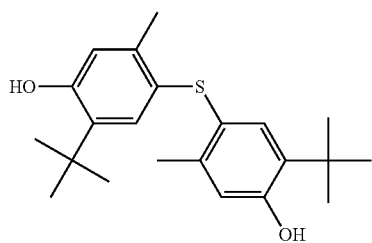

(X-13-2)

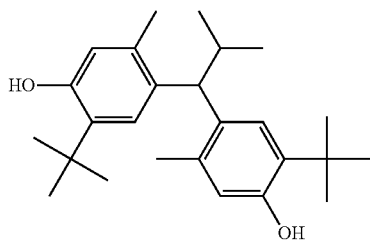

(X-13-3)

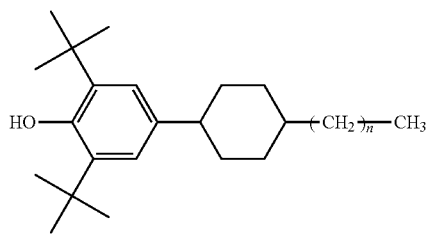

(X-13-4)

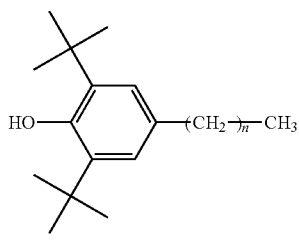

(X-13-5)

-continued
[Chem. 120]
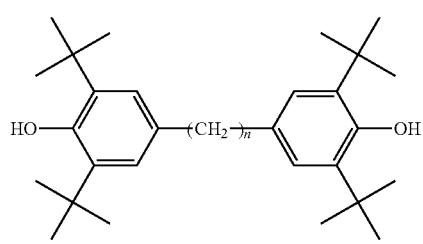
(X-13-6)
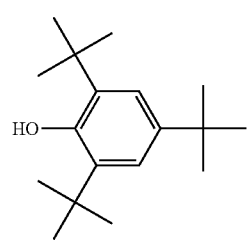
(X-13-7)
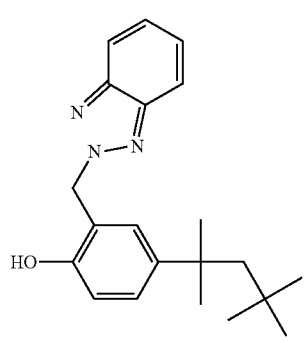
(X-13-8)
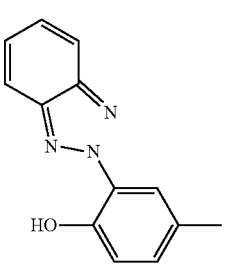
(X-13-9)
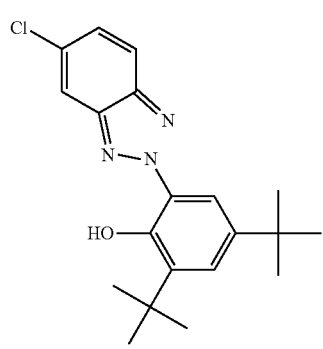
(X-13-10)
[Chem. 121]
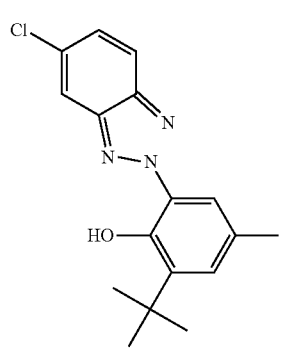
(X-13-11)
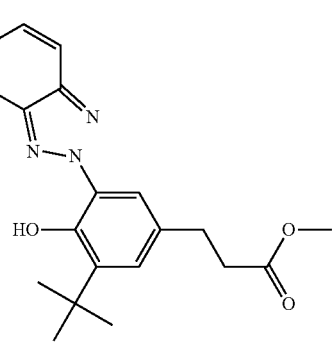
(X-13-12)

(X-13-13)
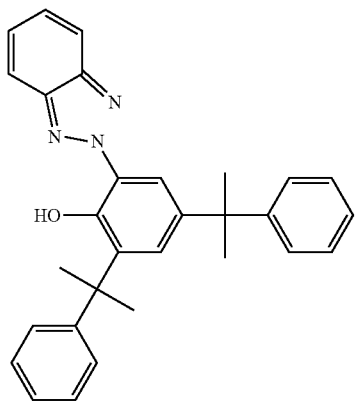
(X-13-14)
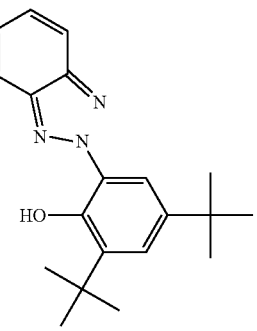
(X-13-15)
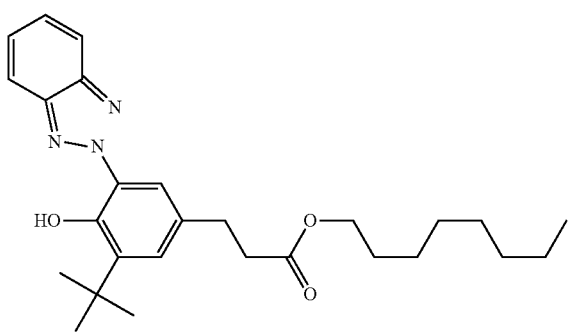
[Chem. 122]
(X-13-16)
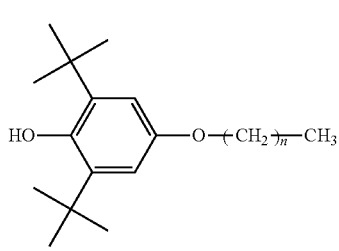
(X-13-17)
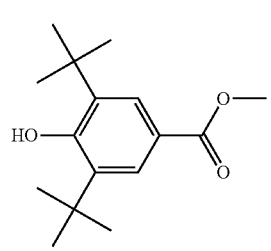
(X-13-18)
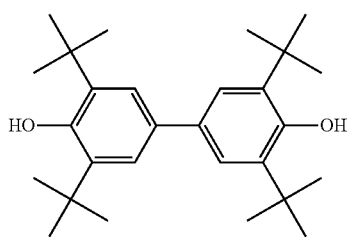
(X-13-19)
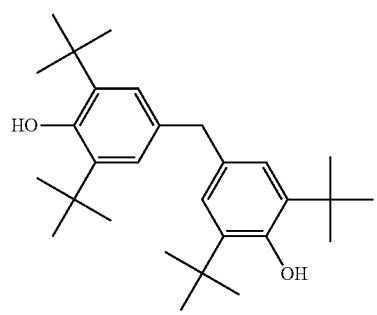
(X-13-20)
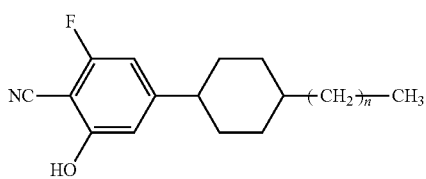

[Chem. 123]
(X-13-21)
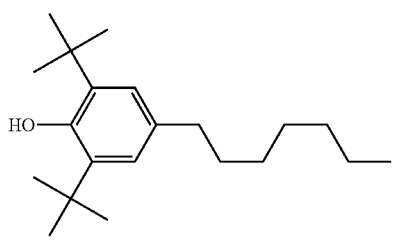
(X-13-22)
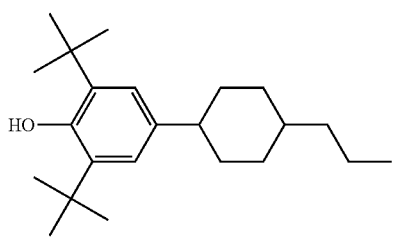
(X-13-23)
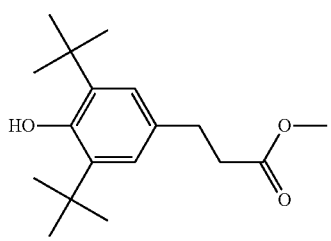
(X-13-24)
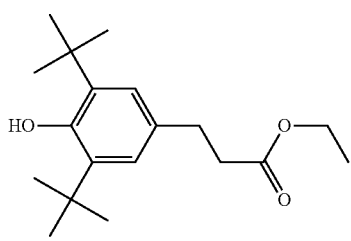
(X-13-25)
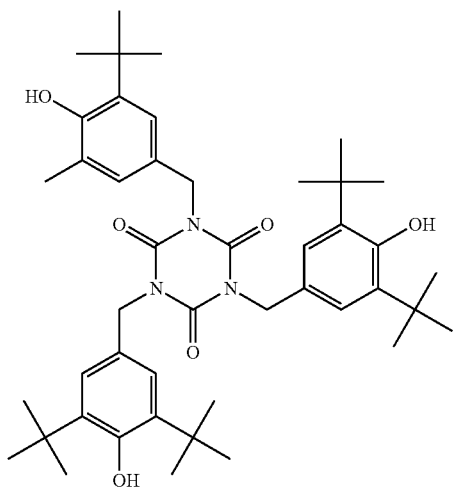
[Chem. 124]
(X-13-26)
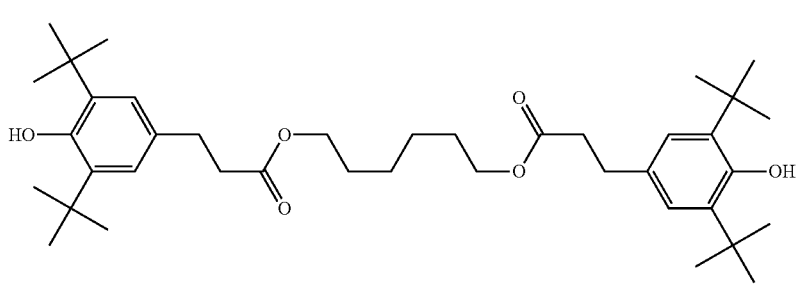
(X-13-27)
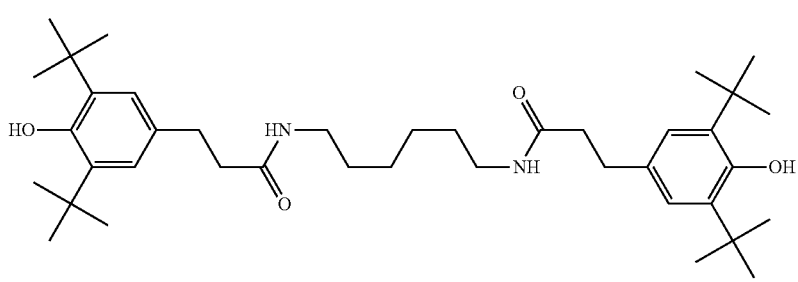

(X-13-28)
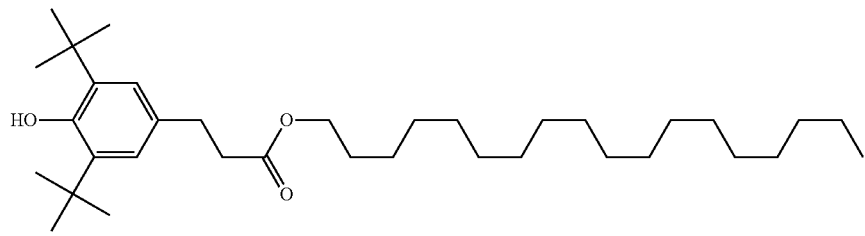
(X-13-29)
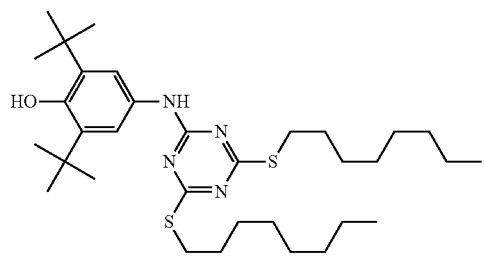
(X-13-30)
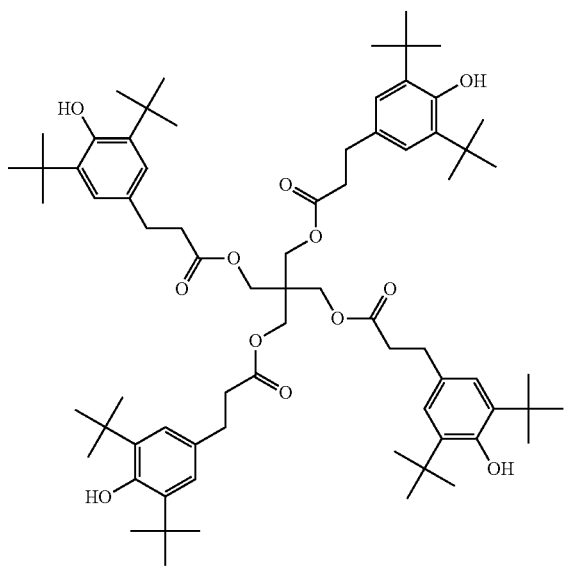
[Chem. 125]
(X-13-31)
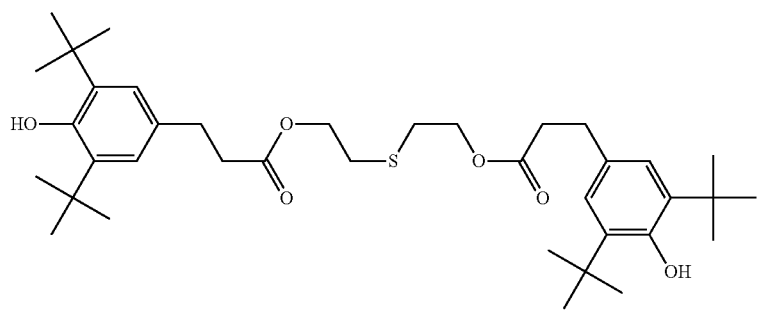
(X-13-32)
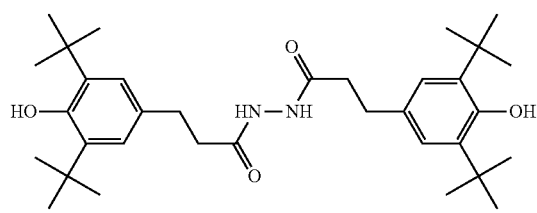
(X-13-33)
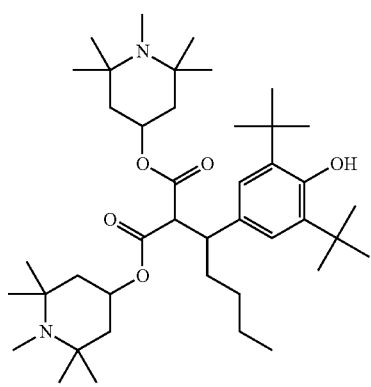

-continued (X-13-34)

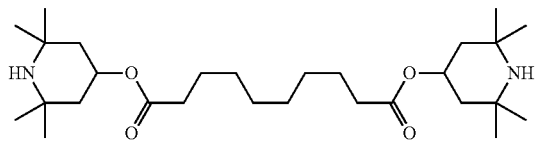

(X-13-35)

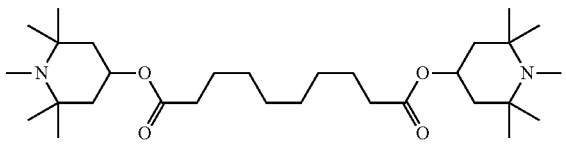

(In the formulae, n represents an integer of 0 to 20.)

In the case where the polymerizable liquid crystal composition containing the compound of the present invention is used in applications for films, optical devices, functional pigments, medicines, cosmetics, coating agents, synthetic resins, etc., metals, metal complexes, dyes, pigments, colorants, fluorescent materials, phosphorescent materials, surfactants, leveling agents, thixotropic agents, gelling agents, polysaccharides, UV absorbents, IR absorbents, antioxidants, ion-exchange resins, metal oxides such as titanium oxide or the like may be added thereto, depending on the intended purposes.

Polymers to be obtained by polymerizing the polymerizable liquid crystal composition containing the compound of the present invention can be used in various applications. For example, polymers obtained though polymerization with no alignment of the polymerizable liquid crystal composition containing the compound of the present invention are usable as light-scattering plates, depolarizers, moire stripe inhibitors. Polymers obtained by polymerizing the composition after alignment are usable as having optical anisotropy. Such optically anisotropic bodies can be produced, for example, by making the polymerizable liquid crystal composition containing the compound of the present invention supported by a substrate rubbed with cloth or the like, by a substrate with an organic thin film formed thereon, or by a substrate having an alignment film of $SiO_2$ formed thereon through orthorhombic deposition thereon, or by making the composition sandwiched between such substrates, and thereafter polymerizing the polymerizable liquid crystal composition.

The method of making the polymerizable liquid crystal composition supported by a substrate includes methods of spin coating, die coating, extrusion coating, roll coating, wire bar coating, gravure coating, spray coating, dipping, printing, etc. In coating, an organic solvent may be added to the polymerizable liquid crystal composition. The usable organic solvent includes hydrocarbon solvents, halogenohydrocarbon solvents, ether solvents, alcohol solvents, ketone solvents, ester solvents, aprotic solvents. For example, the hydrocarbon solvent include toluene, hexane; the halogenohydrocarbon solvents include methylene chloride; the ether solvents include tetrahydrofuran, acetoxy-2-ethoxyethane, propylene glycol monomethyl ether acetate; alcohol solvents include methanol, ethanol, isopropanol; ketone solvents include acetone, methyl ethyl ketone, cyclohexanone, γ-butyrolactone, N-methylpyrrolidinones; the ester solvents include ethyl acetate, cellosolve; the aprotic solvents include dimethylformamide, acetonitrile. One or more of these may be used either singly or as combined, and may be adequately selected in consideration of the vapor pressure and the solubility of the polymerizable liquid crystal composition therein. The method for evaporating the added organic solvent includes spontaneous drying, drying by heating, drying under reduced pressure, drying by heating under reduced pressure. For further improving the coatability with the polymerizable liquid crystal composition, it is also effective to provide an interlayer such as a polyimide thin layer or the like on a substrate, or to add a leveling agent to the polymerizable liquid crystal material. The method of providing an interlayer such as a polyimide thin layer or the like on a substrate is effective for improving the adhesion between the polymer to be produced through polymerization of the polymerizable liquid crystal material, and a substrate.

Other alignment treatments than the above include use of flow alignment of a liquid crystal material, or use of an electric field or a magnetic field. One alone or two or more of these alignment methods may be used either singly or as combined. Further, as an alignment treatment method in place of rubbing, a photo-alignment method is also employable. Regarding the shape of the substrate, those having a curved constituent part may be used in addition to a flat plate. As the material to constitute the substrate, any of organic materials or inorganic materials can be used. Examples of the organic materials for the substrate include polyethylene terephthalate, polycarbonate, polyimide, polyamide, polymethyl methacrylate, polystyrene, polyvinyl chloride, polytetrafluoroethylene, polychlorotrifluoroethylene, polyarylate, polysulfone, triacetyl cellulose, cellulose, polyether ether ketone, etc. Examples of the inorganic materials include silicon, glass, calcite, etc.

In polymerizing the polymerizable liquid crystal composition containing the compound of the present invention, preferably, the polymerization is carried out rapidly. Accordingly, a method of polymerization with irradiation with active energy rays such as UV rays, electron beams or the like is preferred. In the case of using UV rays, a polarization light source may be used, or a non-polarization light source may be used. In the case where the polymerization is carried out while the liquid crystal composition is sandwiched between two substrates, at least the substrate on the irradiation side must have suitable transparency relative to active energy rays. In addition, a method of polymerizing only a specific part by using a mask during photoirradiation, and thereafter changing the alignment state of the unpolymerized part by changing the condition of an electric field, a magnetic field, a temperature or the like, followed by further irradiation with active energy rays for polymerization may also be employed. The temperature in irradiation is preferably within a temperature range capable of keeping the liquid-crystal state of the polymerizable liquid crystal composition of the present invention. In particular, in the case of producing an optically anisotropic body through photopolymerization, preferably, the polymerization is carried out at a temperature near to room temperature wherever possible, that is, typically at a temperature of 25° C. from the viewpoint of evading induction of any unintended thermal polymerization. The intensity of the active energy rays is preferably 0.1 mW/cm to 2 mW/cm. When the intensity is less than 0.1 mW/cm$^2$, a lot of time is needed to complete the photopolymerization and the productivity is thereby worsened, and when more than 2 mW/cm$^2$, there may occur a risk of degradation of the polymerizable liquid crystal compound or the polymerizable liquid crystal composition.

The optically anisotropic body obtained by polymerization may be heat-treated for reducing the initial characteristic changes thereof to realize stable characteristic expression. The heat treatment temperature is preferably within a range of 50 to 250° C., and the heat treatment time is preferably within 30 seconds to 12 hours.

etc. Ordinary post-treatment is an operation to carry out the intended compound from a reaction liquid, and means an operation generally carried out by those skilled in the art, such as reaction quenching, liquid-liquid separation/extraction, neutralization, washing, drying, condensation, etc.

(Example 1) Production of Compound of Formula (I-1)

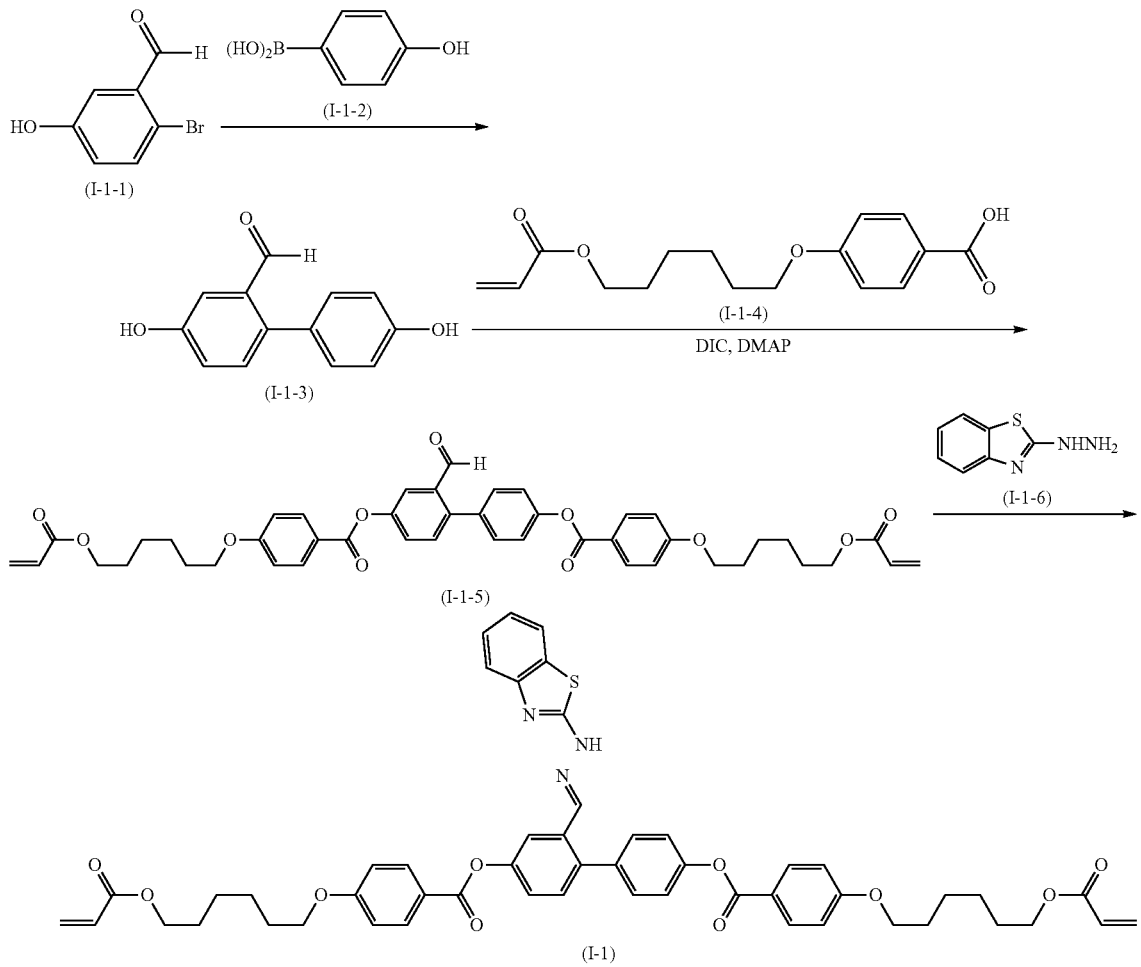

The optically anisotropic body thus produced according to the method as above may be used as a single substance thereof as peeled from the substrate, or may be used without being peeled. The resultant optically anisotropic body may be layered, or may be stuck to any other substrate.

EXAMPLES

Hereinunder present invention is described further with reference to Examples, but the present invention is not limited to these Examples. In the compositions of the following Examples and Comparative Examples, "%" means "% by mass". In handling a substance unstable to oxygen and/or water in each step, the operation is preferably carried out in an inert gas such as nitrogen gas, argon gas, In a nitrogen atmosphere, 2.0 g of a compound represented by the formula (I-1-1), 1.3 g of a compound represented by the formula (I-1-2), 1.9 g of potassium carbonate, 20 mL of ethanol, and 0.2 g of tetrakis(triphenylphosphine)palladium(0) were put into a reactor, and heated and refluxed for 8 hours. This was diluted with ethyl acetate, and washed sequentially with hydrochloric acid and salt solution. This was purified through column chromatography (silica gel, dichloromethane/ethyl acetate) to give 1.5 g of a compound represented by the formula (I-1-3).

1.0 g of the compound represented by the formula (I-1-3), 2.5 g of a compound represented by the formula (I-1-4), 0.1 g of N,N-dimethylaminopyridine, and 15 mL of dichloromethane were put into a reactor. With cooling with ice, 1.2 g of diisopropylcarbodiimide was dropwise added thereto at room temperature and stirred for 8 hours. This was washed sequentially with 1% hydrochloric acid and salt solution, and then purified through column chromatography (silica gel, dichloromethane) and recrystallization (dichloromethane/methanol) to give 2.4 g of a compound represented by the formula (I-1-5).

2.4 g of the compound represented by the formula (I-1-5), 0.5 g of a compound represented by the formula (I-1-6), 0.1 g of (±)-10-camphorsulfonic acid, 20 mL of tetrahydrofuran, and 5 mL of ethanol were put into a reactor, and stirred at room temperature for 20 hours. The solvent was concentrated, and the residue was purified through column chromatography (silica gel, dichloromethane) and recrystallization (dichloromethane/methanol) to give 1.9 g of a compound represented by the formula (I-1).

Phase transition temperature (heating process): C 107 N 217 I $^1$H NMR (CDCl$_3$): 1.52 (m, 8H), 1.74 (quin, 4H), 1.86 (quin, 4H), 4.07 (td, 4H), 4.20 (td, 4H), 5.84 (d, 2H), 6.14 (dd, 2H), 6.42 (d, 2H), 6.99 (d, 4H), 7.11 (t, 1H), 7.21-7.40 (m, 8H), 7.62 (d, 1H), 7.93 (m, 2H), 8.19 (dd, 4H) ppm.

(Example 2) Production of Compound of Formula (I-2)

20 mL of hydrazine monohydrate and 20 mL of ethanol were put into a reactor. 10 mL of a tetrahydrofuran solution of 1.0 g of a compound represented by the formula (I-2-1) was added thereto and heated with stirring at 500° C. for 6 hours. The solvent was evaporated away, and the residue was redissolved in dichloromethane, and washed with salt solution. This was Purified through column chromatography (silica gel, dichloromethane/methanol) and recrystallization (dichloromethane/hexane) to give 0.8 g of a compound represented by the formula (I-2-2).

0.8 g of the compound represented by the formula (I-2-2), 4.3 g of a compound represented by the formula (I-2-3), 0.1 g of (±)-10-camphorsulfonic acid, 15 mL of tetrahydrofuran, and 5 mL of ethanol were put into a reactor and stirred at room temperature for 10 hours. The solvent was evaporated away, and the residue purified through column chromatography (dichloromethane) and recrystallization (dichloromethane/methanol) to give 3.6 g of a compound represented by the formula (I-2).

Phase transition temperature (heating process): C 113 N 171 I $^1$H NMR (CDCl$_3$): 1.48-1.59 (m, 8H), 1.74 (m, 4H), 1.85 (m, 4H), 4.07 (q, 4H), 4.19 (td, 4H), 5.84 (d, 2H), 6.14 (ddd,

[Chem. 127]

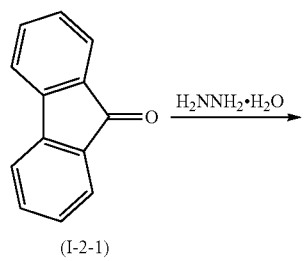

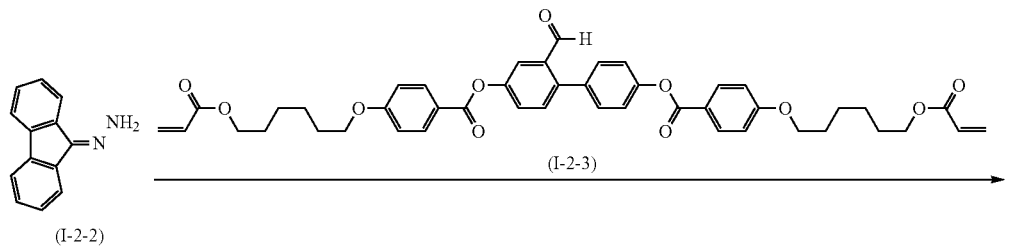

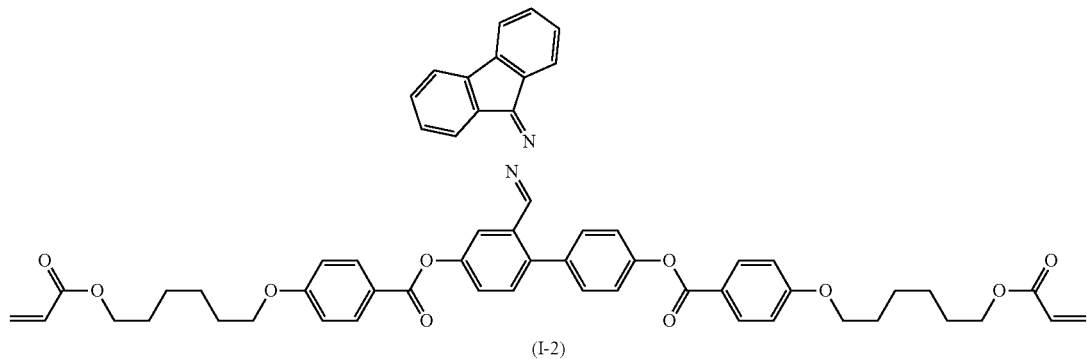

2H), 6.42 (dt, 2H), 7.00 (q, 4H), 7.30 (m, 4H), 7.39-7.46 (m, 5H), 7.51 (d, 1H), 7.61 (dd, 2H), 7.85 (d, 1H), 6.17 (d, 2H), 8.22-8.25 (m, 3H), 8.39 (d, 1H), 8.57 (s, 1H) ppm.

(Example 3) Production of Compound of Formula (I-3)

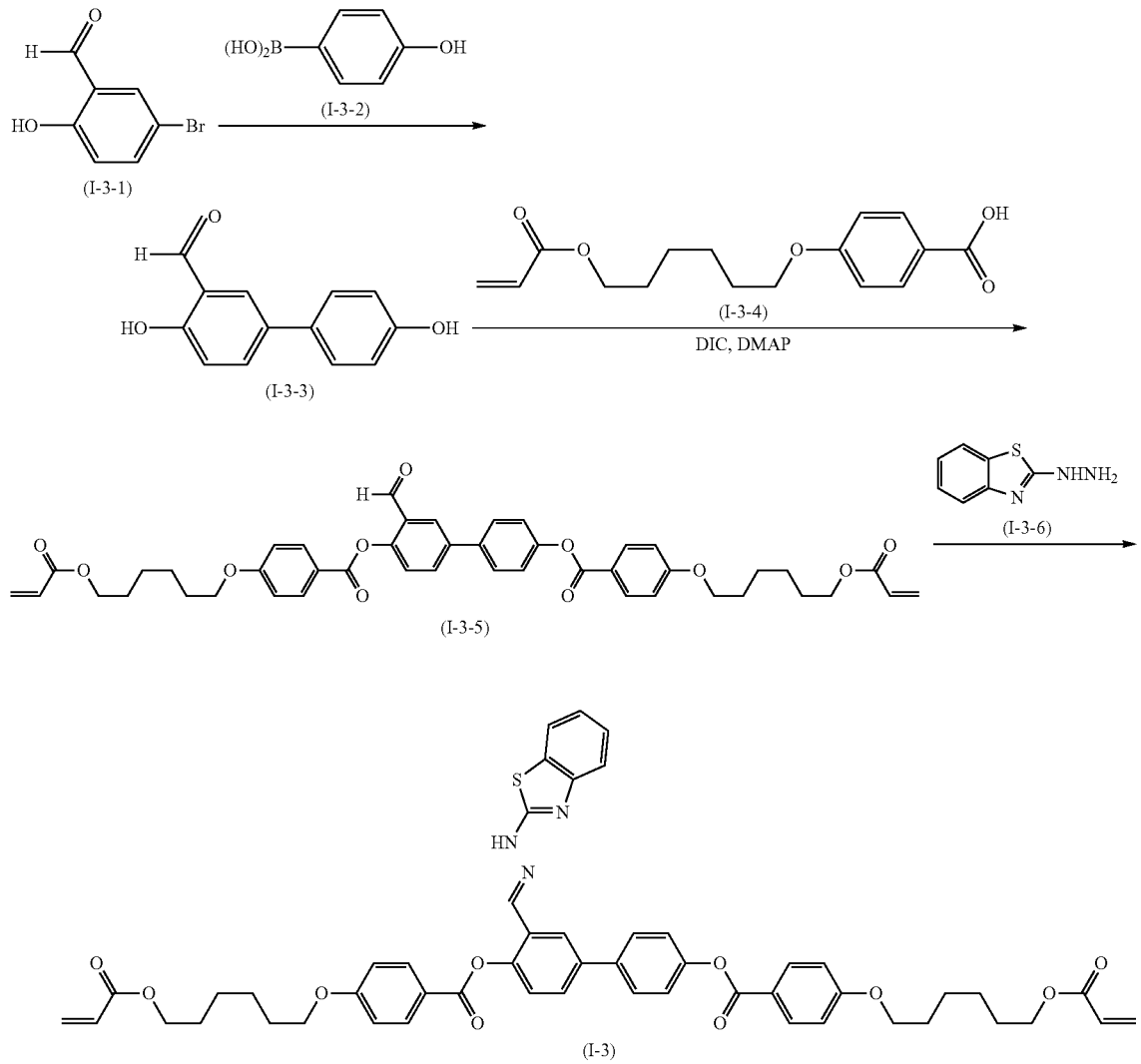

temperature for 8 hours. This was washed sequentially with 1% hydrochloric acid and salt solution, and then purified through column chromatography (silica gel, dichloromethane) and recrystallization (dichloromethane/methanol) to give 2.4 g of a compound represented by the formula (I-3-5).

2.4 g of the compound represented by the formula (I-3-5), 0.5 g of a compound represented by the formula (I-3-6), 0.1

In a nitrogen atmosphere, 2.0 g of a compound represented by the formula (I-3-1), 1.3 g of a compound represented by the formula (I-3-2), 1.9 g of potassium carbonate, 20 mL of ethanol, and 0.2 g of tetrakis(triphenylphosphine)palladium(0) were put into a reactor and heated under reflux for 8 hours. This was diluted with ethyl acetate, and washed sequentially with hydrochloric acid and salt solution. This was purified through column chromatography (silica gel, dichloromethane/ethyl acetate) to give 1.5 g of a compound represented by the formula (I-3-3).

1.0 g of the compound represented by the formula (I-3-3), 2.5 g of a compound represented by the formula (I-3-4), 0.1 g of N,N-dimethylaminopyridine, and 15 mL of dichloromethane were put into a reactor. 1.2 g of diisopropylcarbodiimide was dropwise added thereto and stirred at room g of (±)-10-camphorsulfonic acid, 20 mL of tetrahydrofuran and 5 mL of ethanol were put into a reactor and stirred at room temperature for 20 hours. The solvent was concentrated and the residue was purified through column chromatography (silica gel, dichloromethane) and recrystallization (dichloromethane/methanol) to give 1.9 g of a compound represented by the formula (I-3).

Phase transition temperature (heating process): C 180 N>220 I $^1$H NMR (CDCl$_3$): 1.42-1.60 (m, 8H), 1.68-1.91 (m, 8H), 3.95 (m, 2H), 4.07 (t, 2H), 4.16-4.22 (m, 4H), 5.83 (dd, 2H), 6.09-6.18 (m, 2H), 6.42 (dd, 2H), 6.82 (br, 2H), 7.00 (d, 2H), 7.09 (br, 1H), 7.21 (br, 1H), 7.33 (m, 3H), 7.45 (br, 1H), 7.62 (m, 2H), 7.70 (d, 2H), 8.02 (br, 2H), 8.19 (d, 3H), 8.25 (br, 1H) ppm.

(Example 4: Production of Compound of Formula (I-4))

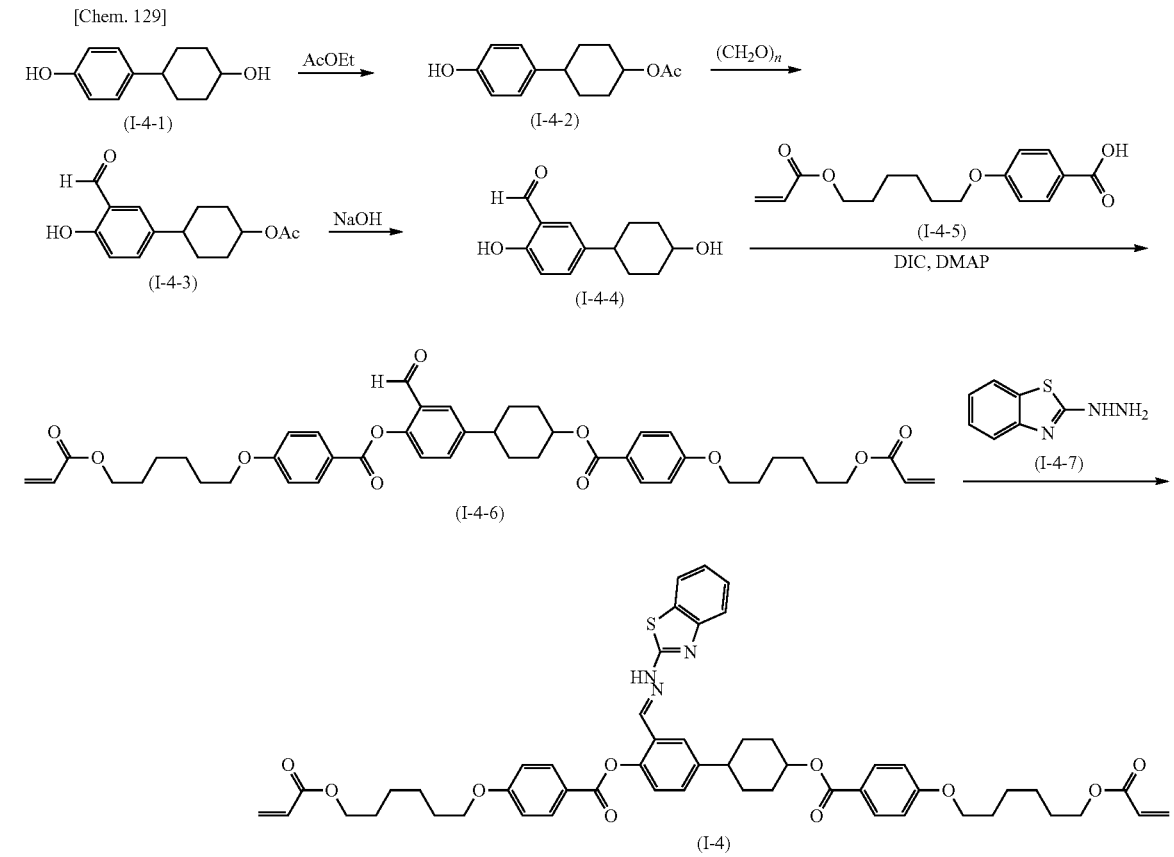

5.0 g of a compound represented by the formula (I-4-1), 0.5 g of p-toluenesulfonic acid hydrate, and 50 mL of ethyl acetate were put into a reactor, and heated under reflux while the solvent was kept changed. This was washed with aqueous sodium hydrogencarbonate solution and salt solution, and then purified through column chromatography (alumina, ethyl acetate) to give 5.4 g of a compound represented by the formula (I-4-2).

5.4 g of the compound represented by the formula (I-4-2), 2.1 g of paraformaldehyde, 3.3 g of magnesium chloride, 30 mL of triethylamine, and 90 mL of acetonitrile were put into a reactor, and heated with stirring at 60° C. for 10 hours. This was diluted with dichloromethane, then washed sequentially with 1% hydrochloric acid, water and salt solution, and thereafter purified through column chromatography (silica gel, dichloromethane/hexane) to give 4.3 g of a compound represented by the formula (I-4-3).

4.3 g of the compound represented by the formula (I-4-3), 30 mL of methanol and 20 mL of aqueous sodium hydroxide solution were put into a reactor, and heated with stirring at 50° C. for 3 hours. This was neutralized with 1% hydrochloric acid, diluted with dichloromethane, and washed sequentially with water and salt solution. This was purified through column chromatography (silica gel, dichloromethane/ethyl acetate) to give 3.2 g of a compound represented by the formula (I-4-4).

1.5 g of the compound represented by the formula (I-4-4), 4.0 g of a compound represented by the formula (I-4-5), 0.2 g of N,N-dimethylaminopyridine, and 30 mL of dichloromethane were put into a reactor. With cooling with ice, 1.9 g of diisopropylcarbodiimide was dropwise added thereto and stirred at room temperature for 10 hours. This was washed sequentially with 1% hydrochloric acid, water and salt solution, and then purified through column chromatography (silica gel, dichloromethane) and recrystallization (dichloromethane/methanol) to give 3.7 g of a compound represented by the formula (I-4-6).

3.7 g of the compound represented by the formula (I-4-6), 0.8 g of a compound represented by the formula (I-4-7), 0.3 g of (±)-10-camphorsulfonic acid, 30 mL of tetrahydrofuran, and 10 mL of ethanol were put into a reactor, and stirred at room temperature for 20 hours. The solvent was evaporated away, and the residue was purified through column chromatography (dichloromethane) and recrystallization (dichloromethane/methanol) to give 3.1 g of a compound represented by the formula (I-4).

Phase transition temperature (heating process): C 60-80 N 206 I $^1$H NMR (CDCl$_3$): 1.44-1.60 (m, 9H), 1.66-1.90 (m, 13H), 2.07 (m, 2H), 2.29 (m, 2H), 2.68 (m, 1H), 4.03 (td, 4H), 4.19 (td, 4H), 5.07 (m, 1H), 5.84 (dt, 2H), 6.13 (dd, 2H), 6.42 (dd, 2H), 6.86 (d, 2H), 6.93 (d, 2H), 7.06-7.22 (m, 3H), 7.30 (dd, 1H), 7.45 (d, 1H), 7.63 (d, 1H), 7.90 (s, 1H), 8.04 (m, 4H), 8.11 (s, 1H) ppm.

(Example 5) Production of Compound of Formula (I-5)
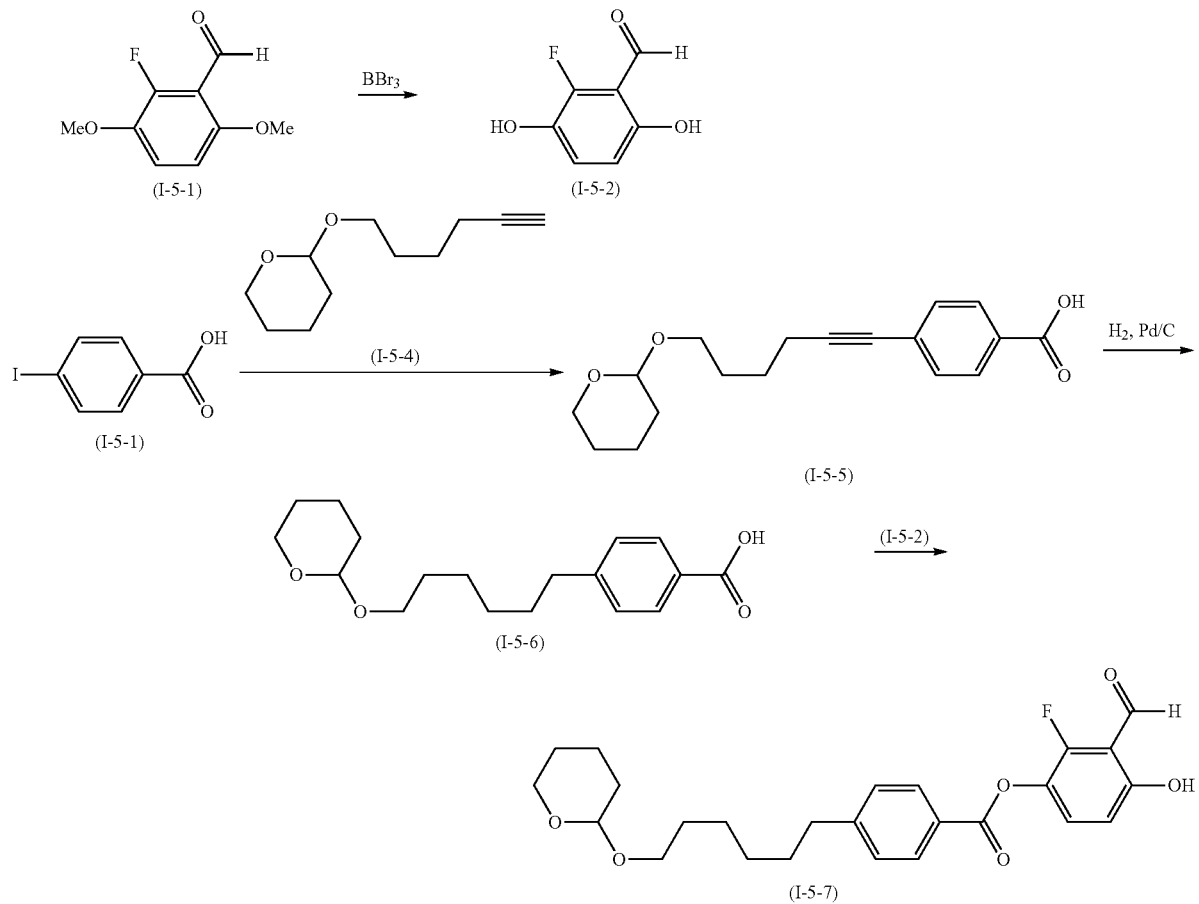
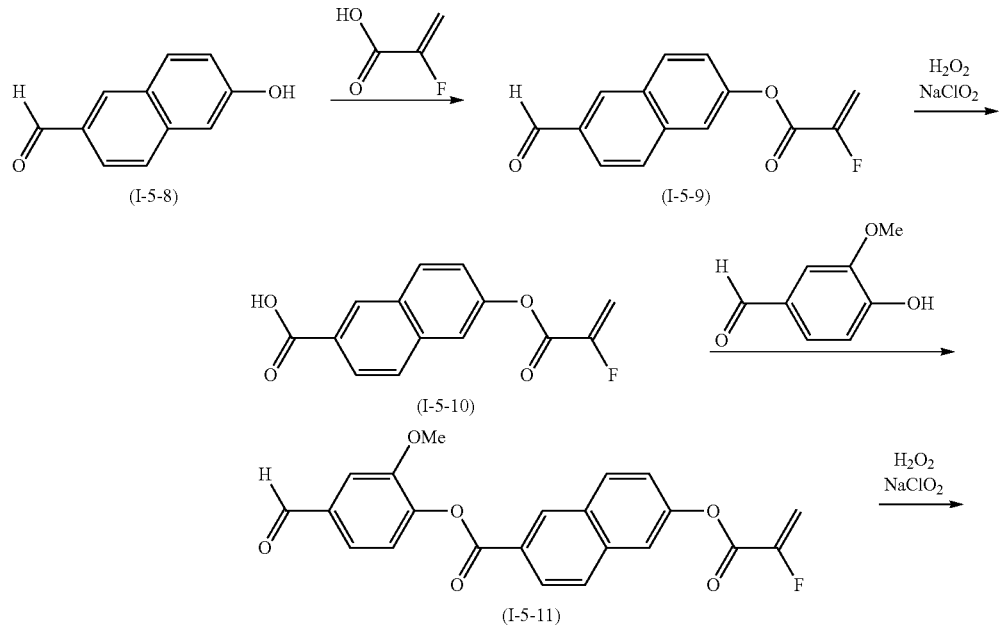

-continued
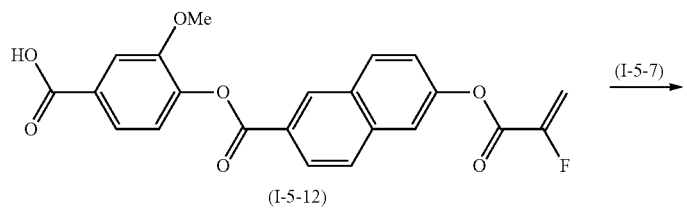
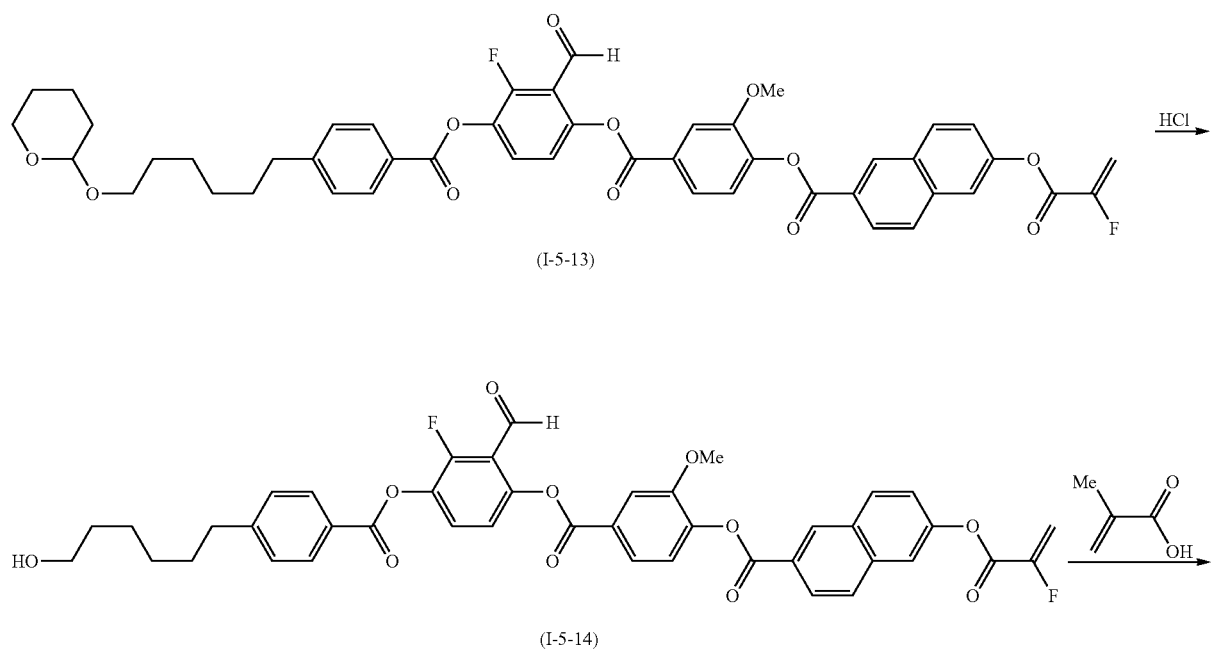
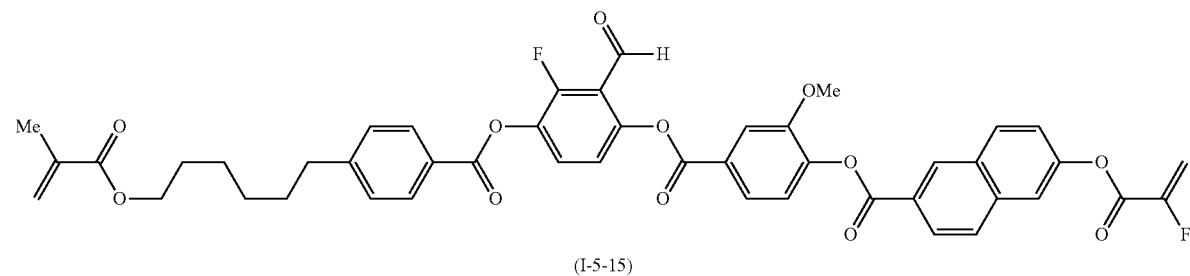
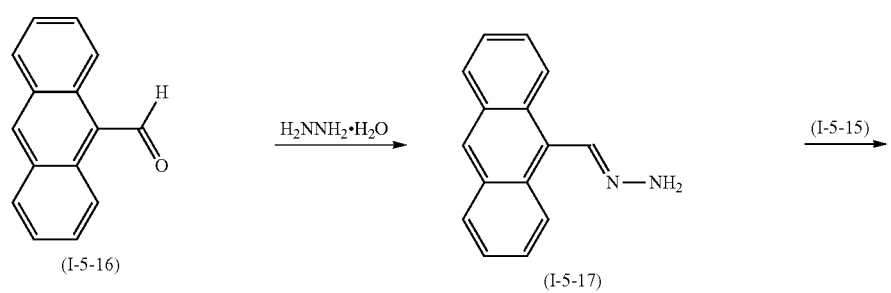

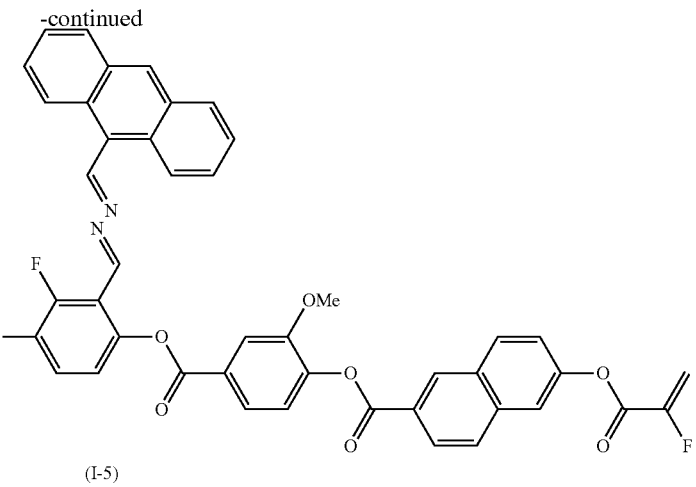

(I-5)

According to the method described in a journal, Bioorganic & Medicinal Chemistry Letters, 2005, Vol. 15, No. 6, pp. 1675-1681, a compound represented by the formula (I-5-1) was produced. 2.0 g of the compound represented by the formula (I-5-1), and 20 mL of dichloromethane were put into a reactor. The reactor was cooled to −78° C., and 8.2 g of boron tribromide was dropwise added thereto and stirred. After poured into water, this was diluted with ethyl acetate, and washed with salt solution. This was purified through column chromatography (dichloromethane/methanol) to give 1.6 g of a compound represented by the formula (I-5-2).

In a nitrogen atmosphere, 3.0 g of a compound represented by the formula (I-5-3), 2.2 g of a compound represented by the formula (I-5-4), 0.05 g of copper(I) iodide, 0.14 g of tetrakis(triphenylphosphine)palladium(0), 10 mL of triethylamine, and 30 mL of N,N-dimethylformamide were put into a reactor, and heated with stirring at 80° C. for 5 hours. After diluted with ethyl acetate, this was washed sequentially with 5% hydrochloric acid, water and salt solution. This was purified through column chromatography (alumina, ethyl acetate) to give 2.6 g of a compound represented by the formula (I-5-5).

2.6 g of the compound represented by the formula (I-5-5), 0.3 g of 5% palladium carbon, and 50 mL of tetrahydrofuran were put into a reactor. This was stirred under a hydrogen pressure of 0.5 MPa at 50° C. for 6 hours. The catalyst was filtered away, and the residue was purified through column chromatography (alumina, ethyl acetate) to give 2.4 g of a compound represented by the formula (I-5-6).

2.9 g of the compound represented by the formula (I-5-6), 1.5 g of the compound represented by the formula (I-5-2), 0.3 g of N,N-dimethylaminopyridine, and 30 mL of dichloromethane were put into a reactor. With cooling with ice, 1.5 g of diisopropylcarbodiimide was dropwise added and stirred at room temperature for 8 hours. This was washed sequentially with 1% hydrochloric acid, water and salt solution, and then purified through column chromatography (dichloromethane/hexane) and recrystallization (dichloromethane/hexane) to give 2.1 g of a compound represented by the formula (I-5-7).

7.0 g of a compound represented by the formula (I-5-8), 3.7 g of 2-fluoroacrylic acid, 0.1 g of N,N-dimethylaminopyridine, and 30 mL of dichloromethane were put into a reactor. 6.7 g of diisopropylcarbodiimide was dropwise added thereto and stirred. After ordinary post-treatment, this was purified through column chromatography and recrystallization to give 3.9 g of a compound represented by the formula (I-5-9).

3.9 g of the compound represented by the formula (I-5-9), 3.5 g of sodium dihydrogenphosphate dihydrate, sodium chlorite, hydrogen peroxide solution, 20 mL of methanol, and 10 mL of water were put into a reactor, and heated with stirring at 50° C. for 6 hours. After ordinary post-treatment, this was purified through column chromatography to give 3.8 g of a compound represented by the formula (I-5-10).

1.0 g of the compound represented by the formula (I-5-10), 0.6 g of vanillin, 0.3 g of N,N-dimethylaminopyridine, and 20 mL of dichloromethane were put into a reactor. 0.6 g of diisopropylcarbodiimide was dropwise added thereto and stirred. After ordinary post-treatment, this was purified through column chromatography and recrystallization to give 1.2 g of a compound represented by the formula (I-5-11).

1.2 g of the compound represented by the formula (I-5-11), sodium dihydrogenphosphate dihydrate, sodium chlorite, hydrogen peroxide solution, 20 mL of methanol, and 10 mL of water were put into a reactor, and heated with stirring at 50° C. for 6 hours. After ordinary post-treatment, this was purified through column chromatography to give 1.2 g of a compound represented by the formula (I-5-12).

1.2 g of the compound represented by the formula (I-5-12), 1.3 g of the compound represented by the formula (I-5-7), 0.2 g of N,N-dimethylaminopyridine, and 20 mL of dichloromethane were put into a reactor. 0.4 g of diisopropylcarbodiimide was dropwise added thereto and stirred. After ordinary post-treatment, this was purified through column chromatography and recrystallization to give 1.7 g of a compound represented by the formula (I-5-13).

1.7 g of the compound represented by the formula (I-5-13), 10 mL of methanol, 20 mL of tetrahydrofuran, and 1 mL of concentrated hydrochloric acid were put into a reactor and stirred. After ordinary post-treatment, this was purified through column chromatography and recrystallization to give 1.4 g of a compound represented by the formula (I-5-14).

1.4 g of the compound represented by the formula (I-5-14), 0.2 g of methacrylic acid, 0.1 g of N,N-dimethylaminopyridine, and 20 mL of dichloromethane were put into a reactor. 0.3 g of diisopropylcarbodiimide was dropwise added thereto and stirred. After ordinary post-treatment, this was purified through column chromatography and recrystallization to give 1.2 g of a compound represented by the formula (I-5-15).

20 mL of hydrazine monohydrate, and 20 mL of ethanol were put into a reactor. 20 mL of a tetrahydrofuran solution of 1.0 g of a compound represented by the formula (I-5-16) was added thereto and stirred. After ordinary post-treatment, this was purified through recrystallization to give 1.0 g of a compound represented by the formula (I-5-17).

0.3 g of the compound represented by the formula (I-5-17), 1.2 g of the compound represented by the formula (I-5-15), 0.1 g of (±)-10-camphorsulfonic acid, 10 mL of tetrahydrofuran, and 5 mL of ethanol were put into a reactor and stirred. After ordinary post-treatment, this was purified through column chromatography and recrystallization to give 1.1 g of a compound represented by the formula (I-5).

LCMS: 1023 [M+1]

(Example 6) Production of Compound of Formula (I-6)

[Chem. 132]

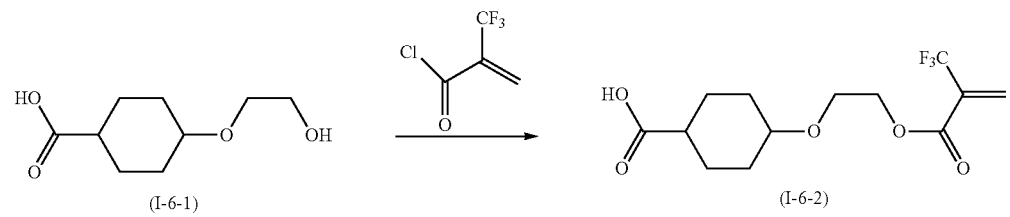

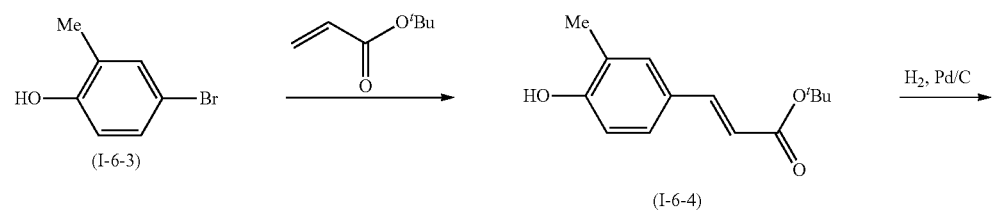

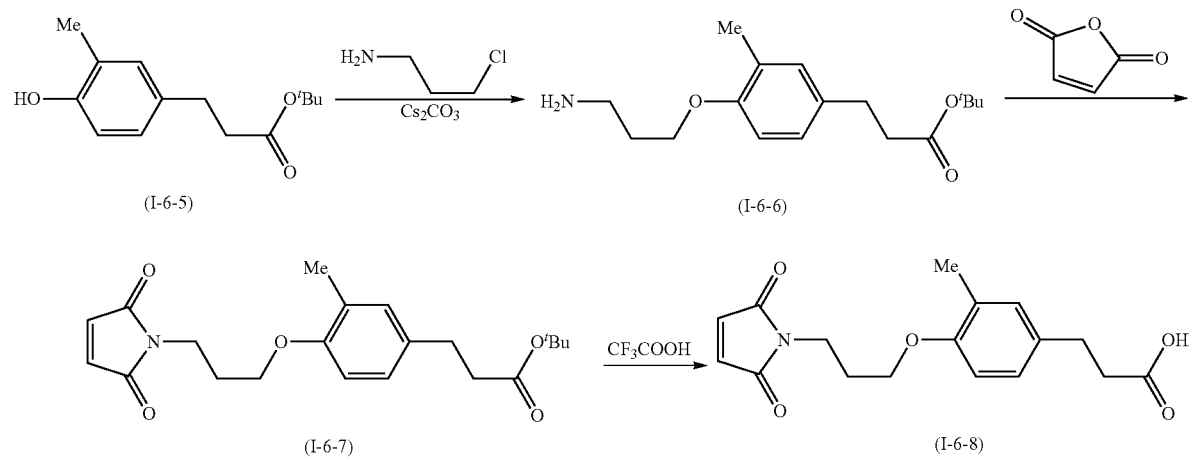

[Chem. 133]

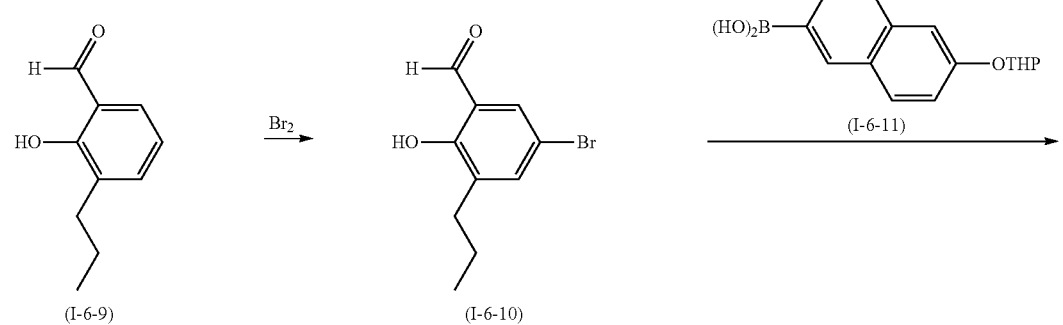

-continued
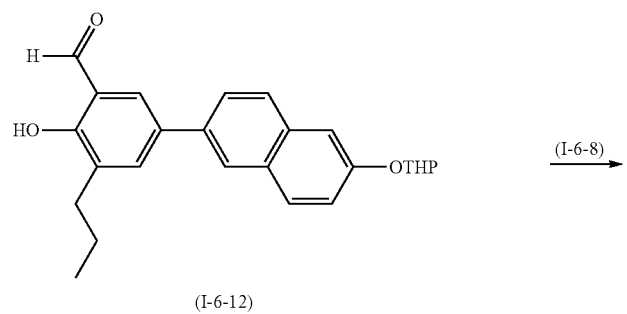
(I-6-12)
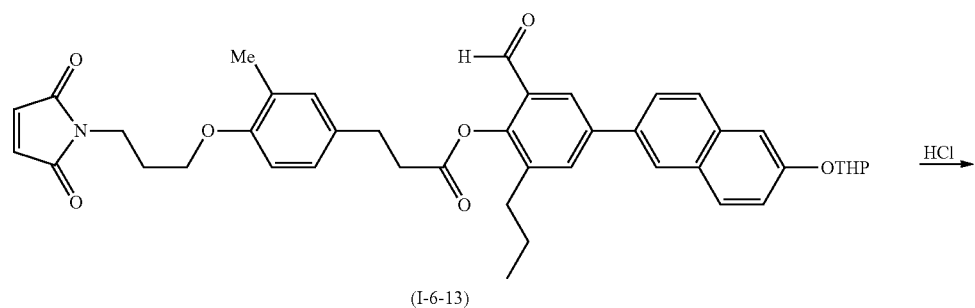
(I-6-13)
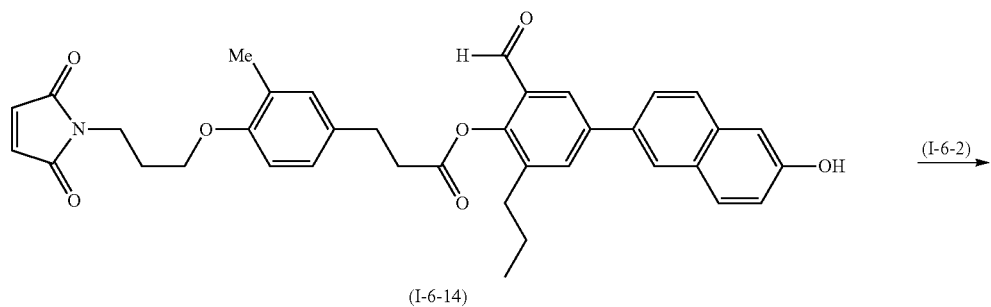
(I-6-14)
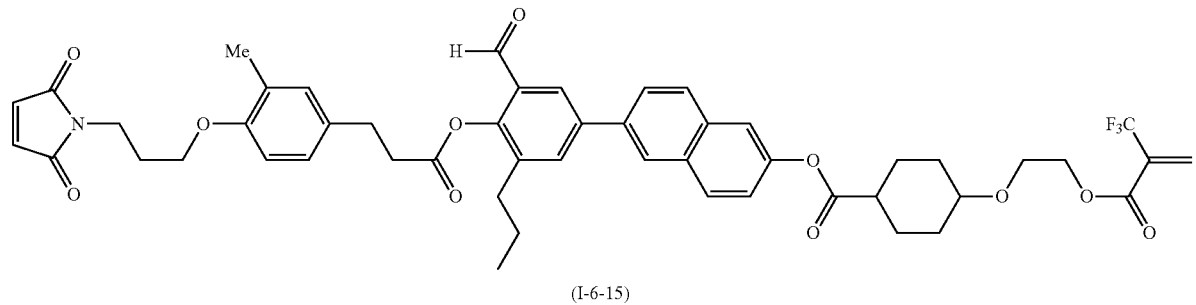
(I-6-15)
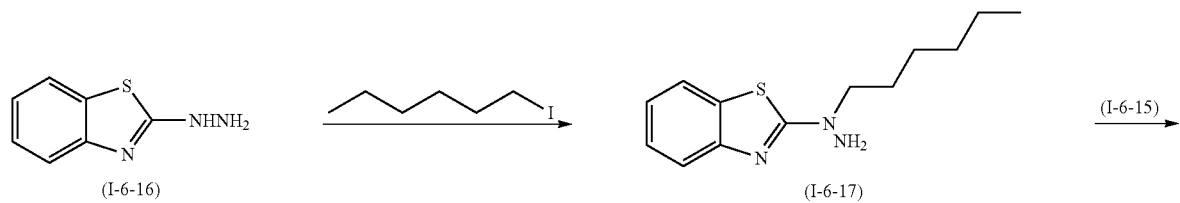

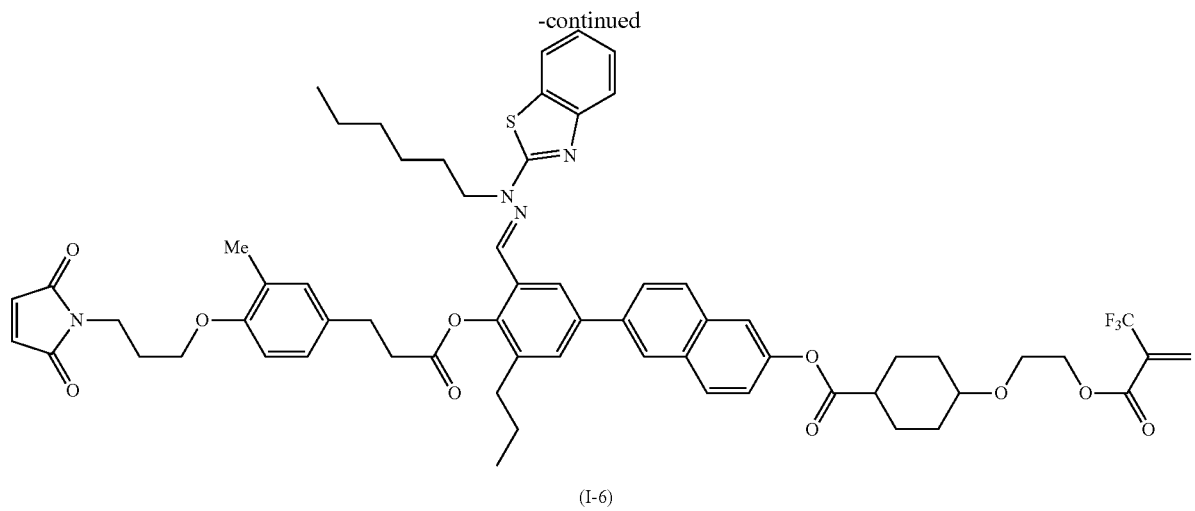

(I-6)

In a nitrogen atmosphere, 5.0 g of a compound represented by the formula (I-6-1), 3.2 g of triethylamine, and 30 mL of dichloromethane were put into a reactor. With cooling with ice, 4.6 g of 2-(trifluoromethyl)acryloyl chloride was dropwise added thereto and stirred. After ordinary post-treatment, this was purified through column chromatography to give 6.6 g of a compound represented by the formula (I-6-2).

In a nitrogen atmosphere, 5.0 g of a compound represented by the formula (I-6-3), 4.1 g of tert-butyl acrylate, 3.3 g of sodium acetate, 30 mL of N,N-dimethylformamide, and 0.1 g of palladium(II) acetate were put into a reactor, and heated with stirring. After ordinary post-treatment, this was purified through column chromatography to give 5.0 g of a compound represented by the formula (I-6-4).

5.0 g of the compound represented by the formula (I-6-4), 0.5 g of 5% palladium carbon, and 50 mL of ethanol were put into a reactor, and stirred in a hydrogen atmosphere (0.5 MPa). The catalyst was filtered away, and the residue was purified through column chromatography to give 4.5 g of a compound represented by the formula (I-6-5).

In a nitrogen atmosphere, 4.5 g of a compound represented by the formula (I-6-5), 2.1 g of 3-chloropropylamine, 9.4 g of cesium carbonate, and 40 mL of dimethyl sulfoxide were put into a reactor and heated with stirring. After ordinary post-treatment, this was purified through column chromatography to give 4.5 g of a compound represented by the formula (I-6-6).

4.5 of the compound represented by the formula (I-6-6), 1.5 g of maleic anhydride, and 20 mL of acetic acid were put into a reactor, and heated with stirring. After ordinary post-treatment, this was purified through column chromatography to give 5.2 g of a compound represented by the formula (I-6-7).

5.2 g of the compound represented by the formula (I-6-7), and 40 mL of dichloromethane were put into a reactor. With cooling with ice, 10 mL of trifluoroacetic acid was added and stirred. After ordinary post-treatment, this was purified through column chromatography to give 4.0 g of a compound represented by the formula (I-6-8).

A compound represented by the formula (I-6-9) was produced according to the method described in JP 2011-207765 A. 2.0 g of the compound represented by the formula (I-6-9), and 30 mL of dichloromethane were put into a reactor. With cooling with ice, 2.1 g of bromine was added thereto and stirred. After ordinary post-treatment, this was purified through column chromatography to give 2.4 g of a compound represented by the formula (I-6-10).

In a nitrogen atmosphere, 2.4 g of the compound represented by the formula (I-6-10), 2.7 g of a compound represented by the formula (I-6-11), 2.0 g of potassium carbonate, 30 mL of ethanol, and 0.1 g of tetrakis(triphenylphosphine) palladium(0) were put into a reactor and heated with stirring. After ordinary post-treatment, this was purified through column chromatography to give 3.0 g of a compound represented by the formula (I-6-12).

In a nitrogen atmosphere, 3.0 g of the compound represented by the formula (I-6-12), 2.5 g of the compound represented by the formula (I-6-8), 0.2 g of N,N-dimethylaminopyridine, and 30 mL of dichloromethane were put into a reactor. With cooling with ice, 1.2 g of diisopropylcarbodiimide was added thereto and stirred. After ordinary post-treatment, this was purified through column chromatography to give 4.3 g of a compound represented by the formula (I-6-13).

4.3 g of the compound represented by the formula (I-6-13), 30 mL of tetrahydrofuran, 20 mL of methanol, and 1 mL of concentrated hydrochloric acid were put into a reactor and stirred. After ordinary post-treatment, this was purified through column chromatography and recrystallization to give 3.4 g of a compound represented by the formula (I-6-14).

In a nitrogen atmosphere, 3.4 g of the compound represented by the formula (I-6-14), 1.7 g of the compound represented by the formula (I-6-2), 0.1 g of N,N-dimethylaminopyridine, and 30 mL of dichloromethane were put into a reactor. With cooling with ice, 0.8 g of diisopropylcarbodiimide was added thereto and stirred. After ordinary post-treatment, this was purified through column chromatography and recrystallization to give 4.0 g of a compound represented by the formula (I-6-15).

3.0 g of a compound represented by the formula (I-6-16), 4.6 g of 1-iodohexane, 8.9 g of cesium carbonate, and 20 mL of dimethyl sulfoxide were put into a reactor and heated with stirring. After ordinary post-treatment, this was purified through column chromatography to give 2.3 g of a compound represented by the formula (I-6-17).

0.6 g of the compound represented by the formula (I-6-17), 2.0 g of the compound represented by the formula (I-6-15), 0.3 g of (±)-10-camphorsulfonic acid, 20 mL of tetrahydrofuran, and 10 mL of ethanol were put into reactor and stirred. After ordinary post-treatment, this was purified through column chromatography and recrystallization to give 1.8 g of a compound represented by the formula (I-6).

LCMS: 1129 [M+1]

(Example 7) Production of Compound of Formula (I-7)
[Chem. 134]
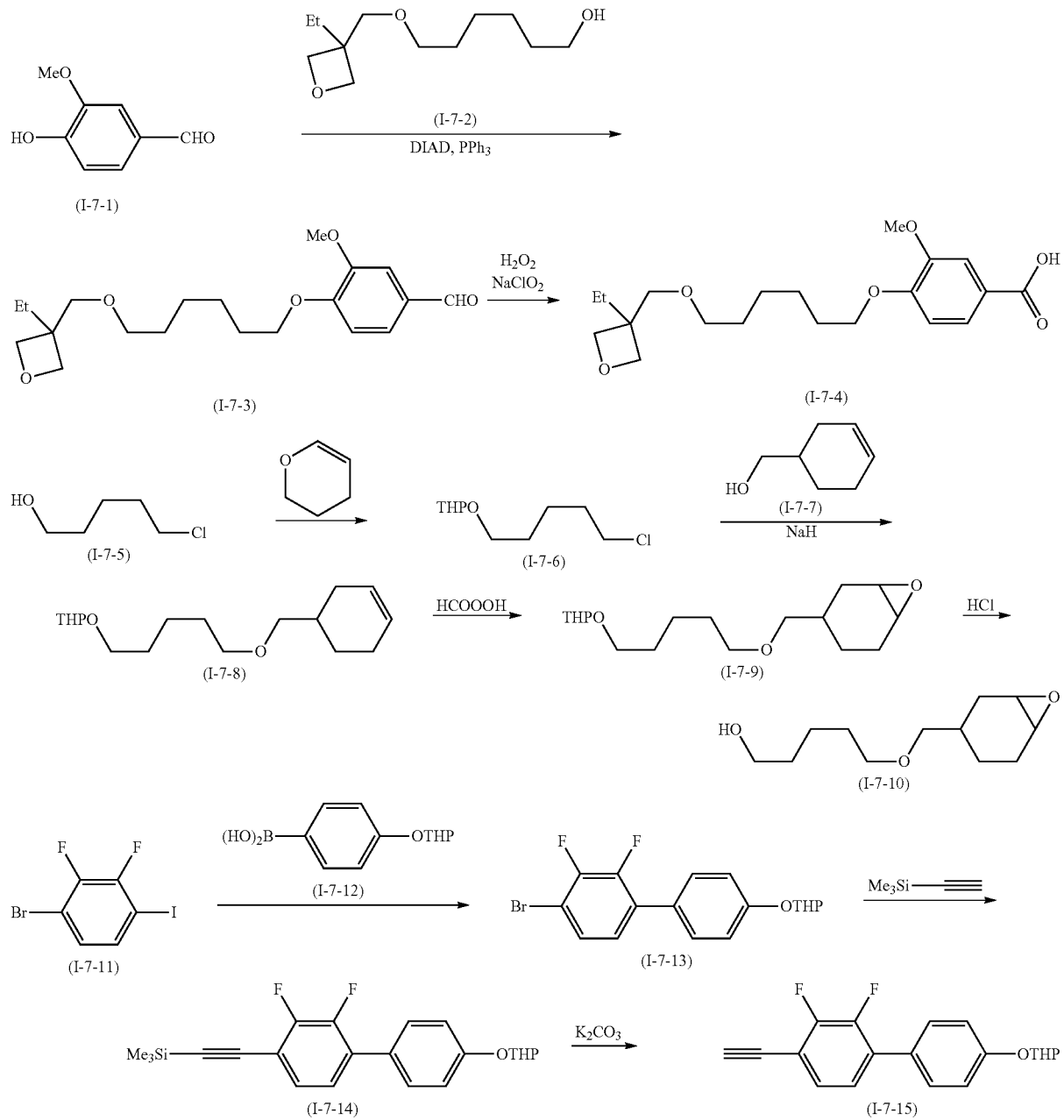
[Chem. 135]
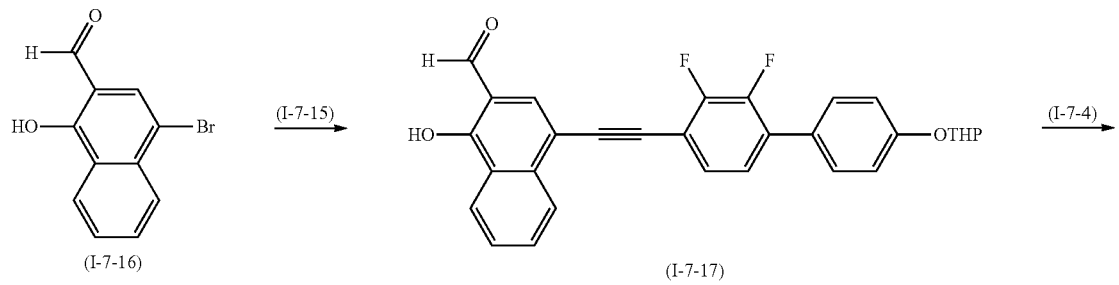

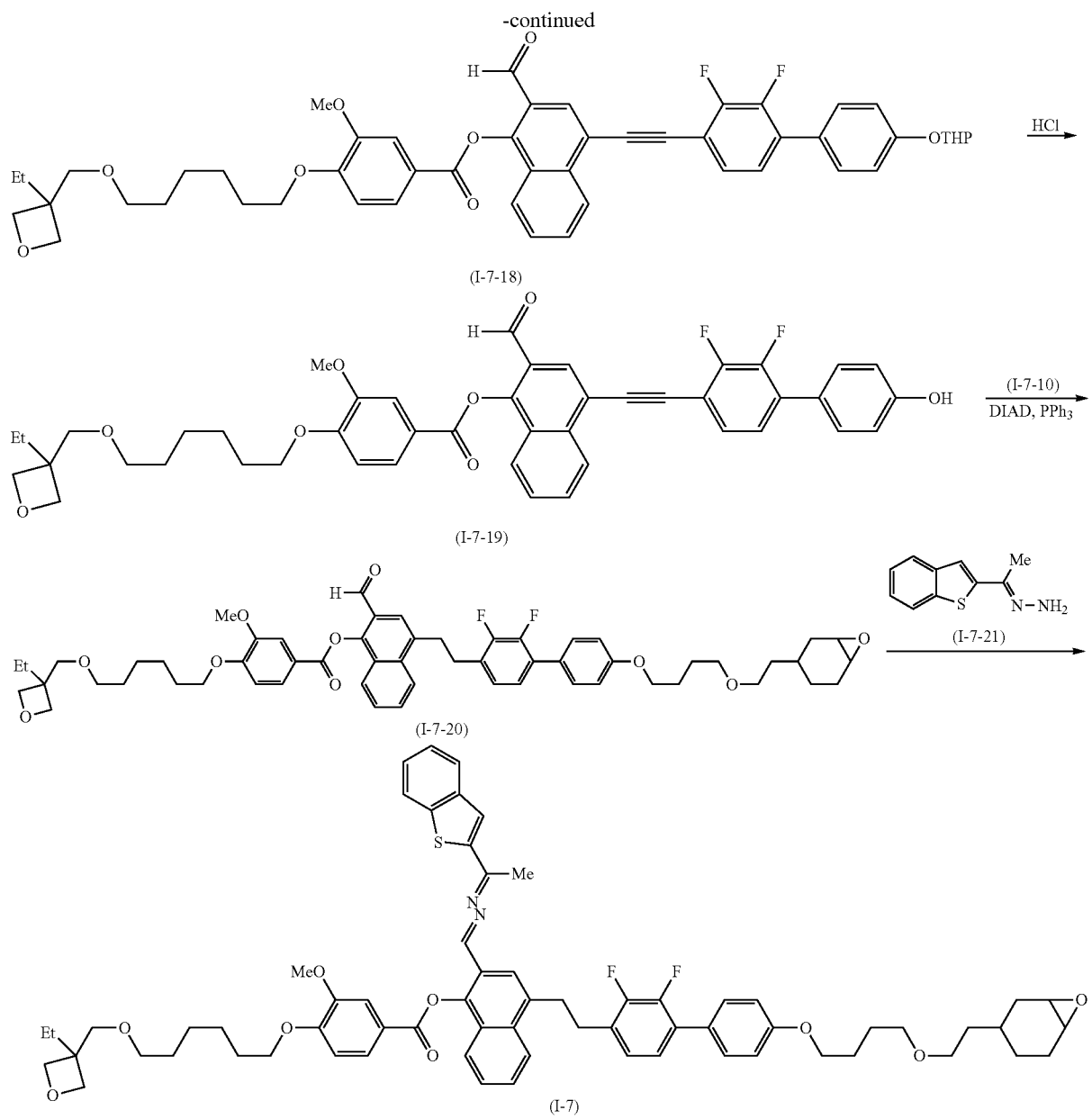

According to the method described in a journal, Macromolecular Chemistry and Physics, 2009, Vol. 210, No. 7, pp. 531-541, a compound represented by the formula (I-7-2) was produced. In a nitrogen atmosphere, 5.0 g of a compound represented by the formula (I-7-1), 7.1 g of the compound represented by the formula (I-7-2), 9.5 g of triphenylphosphine, and 60 mL of tetrahydrofuran were put into a reactor. With cooling with ice, 7.3 g of diisopropyl azodicarboxylate was added thereto and stirred. After ordinary post-treatment, this was purified through column chromatography to give 8.1 g of a compound represented by the formula (I-7-3).

8.1 g of the compound represented by the formula (I-7-3), sodium dihydrogenphosphate dihydrate, methanol, water and hydrogen peroxide solution were put into a reactor. An aqueous solution of sodium chlorite was dropwise added thereto and heated with stirring. This was cooled with water added, and the precipitate was taken out through filtration. This was dried to give 6.7 g of a compound represented by the formula (I-7-4).

In a nitrogen atmosphere, 5.0 g of a compound represented by the formula (I-7-5), 0.5 g of pyridinium p-toluenesulfonate, and 30 mL of dichloromethane were put into a reactor. With cooling with ice, 3.8 g of 3,4-dihydro-2H-pyran was added thereto and stirred. After ordinary post-treatment, this was purified through column chromatography to give 7.6 g of a compound represented by the formula (I-7-6).

4.1 g of a compound represented by the formula (I-7-7), 20 mL of tetrahydrofuran, and 0.9 g of sodium hydride were put into a reactor and stirred. A tetrahydrofuran solution of 7.6 g of the compound represented by the formula (I-7-6) was dropwise added thereto and heated with stirring. Water was dropwise added thereto, and after ordinary post-treatment, this was purified through column chromatography to give 7.2 g of a compound represented by the formula (I-7-8).

30 mL of formic acid, and 30 mL of hydrogen peroxide were put into a reactor and stirred. A dichloromethane solution of 7.2 g of the compound represented by the formula (I-7-8) was dropwise added thereto and heated with stirring. After ordinary post-treatment, this was purified through column chromatography to give 6.9 g of a compound represented by the formula (I-7-9).

6.9 g of the compound represented by the formula (I-7-9), 30 mL of methanol, 30 mL of tetrahydrofuran, and 1 mL of concentrated hydrochloric acid were put into a reactor and heated with stirring. After ordinary post-treatment, this was purified through column chromatography to give 4.5 g of a compound represented by the formula (I-7-10).

In a nitrogen atmosphere, 5.0 g of a compound represented by the formula (I-7-11), 3.5 g of a compound represented by the formula (I-7-12), 3.2 g of potassium carbonate, 30 mL of tetrahydrofuran, 30 mL of water, and 0.2 g of tetrakis(triphenylphosphine)palladium(0) were put in a reactor and heated with stirring. After ordinary post-treatment, this was purified through column chromatography to give 4.6 g of a compound represented by the formula (I-7-13).

In a nitrogen atmosphere, 4.6 g of the compound represented by the formula (I-7-13), 1.5 g of trimethylsilylacetylene, 0.05 g of copper(I) iodide, 30 mL of triethylamine, 90 mL of N,N-dimethylformamide, and 0.1 g of tetrakis(triphenylphosphine)palladium(0) were put into a reactor and heated with stirring. After ordinary post-treatment, this was purified through column chromatography to give 3.4 g of a compound represented by the formula (I-7-14).

3.4 g of the compound represented by the formula (I-7-14), 50 mL of methanol and 3.6 g of potassium carbonate were put into a reactor and stirred. After ordinary post-treatment, this was purified through column chromatography to give 2.5 g of a compound represented by the formula (I-7-15).

A compound represented by the formula (I-7-16) was produced according to the method described in a journal, Synthetic Communications, 2011, Vol. 41, No. 9, pp. 1381-1393. In a nitrogen atmosphere, 2.0 g of the compound represented by the formula (I-7-16), 2.5 g of the compound represented by the formula (I-7-15), 0.03 g of copper(I) iodide, 30 mL of triethylamine, 90 mL of N,N-dimethylformamide, and 0.1 g of tetrakis(triphenylphosphine)palladium (0) were put in a reactor and heated with stirring. After ordinary post-treatment, this was purified through column chromatography to give 2.7 g of a compound represented by the formula (I-7-17).

In a nitrogen atmosphere, 2.7 g of the compound represented by the formula (I-7-17), 1.5 g of the compound represented by the formula (I-7-4), 0.2 g of N,N-dimethylaminopyridine, and 30 mL of dichloromethane were put in a reactor. With cooling with ice, 0.8 g of diisopropylcarbodiimide was added thereto and stirred. After ordinary post-treatment, this was purified through column chromatography and recrystallization to give 3.7 g of a compound represented by the formula (I-7-18).

3.7 g of the compound represented by the formula (I-7-18), 30 mL of tetrahydrofuran, 30 mL of methanol and 1 mL of concentrated hydrochloric acid were put in a reactor and stirred. After ordinary post-treatment, this was purified through column chromatography and recrystallization to give 3.0 g of a compound represented by the formula (I-7-19).

In a nitrogen atmosphere, 3.0 g of the compound represented by the formula (I-7-19), 0.9 g of the compound represented by the formula (I-7-10), 1.3 g of triphenyl phosphine, and 30 mL of tetrahydrofuran were put in a reactor. With cooling with ice, 1.0 g of diisopropyl azodicarboxylate was added thereto and stirred. After ordinary post-treatment, this was purified through column chromatography to give 2.7 g of a compound represented by the formula (I-7-20).

A compound represented by the formula (I-7-21) was produced according to the method described in WO2012-141245 A1. 2.7 g of the compound represented by the formula (I-7-20), 0.5 g of the compound represented by the formula (I-7-21), 0.3 g of (±)-10-camphorsulfonic acid, 30 mL of tetrahydrofuran, and 20 mL of ethanol were put in a reactor and stirred. After ordinary post-treatment, this was purified through column chromatography and recrystallization to give 2.2 g of a compound represented by the formula (I-7).

LCMS: 1121 [M+1]

(Example 8) Production of Compound of Formula (I-8)

[Chem. 136]

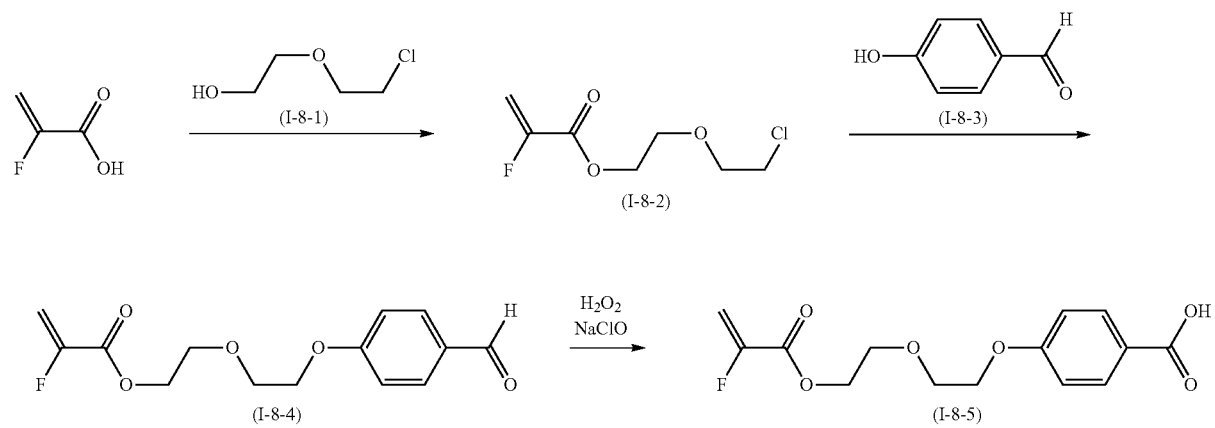

-continued
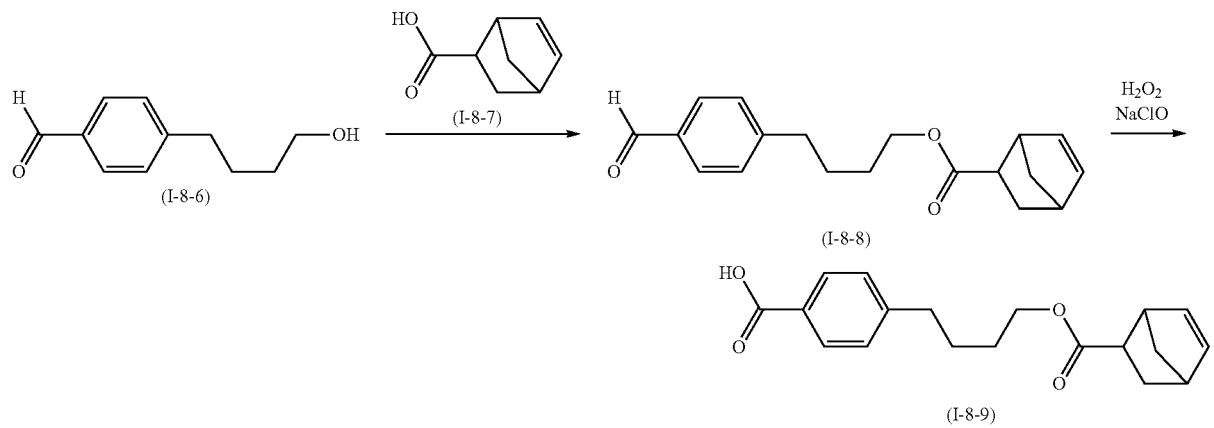
[Chem. 137]
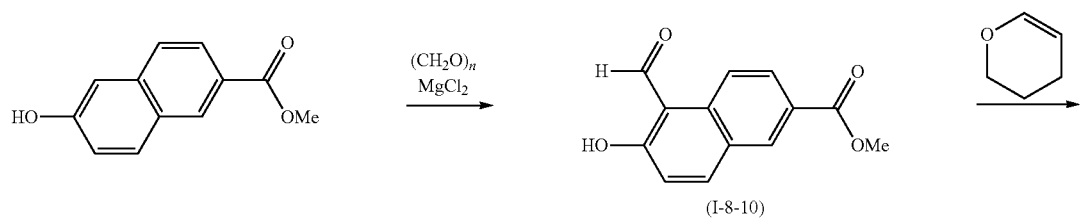
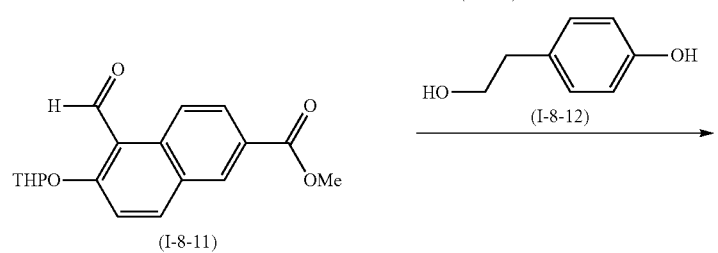
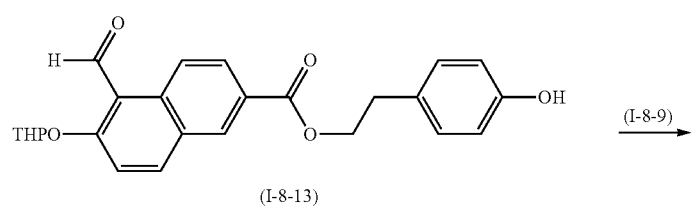
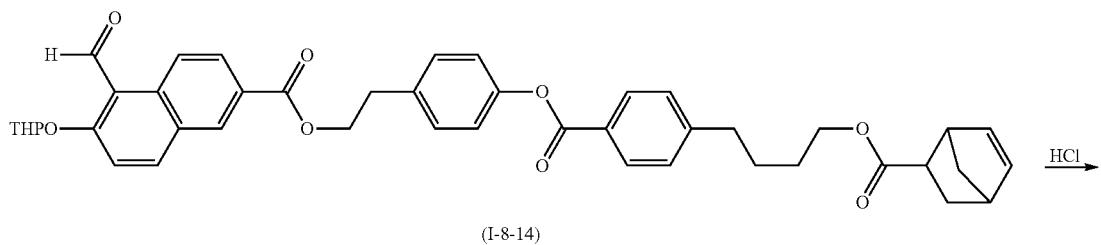
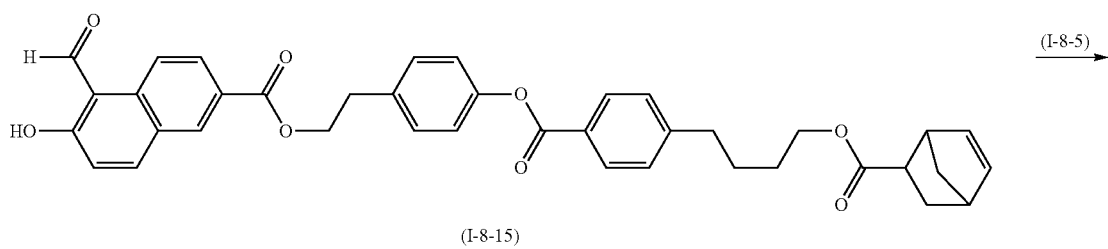

-continued

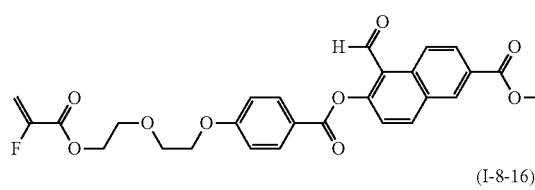
(I-8-16)

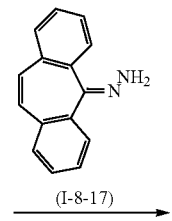
(I-8-17)

(I-8)

In a nitrogen atmosphere, 3.0 g of 2-fluoroacrylic acid, 4.2 g of a compound represented by the formula (I-8-1), 0.2 g of N,N-dimethylaminopyridine, and 40 mL o dichloromethane were put in a reactor. With cooling with ice, 5.0 g of diisopropylcarbodiimide was added thereto and stirred. After ordinary post-treatment, this was purified through column chromatography to give 5.2 g of a compound represented by the formula (I-8-2).

5.2 g of the compound represented by the formula (I-8-2), 3.2 g of a compound represented by the formula (I-8-3), 13.0 g of cesium carbonate, and 50 mL of dimethyl sulfoxide were put in a reactor and heated with stirring. After ordinary post-treatment, this was purified through column chromatography to give 6.0 g of a compound represented by the formula (I-8-4).

6.0 g of the compound represented by the formula (I-8-4), sodium dihydrogenphosphate dihydrate, 50 mL of methanol, 10 mL of water, and 30 mL of hydrogen peroxide solution were put in a reactor. 30 mL of an aqueous solution of sodium chlorite was dropwise added thereto and heated with stirring. This was cooled with water added, and the precipitate was taken out through filtration. This was dried to give 5.1 g of a compound represented by the formula (I-8-5).

In a nitrogen atmosphere, 3.0 g of a compound represented by the formula (I-8-6), 2.3 g of a compound represented by the formula (I-8-7), 0.3 g of N,N-dimethylaminopyridine, and 30 mL of dichloromethane were put in a reactor. With cooling with ice, 2.6 g of diisopropylcarbodiimide was added thereto and stirred. After ordinary post-treatment, this was purified through column chromatography to give 4.0 g of a compound represented by the formula (I-8-8).

4.0 g of the compound represented by the formula (I-8-8), sodium dihydrogenphosphate dihydrate, 30 mL of methanol, 10 mL of water and 20 mL of hydrogen peroxide solution were put in a reactor. 20 mL of an aqueous solution of sodium chloride was dropwise added thereto and heated with stirring. This was cooled with water added, and the precipitate was taken out through filtration. This was dried to give 3.4 g of a compound represented by the formula (I-8-9).

5.0 g of methyl 6-hydroxy-2-naphthalenecarboxylate, 3.0 g of paraformaldehyde, 20 mL of triethylamine, 3.5 g of magnesium chloride, and 30 mL of acetonitrile were put in a reactor and heated with stirring. The reaction liquid was poured into hydrochloric acid, and after ordinary post-treatment, this was purified through column chromatography to give 4.5 g of a compound represented by the formula (I-8-10).

In a nitrogen atmosphere, 4.5 g of the compound represented by the formula (I-8-10), 0.5 g of pyridinium p-toluenesulfonate, and 30 mL of dichloromethane were put in a reactor. With cooling with ice, 1.8 g of 3,4-dihydro-2H-pyran was added thereto and stirred. After ordinary post-treatment, this was purified through column chromatography to give 5.6 g of a compound represented by the formula (I-8-11).

5.6 g of the compound represented by the formula (I-8-11), 2.5 g of a compound represented by the formula (I-8-12), 0.5 g of dibutyltin oxide, and 30 mL of xylene were put in a reactor and heated with stirring. After ordinary post-treatment, this was purified through column chromatography to give 6.0 g of a compound represented by the formula (I-8-13).

In a nitrogen atmosphere, 6.0 g of the compound represented by the formula (I-8-13), 4.5 g of the compound represented by the formula (I-8-9), 0.2 g of N,N-dimethylaminopyridine, and 30 mL of dichloromethane were put in a reactor. With cooling with ice, 2.2 g of diisopropylcarbodiimide was added thereto and stirred. After ordinary post-treatment, this was purified through column chromatography and recrystallization to give 8.2 g of a compound represented by the formula (I-8-14).

3.0 g of the compound represented by the formula (I-8-14), 30 mL of tetrahydrofuran, 10 mL of methanol and 1 mL of concentrated hydrochloric acid were put in a reactor and stirred. After ordinary post-treatment, this was purified through column chromatography and recrystallization to give 2.4 g of a compound represented by the formula (I-8-15).

In a nitrogen atmosphere, 2.4 g of the compound represented by the formula (I-8-15), 1.1 g of the compound represented by the formula (I-8-5), 0.1 g of N, N-dimethylaminopyiridine, and 30 mL of dichloromethane were put in a reactor. With cooling with ice, 0.6 g of diisopropylcarbodiimide was added thereto and stirred. After ordinary post-treatment, this was purified through column chromatography and recrystallization to give 2.8 g of a compound represented by the formula (I-8-16).

A compound represented by the formula (I-8-17) was produced according to the method described in WO2012-141245 A1. 2.8 g of the compound represented by the formula (I-8-16), 0.7 g of the compound represented by the formula (I-8-17), 0.3 g of (±)-10-camphorsulfonic acid, 30 mL of tetrahydrofuran, and 20 mL of ethanol were put in a reactor and stirred. After ordinary post-treatment, this was purified through column chromatography and recrystallization to give 2.4 g of a compound represented by the formula (I-8).

LCMS: 1115 [M+1]

(Example 9) Production of Compound of Formula (I-9)

[Chem. 138]

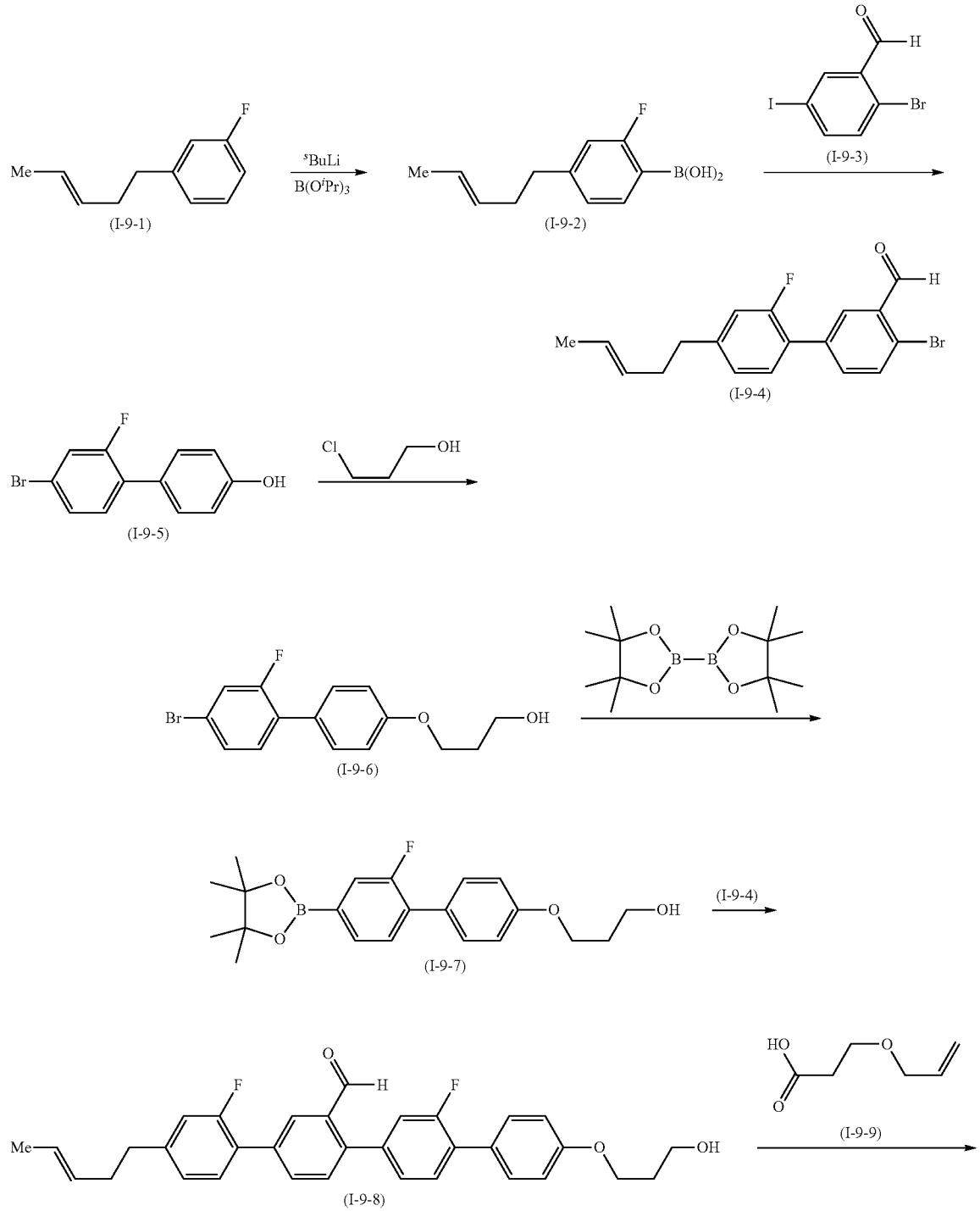

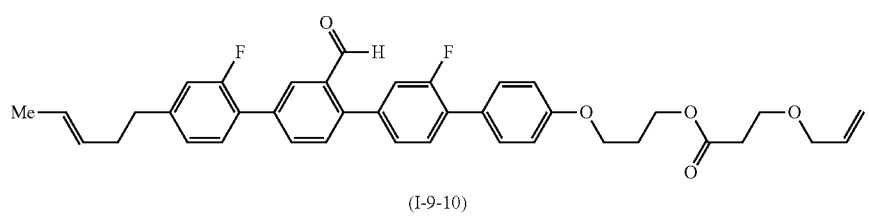

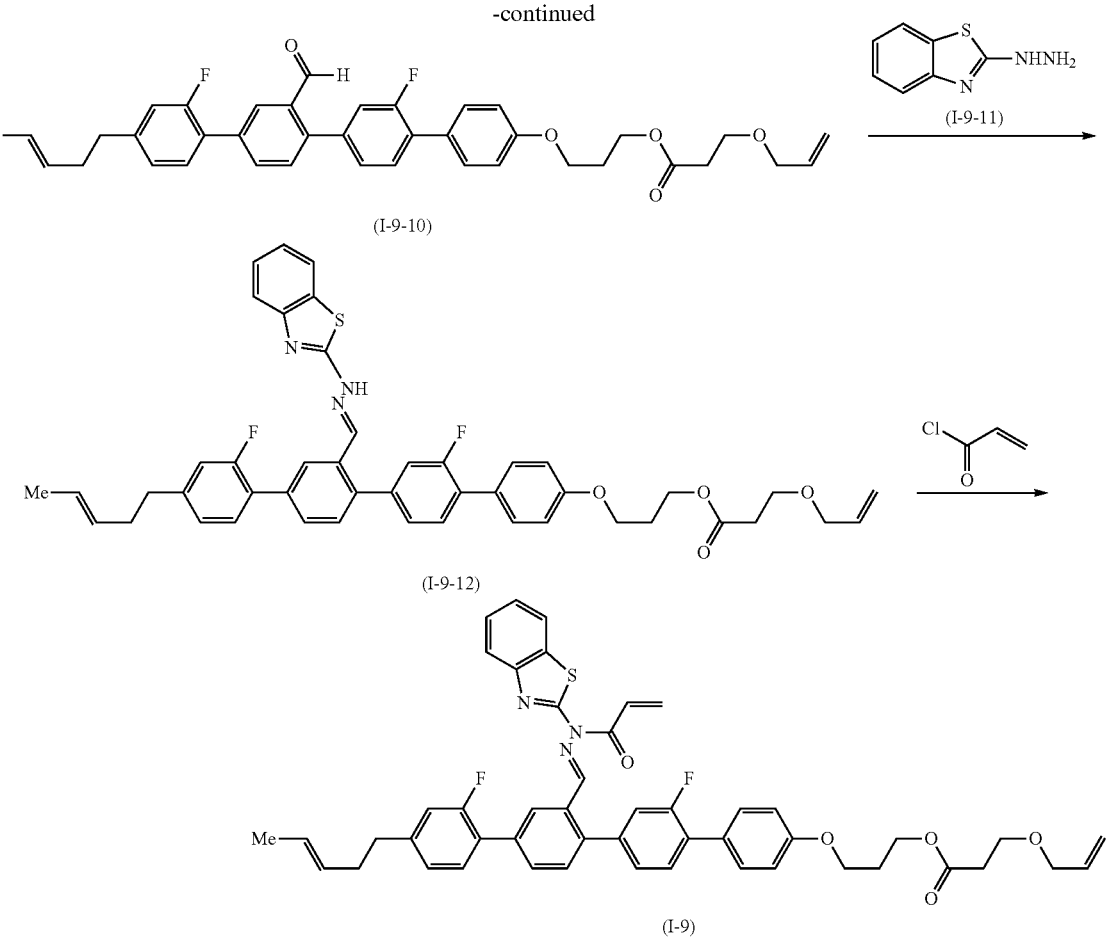

In a nitrogen atmosphere, 5.0 g of a compound represented by the formula (I-9-1), and tetrahydrofuran were put in a reactor. This was cooled to −78° C., and a hexane solution of s-butyl lithium was added thereto and stirred. 6.3 g of triisopropyl borate was added and stirred. Heated up to 5° C., hydrochloric acid was added thereto and stirred. After ordinary post-treatment, this was dried to give 5.1 g of a compound represented by the formula (I-9-2).

According to the method described in a journal, European Journal of Organic Chemistry, 2008, No. 10, pp. 1797-1801, a compound represented by the formula (I-9-3) was produced. In a nitrogen atmosphere, 2.0 g of the compound represented by the formula (I-9-2), 3.0 g of the compound represented by the formula (I-9-3), 2.0 g of potassium carbonate, 20 mL of tetrahydrofuran, 20 mL of water, and 0.1 g of tetrakis(triphenylphosphine)palladium(0) were put in a reactor and heated with stirring. After ordinary post-treatment, this was purified through column chromatography to give 2.3 g of a compound represented by the formula (I-9-4).

According to the method described in JP 2012-240945 A, a compound represented by the formula (I-9-5) was produced. 2.0 g of the compound represented by the formula (I-9-5), 0.8 g of 3-chloropropanol, 3.7 g of cesium carbonate, and 30 mL of dimethyl sulfoxide were put in a reactor and heated with stirring. After ordinary post-treatment, this was purified through column chromatography and recrystallization to give 1.9 g of a compound represented by the formula (I-9-6).

In a nitrogen atmosphere, 1.9 g of the compound represented by the formula (I-9-6), 1.5 g of bis(pinacolato)diboron, 0.9 g of potassium acetate, 20 mL of dimethyl sulfoxide, and 0.1 g of bis(triphenylphosphine) palladium (II) dichloride were put in a reactor and heated with stirring. After ordinary post-treatment, this gave 1.8 g of a compound represented by the formula (I-9-7).

In a nitrogen atmosphere, 1.8 g of the compound represented by the formula (I-9-7), 1.7 g of the compound represented by the formula (I-9-4), 1.0 g of potassium carbonate, 20 mL of tetrahydrofuran, 10 mL of water, and 0.1 g of tetrakis(triphenylphosphine)palladium(0) were put in a reactor and heated with stirring. After ordinary post-treatment, this was purified through column chromatography and recrystallization to give 2.0 g of a compound represented by the formula (I-9-8).

In a nitrogen atmosphere, 2.0 g of the compound represented by the formula (I-9-8), 0.5 g of a compound represented by the formula (I-9-9), 0.1 g of N,N-dimethylaminopyridine, and 20 mL of dichloromethane were put in a reactor. With cooling with ice, 0.6 g of diisopropylcarbodiimide was added thereto and stirred. After ordinary post-treatment, this was purified through column chromatography and recrystallization to give 1.9 g of a compound represented by the formula (I-9-10).

1.9 g of the compound represented by the formula (I-9-10), 0.5 g of a compound represented by the formula (I-9-11), 0.3 g of (±)-10-camphorsulfonic acid, 20 mL of tetrahydrofuran, and 10 mL of ethanol were put in a reactor and stirred. After ordinary post-treatment, this was purified through column chromatography and recrystallization to give 1.6 g of a compound represented by the formula (I-9-12).

In a nitrogen atmosphere, 1.6 g of the compound represented by the formula (I-9-12), 0.3 g of triethylamine, and 20 mL of dichloromethane were put in a reactor. With cooling with ice, 0.5 g of acryloyl chloride was added thereto and stirred. After ordinary post-treatment, this was purified through column chromatography and recrystallization to give 1.4 g of a compound represented by the formula (I-9).

LCMS: 826 [M+1]

(Example 10) Production of Compound of Formula (I-10)

[Chem. 139]

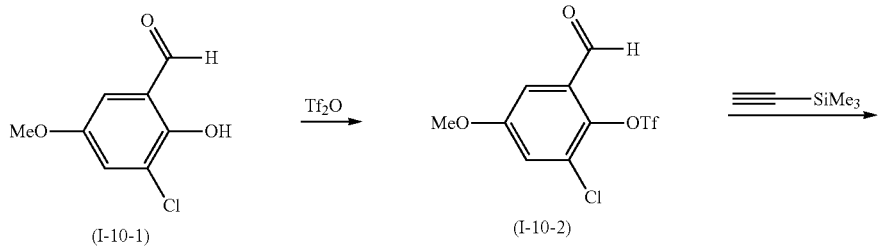

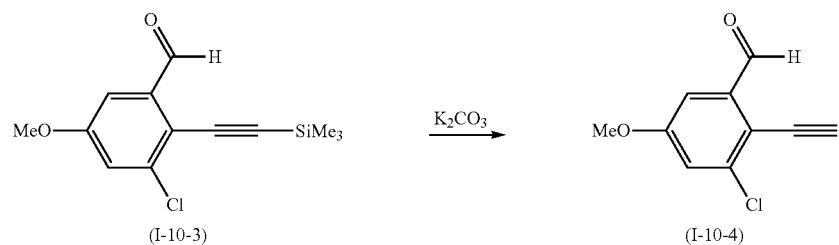

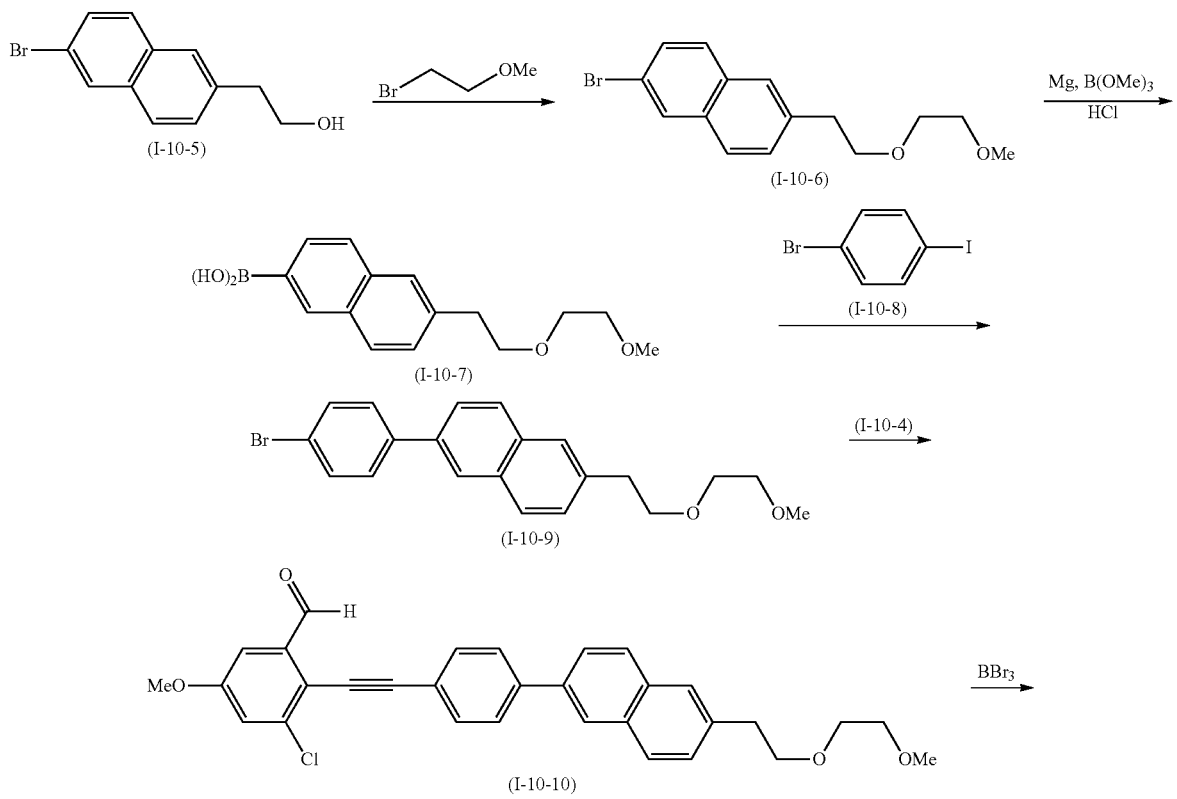

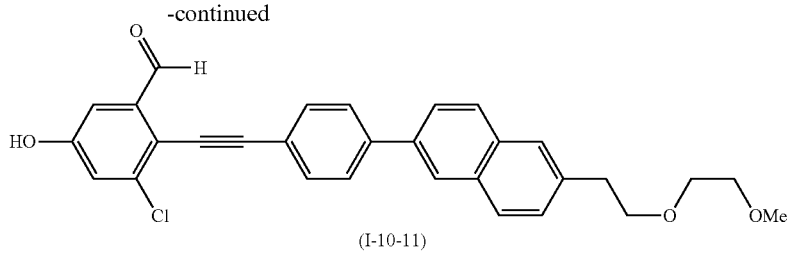
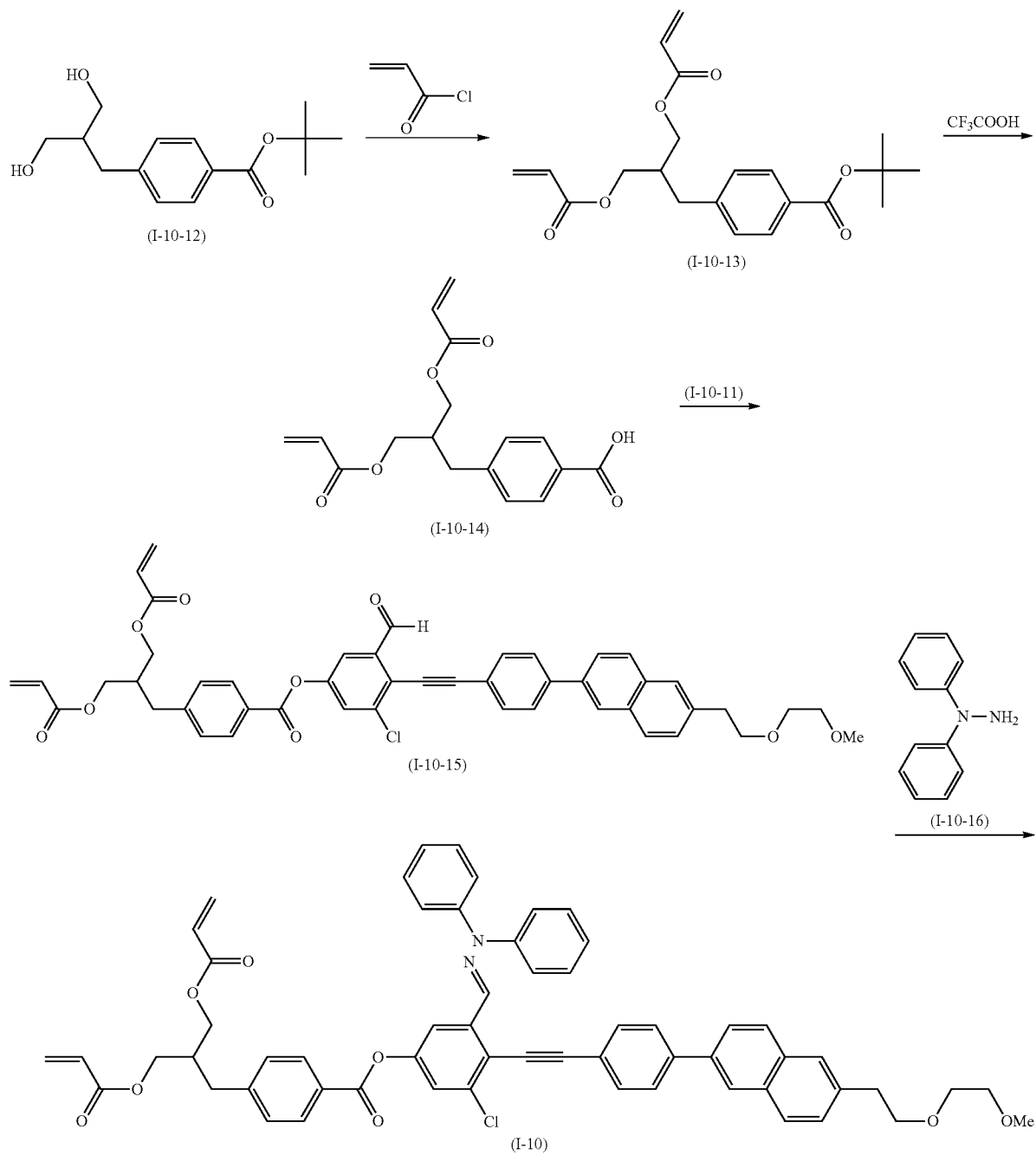
According to the method described in a journal, Organic Letters, 2014, Vol. 16, No. 13, pp. 3544-3547, a compound represented by the formula (I-10-1) was produced. In a nitrogen atmosphere, 5.0 g of the compound represented by the formula (I-10-1), 2.3 g of pyridine and 50 mL of dichloromethane were put in a reactor. With cooling with ice, 8.3 g of trifluoromethanesulfonic acid anhydride was added thereto and stirred. After ordinary post-treatment, this was purified through column chromatography to give 7.7 g of a compound represented by the formula (I-10-2).

In a nitrogen atmosphere, 7.7 g of the compound represented by the formula (I-10-2), 2.6 g of trimethylsilylacetylene, 0.09 g of copper(I) iodide, 20 mL of triethylamine, 60 mL of N,N-dimethylformamide, and 0.3 g of tetrakis(triphenylphosphine)palladium(0) were put in a reactor and heated with stirring. After ordinary post-treatment, this was purified through column chromatography to give 4.5 g of a compound represented by the formula (I-10-3).

4.5 g of the compound represented by the formula (I-10-3), 50 mL of methanol, and 4.7 g of potassium carbonate were put in a reactor and stirred. After ordinary post-treatment, this was purified through column chromatography to give 2.9 g of a compound represented by the formula (I-10-4).

In a nitrogen atmosphere, 2.0 g of a compound represented by the formula (I-10-5), and 30 mL of tetrahydrofuran were put in a reactor. 0.6 g of sodium hydride was added thereto and stirred. 1.1 g of 2-bromoethyl methyl ether was added and heated with stirring. After ordinary post-treatment, this was purified through column chromatography to give 1.7 g of a compound represented by the formula (I-10-6).

In a nitrogen atmosphere, 0.2 g of magnesium, and 1 mL of tetrahydrofuran were put in a reactor. A tetrahydrofuran solution of 1.7 g of the compound represented by the formula (I-10-6) was added thereto to prepare a Grignard reagent. 0.6 g of trimethyl borate was added and stirred. Hydrochloric acid was added and stirred. After ordinary post-treatment, this gave 1.2 g of a compound represented by the formula (I-10-7).

In a nitrogen atmosphere, 1.2 g of the compound represented by the formula (I-10-7), 1.3 g of a compound represented by the formula (I-10-8), 0.9 g of potassium carbonate, 20 mL of tetrahydrofuran, 10 mL of water, and 0.05 g of tetrakis(triphenylphosphine)palladium(0) were put in a reactor and heated with stirring. After ordinary post-treatment, this was purified through column chromatography and recrystallization to give 1.4 g of a compound represented by the formula (I-10-9).

In a nitrogen atmosphere, 1.4 g of the compound represented by the formula (I-10-9), 0.7 g of the compound represented by the formula (I-10-4), 0.01 g of copper(I) iodide, 10 mL of triethylamine, 30 mL of N,N-dimethylformamide, and 0.04 g of tetrakis(triphenylphosphine)palladium(0) were put in a reactor and heated with stirring. After ordinary post-treatment, this was purified through column chromatography and recrystallization to give 1.4 g of a compound represented by the formula (I-10-10).

In a nitrogen atmosphere, 1.4 g of the compound represented by the formula (I-10-10), and 30 mL of dichloromethane were put in a reactor. This was cooled to −78° C., and 2.1 g of boron tribromide was added thereto and stirred. After ordinary post-treatment, this was purified through column chromatography and recrystallization to give 1.1 g of a compound represented by the formula (I-10-11).

According to the method described in WO2008-010985, a compound represented by the formula (I-10-12) was produced. In a nitrogen atmosphere, 3.0 g of the compound represented by the formula (I-10-12), 3.5 g of N-ethyldiisopropylamine, and 30 mL of dichloromethane were put in a reactor. With cooling with ice, 2.1 g of acryloyl chloride was added thereto and stirred. After ordinary post-treatment, this was purified through column chromatography to give 3.4 g of a compound represented by the formula (I-10-13).

3.4 g of the compound represented by the formula (I-10-13), and 30 mL of dichloromethane were put in a reactor. With cooling with ice, 20 mL of trifluoroacetic acid was added and stirred. After ordinary post-treatment, this was dried to give 2.3 g of a compound represented by the formula (I-10-14).

In a nitrogen atmosphere, 0.7 g of the compound represented by the formula (I-10-14), 1.1 g of the compound represented by the formula (I-10-11), 0.1 g of N,N-dimethylaminopyridine, and 20 mL of dichloromethane were put in a reactor. With cooling with ice, 0.3 g of diisopropylcarbodiimide was added thereto and stirred. After ordinary post-treatment, this was purified through column chromatography and recrystallization to give 1.4 g of a compound represented by the formula (I-10-15).

1.4 g of the compound represented by the formula (I-10-15), 0.3 g of a compound represented by the formula (I-10-16), 0.2 g of (±)-10-camphorsulfonic acid, 20 mL of tetrahydrofuran, and 10 mL of ethanol were put in a reactor and stirred. After ordinary post-treatment, this was purified through column chromatography and recrystallization to give 1.4 g of a compound represented by the formula (I-10).

LCMS: 951 [M+1]

(Example 11) Production of Compound of Formula (I-111)

[Chem. 141]

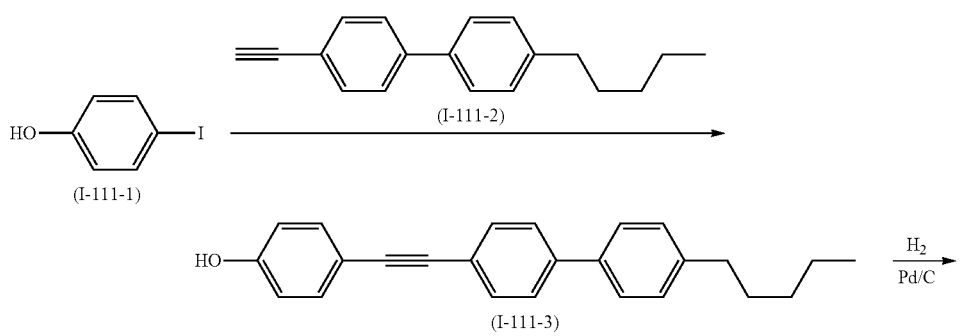

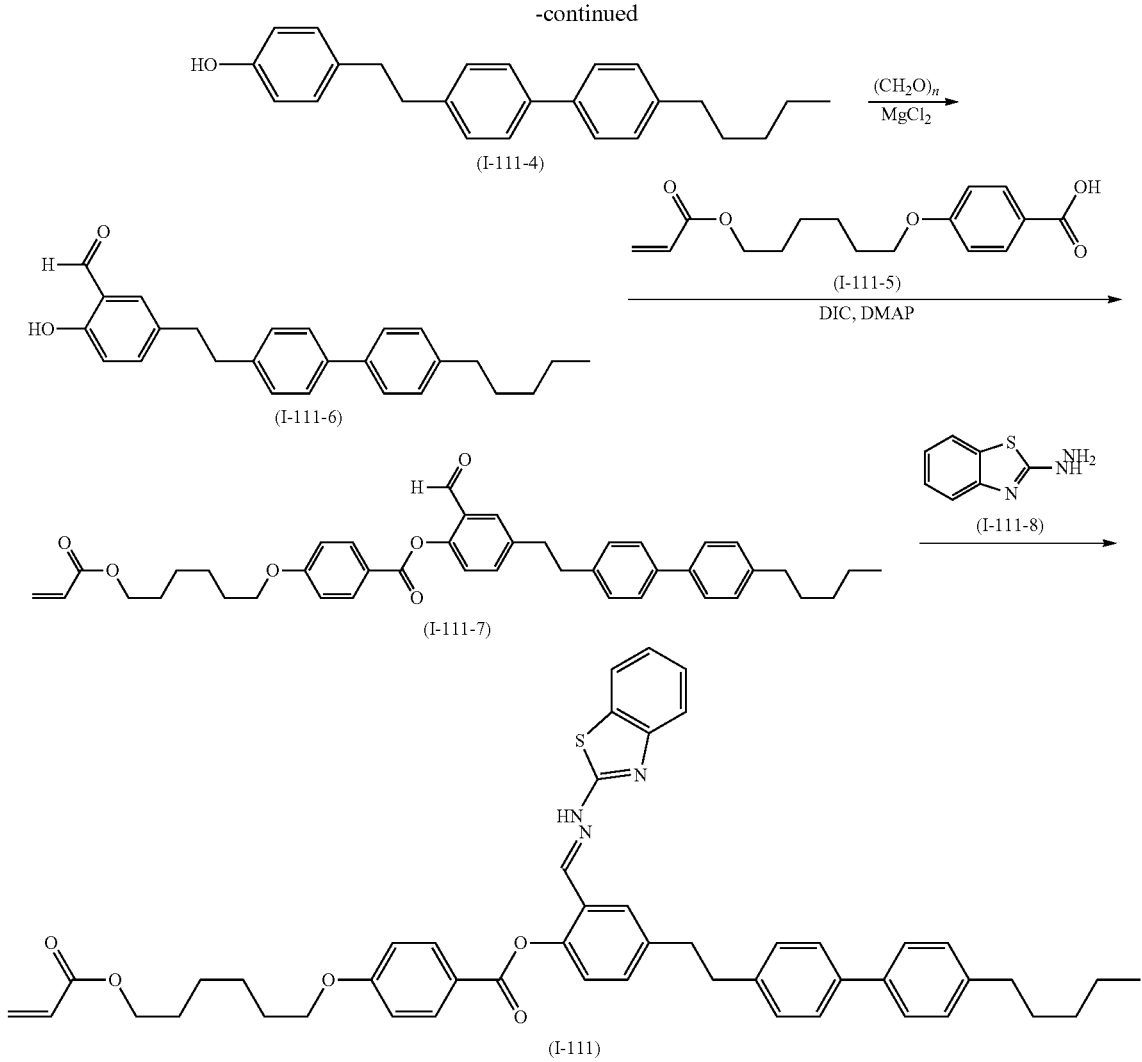
According to the same method as described above, a compound represented by the formula (I-111) was produced.
Transition temperature (heating at 5° C./min): C 159 N 167 I
MS(m/z): 794 [M$^+$+1]
(Example 12) Production of Compound of Formula (I-112)
[Chem. 142]
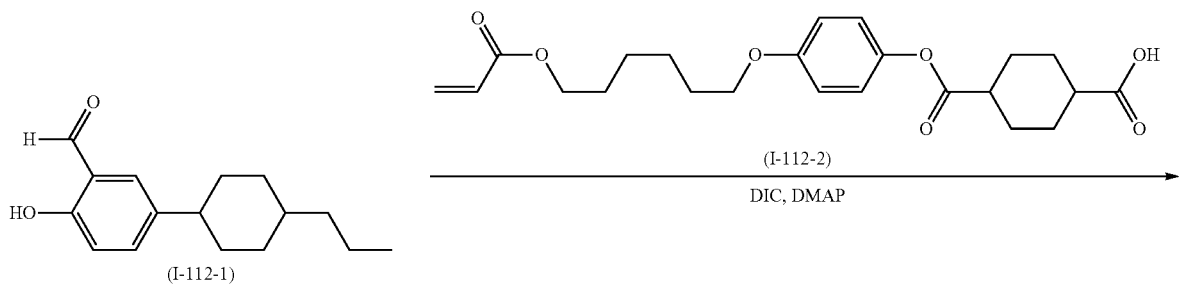

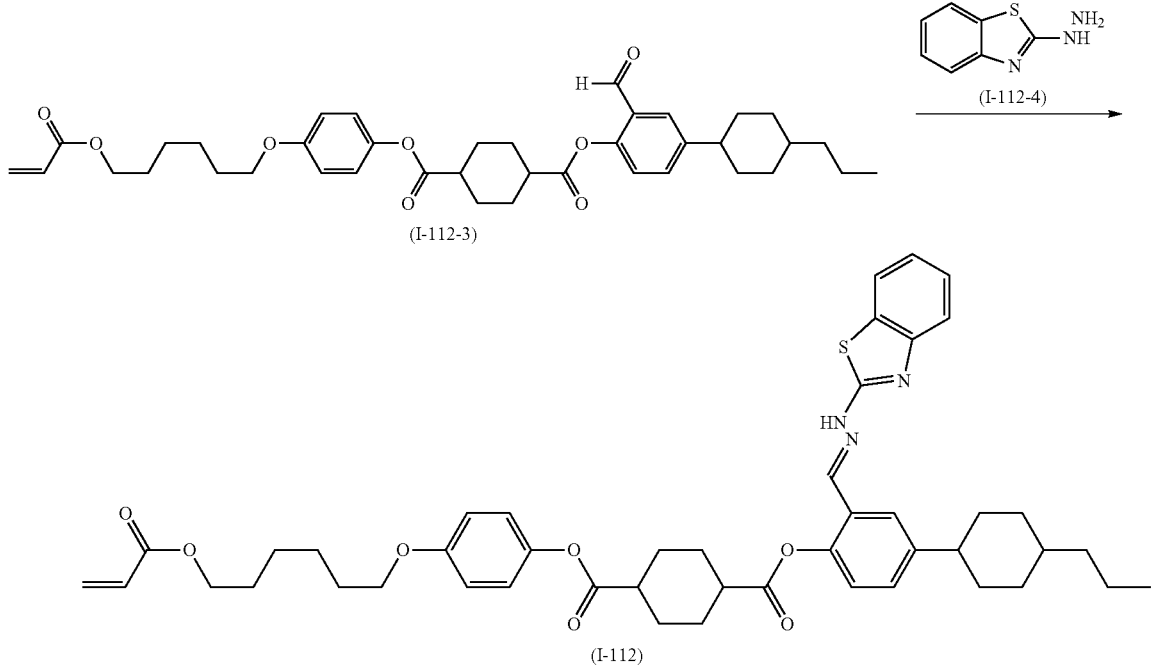

According to the method described in JP 2010-31223 A, a compound represented by the formula (I-112-2) was produced. 2.0 g of a compound represented by the formula (I-112-1), 3.4 g of the compound represented by the formula (I-112-2), 0.4 g of N,N-dimethylaminopyridine, and 30 mL of dichloromethane were put in a reactor. With cooling with ice, 1.3 g of diisopropylcarbodiimide was dropwise added thereto and stirred at room temperature. The precipitate was taken out through filtration, and the filtrate was washed with hydrochloric acid, water and salt solution. This was purified through column chromatography (silica gel) and recrystallization to give 3.7 g of a compound represented by the formula (I-112-3).

3.0 g of the compound represented by the formula (I-112-3), 0.8 g of a compound represented by the formula (I-112-4), 0.3 g of (±)-10-camphorsulfonic acid, 20 mL of tetrahydrofuran, and 20 mL of ethanol were put in a reactor. After this was stirred, the solvent was evaporated away, and the residue was washed through dispersion in methanol. This was purified through column chromatography (silica gel) and recrystallization (dichloromethane/methanol) to give 2.2 g of a compound represented by the formula (I-112).

Transition temperature (heating at 5° C./min): C 117 N 220 I $^1$H NMR (CDCl$_3$) δ 0.92 (t, 3H), 1.07 (q, 2H), 1.24-2.06 (m, 27H), 2.35 (m, 2H), 2.55 (t, 1H), 3.95 (t, 2H), 4.18 (t, 2H), 5.83 (dd, 1H), 6.13 (dd, 1H), 6.42 (dd, 1H), 6.88 (d, 2H), 6.98 (m, 3H), 7.19-7.26 (m, 2H), 7.35 (m, 1H), 7.51 (m, 1H), 7.68 (m, 1H), 7.89 (m, 1H), 8.08 (m, 1H) ppm.

MS(m/z): 794 [M$^+$+1]

(Example 13) Production of Compound of Formula (I-113)

[Chem. 143]

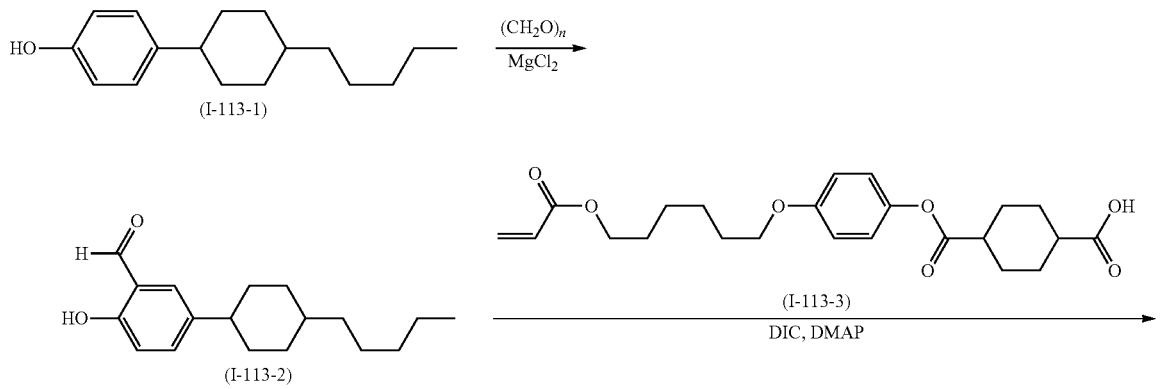

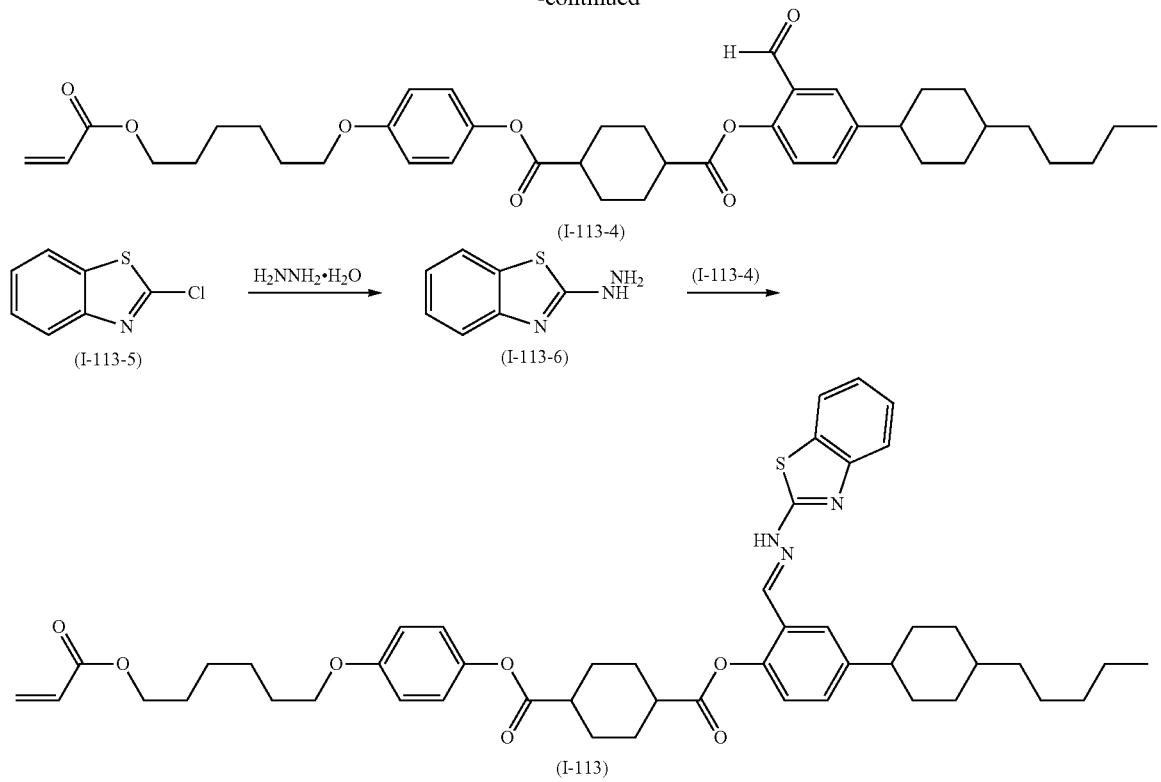

3.0 g of a compound represented by the formula (I-113-1), 1.7 g of magnesium chloride, 1.8 g of paraformaldehyde, 15 mL of triethylamine, and 50 mL of tetrahydrofuran were put in a reactor equipped with a condenser. With adequately adding paraformaldehyde thereto, this was heated under reflux. The reaction liquid was poured into hydrochloric acid, extracted with ethyl acetate and washed with water and salt solution. This was purified through column chromatography (silica gel) to give 2.3 g of a compound represented by the formula (I-113-2).

According to the same method as above, a compound represented by the formula (I-113) was produced.

Transition temperature (heating at 5° C./min): C 90 S 156 N $^1$H NMR (CDCl$_3$) δ 0.92 (t, 3H), 1.09 (m, 2H), 1.31 (m, 13H), 1.48 (m, 6H), 1.74 (t, 3H), 1.81 (t, 3H), 1.93 (m, 6H), 2.54 (t, 1H), 2.72 (t, 1H), 3.94 (t, 2H), 4.18 (t, 2H), 5.81 (d, 1H), 6.13 (q, 1H), 6.41 (d, 1H), 6.41 (d, 1H), 6.88 (d, 2H), 6.96 (d, 2H), 7.20 (t, 1H), 7.26 (d, 1H), 7.45 (d, 1H), 7.57 (d, 1H), 7.84 (s, 1H), 8.07 (d, 3H) ppm.

MS(m/z): 822 [M$^+$+1]

(Example 14) Production of Compound of Formula (I-114)

[Chem. 144]

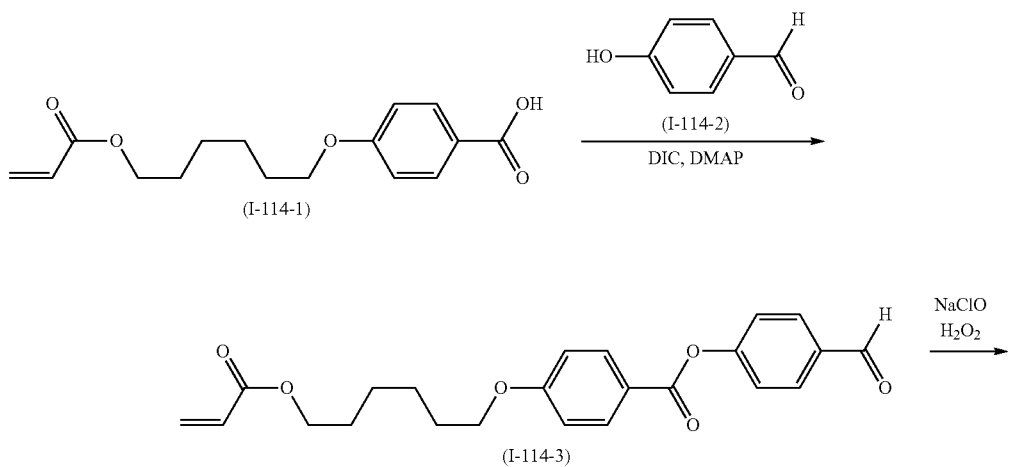

-continued

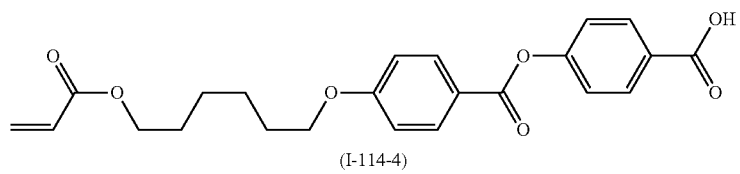
(I-114-4)

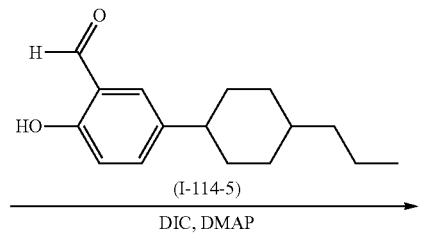
(I-114-5)

DIC, DMAP

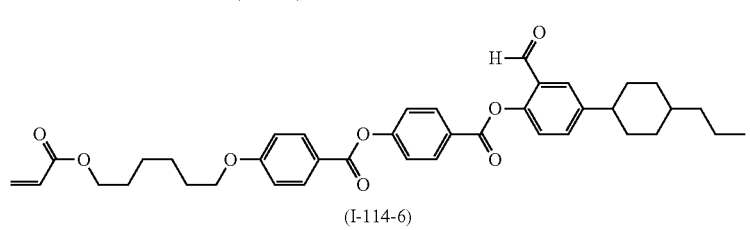
(I-114-6)

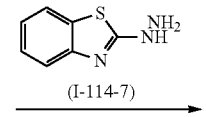
(I-114-7)

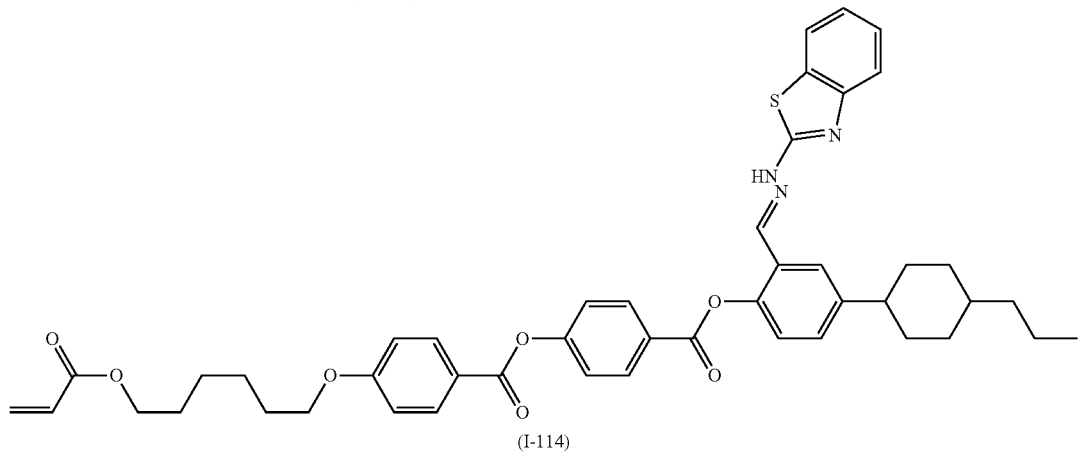
(I-114)

In a nitrogen atmosphere, 4.0 g of a compound represented by the formula (I-114-1), 1.7 g of a compound represented by the formula (I-114-2), 0.3 g of N,N-dimethylaminopyridine, and 30 mL of dichloromethane were put in a reactor. With cooling with ice, 2.1 g of diisopropylcarbodiimide was dropwise added thereto and stirred at room temperature. The precipitate was taken out through filtration, and the filtrate was washed with hydrochloric acid, water and salt solution. This was purified through column chromatography (silica gel) and recrystallization (dichloromethane/methanol) to give 4.3 g of a compound represented by the formula (I-114-3).

4.3 g of the compound represented by the formula (I-114-3), 30 mL of methanol, 10 mL of water, 5.0 g of sodium dihydrogenphosphate dehydrate, and 30 mL of 30% hydrogen peroxide solution were put in a reactor. An aqueous solution of sodium chlorite was dropwise added thereto and heated with stirring at 40° C. Cooled by adding water, the solid was taken out through filtration and washed. This was dried to give 4.1 g of a compound represented by the formula (I-114-4).

In a nitrogen atmosphere, 4.1 g of the compound represented by the formula (I-114-4), 2.4 g of a compound represented by the formula (I-114-5), 0.2 g of N,N-dimethylaminopyridine, and 40 mL of dichloromethane were put in a reactor. With cooling with ice, 1.5 g of diisopropylcarbodiimide was dropwise added thereto and stirred at room temperature. The precipitate was taken out through filtration, and the filtrate was washed with hydrochloric acid, water, and salt solution. This was purified through column chromatography (silica gel) and recrystallization (dichloromethane/methanol) to give 5.0 g of a compound represented by the formula (I-114-6).

3.0 g of the compound represented by the formula (I-114-6), 0.8 g of a compound represented by the formula (I-114-7), 0.2 g of (±)-10-camphorsulfonic acid, 20 mL of tetrahydrofuran, and 10 mL of ethanol were put in a reactor. After this was stirred, the solvent was evaporated away, and the residue was washed through dispersion in methanol. This was purified through column chromatography (silica gel) and recrystallization (dichloromethane/methanol) to give 2.5 g of a compound represented by the formula (I-114).

Transition temperature (heating at 5° C./min): C 64-77 N>220 I $^1$H NMR (CDCl$_3$) δ 0.92 (t, 3H), 1.07 (q, 2H), 1.23 (m, 2H), 1.37 (m, 3H), 1.48-1.60 (m, 6H), 1.74 (quin, 2H), 1.83-1.90 (m, 4H), 1.97 (d, 2H), 2.56 (tt, 1H), 4.07 (t, 2H), 4.19 (t, 2H), 5.83 (dd, H), 6.13 (dd, 1H), 6.42 (dd, 1H), 7.00 (d, 2H), 7.11 (q, 1H), 7.12 (d, 1H), 7.19-7.31 (m, 4H), 7.46 (d, 1H), 7.61 (d, H), 7.85 (d, H), 8.09 (s, 1H), 8.17 (m, 4H) ppm.

MS(m/z): 788 [M$^+$+1]

(Example 15) Production of Compound of Formula (I-115)

[Chem. 145]

According to the same method as above, a compound represented by the formula (I-115) was produced.

Transition temperature (heating at 5° C./min): C 190 N 260 I $^1$H NMR(CDCl$_3$) δ 0.89 (t, 1H), 1.05 (t, 2H), 1.31 (q, 2H), 1.50 (m, 6H), 1.74, (m, 15H), 2.54 (t, 1H), 4.03 (t, 2H), 4.19 (t, 2H), 5.81 (d, 1H), 6.13 (q, 1H), 6.41 (d, 1H), 6.43 (d, 1H), 7.09 (d, 2H), 7.11 (d, 2H), 7.20 (t, 1H), 7.26 (d, H), 7.45 (d, 1H), 7.57 (d, 1H), 7.84 (s, 1H), 8.07 (d, 3H) ppm.

MS(m/z): 750 [M$^+$+1]

(Example 16) Production of Compound of Formula (I-116)

[Chem. 146]

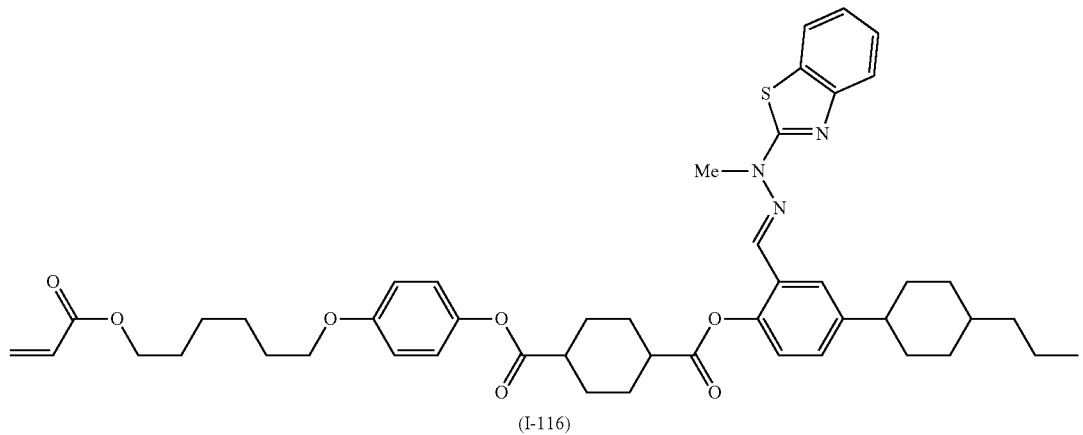

(I-116)

2.5 g of a compound represented by the formula (I-116-1), 0.7 g of a compound represented by the formula (I-116-2), 0.2 g of (±)-10-camphorsulfonic acid, 20 mL of tetrahydrofuran, and 10 mL of ethanol were put in a reactor. This was heated with stirring at 50° C., then the solvent was evaporated away, and the residue was washed through dispersion in methanol. This was purified through column chromatography (silica gel) and recrystallization (dichloromethane/methanol) to give 2.2 g of a compound represented by the formula (I-116).

Transition temperature (heating at 5° C./min): C 147-156 N 173 I $^1$H NMR (CDCl$_3$) δ 0.92 (t, 3H), 1.11 (q, 2H), 1.25 (m, 2H), 1.37-1.55 (m, 9H), 1.71 (m, 6H), 1.78 (m, 2H), 1.94 (m, 4H), 2.33 (m, 4H), 2.56 (m, 2H), 2.70 (m, 1H), 3.72 (s, 3H), 3.94 (t, 2H), 4.17 (t, 2H), 5.82 (dd, 1H), 6.13 (dd, 1H), 6.40 (dd, 1H), 6.88 (d, 2H), 6.98 (m, 3H), 7.17 (t, 1H), 7.24 (dd, 1H), 7.35 (t, 1H), 7.66-7.72 (m, 3H), 7.88 (d, 1H) ppm.

MS(m/z): 808 [M$^+$+1]

(Example 17) Production of Compound of Formula (I-117)

[Chem. 147]

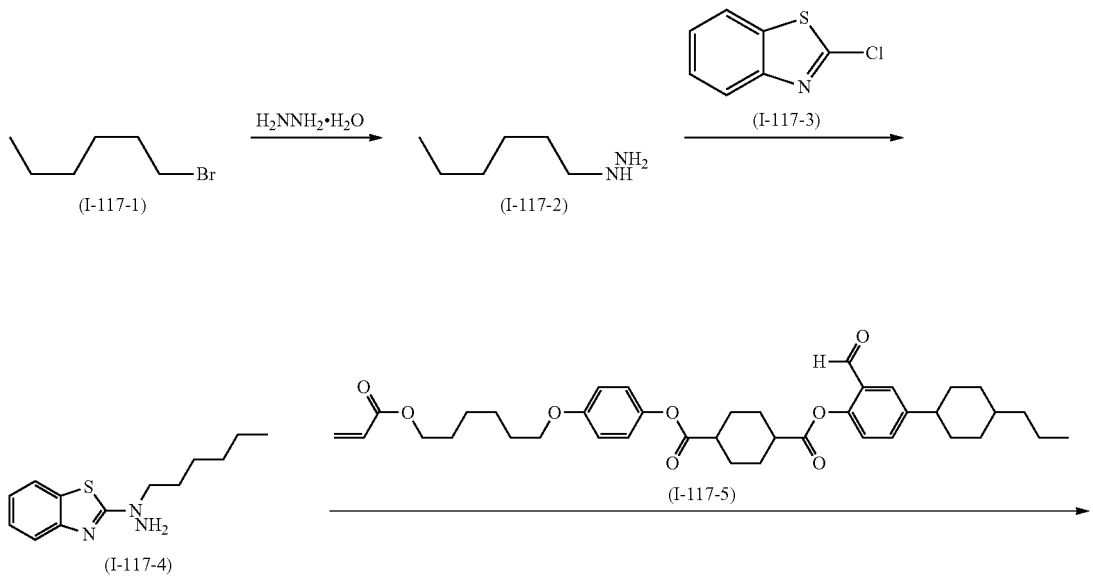

-continued

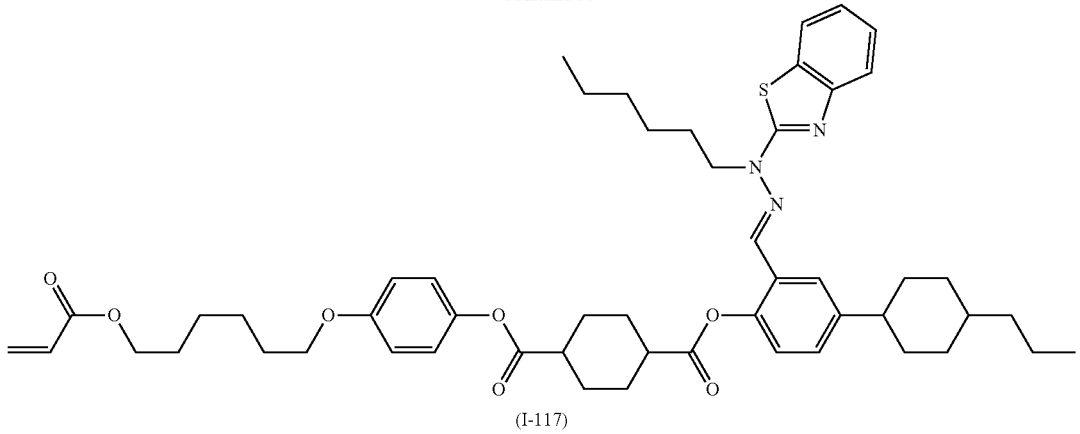

(I-117)

In a nitrogen atmosphere, 50 mL of hydrazine monohydrate, and 50 mL of ethanol were put in a reactor. An ethanol solution of 5.0 g of a compound represented by the formula (I-117-1) was dropwise added thereto and heated with attiring at 50° C. This was diluted with dichloromethane, and washed with water and salt solution. After this was dried with sodium sulfate, and the solvent was evaporated away to give 2.8 g of a compound represented by the formula (I-117-2).

In a nitrogen atmosphere, 4.1 g of a compound represented by the formula (I-117-3), 20 mL of 1,2-dimethoxyethane, and 10 mL of triethylamine were put in a reactor. 2.8 g of the compound represented by the formula (I-117-2) was dropwise added thereto and heated with stirring at 50° C. The reaction liquid was poured into water, and the precipitated solid was washed with water and hexane to give 3.0 g of a compound represented by the formula (I-117-4).

1.0 g of the compound represented by the formula (I-117-4), 2.6 g of a compound represented by the formula (I-117-5), 0.6 g of (±)-10-camphorsulfonic acid, 20 mL of tetrahydrofuran, and 10 mL of ethanol were put in a reactor. After this was heated with stirring at 50° C., the solvent was evaporated away, and the residue was washed through dispersion in methanol. This was purified through column chromatography (silica gel) and recrystallization (dichloromethane/methanol) to give 2.5 g of a compound represented by the formula (I-117).

Transition temperature (heating at 5° C./min): C 117-122 N 146 I $^1$H NMR (CDCl$_3$) δ 0.91 (m, 6H), 1.10 (q, 2H), 1.23-1.56 (m, 18H), 1.68-1.81 (m, 9H), 1.94 (t, 4H), 2.32 (m, 4H), 2.56-2.70 (m, 3H), 3.94 (t, 2H), 4.18 (t, 2H), 4.29 (t, 2H), 5.82 (dd, 1H), 6.13 (dd, 1H), 6.40 (dd, 1H), 6.89 (d, 2H), 6.99 (m, 3H), 7.16 (t, 1H), 7.23 (dd, 1H), 7.34 (t, 1H), 7.66-7.72 (m, 3H), 7.90 (d, 1H) ppm.

MS(m/z): 878 [M$^+$+1]

(Example 18) Production of Compound of Formula (I-118)

[Chem. 148]

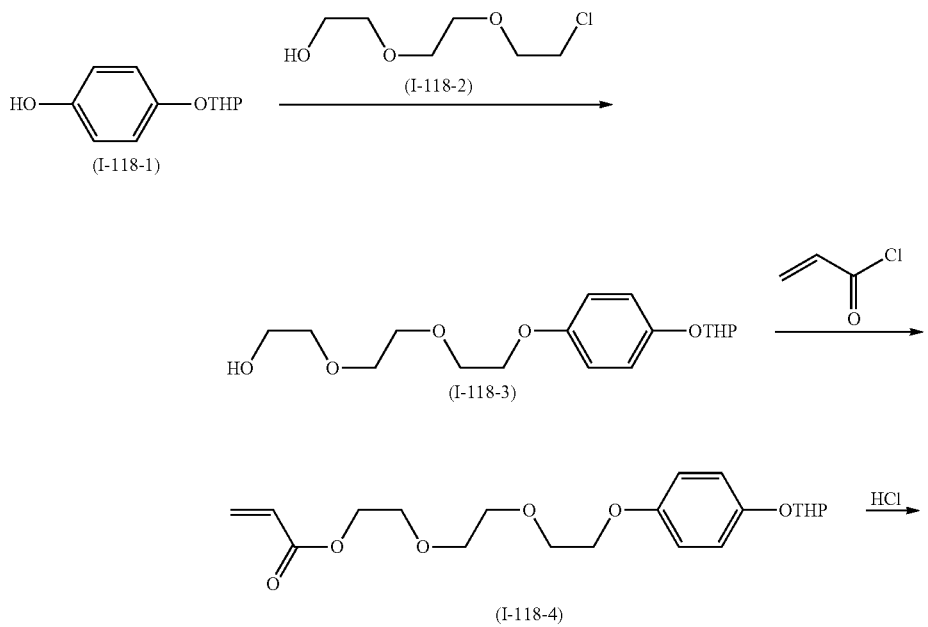

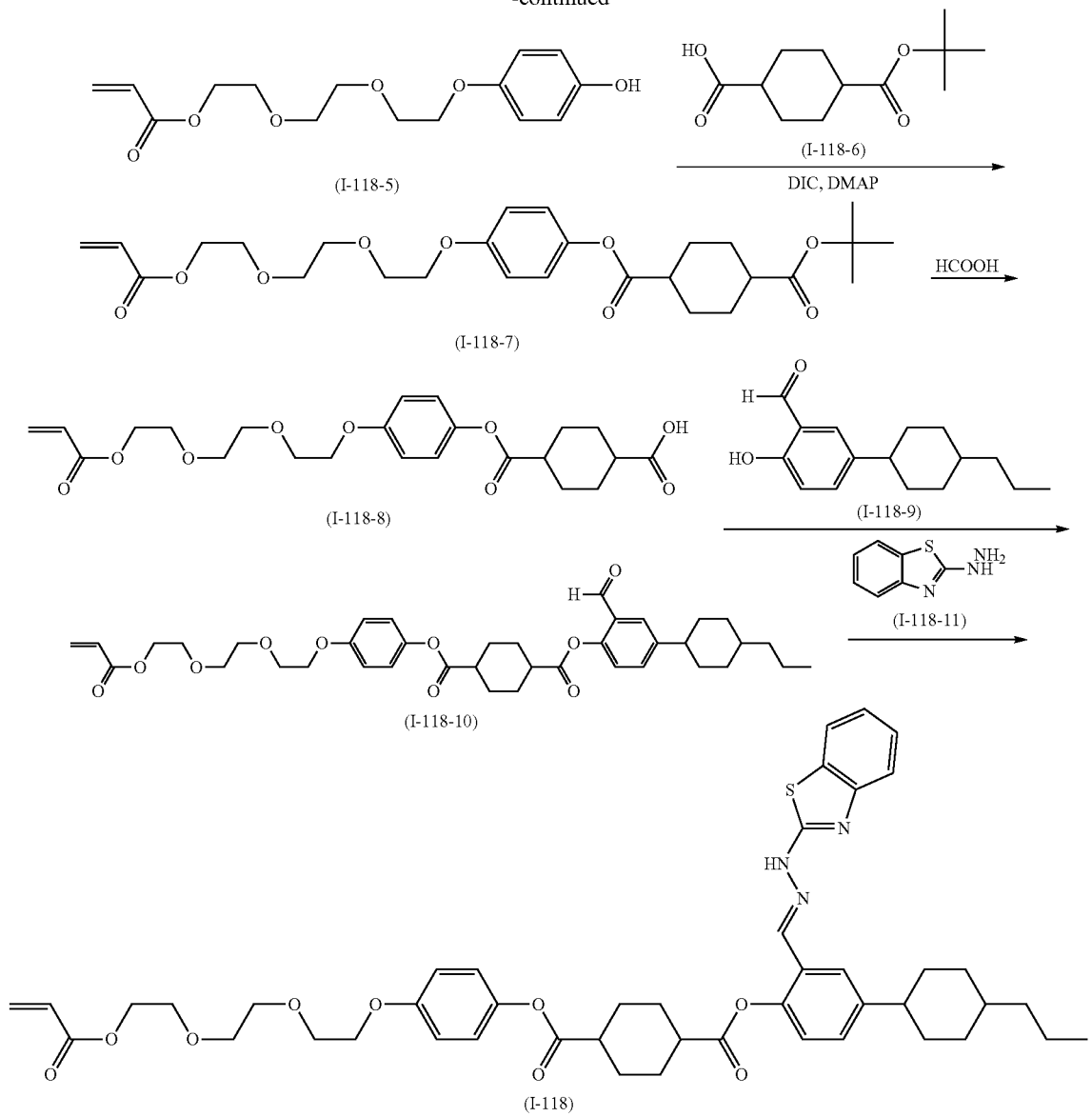

115.9 g of a compound represented by the formula (I-118-1), 120.7 g of a compound represented by the formula (I-118-2), 272.2 g of cesium carbonate, and 580 mL of N,N-dimethylformamide were put in a reactor, and stirred at 60° C. for 10 hours. The reaction liquid was diluted with dichloromethane, and washed sequentially with water and salt solution. This was purified through column chromatography (alumina) to give 166.5 g of a compound represented by the formula (I-118-3).

166.5 g of the compound represented by the formula (I-118-3), 77.4 g of triethylamine, and 830 mL of dichloromethane were put in a reactor. 55.4 g of acryloyl chloride was dropwise added thereto with cooling with ice, and stirred at room temperature for 4 hours. The reaction liquid was washed with salt solution, and purified through column chromatography (alumina) to give an oily substance. 35 mL of 10% hydrochloric acid, 580 mL of methanol, and 580 mL of tetrahydrofuran were added thereto, and stirred at room temperature for 2 hours. The reaction liquid was washed sequentially with an aqueous solution of saturated sodium hydrogencarbonate, water and salt solution, and the solvent was evaporated away. This was purified through column chromatography (silica gel) to give 116.8 g of a compound represented by the formula (I-118-5).

60.0 g of the compound represented by the formula (I-118-5), 46.2 g of a compound represented by the formula (I-118-6), 0.2 g of N,N-dimethylaminopyridine, and 300 mL of dichloromethane were put in a reactor. 30.7 g of diisopropylcarbodiimide was dropwise added thereto with cooling with ice, and stirred at room temperature for 2 hours. The reaction liquid was filtered, and the filtrate was washed sequentially with hydrochloric acid, water and salt solution. This was purified through column chromatography (silica gel) and recrystallization (dichloromethane/hexane) to give 78.4 g of a compound represented by the formula (I-118-7).

42.5 g of the compound represented by the formula (I-118-7), 170 mL of formic acid, and 210 mL of dichloromethane were put in a reactor, and stirred at room temperature for 3 hours. Dichloromethane was evaporated away from the reaction liquid, diisopropyl ether was added thereto for crystal precipitation to give 31.6 g of a compound represented by the formula (I-118-8).

20.0 g of the compound represented by the formula (I-118-8), 10.9 g of a compound represented by the formula (I-118-9), 50 mg of N,N-dimethylaminopyridine, and 100 mL of dichloromethane were put in a reactor. 6.7 g of diisopropylcarbodiimide was dropwise added thereto with cooling with ice, and stirred at room temperature for 3 hours. The reaction liquid was filtered, the filtrate was washed sequentially with hydrochloric acid, water and salt solution. This was purified through column chromatography (silica gel) and recrystallization (dichloromethane/hexane, dichloromethane/methanol) to give 18.4 g of a compound represented by the formula (I-118-10).

10.0 g of the compound represented by the formula (I-118-10), 2.4 g of a compound represented by the formula (I-118-11), 70 mg of (±)-10-camphorsulfonic acid, 40 mL of tetrahydrofuran, and 10 mL of methanol were put in a reactor, and stirred at room temperature for 5 hours. The solvent was evaporated away from the reaction liquid. This was purified through column chromatography (silica gel, alumina) and recrystallization (dichloromethane/methanol) to give 7.9 g of a compound represented by the formula (I-118).

Transition temperature (heating at 5° C./min): C 75-108 N 180 I $^1$H NMR (CDCl$_3$) δ 0.94 (t, 3H), 1.10 (m, 2H), 1.25 (m, 2H), 1.29-1.57 (m, 11H), 1.80-2.08 (m, 6H), 2.30 (m, 2H), 2.54 (m, 1H), 3.67-3.78 (m, 6H), 3.85 (t, 2H), 4.11 (t, 2H), 4.32 (t, 2H), 5.84 (dd, 1H), 6.15 (dd, 1H), 6.40 (dd, 1H), 6.82-7.00 (m, 4H), 7.08-7.60 (m, 4H), 7.65-8.10 (m, 3H), 8.40 (s, 1H), 11.6 (s, 1H) ppm.

(Example 19) Production of Compound of Formula (I-119)

2.5 g of a compound represented by the formula (I-119-1), 1.0 g of a compound represented by the formula (I-119-2), 0.5 g of (+)-10-camphorsulfonic acid, 10 mL of tetrahydrofuran, and 10 mL of ethanol were put into a reactor. This was heated with stirring at 50° C., the solvent was evaporated away, and the residue was washed through dispersion in methanol. This was purified through column chromatography (silica gel) and recrystallization to give 2.0 g of a compound represented by the formula (I-119).

Transition temperature (heating at 5° C./min): C 106 N 125 I $^1$H NMR (CDCl$_3$) δ 0.92 (t, 3H), 1.05-1.83 (m, 22H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.82 (dd, 1H), 6.12 (dd, 1H), 6.40 (dd, 1H), 6.88 (d, 2H), 6.99 (m, 3H), 7.17 (t, 1H), 7.23 (dd, 1H), 7.34 (t, 1H), 7.66 (d, H), 7.71 (d, 1H), 7.89 (d, H), 8.02 (s, 1H) ppm.

[Chem. 149]

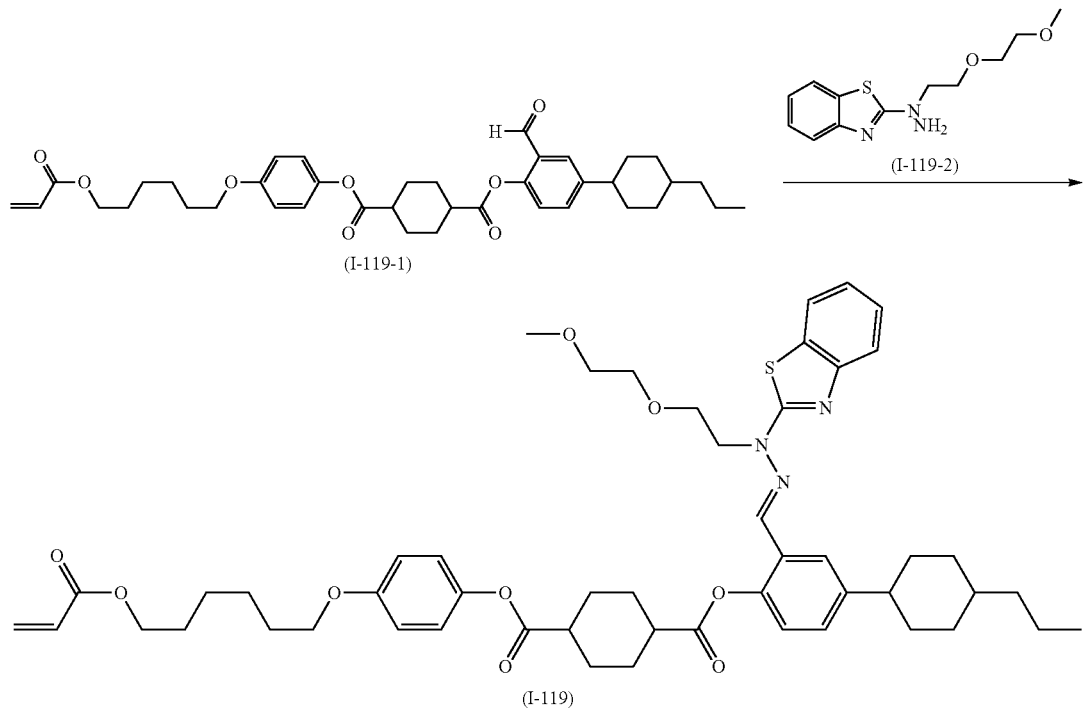

LCMS: 826 [M+1]

(Example 20) Production of Compound of Formula (I-120)

[Chem. 150]

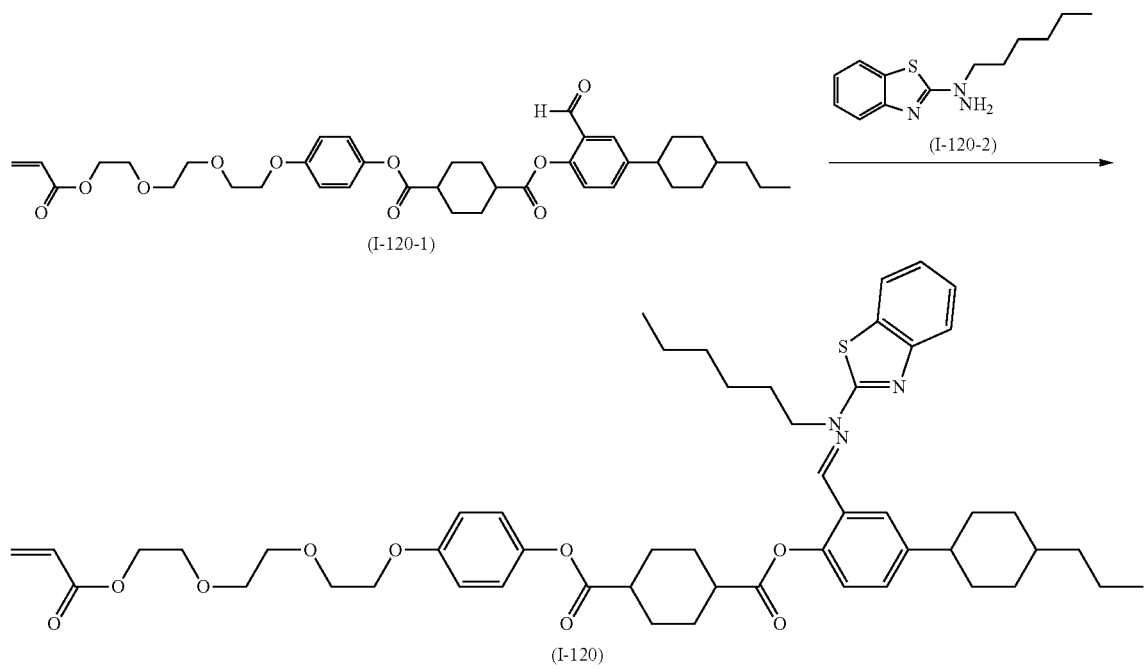

1.0 g of a compound represented by the formula (I-120-1), 0.4 g of a compound represented by the formula (I-120-2), 0.5 g of (±)-10-camphorsulfonic acid, 20 mL of tetrahydrofuran, and 10 mL of ethanol were put in a reactor, and stirred at 50° C. The solvent was evaporated away from the reaction liquid, and the residue was washed through dispersion in methanol. This was purified through column chromatography (silica gel) and recrystallization (dichloromethane/methanol) to give 0.9 g of a compound represented by the formula (I-120).

Transition temperature (heating at 5° C./min): C 131 I
$^1$H NMR (CDCl$_3$) δ 0.88-0.94 (m, 6H), 1.10 (m, 2H), 1.22-1.52 (m, 13H), 1.72 (m, 6H), 1.94 (t, 4H), 2.32 (m, 4H), 2.53-2.62 (m, 3H), 3.69-3.77 (m, 6H), 3.86 (t, 2H), 4.12 (t, 2H), 4.27-4.34 (m, 4H), 5.83 (dd, 1H), 6.16 (dd, 1H), 6.43 (dd, 1H), 6.91 (d, 2H), 6.97-7.02 (m, 3H), 7.16 (t, 1H), 7.23 (dd, 1H), 7.33 (t, 1H), 6.66-7.72 (m, 3H), 7.90 (d, 1H) ppm.
LCMS: 910 [M+1]

(Example 21) Production of Compound of Formula (I-121)

[Chem. 151]

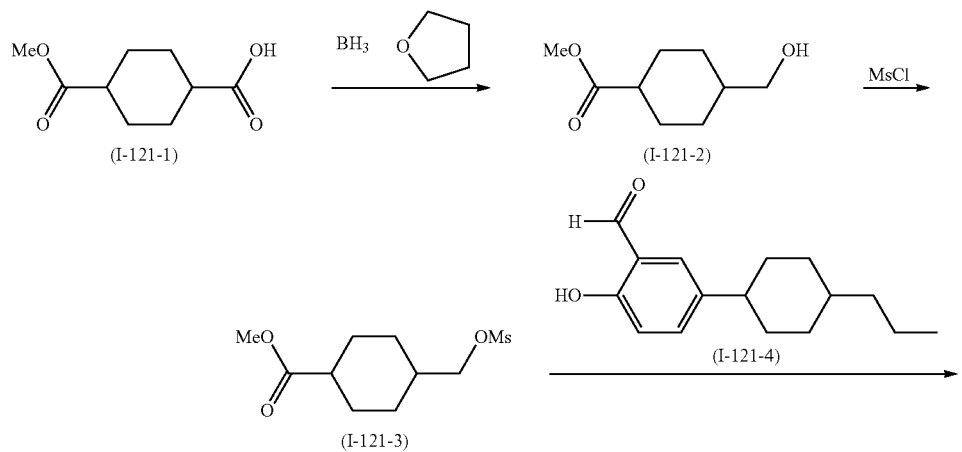

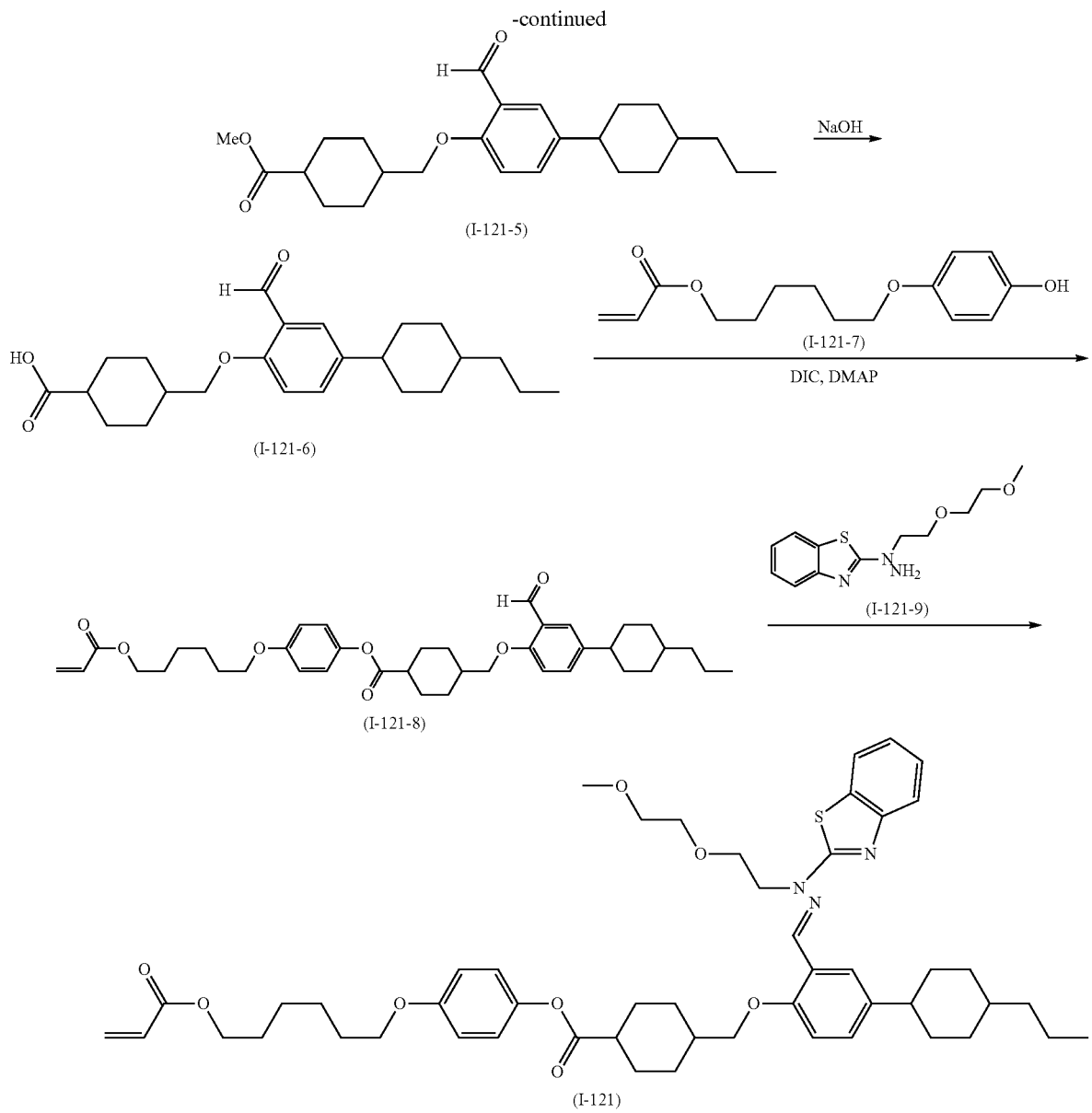

In a nitrogen atmosphere, 20.0 g of a compound represented by the formula (I-121-1), and 120 mL of tetrahydrofuran were put in a reactor. With cooling with ice, 143 mL of borane-tetrahydrofuran complex (0.9 mol/L) was dropwise added thereto and stirred for 2 hours. This was poured into 200 mL of 5% hydrochloric acid, and processed with 200 mL of ethyl acetate for liquid-liquid separation. This was dried with sodium sulfate, and the solvent was evaporated away to give 17.6 g of a compound represented by the formula (I-121-2).

In a nitrogen atmosphere, 17.6 g of the compound represented by the formula (I-121-2), 12.1 g of pyridine, and 100 mL of dichloromethane were put in a reactor. With cooling with ice, 12.9 g of methanesulfonyl chloride was dropwise added thereto and stirred at room temperature for 8 hours. After poured into 5% hydrochloric acid, this was processed for liquid-liquid separation. This was purified through column chromatography (silica gel) to give 23.0 g of a compound represented by the formula (I-121-3).

4.0 g of the compound represented by the formula (I-121-3), 3.9 g of a compound represented by the formula (I-121-4), 3.5 g of potassium carbonate, and 30 mL of N,N-dimethylformamide were put in a reactor, and heated with stirring at 90° C. for 12 hours. This was diluted with dichloromethane and washed with water and salt solution. This was purified through column chromatography (silica gel) and recrystallization to give 5.1 g of a compound represented by the formula (I-121-5).

5.1 g of the compound represented by the formula (I-121-5), 30 mL of tetrahydrofuran, 30 mL of methanol, and 10 mL of an aqueous solution of 25% sodium hydroxide were put in a reactor, and stirred at 60° C. Hydrochloric acid was added thereto and the solvent was evaporated away. This was washed with water and dried to give 4.9 g of a compound represented by the formula (I-121-6).

In a nitrogen atmosphere, 4.9 g of the compound represented by the formula (I-121-6), 3.4 g of a compound represented by the formula (I-121-7), 0.1 g of N,N-dimethylaminopyridine, and 40 mL of dichloromethane were put in a reactor. With cooling with ice, 1.6 g of diisopropylcarbodiimide was dropwise added and stirred. This was purified through column chromatography (silica gel) and recrystallization to give 5.7 g of a compound represented by the formula (I-121-8).

2.5 g of the compound represented by the formula (I-121-8), 1.1 g of a compound represented by the formula (I-121-9), 0.5 g of (±)-10-camphorsulfonic acid, 10 mL of tetrahydrofuran and 10 mL of ethanol were put in a reactor. This was heated with stirring at 50° C., the solvent was evaporated away, and the residue was washed through dispersion in methanol. This was purified through column chromatography (silica gel) and recrystallization to give 2.1 g of a compound represented by the formula (I-121).

Transition temperature (heating at 5° C./min, cooling at 5° C./min): C 101-105 (N 82)I $^1$H NMR (CDCl$_3$) δ 0.92 (t, 3H), 1.08-1.91 (m, 26H), 2.06 (d, 2H), 2.24 (d, 2H), 2.51 (m, 2H), 3.30 (s, 3H), 3.51 (dd, 2H), 3.67 (dd, 2H), 3.87 (quin, 4H), 3.94 (t, 2H), 4.17 (t, 2H), 4.54 (t, 2H), 5.82 (dd, 1H), 6.12 (dd, 1H), 6.40 (dd, 1H), 6.86 (m, 3H), 6.97 (m, 2H), 7.16 (m, 2H), 7.32 (t, 1H), 7.65 (d, 1H), 7.70 (d, 1H), 7.82 (d, 1H), 8.36 (s, 1H) ppm.

(Example 22) Production of Compound of Formula (I-122)

[Chem. 152]

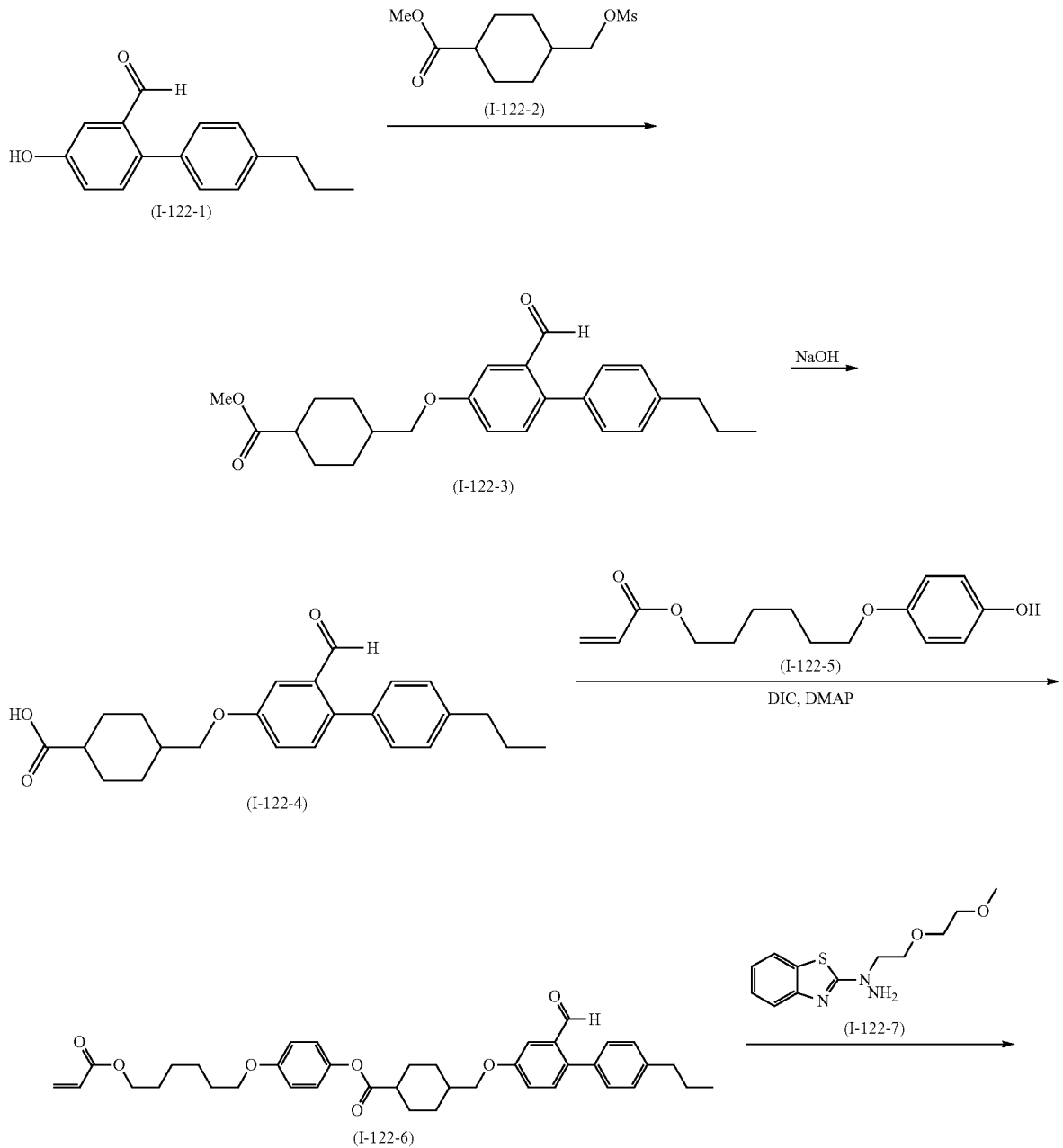

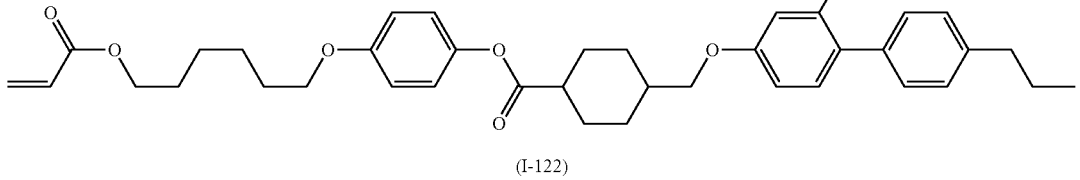

(I-122)

4.0 g of a compound represented by the formula (I-122-1), 4.2 g of a compound represented by the formula (I-122-2), 3.5 g of potassium carbonate, and 30 mL of N,N-dimethylformamide were put in a reactor, and heated with stirring at 90° C. for 12 hours. This was diluted with dichloromethane and washed with water and salt solution. This was purified through column chromatography (silica gel) and recrystallization to give 4.6 g of a compound represented by the formula (I-122-3).

4.6 g of the compound represented by the formula (I-122-3), 30 mL of tetrahydrofuran, 30 mL of methanol and 10 mL of an aqueous solution of 25% sodium hydroxide were put in a reactor and stirred at 60° C. Hydrochloric acid was added thereto and the solvent was evaporated away. This was washed with water and dried to give 4.4 g of a compound represented by the formula (I-122-4).

In a nitrogen atmosphere, 4.4 g of the compound represented by the formula (I-122-4), 3.1 g of a compound represented by the formula (I-122-5), 0.1 g of N,N-dimethylaminopyridine, and 40 mL of dichloromethane were put in a reactor. With cooling with ice, 1.8 g of diisopropylcarbodiimide was dropwise added thereto and stirred. This was purified through column chromatography (silica gel) and recrystallization to give 5.1 g of a compound represented by the formula (I-122-6).

2.5 g of the compound represented by the formula (I-122-6), 1.1 g of a compound represented by the formula (I-122-7), 0.5 g of (±)-10-camphorsulfonic acid, 10 mL of tetrahydrofuran, and 10 mL of ethanol were put in a reactor. This was heated with stirring at 50° C., the solvent was evaporated away, and the residue was washed through dispersion in methanol. This was purified through column chromatography (silica gel) and recrystallization to give 1.8 g of a compound represented by the formula (I-122).

Transition temperature (heating at 5° C./min): C 67-100 I $^1$H NMR (CDCl$_3$) δ 1.00 (t, 3H), 1.28 (m, 2H), 1.45-1.81 (m, 12H), 1.97 (br, 1H), 2.13 (m, 2H), 2.26 (m, 2H), 2.57 (tt, 1H), 2.65 (t, 2H), 3.27 (s, 3H), 3.37 (m, 2H), 3.50 (m, 2H), 3.70 (t, 2H), 3.95 (q, 4H), 4.17 (t, 2H), 4.33 (t, 2H), 5.82 (dd, 1H), 6.12 (dd, 1H), 6.40 (dd, 1H), 6.87 (d, 2H), 6.98 (m, 3H), 7.15 (t, 1H), 7.25 (m, 5H), 7.32 (t, 1H), 7.64 (m, 2H), 7.69 (d, 1H), 7.91 (s, 1H) ppm.

Using the same method as in Example 1 to Example 22, or using the same method according to the same method as a known method, compounds represented by the formulae (I-11) to (I-110), and formulae (I-123) to (I-133) were produced.

Examples 23 to 44, Comparative Examples 1 to 3

The compounds of formulae (I-1) to (I-10), and formulae (I-111) to (I-122) of Example 1 to Example 22, the compound (R-1) described in PTL 1, the compound (R-2) described in PTL 2 and the compound (R-3) described in PTL 3 were targeted for evaluation.

[Chem. 153]

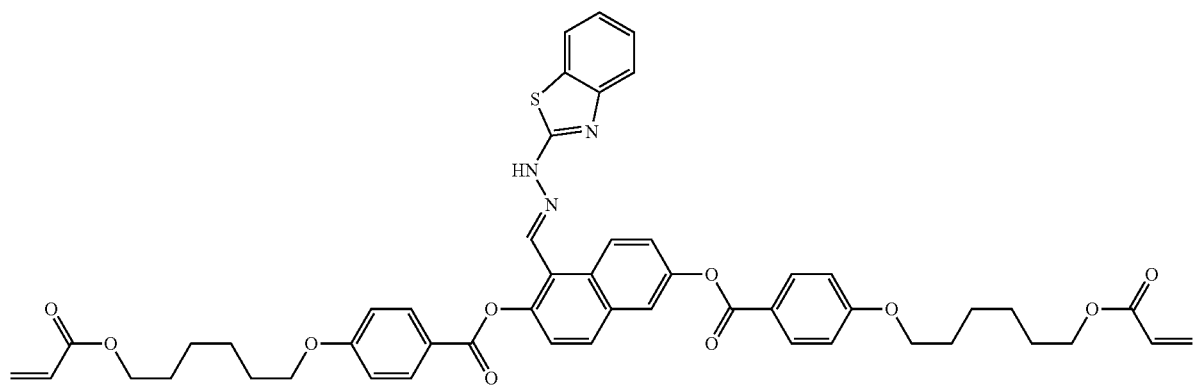

(R-1)

(R-2)

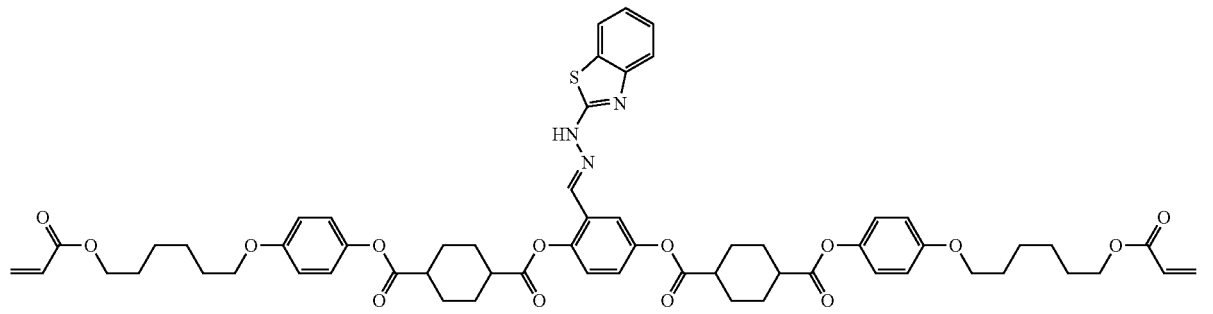

(R-3)

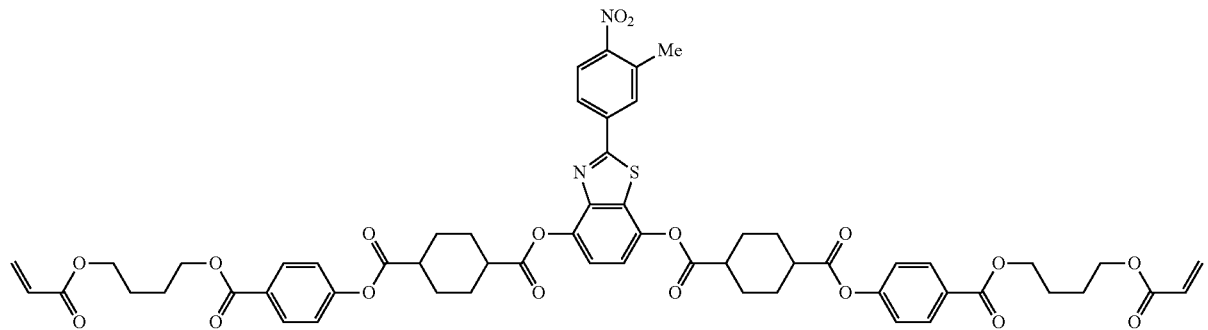

For evaluation of storage stability, the stable storage concentration of the targeted compound was measured. Regarding the stable storage concentration, the targeted compound was added to the mother liquid crystal to have a concentration of 5% to 25% at intervals of 5% to prepare different compositions, and the thus-prepared compositions were left at 17.5° C. for 10 weeks. The maximum addition concentration of the compound not having caused crystal precipitation was defined as the stable storage concentration of the compound. The compound having a large value of the maximum addition concentration has a large stable storage concentration, therefore meaning that the compound is free from crystal precipitation in long-term storage.

For measuring the stable storage concentration, a liquid crystal composition composed of 30% of the compound (X-1) described in JP 2005-015473 A, 30% of the compound (X-2) described in WO2009/122868 A1 and 40% of the compound (x-3) described in JP 2002-542219 A was used as a mother liquid crystal (X). The evaluation results are shown in the following Table.

[Chem. 154]

(X-1)

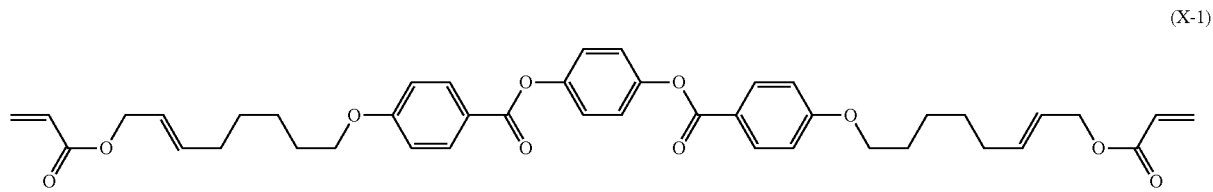

(X-2)

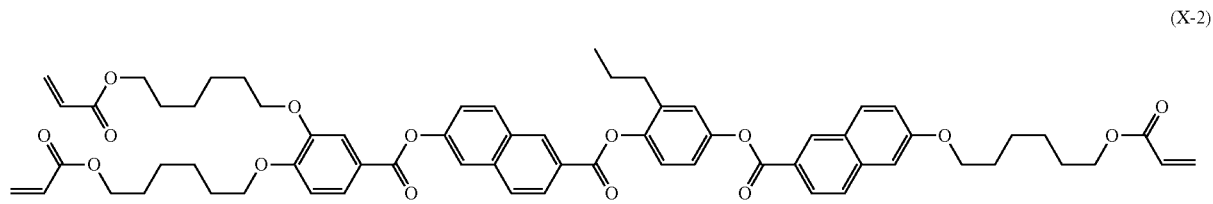

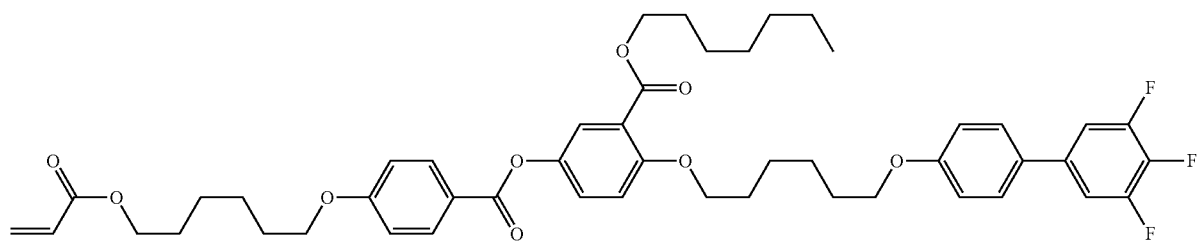

(X-3)

TABLE 1

| | Target Compound | Stable Storage Concentration |
|---|---|---|
| Example 23 | Inventive Compound (I-1) | 25% |
| Example 24 | Inventive Compound (I-2) | 25% |
| Example 25 | Inventive Compound (I-3) | 20% |
| Example 26 | Inventive Compound (I-4) | 20% |
| Example 27 | Inventive Compound (I-5) | 15% |
| Example 28 | Inventive Compound (I-6) | 15% |
| Example 29 | Inventive Compound (I-7) | 15% |
| Example 30 | Inventive Compound (I-8) | 15% |
| Example 31 | Inventive Compound (I-9) | 20% |
| Example 32 | Inventive Compound (I-10) | 10% |
| Example 33 | Inventive Compound (I-111) | 20% |
| Example 34 | Inventive Compound (I-112) | 25% |
| Example 35 | Inventive Compound (I-113) | 25% |
| Example 36 | Inventive Compound (I-114) | 15% |
| Example 37 | Inventive Compound (I-115) | 15% |
| Example 38 | Inventive Compound (I-116) | 20% |
| Example 39 | Inventive Compound (I-117) | 20% |
| Example 40 | Inventive Compound (I-118) | 20% |
| Example 41 | Inventive Compound (I-119) | 25% |
| Example 42 | Inventive Compound (I-120) | 20% |
| Example 43 | Inventive Compound (I-121) | 20% |
| Example 44 | Inventive Compound (I-122) | 20% |
| Comparative Example 1 | Comparative Compound (R-1) | <5% |
| Comparative Example 2 | Comparative Compound (R-2) | 5% |
| Comparative Example 3 | Comparative Compound (R-3) | <5% |

From the Table, it is known that the compounds of the present invention of Example 23 to Example 44 all have a high maximum addition concentration not causing crystal precipitation, and therefore have high storage stability.

Examples 45 to 66, Comparative Examples 4 to 6

According to a spin coating method, a polyimide solution for alignment film was applied onto a glass substrate having a thickness of 0.7 mm, dried at 100° C. for 10 minutes, and baked at 200° C. for 60 minutes to form a coating film thereon. The resultant film was rubbed. For the rubbing, a commercially-available rubbing device was used.

The target compound was added to the mother liquid crystal (X) in a ratio of 50% to prepare a composition. A photopolymerization initiator, Irgacure 907 (manufactured by BASF) in a ratio of 1%, 4-methoxyphenol in a ratio of 0.1% and chloroform in a ratio of 80% were added to the resultant composition to prepare a coating liquid. The coating liquid was applied onto the rubbed glass substrate according to a spin coating method. This was dried at 80° C. for 1 minute and further dried at 120° C. for 1 minute. Subsequently, using a high-pressure mercury lamp, this was irradiated with UV rays at an intensity of 40 mW/cm² for 25 seconds. In that manner, 10 sheets of evaluation target films were produced for every target compound. Example numbers of the films and the target compound used therein are shown in the following Table.

TABLE 2

| Film | Target Compound Used |
|---|---|
| Example 45 | Inventive Compound (I-1) |
| Example 46 | Inventive Compound (I-2) |
| Example 47 | Inventive Compound (I-3) |
| Example 48 | Inventive Compound (I-4) |
| Example 49 | Inventive Compound (I-5) |
| Example 50 | Inventive Compound (I-6) |
| Example 51 | Inventive Compound (I-7) |
| Example 52 | Inventive Compound (I-8) |
| Example 53 | Inventive Compound (I-9) |
| Example 54 | Inventive Compound (I-10) |
| Example 55 | Inventive Compound (I-111) |
| Example 56 | Inventive Compound (I-112) |
| Example 57 | Inventive Compound (I-113) |
| Example 58 | Inventive Compound (I-114) |
| Example 59 | Inventive Compound (I-115) |
| Example 60 | Inventive Compound (I-116) |
| Example 61 | Inventive Compound (I-117) |
| Example 62 | Inventive Compound (I-118) |
| Example 63 | Inventive Compound (I-119) |
| Example 64 | Inventive Compound (I-120) |
| Example 65 | Inventive Compound (I-121) |
| Example 66 | Inventive Compound (I-122) |
| Comparative Example 4 | Comparative Compound (R-1) |
| Comparative Example 5 | Comparative Compound (R-2) |
| Comparative Example 6 | Comparative Compound (R-3) |

Next, using a xenon lamp irradiation tester (Suntest XLS, manufactured by Atlas), the produced 10 films were tested for exposure at 60 mW/cm², 26° C. and 120 J. The resultant films were visually checked for outward appearance including discoloration, peeling, etc.

<Discoloration>

The tested 10 films were analyzed to measure the yellow index (YI) thereof. The difference between the YI mean value of the 10 films before the test and the YI mean value of the 10 films after the test (ΔYI) was calculated. Briefly, the absorption spectrum of the polymer was measured using JASCO UV/VIS Spectrophotometer V-560, and the yellow index (YI) was calculated using the accompanying color diagnostic program. The calculation expression is:

$$YI = 100(1.28X - 1.06Z)/Y \text{ (JIS K7373)}$$

(where X, Y and Z each indicates the tristimulus values in the XYZ color system).

A larger ΔYI value means that the film discolored more after the exposure test.

<Peeling>

Each film was cross-cut in 10 cuts in length×10 cuts in width, totaling 100 cuts. After the exposure test, the number of the peeled cuts was counted in every film, and expressed as a ratio (%) of the peeled cuts to the total 1000 cuts (100 cuts/sheet×10 sheets).

The results are shown in the following Table.

TABLE 3

| Film | ΔYI | Peel Ratio |
|---|---|---|
| Example 45 | 0.5 | 0% |
| Example 46 | 0.6 | 0% |
| Example 47 | 0.6 | 0% |
| Example 48 | 0.5 | 0% |
| Example 49 | 1.6 | 0.6% |
| Example 50 | 1.6 | 0.3% |
| Example 51 | 1.4 | 0.4% |
| Example 52 | 1.8 | 0.6% |
| Example 53 | 1.2 | 0.3% |
| Example 54 | 1.7 | 0.5% |
| Example 55 | 0.8 | 0.6% |
| Example 56 | 0.6 | 0.4% |
| Example 57 | 0.6 | 0.6% |
| Example 58 | 1.0 | 0.8% |
| Example 59 | 1.0 | 0.9% |
| Example 60 | 0.6 | 0.6% |
| Example 61 | 0.6 | 0.6% |
| Example 62 | 0.8 | 0.3% |
| Example 63 | 0.5 | 0% |
| Example 64 | 0.7 | 0.3% |
| Example 65 | 0.6 | 0% |
| Example 66 | 0.6 | 0% |
| Comparative Example 4 | 1.8 | 3.2% |
| Comparative Example 5 | 2.7 | 4.1% |
| Comparative Example 6 | 5.2 | 4.9% |

From the Table, it is known that the films of Example 45 to Example 66 produced using the compounds of the present invention all hardly discolored or peeled from the substrate when exposed to UV light. Accordingly, the compounds of the present invention are useful as a constituent component of polymerizable compositions. In addition, the optically anisotropic bodies using the polymerizable liquid crystal compositions containing the compound of the present invention are useful for optical films, etc.

The invention claimed is:

1. A compound represented by the general formula (I):

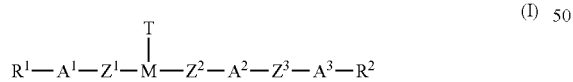

(I)

wherein $R^1$ and $R^2$ each independently represent a polymerizable group represented by general formula (I-R),

(I-R)

in the general formula (I-R), P represents a polymerizable group;

Sp represents a single bond, or an alkylene group having 1 to 20 carbon atoms in which one —CH$_2$— or two or more of (—CH$_2$—)'s which are not adjacent to each other may be each independently substituted with —O—, —COO—, —OCO—, —OCO—O—, —CO—NH—, —NH—CO—, —CH=CH— or —C≡C—, in which when plural Sp's exist, said plural Sp's may be the same or different;

X represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C— or a single bond, in which when plural X's exist, said plural X's may be the same or different, wherein P-(Sp-X)$_k$— does not contain an —O—O— bond;

k represents an integer of 0 to 10;

$A^1$, $A^2$ and $A^3$ each independently represent a 1,4-phenylene group, a 1,4-cyclohexylene group, a pyridine-2,5-diyl group, a pyrimidine-2,5-diyl group, a naphthalene-2,6-diyl group, a naphthalane-1,4-diyl group, a tetrahydronaphthalene-2,6-diyl group, a decahydronaphthalane-2,6-diyl group or a 1,3-dioxane-2,5-diyl group, which may be unsubstituted or substituted with one or more of substituents L's, $Z^1$, $Z^2$ and $Z^3$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C— or a single bond, M represents an optionally-substituted trivalent aromatic group;

T represents a group selected from the following formula (T-1) or formula (T-2):

(T-1)

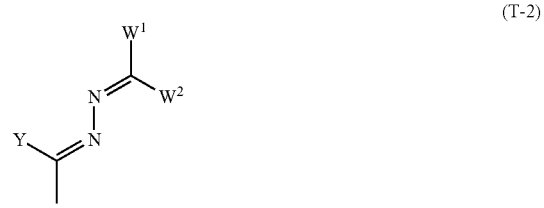

(T-2)

wherein $W^1$ represents a group including an aromatic group and/or a non-aromatic group optionally substituted and having 1 to 80 carbon atoms, in which the aromatic group may be a hydrocarbon ring or a hetero ring, the non-aromatic group may be a hydrocarbon group or a hydrocarbon group where one or more of arbitrary carbon atoms is substituted with a hetero atom, wherein the oxygen atoms therein do not directly bond to each other, and the group may be unsubstituted or substituted with one or more of substituents $L^W$'s, $W^2$ represents a hydrogen atom, or a linear or branched alkyl group having 1 to 20 carbon atoms, in which one —$CH_2$— or two or more of (—$CH_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and one or more of arbitrary hydrogen atoms in the alkyl group may be substituted with a fluorine atom, or $W^2$ represents a group including an aromatic group and/or a non-aromatic group optionally substituted and having 1 to 80 carbon atoms, in which the aromatic group may be a hydrocarbon ring or a hetero ring, and the non-aromatic group may be a hydrocarbon group or a hydrocarbon group where one or more of arbitrary carbon atoms is substituted with a hetero atom (in which the oxygen atoms therein do not directly bond to each other, and the group may be unsubstituted or substituted with one or more of substituents $L^W$'s, or $W^2$ may represent a group represented by $P^W$-($Sp^W$-$X^W$)$_{kW}$—, where $P^W$ represents a polymerizable group, $Sp^W$ represents a spacer group or a single bond, and plural $Sp^W$'s, if any, may be the same or different, $X^W$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, plural $X^W$'s, if any, may be the same or different in which $P^W$-($Sp^W$-$X^W$)$_{kW}$— does not contain an —O—O— bond, kW represents an integer of 0 to 10, and $W^1$ and $W^2$ may together form a cyclic structure, $L^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more of (—$CH_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and one or more of arbitrary hydrogen atoms in the alkyl group may be substituted with a fluorine atom, or $L^W$ represents a group represented by $P^{LW}$-($Sp^{LW}$-$X^{LW}$)$_{kLW}$— where $P^{LW}$ represents a polymerizable group, $Sp^{LW}$ represents a spacer group or a single bond, plural $Sp^{LW}$'s, if any, may be the same or different, $X^{LW}$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, plural $X^{LW}$'s, if any, may be the same or different in which $P^{LW}$-($Sp^{LW}$-$X^{LW}$)$_{kLW}$— does not contain an —O—O— bond, kLW represents an integer of 0 to 10, and plural $L^W$'s, if any, in the compound may be the same or different, Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more of (—$CH_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and one or more of arbitrary hydrogen atoms in the alkyl group may be substituted with a fluorine atom, or Y represents a group represented by $P^Y$-($Sp^Y$-$X^Y$)$_{kY}$— where $P^Y$ represents a polymerizable group, $Sp^Y$ represents a spacer group or a single bond, plural $Sp^Y$'s, if any, may be the same or different, $X^Y$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, plural $X^Y$'s, if any, may be the same or different in which $P^Y$-($Sp^Y$-$X$)$_{kY}$— does not contain an —O—O— bond, kY represents an integer of 0 to 10;

L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH$_2$— or two or more of (—CH$_2$—)'s which are not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and one or more of arbitrary hydrogen atoms in the alkyl group may be substituted with a fluorine atom, or L represents a group represented by $P^L$-$(Sp^L$-$X^L)_{kL}$— where $P^L$ represents a polymerizable group, $Sp^L$ represents a spacer group or a single bond, plural $Sp^L$'s, if any, may be the same or different, $X^L$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C— or a single bond, plural $X^L$'s, if any, may be the same or different in which $P^L$-$(Sp^L$-$X^L)_{kL}$— does not contain an —O—O— bond, kL represents an integer of 0 to 10, plural L's, if any, in the compound may be the same or different; and the group that links T-M may be a single bond or a double bond.

2. The compound according to claim 1, wherein in the general formula (I), at least one of $R^1$ and $R^2$ represents a group represented by the following general formula (I-R):

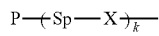
(I-R)

wherein P represents a polymerizable group, Sp represents a spacer group or a single bond, and plural Sp's, if any, may be the same or different; X represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C— or a single bond, and plural X's, if any, may be the same or different, in which P-(Sp-X)$_k$— does not contain an —O—O— bond; and k represents an integer of 0 to 10.

3. The compound according to claim 2, wherein in the formula (I-R), P represents a group selected from the following formula (P-1) to formula (P-20):

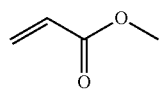
(P-1)

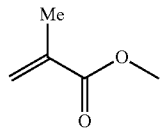
(P-2)

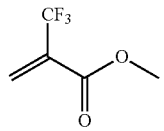
(P-3)

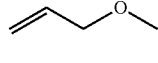
(P-4)

(P-5)

(P-6)

(P-7)

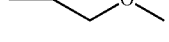
(P-8)

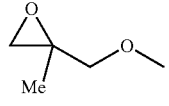
(P-9)

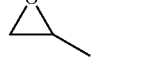
(P-10)

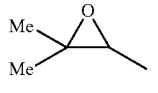
(P-11)

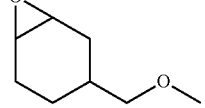
(P-12)

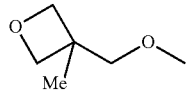
(P-13)

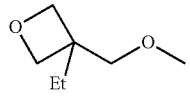
(P-14)

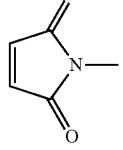
(P-15)

HS—

(P-16)

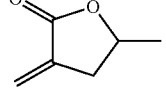

-continued (P-17) 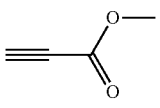

(P-18) 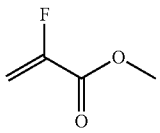

(P-19) 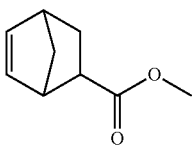

(P-20) 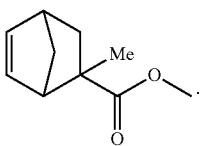

4. The compound according to claim 2, wherein in the formula (I-R), Sp each independently represents an alkylene group having 1 to 20 carbon atoms in which one —$CH_2$— or two or more of (—$CH_2$—)'s which are not adjacent to each other may be each independently substituted with —O—, —COO—, —OCO—, —OCO—O—, —CO—NH—, —NH—CO—, —CH=CH— or —C≡C—.

5. A composition containing the compound of claim 1.

6. A liquid crystal composition containing the compound of claim 1.

7. A polymer obtained through polymerization of the composition of claim 5.

8. An optically anisotropic body using the polymer of claim 7.

9. Resins, resin additives, oils, filters, adhesives, pressure-sensitive adhesives, oils and fats, inks, medicines, cosmetics, detergents, building materials, wrapping or packaging materials, liquid crystal materials, organic EL materials, organic semiconductor materials, electronic materials, display devices, electronic devices, communication instruments, automobile parts, airplane parts, machine parts, agricultural chemicals and foods using the compound of claim 1.

* * * * *